US009428784B2

(12) United States Patent
Choi et al.

(10) Patent No.: US 9,428,784 B2
(45) Date of Patent: Aug. 30, 2016

(54) METHODS FOR INCREASING N-GLYCAN OCCUPANCY AND REDUCING PRODUCTION OF HYBRID N-GLYCANS IN PICHIA PASTORIS STRAINS LACKING ALG3 EXPRESSION

(71) Applicant: MERCK SHARP & DOHME CORP., Rahway, NJ (US)

(72) Inventors: Byung-Kwon Choi, Norwich, VT (US); Stephen R. Hamilton, Enfield, NH (US); Natarajan Sethuraman, Hanover, NH (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 83 days.

(21) Appl. No.: 14/354,160

(22) PCT Filed: Oct. 23, 2012

(86) PCT No.: PCT/US2012/061428
§ 371 (c)(1),
(2) Date: Apr. 25, 2014

(87) PCT Pub. No.: WO2013/062939
PCT Pub. Date: May 2, 2013

(65) Prior Publication Data
US 2014/0329276 A1 Nov. 6, 2014

Related U.S. Application Data

(60) Provisional application No. 61/679,212, filed on Aug. 3, 2012, provisional application No. 61/552,720, filed on Oct. 28, 2011.

(51) Int. Cl.
| | |
|---|---|
| C12P 19/18 | (2006.01) |
| C12P 21/00 | (2006.01) |
| C07K 14/62 | (2006.01) |
| C07K 16/10 | (2006.01) |
| C07K 16/32 | (2006.01) |
| C07K 14/39 | (2006.01) |
| C07K 14/395 | (2006.01) |
| C12N 9/10 | (2006.01) |
| C07K 14/47 | (2006.01) |
| C07K 16/00 | (2006.01) |
| C12N 15/81 | (2006.01) |

(52) U.S. Cl.
CPC .............. *C12P 21/005* (2013.01); *C07K 14/39* (2013.01); *C07K 14/395* (2013.01); *C07K 14/4725* (2013.01); *C07K 14/62* (2013.01); *C07K 16/00* (2013.01); *C07K 16/1027* (2013.01); *C07K 16/32* (2013.01); *C12N 9/1051* (2013.01); *C12N 15/815* (2013.01); *C07K 2317/14* (2013.01); *C07K 2317/21* (2013.01); *C07K 2317/41* (2013.01); *Y02P 20/52* (2015.11)

(58) Field of Classification Search
CPC ..... C12N 9/1051; C12P 21/005; C12P 19/18
See application file for complete search history.

(56) References Cited

U.S. PATENT DOCUMENTS
2010/0279356 A1 11/2010 Hamilton

FOREIGN PATENT DOCUMENTS
WO WO2013062939 5/2013

OTHER PUBLICATIONS

Clerc et al. 2009; HTM 1 protein generates the N-glycan signal for glycoprotein degradation in the endoplasmic reticulum. J. Cell Biol. 184(1): 159-172; the 1 page Supplemental Material Only is being sent.*
Nasab et al. 2008; All in one: Leishmania major STT3 protein substitute for the whole oligosaccharyltransferase complex in Saccharomyces cerevisiae. Molecular Biology of the Cell. 19: 3758-3768.*
Davidson et al. 2004; Functional analysis of the ALG3 gene encoding the Dol-P-Man:Man5GlcNac2-PP-Dol mannosyltransferase enzyme of P. pastoris. Glycobiology. 14(5): 399-407.*
Clerc, Htm1 protein generates the N-glycan signal for glycoprotein degradation in the endoplasmic reticulum, J. Cell Biol., 2009, pp. 159-172, 184(1).
Davidson, Functional analysis of the ALG3 gene encoding the Dol-P-Man: Man5GlcNAc2-PP-Dol mannosyltransferase enzyme of P. pastoris, Glycobiology, 2004, pp. 399-407, 14(5).
Denic, A Luminal Surveillance Complex that Selects Misfolded Glycoproteins for ER-Associated Degradation, Cell, 2006, pp. 349-359, 126(2).

(Continued)

*Primary Examiner* — Karen Cochrane Carlson
(74) *Attorney, Agent, or Firm* — Gloria Fuentes; John David Reilly

(57) ABSTRACT

Methods for increasing the yield and N-glycosylation site occupancy of paucimannose or complex N-glycans of recombinant glycoproteins produced in a recombinant host cell lacking dolichyl-P-Man:Man5GlcNAc2-PP-dolichyl alpha-1,3 mannosyltransferase (Alg3p) activity are disclosed. In particular, recombinant host cells are provided that comprise a disruption of the expression of an OS-9 family gene in the host cell. These recombinant host cells may then be used for producing recombinant glycoproteins. In further embodiments, the recombinant host cells further overexpress at least one heterologous single-subunit oligosaccharyltransferase, which in particular embodiments is capable of functionally suppressing the lethal phenotype of a mutation of at least one essential protein of the yeast oligosaccharyltransferase (OTase) complex.

14 Claims, 25 Drawing Sheets

(56) References Cited

OTHER PUBLICATIONS

Finger, Analysis of two mutated vacuolar proteins reveals a degradation pathway in the endoplasmic reticulum or a related compartment of yeast, Eur. J. Biochem., 1993, pp. 565-574, 218(2).

Friedmann, YOS9, the Putative Yeast Homolog of a Gene Amplified inOsteosarcomas, Is Involved in the Endoplasmic Reticulum (ER)-Golgi Transport of GPI-anchored Proteins*, J. Biol. Chem., 2002, pp. 35274-81, 277 (38).

International Search Report—Mailing date of Mar. 5, 2013.

* cited by examiner

YGLY8323
[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1::lacZ bmt3::lacZ-URA5-lacZ
PRO1::ARG1/AOX1p-TrMDS1

↓ pGLY6564

YGLY14401
[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1::lacZ bmt3::lacZ-URA5-lacZ
PRO1::ARG1/AOX1p-TrMDS1]
TRP2::Sh ble/AOX1p-anti-RSV-Ab]

↓ Counterselect on 5-FOA

YGLY15820
[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1::lacZ bmt3::lacZ
PRO1::ARG1/AOX1p-TrMDS1]
TRP2::Sh ble/AOX1p-anti-RSV-Ab]

↓ pGLY7140

FIG.1A

YGLY15019

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1::lacZ bmt3::lacZ
PRO1::ARG1/AOX1p-TrMDS1]
TRP2::Sh ble/AOX1p-anti-RSV-Ab
yos9Δ::lacZ-URA5-LacZ]

pGLY6294 ↓

YGLY17327

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1::lacZ bmt3::lacZ
PRO1::ARG1/AOX1p-TrMDS1]
TRP2::Sh ble/AOX1p-anti-RSV-Ab
yos9Δ::lacZ-URA5-LacZ TRP1::Nat$^R$GAPDHp-LmSTT3d]

↓ Counterselect on 5-FOA

YGLY17331

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1::lacZ bmt3::lacZ
PRO1::ARG1/AOX1p-TrMDS1]
TRP2::Sh ble/AOX1p-anti-RSV-Ab
yos9Δ::lacZ TRP1::Nat$^R$GAPDHp-LmSTT3d]

FIG.1B

Glossary:

| | |
|---|---|
| ScSUC2 | S. cerevisiae Invertase |
| OCH1 | Alpha-1,6-mannosyltransferase |
| KIMNN2-2: | K. lactis UDP-GlcNAc transporter |
| BMT1: | Beta-mannose-transfer (beta- mannose elimination) |
| BMT2: | Beta-mannose-transfer (beta- mannose elimination) |
| BMT3: | Beta-mannose-transfer (beta- mannose elimination) |
| BMT4: | Beta-mannose-transfer (beta- mannose elimination) |
| MNN4L1: | MNN4-like 1 (charge elimination) |
| MmSLC35A3 | Mouse homologue of UDP-GlcNAc transporter |
| PNO1: | Phosphomannosylation of N-linked oligosaccharides (charge elimination) |
| MNN4: | Mannosyltransferase (charge elimination) |
| ScGAL10 | UDP-glucose 4-epimerase |
| XB33 | Truncated HsGalT1 fused to ScKRE2 leader |
| DmUGT | UDP-Galactose transporter |
| KD53 | Truncated DmMNSII fused to ScMNN2 leader |
| TC54 | Truncated RnGNTII fused to ScMNN2 leader |
| NA10 | Truncated HsGNTI fused to PpSEC12 leader |
| FB8: | Truncated MmMNS1A fused to ScSEC12 leader |
| TrMDS1: | Secreted T. reseei MNS1 |
| NatR | Nourseothricin resistance marker |

FIG.1E

YGLY27300-27302
[ ura5Δ::ScSUC2 och1Δ::lacZ bmt2Δ::lacZ/KlMNN2-2
mnn4L1Δ::lacZ/MmSLC35A3 pno1Δ mnn4Δ::lacZ
bmt1Δ::lacZ bmt4Δ::lacZ bmt3Δ PRO1::lacZ/TrMDS1
yos9Δ::lacZ alg3Δ::lacZ-URA5-LacZ
TRP2::Sh ble/AOX1p-anti-Her2-Ab
URA6::ScARR3/AOX1p-LmSTT3c ]

YGLY27297-27299
[ ura5Δ::ScSUC2 och1Δ::lacZ bmt2Δ::lacZ/KlMNN2-2
mnn4L1Δ::lacZ/MmSLC35A3 pno1Δ mnn4Δ::lacZ
bmt1Δ::lacZ bmt4Δ::lacZ bmt3Δ PRO1::lacZ/TrMDS1
yos9Δ::lacZ alg3Δ::lacZ-URA5-LacZ
TRP2::Sh ble/AOX1p-anti-Her2-Ab
URA6::ScARR3/AOX1p-LmSTT3c ]

YGLY24558

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
bmt1Δ::lacZ bmt4Δ::lacZ bmt3Δ PRO1::lacZ/TrMDS1
yos9Δ::lacZ alg3Δ::lacZ-URA5-LacZ
URA6::ScARR3/AOX1p-LmSTT3a/AOX1p-LmSTT3b/AOX1p-LmSTT3c]

pGLY6833 

YGLY26363-26364

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
bmt1Δ::lacZ bmt4Δ::lacZ bmt3Δ PRO1::lacZ/TrMDS1
yos9Δ::lacZ alg3Δ::lacZ-URA5-LacZ
URA6::ScARR3/AOX1p-LmSTT3a/AOX1p-LmSTT3b/AOX1p-LmSTT3d
TRP2::Sh ble/AOX1p-anti-Her2-Ab]

B

YGLY25636

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
bmt1Δ::lacZ bmt4Δ::lacZ bmt3Δ PRO1::lacZ/TrMDS1
yos9Δ::lacZ alg3Δ::lacZ-URA5-LacZ
URA6::ScARR3/AOX1p-LmSTT3d]

pGLY6833 

YGLY26365

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
bmt1Δ::lacZ bmt4Δ::lacZ bmt3Δ PRO1::lacZ/TrMDS1
yos9Δ::lacZ alg3Δ::lacZ-URA5-LacZ
URA6::ScARR3/AOX1p-LmSTT3d
TRP2::Sh ble/AOX1p-anti-Her2-Ab]

FIG. 7E

SEQUENCE LISTING

<160> NUMBER OF SEQ ID NOS: 56

<210> SEQ ID NO 1
<211> LENGTH: 857
<212> TYPE: PRT
<213> ORGANISM: Leishmania major

<400> SEQUENCE: 1

Met Gly Lys Arg Lys Gly Asn Ser Leu Gly Asp Ser Gly Ser Ala Ala
1               5                   10                  15

Thr Ala Ser Arg Glu Ala Ser Ala Gln Ala Glu Asp Ala Ala Ser Gln
            20                  25                  30

```
Thr Lys Thr Ala Ser Pro Pro Ala Lys Val Ile Leu Leu Pro Lys Thr
             35                  40                  45

Leu Thr Asp Glu Lys Asp Phe Ile Gly Ile Phe Pro Phe Pro Phe Trp
 50                  55                  60

Pro Val His Phe Val Leu Thr Val Ala Leu Phe Val Leu Ala Ala
 65                  70                  75                  80

Ser Cys Phe Gln Ala Phe Thr Val Arg Met Ile Ser Val Gln Ile Tyr
                 85                  90                  95

Gly Tyr Leu Ile His Glu Phe Asp Pro Trp Phe Asn Tyr Arg Ala Ala
                100                 105                 110

Glu Tyr Met Ser Thr His Gly Trp Ser Ala Phe Phe Ser Trp Phe Asp
            115                 120                 125

Tyr Met Ser Trp Tyr Pro Leu Gly Arg Pro Val Gly Ser Thr Thr Tyr
130                 135                 140

Pro Gly Leu Gln Leu Thr Ala Val Ala Ile His Arg Ala Leu Ala Ala
145                 150                 155                 160

Ala Gly Met Pro Met Ser Leu Asn Asn Val Cys Val Leu Met Pro Ala
                165                 170                 175

Trp Phe Gly Ala Ile Ala Thr Ala Thr Leu Ala Phe Cys Thr Tyr Glu
                180                 185                 190

Ala Ser Gly Ser Thr Val Ala Ala Ala Ala Ala Leu Ser Phe Ser
195                 200                 205

Ile Ile Pro Ala His Leu Met Arg Ser Met Ala Gly Glu Phe Asp Asn
    210                 215                 220

Glu Cys Ile Ala Ala Ala Met Leu Leu Thr Phe Tyr Cys Trp Val
225                 230                 235                 240

Arg Ser Leu Arg Thr Arg Ser Ser Trp Pro Ile Gly Val Leu Thr Gly
                245                 250                 255

Val Ala Tyr Gly Tyr Met Ala Ala Trp Gly Gly Tyr Ile Phe Val
                260                 265                 270

Leu Asn Met Val Ala Met His Ala Gly Ile Ser Ser Met Val Asp Trp
    275                 280                 285

Ala Arg Asn Thr Tyr Asn Pro Ser Leu Leu Arg Ala Tyr Thr Leu Phe
290                 295                 300

Tyr Val Val Gly Thr Ala Ile Ala Val Cys Val Pro Pro Val Gly Met
305                 310                 315                 320

Ser Pro Phe Lys Ser Leu Glu Gln Leu Gly Ala Leu Leu Val Leu Val
                325                 330                 335

Phe Leu Cys Gly Leu Gln Val Cys Glu Val Leu Arg Ala Arg Ala Gly
                340                 345                 350

Val Glu Val Arg Ser Arg Ala Asn Phe Lys Ile Arg Val Arg Val Phe
                355                 360                 365

Ser Val Met Ala Gly Val Ala Ala Leu Ala Ile Ser Val Leu Ala Pro
370                 375                 380

Thr Gly Tyr Phe Gly Pro Leu Ser Val Arg Val Arg Ala Leu Phe Val
385                 390                 395                 400

Glu His Thr Arg Thr Gly Asn Pro Leu Val Asp Ser Val Ala Glu His
                405                 410                 415

Gln Pro Ala Ser Pro Glu Ala Met Trp Ala Phe Leu His Val Cys Gly
                420                 425                 430

Val Thr Trp Gly Leu Gly Ser Ile Val Leu Ala Val Ser Thr Phe Val
                435                 440                 445

His Tyr Ser Pro Ser Lys Val Phe Trp Leu Leu Asn Ser Gly Ala Val
```

```
            450                 455                 460
Tyr Tyr Phe Ser Thr Arg Met Ala Arg Leu Leu Leu Ser Gly Pro
465                 470                 475                 480

Ala Ala Cys Leu Ser Thr Gly Ile Phe Val Gly Thr Ile Leu Glu Ala
            485                 490                 495

Ala Val Gln Leu Ser Phe Trp Asp Ser Asp Ala Thr Lys Ala Lys Lys
            500                 505                 510

Gln Gln Lys Gln Ala Gln Arg His Gln Arg Gly Ala Gly Lys Gly Ser
            515                 520                 525

Gly Arg Asp Asp Ala Lys Asn Ala Thr Thr Ala Arg Ala Phe Cys Asp
            530                 535                 540

Val Phe Ala Gly Ser Ser Leu Ala Trp Gly His Arg Met Val Leu Ser
545                 550                 555                 560

Ile Ala Met Trp Ala Leu Val Thr Thr Thr Ala Val Ser Phe Phe Ser
                565                 570                 575

Ser Glu Phe Ala Ser His Ser Thr Lys Phe Ala Glu Gln Ser Ser Asn
            580                 585                 590

Pro Met Ile Val Phe Ala Ala Val Gln Asn Arg Ala Thr Gly Lys
            595                 600                 605

Pro Met Asn Leu Leu Val Asp Asp Tyr Leu Lys Ala Tyr Glu Trp Leu
            610                 615                 620

Arg Asp Ser Thr Pro Glu Asp Ala Arg Val Leu Ala Trp Trp Asp Tyr
625                 630                 635                 640

Gly Tyr Gln Ile Thr Gly Ile Gly Asn Arg Thr Ser Leu Ala Asp Gly
                645                 650                 655

Asn Thr Trp Asn His Glu His Ile Ala Thr Ile Gly Lys Met Leu Thr
            660                 665                 670

Ser Pro Val Val Glu Ala His Ser Leu Val Arg His Met Ala Asp Tyr
            675                 680                 685

Val Leu Ile Trp Ala Gly Gln Ser Gly Asp Leu Met Lys Ser Pro His
            690                 695                 700

Met Ala Arg Ile Gly Asn Ser Val Tyr His Asp Ile Cys Pro Asp Asp
705                 710                 715                 720

Pro Leu Cys Gln Gln Phe Gly Phe His Arg Asn Asp Tyr Ser Arg Pro
                725                 730                 735

Thr Pro Met Met Arg Ala Ser Leu Leu Tyr Asn Leu His Glu Ala Gly
                740                 745                 750

Lys Arg Lys Gly Val Lys Val Asn Pro Ser Leu Phe Gln Glu Val Tyr
            755                 760                 765

Ser Ser Lys Tyr Gly Leu Val Arg Ile Phe Lys Val Met Asn Val Ser
            770                 775                 780

Ala Glu Ser Lys Lys Trp Val Ala Asp Pro Ala Asn Arg Val Cys His
785                 790                 795                 800

Pro Pro Gly Ser Trp Ile Cys Pro Gly Gln Tyr Pro Pro Ala Lys Glu
                805                 810                 815

Ile Gln Glu Met Leu Ala His Arg Val Pro Phe Asp Gln Val Thr Asn
            820                 825                 830

Ala Asp Arg Lys Asn Asn Val Gly Ser Tyr Gln Glu Glu Tyr Met Arg
            835                 840                 845

Arg Met Arg Glu Ser Glu Asn Arg Arg
850                 855

<210> SEQ ID NO 2
```

<211> LENGTH: 2577
<212> TYPE: DNA
<213> ORGANISM: Leishmania major

<400> SEQUENCE: 2

| | | | | | |
|---|---|---|---|---|---|
| atgggtaaaa | gaaagggaaa | ctccttggga | gattctggtt | ctgctgctac | tgcttccaga | 60 |
| gaggcttctg | ctcaagctga | agatgctgct | tcccagacta | agactgcttc | tccacctgct | 120 |
| aaggttatct | tgttgccaaa | gactttgact | gacgagaagg | acttcatcgg | tatcttccca | 180 |
| tttccattct | ggccagttca | cttcgttttg | actgttgttg | ctttgttcgt | tttggctgct | 240 |
| tcctgtttcc | aggctttcac | tgttagaatg | atctccgttc | aaatctacgg | ttacttgatc | 300 |
| cacgaatttg | acccatggtt | caactacaga | gctgctgagt | acatgtctac | tcacggatgg | 360 |
| agtgcttttt | tctcctggtt | cgattacatg | tcctggtatc | cattgggtag | accagttggt | 420 |
| tctactactt | acccaggatt | gcagttgact | gctgttgcta | tccatagagc | tttggctgct | 480 |
| gctggaatgc | caatgtcctt | gaacaatgtt | tgtgttttga | tgccagcttg | gtttggtgct | 540 |
| atcgctactc | ctactttggc | tttctgtact | tacgaggctt | ctggttctac | tgttgctgct | 600 |
| gctgcagctg | ctttgtcctt | ctccattatc | cctgctcact | tgatgagatc | catggctggt | 660 |
| gagttcgaca | cgagtgtat | tgctgttgct | gctatgttgt | tgactttcta | ctgttgggtt | 720 |
| cgttccttga | aactagatc | ctcctggcca | atcggtgttt | tgacaggtgt | tgcttacggt | 780 |
| tacatgctg | ctgcttgggg | aggttacatc | ttcgttttga | acatggttgc | tatgcacgct | 840 |
| ggtatctctt | ctatggttga | ctgggctaga | aacacttaca | acccatcctt | gttgagagct | 900 |
| tacactttgt | tctacgttgt | tggtactgct | atcgctgttt | gtgttccacc | agttggaatg | 960 |
| tctccattca | agtccttgga | gcagttggga | gctttgttgg | ttttggtttt | cttgtgtgga | 1020 |
| ttgcaagttt | gtgaggtttt | gagagctaga | gctggtgttg | aagttagatc | cagagctaat | 1080 |
| ttcaagatca | gagttagagt | tttctccgtt | atggctggtg | ttgctgctttt | ggctatctct | 1140 |
| gttttggctc | caactggtta | ctttggtcca | ttgtctgtta | gagttagagc | tttgtttgtt | 1200 |
| gagcacacta | gaactggtaa | cccattggtt | gactccgttg | ctgaacatca | accagcttct | 1260 |
| ccagaggcta | tgtgggcttt | cttgcatgtt | tgtggtgtta | cttggggatt | gggttccatt | 1320 |
| gttttggctg | tttccacttt | cgttcactac | tcccccatcta | aggttttctg | gttgttgaac | 1380 |
| tccggtgctg | tttactactt | ctccactaga | atggctagat | tgttgttgtt | gtccggtcca | 1440 |
| gctgcttgtt | tgtccactgg | tatcttcgtt | ggtactatct | tggaggctgc | tgttcaattg | 1500 |
| tctttctggg | actccgatgc | tactaaggct | aagaagcagc | aaaagcaggc | tcaaagacac | 1560 |
| caaagaggtg | ctggtaaagg | ttctggtaga | gatgacgcta | agaacgctac | tactgctaga | 1620 |
| gcttctgtg | acgttttcgc | tggttcttct | ttggcttggg | gtcacagaat | ggttttgtcc | 1680 |
| attgctatgt | gggctttggt | tactactact | gctgtttcct | tcttctcctc | cgaatttgct | 1740 |
| tctcactcca | ctaagttcgc | tgaacaatcc | tccaacccaa | tgatcgtttt | cgctgctgtt | 1800 |
| gttcagaaca | gagctactgg | aaagccaatg | aacttgttgg | ttgacgacta | cttgaaggct | 1860 |
| tacgagtggt | tgagagactc | tactccagag | gacgctagag | ttttggcttg | gtgggactac | 1920 |
| ggttaccaaa | tcactggtat | cggtaacaga | acttccttgg | ctgatggtaa | cacttggaac | 1980 |
| cacgagcaca | ttgctactat | cggaaagatg | ttgacttccc | cagttgttga | agctcactcc | 2040 |
| cttgttagac | acatggctga | ctacgttttg | atttgggctg | tcaatctgg | tgacttgatg | 2100 |
| aagtctccac | acatggctag | aatcggtaac | tctgtttacc | acgacatttg | tccagatgac | 2160 |
| ccattgtgtc | agcaattcgg | tttccacaga | aacgattact | ccagaccaac | tccaatgatg | 2220 |

| | | |
|---|---|---|
| agagcttcct tgttgtacaa cttgcacgag gctggaaaaa gaaagggtgt taaggttaac | 2280 |
| ccatctttgt tccaagaggt ttactcctcc aagtacggac ttgttagaat cttcaaggtt | 2340 |
| atgaacgttt ccgctgagtc taagaagtgg gttgcagacc cagctaacag agtttgtcac | 2400 |
| ccacctggtt cttggatttg tcctggtcaa tacccacctg ctaaagaaat ccaagagatg | 2460 |
| ttggctcaca gagttccatt cgaccaggtt acaaacgctg acagaaagaa caatgttggt | 2520 |
| tcctaccaag aggaatacat gagaagaatg agagagtccg agaacagaag ataatag | 2577 |

<210> SEQ ID NO 3
<211> LENGTH: 934
<212> TYPE: DNA
<213> ORGANISM: Artificial Sequence
<220> FEATURE:
<223> OTHER INFORMATION: Pichia pastoris AOX1 promoter

<400> SEQUENCE: 3

| | | |
|---|---|---|
| aacatccaaa gacgaaaggt tgaatgaaac cttttttgcca tccgacatcc acaggtccat | 60 |
| tctcacacat aagtgccaaa cgcaacagga ggggatacac tagcagcaga ccgttgcaaa | 120 |
| cgcaggacct ccactcctct tctcctcaac acccactttt gccatcgaaa accagccca | 180 |
| gttattgggc ttgattggag ctcgctcatt ccaattcctt ctattaggct actaacacca | 240 |
| tgactttatt agcctgtcta tcctggcccc cctggcgagg ttcatgtttg tttatttccg | 300 |
| aatgcaacaa gctccgcatt acacccgaac atcactccag atgagggctt tctgagtgtg | 360 |
| gggtcaaata gtttcatgtt ccccaaatgg cccaaaactg acagtttaaa cgctgtcttg | 420 |
| gaacctaata tgacaaaagc gtgatctcat ccaagatgaa ctaagtttgg ttcgttgaaa | 480 |
| tgctaacggc cagttggtca aaaagaaact tccaaaagtc ggcataccgt tgtcttgtt | 540 |
| tggtattgat tgacgaatgc tcaaaaataa tctcattaat gcttagcgca gtctctctat | 600 |
| cgcttctgaa ccccggtgca cctgtgccga aacgcaaatg gggaaacacc cgcttttttgg | 660 |
| atgattatgc attgtctcca cattgtatgc ttccaagatt ctggtgggaa tactgctgat | 720 |
| agcctaacgt tcatgatcaa aatttaactg ttctaacccc tacttgacag caatatataa | 780 |
| acagaaggaa gctgccctgt cttaaaccctt ttttttttatc atcattatta gcttactttc | 840 |
| ataattgcga ctggttccaa ttgacaagct tttgatttta acgacttttta acgacaactt | 900 |
| gagaagatca aaaaacaact aattattcga aacg | 934 |

<210> SEQ ID NO 4
<211> LENGTH: 293
<212> TYPE: DNA
<213> ORGANISM: Artificial Sequence
<220> FEATURE:
<223> OTHER INFORMATION: Sacharomyces cerevisiea CYC transcription
    termination sequence

<400> SEQUENCE: 4

| | | |
|---|---|---|
| acaggcccct tttcctttgt cgatatcatg taattagtta tgtcacgctt acattcacgc | 60 |
| cctcctccca catccgctct aaccgaaaag gaaggagtta gacaacctga agtctaggtc | 120 |
| cctatttatt tttttaata gttatgttag tattaagaac gttatttata tttcaaattt | 180 |
| ttcttttttt tctgtacaaa cgcgtgtacg catgtaacat tatactgaaa accttgcttg | 240 |
| agaaggtttt gggacgctcg aaggctttaa tttgcaagct gccggctctt aag | 293 |

<210> SEQ ID NO 5
<211> LENGTH: 1215

<212> TYPE: DNA
<213> ORGANISM: Saccharomyces cerevisea

<400> SEQUENCE: 5

```
atgtcagaag atcaaaaaag tgaaaattcc gtaccttcta aggttaatat ggtgaatcgc      60
accgatatac tgactacgat caagtcattg tcatggcttg acttgatgtt gccatttact     120
ataattctct ccataatcat tgcagtaata atttctgtct atgtgccttc ttcccgtcac     180
acttttgacg ctgaaggtca tcccaatcta atgggagtgt ccattccttt gactgttggt     240
atgattgtaa tgatgattcc cccgatctgc aaagtttcct gggagtctat tcacaagtac     300
ttctacagga gctatataag gaagcaacta gccctctcgt tattttgaa ttgggtcatc      360
ggtcctttgt tgatgacagc attggcgtgg atggcgctat tcgattataa ggaataccgt     420
caaggcatta ttatgatcgg agtagctaga tgcattgcca tggtgctaat ttggaatcag     480
attgctggag gagacaatga tctctgcgtc gtgcttgtta ttacaaactc gcttttacag     540
atggtattat atgcaccatt gcagatattt tactgttatg ttatttctca tgaccacctg     600
aatacttcaa atagggtatt attcgaagag gttgcaaagt ctgtcggagt ttttctcggc     660
ataccactgg gaattggcat tatcatacgt ttgggaagtc ttaccatagc tggtaaaagt     720
aattatgaaa atacatttt gagatttatt tctccatggg caatgatcgg atttcattac      780
actttatttg ttattttat tagtagaggt tatcaattta tccacgaaat tggttctgca      840
atattgtgct ttgtcccatt ggtgctttac ttctttattg catggttttt gaccttcgca     900
ttaatgaggt acttatcaat atctaggagt gatacacaaa gagaatgtag ctgtgaccaa     960
gaactacttt taagagggt ctggggaaga aagtcttgtg aagctagctt ttctattacg     1020
atgacgcaat gtttcactat ggcttcaaat aattttgaac tatccctggc aattgctatt    1080
tccttatatg gtaacaatag caagcaagca atagctgcaa catttgggcc gttgctagaa    1140
gttccaattt tattgatttt ggcaatagtc gcgagaatcc ttaaaccata ttatatatgg    1200
aacaatagaa attaa                                                     1215
```

<210> SEQ ID NO 6
<211> LENGTH: 600
<212> TYPE: DNA
<213> ORGANISM: Artificial Sequence
<220> FEATURE:
<223> OTHER INFORMATION: Pichia pastoris RPL10 promoter

<400> SEQUENCE: 6

```
gttcttcgct tggtcttgta tctccttaca ctgtatcttc ccatttgcgt ttaggtggtt      60
atcaaaaact aaaaggaaaa atttcagatg tttatctcta aggttttttc tttttacagt     120
ataacacgtg atgcgtcacg tggtactaga ttacgtaagt tattttggtc cggtgggtaa     180
gtgggtaaga atagaaagca tgaaggttta caaaaacgca gtcacgaatt attgctactt     240
cgagcttgga accaccccaa agattatatt gtactgatgc actaccttct cgattttgct     300
cctccaagaa cctacgaaaa acatttcttg agccttttca acctagacta cacatcaagt     360
tatttaaggt atgttccgtt aacatgtaag aaaaggagag gatagatcgt ttatggggta     420
cgtcgcctga ttcaagcgtg accattcgaa gaataggcct cgaaagctg aataaagcaa      480
atgtcagttg cgattggtat gctgacaaat tagcataaaa agcaatagac tttctaacca     540
cctgtttttt tccttttact ttatttatat tttgccaccg tactaacaag ttcagacaaa     600
```

<210> SEQ ID NO 7

```
<211> LENGTH: 1144
<212> TYPE: DNA
<213> ORGANISM: Pichia pastoris

<400> SEQUENCE: 7
caaatgcaag aggacattag aaatgtgttt ggtaagaaca tgaagccgga ggcatacaaa      60
cgattcacag atttgaagga ggaaaacaaa ctgcatccac cggaagtgcc agcagccgtg     120
tatgccaacc ttgctctcaa aggcattcct acggatctga gtgggaaata tctgagattc     180
acagacccac tattggaaca gtaccaaacc tagtttggcc gatccatgat tatgtaatgc     240
atatagtttt tgtcgatgct cacccgtttc gagtctgtct cgtatcgtct tacgtataag     300
ttcaagcatg tttaccaggt ctgttagaaa ctccttttgtg agggcaggac ctattcgtct     360
cggtcccgtt gtttctaaga gactgtacag ccaagcgcag aatggtggca ttaaccataa     420
gaggattctg atcggacttg gtctattggc tattggaacc acccttacg ggacaaccaa     480
ccctaccaag actcctattg catttgtgga accagccacg gaaagagcgt taaggacgg     540
agacgtctct gtgattttg ttctcggagg tccaggagct ggaaaaggta cccaatgtgc     600
caaactagtg agtaattacg gatttgttca cctgtcagct ggagacttgt tacgtgcaga     660
acagaagagg gagggtctta gtatggaga tgattttcc cagtatatca gagatggact     720
gatagtacct caagaggtca ccattgcgct cttggagcag gccatgaagg aaaacttcga     780
gaaagggaag acacggttct tgattgatgg attccctcgt aagatggacc aggccaaaac     840
ttttgaggaa aaagtcgcaa agtccaaggt gacacttttc tttgattgtc ccgaatcagt     900
gctccttgag agattactta aagaggaca gcaagcgga agagaggatg ataatgcgga     960
gagtatcaaa aaagattca aacattcgt ggaaacttcg atgcctgtgg tggactattt    1020
cgggaagcaa ggacgcgttt tgaaggtatc ttgtgaccac cctgtggatc aagtgtattc    1080
acaggttgtg tcggtgctaa agagaaggg gatctttgcc gataacgaga cggagaataa    1140
ataa                                                                 1144

<210> SEQ ID NO 8
<211> LENGTH: 486
<212> TYPE: DNA
<213> ORGANISM: Artificial Sequence
<220> FEATURE:
<223> OTHER INFORMATION: Pichia pastoris GAPDH promoter

<400> SEQUENCE: 8
tttttgtaga aatgtcttgg tgtcctcgtc caatcaggta gccatctctg aaatatctgg      60
ctccgttgca actccgaacg acctgctggc aacgtaaaat tctccggggt aaaacttaaa     120
tgtggagtaa tggaaccaga aacgtctctt cccttctctc tccttccacc gcccgttacc     180
gtccctagga aattttactc tgctggagag cttcttctac ggccccttg cagcaatgct     240
cttcccagca ttacgttgcg ggtaaaacgg aggtcgtgta cccgacctag cagcccaggg     300
atggaaaagt cccggccgtc gctggcaata atagcgggcg gacgcatgtc atgagattat     360
tggaaaccac cagaatcgaa tataaaaggc gaacaccttt cccaattttg gtttctcctg     420
acccaaagac tttaaattta atttatttgt ccctatttca atcaattgaa caactatcaa     480
aacaca                                                               486

<210> SEQ ID NO 9
<211> LENGTH: 573
<212> TYPE: DNA
<213> ORGANISM: Artificial Sequence
```

<220> FEATURE:
<223> OTHER INFORMATION: Nat resistance ORF

<400> SEQUENCE: 9

```
atgggtacca ctcttgacga cacggcttac cggtaccgca ccagtgtccc gggggacgcc        60
gaggccatcg aggcactgga tgggtccttc accaccgaca ccgtcttccg cgtcaccgcc       120
accggggacg gcttcaccct gcgggaggtg ccggtggacc cgcccctgac caaggtgttc       180
cccgacgacg aatcggacga cgaatcggac gacggggagg acggcgaccc ggactcccgg       240
acgttcgtcg cgtacgggga cgacggcgac ctggcgggct tcgtggtcat ctcgtactcg       300
gcgtggaacc gccggctgac cgtcgaggac atcgaggtcg ccccggagca ccgggggcac       360
ggggtcgggc gcgcgttgat ggggctcgcg acggagttcg ccggcgagcg ggcgccggg        420
cacctctggc tggaggtcac caacgtcaac gcaccggcga tccacgcgta ccggcggatg       480
gggttcaccc tctgcggcct ggacaccgcc ctgtacgacg caccgcctc ggacggcgag        540
cggcaggcgc tctacatgag catgccctgc ccc                                    573
```

<210> SEQ ID NO 10
<211> LENGTH: 388
<212> TYPE: DNA
<213> ORGANISM: Artificial Sequence
<220> FEATURE:
<223> OTHER INFORMATION: Ashbya gossypii TEF1 promoter

<400> SEQUENCE: 10

```
gatctgttta gcttgcctcg tccccgccgg gtcacccggc cagcgacatg gaggcccaga        60
ataccctcct tgacagtctt gacgtgcgca gctcaggggc atgatgtgac tgtcgcccgt       120
acatttagcc catacatccc catgtataat catttgcatc catacatttt gatggccgca       180
cggcgcgaag caaaaattac ggctcctcgc tgcagacctg cgagcaggga aacgctcccc       240
tcacagacgc gttgaattgt ccccacgccg cgcccctgta gagaaatata aaaggttagg       300
atttgccact gaggttcttc tttcatatac ttccttttaa aatcttgcta ggatacagtt       360
ctcacatcac atccgaacat aaacaacc                                          388
```

<210> SEQ ID NO 11
<211> LENGTH: 247
<212> TYPE: DNA
<213> ORGANISM: Artificial Sequence
<220> FEATURE:
<223> OTHER INFORMATION: Ashbya gossypii TEF1 transcription termination
      sequence

<400> SEQUENCE: 11

```
taatcagtac tgacaataaa aagattcttg ttttcaagaa cttgtcattt gtatagtttt        60
tttatattgt agttgttcta ttttaatcaa atgttagcgt gatttatatt ttttttcgcc       120
tcgacatcat ctgcccagat gcgaagttaa gtgcgcagaa agtaatatca tgcgtcaatc       180
gtatgtgaat gctggtcgct atactgctgt cgattcgata ctaacgccgc catccagtgt       240
cgaaaac                                                                 247
```

<210> SEQ ID NO 12
<211> LENGTH: 672
<212> TYPE: DNA
<213> ORGANISM: Artificial Sequence
<220> FEATURE:
<223> OTHER INFORMATION: Pichia pastoris TRP1 5' region and ORF

<400> SEQUENCE: 12

```
gcggaaacgg cagtaaacaa tgagcttca ttagtgggtg ttattatggt ccctggccgg      60
gaacgaacgg tgaaacaaga ggttgcgagg gaaatttcgc agatggtgcg ggaaaagaga    120
atttcaaagg gctcaaaata cttggattcc agacaactga ggaaagagtg ggacgactgt    180
cctctggaag actggtttga gtacaacgtg aaagaaataa acagcagtgg tccattttta    240
gttggagttt ttcgtaatca aagtatagat gaaatccagc aagctatcca cactcatggt    300
ttggatttcg tccaactaca tgggtctgag gattttgatt cgtatatacg caatatccca    360
gttcctgtga ttaccagata cacagataat gccgtcgatg tcttaccgg agaagacctc     420 gctataaata gggcccctggt gctactggac agcgagcaag gaggtgaagg aaaaaccatc   480
gattgggctc gtgcacaaaa atttggagaa cgtagaggaa atatttact agccggaggt     540 ttgacacctg ataatgttgc tcatgctcga tctcatactg gctgtattgg tgttgacgtc    600
tctggtgggg tagaaacaaa tgcctcaaaa gatatggaca agatcacaca atttatcaga    660
aacgctacat aa                                                        672

<210> SEQ ID NO 13
<211> LENGTH: 376
<212> TYPE: DNA
<213> ORGANISM: Artificial Sequence
<220> FEATURE:
<223> OTHER INFORMATION: Pichia pastoris ALG3 transcription termination
      sequence

<400> SEQUENCE: 13
atttacaatt agtaatatta aggtggtaaa aacattcgta gaattgaaat gaattaatat     60
agtatgacaa tggttcatgt ctataaatct ccggcttcgg taccttctcc ccaattgaat   120
acattgtcaa aatgaatggt tgaactatta ggttcgccag tttcgttatt aagaaaactg   180
ttaaaatcaa attccatatc atcggttcca gtgggaggac cagttccatc gccaaaatcc   240
tgtaagaatc cattgtcaga acctgtaaag tcagtttgag atgaaatttt tccggtcttt   300
gttgacttgg aagcttcgtt aaggttaggt gaaacagttt gatcaaccag cggctcccgt   360
tttcgtcgct tagtag                                                    376

<210> SEQ ID NO 14
<211> LENGTH: 834
<212> TYPE: DNA
<213> ORGANISM: Artificial Sequence
<220> FEATURE:
<223> OTHER INFORMATION: Pichia pastoris TRP1 3' region

<400> SEQUENCE: 14
aagtcaatta aatacacgct tgaaaggaca ttacatagct ttcgatttaa gcagaaccag     60
aaatgtagaa ccacttgtca atagattggt caatcttagc aggagcggct gggctagcag   120
ttggaacagc agaggttgct gaaggtgaga aggatggagt ggattgcaaa gtggtgttgg   180
ttaagtcaat ctcaccaggg ctggttttgc caaaaatcaa cttctcccag gcttcacggc   240
attcttgaat gacctcttct gcatacttct tgttcttgca ttcaccagag aaagcaaact   300
ggttctcagg ttttccatca gggatcttgt aaattctgaa ccattcgttg gtagctctca   360
acaagcccgg catgtgcttt tcaacatcct cgatgtcatt gagcttagga gccaatgggt   420
cgttgatgtc gatgacgatg accttccagt cagtctctcc ctcatccaac aaagccataa   480
caccgaggac cttgacttgc ttgacctgtc cagtgtaacc tacggcttca ccaatttcgc   540
aaacgtccaa tggatcattg tcacccttgg ccttggtctc tggatgagtg acgttagggt   600
```

```
cttcccatgt ctgagggaag gcaccgtagt tgtgaatgta tccgtggtga gggaaacagt      660
tacgaacgaa acgaagtttt cccttctttg tgtcctgaag aattgggttc agtttctcct      720
ccttggaaat ctccaacttg gcgttggtcc aacggggggac ttcaacaacc atgttgagaa     780
ccttcttgga ttcgtcagca taaagtggga tgtcgtggaa aggagatacg actt            834
```

<210> SEQ ID NO 15
<211> LENGTH: 1350
<212> TYPE: DNA
<213> ORGANISM: Artificial Sequence
<220> FEATURE:
<223> OTHER INFORMATION: DNA encodes Anti-RSV Heavy chain (VH + IgG1
      constant region)

<400> SEQUENCE: 15

```
caggttacat tgagagaatc cggtccagct ttggttaagc caactcagac tttgactttg       60
acttgtactt tctccggttt ctccttgtct acttccggaa tgtctgttgg atggatcaga     120
caaccacctg gaaaggcttt ggaatggctt gctgacattt ggtgggatga caagaaggac    180
tacaacccat ccttgaagtc cagattgact atctccaagg acacttccaa gaatcaagtt    240
gttttgaagg ttacaaacat ggacccagct gacactgcta cttactactg tgctagatcc    300
atgatcacta actggtactt cgatgtttgg ggtgctggta ctactgttac tgtctcgagt    360
gcttctacta agggaccatc cgttttttcca ttggctccat cctctaagtc tacttccggt    420
ggaaccgctg ctttgggatg tttggttaaa gactacttcc cagagccagt tactgtttct    480
tggaactccg gtgctttgac ttctggtgtt cacactttcc cagctgtttt gcaatcttcc    540
ggtttgtact ctttgtcctc cgttgttact gttccatcct cttccttggg tactcagact    600
tacatctgta acgttaacca caagccatcc aacactaagg ttgacaagag agttgagcca    660
aagtcctgtg acaagacaca tacttgtcca ccatgtccag ctccagaatt gttgggtggt    720
ccatccgttt tcttgttccc accaaagcca aaggacactt tgatgatctc agaactcca     780 gaggttacat gtgttgttgt tgacgtttct cacgaggacc cagaggttaa gttcaactgg    840
tacgttgacg gtgttgaagt tcacaacgct aagactaagc caagagaaga gcagtacaac    900
tccacttaca gagttgtttc cgttttgact gttttgcacc aggactggtt gaacggtaaa    960
gaatacaagt gtaaggtttc caacaaggct ttgccagctc aatcgaaaa gactatctcc     1020 aaggctaagg gtcaaccaag agagccacag gtttacactt tgccaccatc cagagaagag    1080
atgactaaga accaggtttc cttgacttgt ttggttaaag gattctaccc atccgacatt    1140
gctgttgagt gggaatctaa cggtcaacca gagaacaact acaagactac tccaccagtt    1200
ttggattctg atggttcctt cttcttgtac tccaagttga ctgttgacaa gtccagatgg    1260
caacagggta acgttttctc ctgttccgtt atgcatgagg ctttgcacaa ccactacact    1320
caaaagtcct gtctctttgtc ccctggttaa                                     1350
```

<210> SEQ ID NO 16
<211> LENGTH: 699
<212> TYPE: DNA
<213> ORGANISM: Artificial Sequence
<220> FEATURE:
<223> OTHER INFORMATION: DNA encodes Anti-RSV light chain (VL + Kappa
      constant region

<400> SEQUENCE: 16

```
atgagattcc catccatctt cactgctgtt ttgttcgctg cttcttctgc tttggctgac       60
```

```
attcagatga cacagtcccc atctactttg tctgcttccg ttggtgacag agttactatc    120
acttgtaagt gtcagttgtc cgttggttac atgcactggt atcagcaaaa gccaggaaag    180
gctccaaagt tgttgatcta cgacacttcc aagttggctt ccggtgttcc atctagattc    240
tctggttccg gttctggtac tgagttcact ttgactatct cttccttgca accagatgac    300
ttcgctactt actactgttt ccagggttct ggttacccat tcactttcgg tggtggtact    360
aagttggaga tcaagagaac tgttgctgct ccatccgttt tcattttccc accatccgac    420
gaacaattga agtccggtac cgcttccgtt gtttgtttgt tgaacaactt ctacccacgt    480
gaggctaagg ttcagtggaa ggttgacaac gctttgcaat ccggtaactc ccaagaatcc    540
gttactgagc aggattctaa ggattccact tactcattgt cctccacttt gactttgtcc    600
aaggctgatt acgagaagca caaggtttac gcttgcgagg ttacacatca gggtttgtcc    660
tccccagtta ctaagtcctt caacagagga gagtgttaa                          699
```

<210> SEQ ID NO 17
<211> LENGTH: 260
<212> TYPE: DNA
<213> ORGANISM: Artificial Sequence
<220> FEATURE:
<223> OTHER INFORMATION: Pichia pastoris AOX1 transcription termination
      sequence

<400> SEQUENCE: 17

```
tcaagaggat gtcagaatgc catttgcctg agagatgcag gcttcatttt gatacttttt    60
tatttgtaac ctatatagta taggattttt tttgtcattt tgtttcttct cgtacgagct    120
tgctcctgat cagcctatct cgcagctgat gaatatcttg tggtaggggt ttgggaaaat    180
cattcgagtt tgatgttttt cttggtattt cccactcctc ttcagagtac agaagattaa    240
gtgagacgtt cgtttgtgca                                                260
```

<210> SEQ ID NO 18
<211> LENGTH: 375
<212> TYPE: DNA
<213> ORGANISM: Artificial Sequence
<220> FEATURE:
<223> OTHER INFORMATION: DNA encodes Sh ble ORF (Zeocin resistance
      marker)

<400> SEQUENCE: 18

```
atggccaagt tgaccagtgc cgttccggtg ctcaccgcgc gcgacgtcgc cggagcggtc    60
gagttctgga ccgaccggct cgggttctcc cggacttcg tggaggacga cttcgccggt    120
gtggtccggg acgacgtgac cctgttcatc agcgcggtcc aggaccaggt ggtgccggac    180
aacaccctgg cctgggtgtg ggtgcgcggc ctggacgagc tgtacgccga gtggtcggag    240
gtcgtgtcca cgaacttccg ggacgcctcc gggccggcca tgaccgagat cggcgagcag    300
ccgtgggggc gggagttcgc cctgcgcgac ccggccggca actgcgtgca cttcgtggcc    360
gaggagcagg actga                                                     375
```

<210> SEQ ID NO 19
<211> LENGTH: 1430
<212> TYPE: DNA
<213> ORGANISM: Artificial Sequence
<220> FEATURE:
<223> OTHER INFORMATION: 5' region of Pichia pastoris YOS9

<400> SEQUENCE: 19

```
ccatagcctc tgattgatgt aagcaccgac agtacctggc tctaacttgt tagaggtttt    60
```

```
ggtggtcaag acatatctgt tatcacaaat aacataatgg ttatcgggaa agtcattggg      120
atgaacagca agtgtgttca tgatggcaaa ttcattaccc ggagagttga ctatcttcaa      180
tacatgcacc tttggagcat ttctctttgt gaatcccagt ttttccatgg ttgtggcaaa      240
gtgtagagat gttaagtgca gcgagcaaag acaagtagag agactgtatg gtgttctgat      300
gttatagttg tagtgaataa tctataaatg ccttatttga aggtttatgt aatagattta      360
cccgtgtgta gcaagtgtac tgctaagagg tactataaag ttattcatgt ggatatattc      420
agtagataat aacaaagcta caaggagatc aagaaaccat atgagttgtt cgtcacataa      480
gagattacgt aatgacaaat cggggaacta gtaccaattc tgtcttaaag tagtgtctct      540
ctaagcataa cgacctattt gataactggg ctgaactcca agcagcctga tgatgttgac      600
ctgacttatt cagaagggct attggttttg atttccagat attagcataa ttagcaatgc      660
cggaacaata tacatccaat atttttgaat gaatgaacgg ttatcaacat ttacttctgc      720
ctcctcgtct atgacttcct tgagttccag cttgttatcg gatctgattt ttttgatttt      780
cttttctttt cttggtagtt tgggaattgg tgcctgtcga atttgttcaa ctattaggtt      840
aagacctttc tgactagcat cgaagaaggc tacattttcg atgtcgttgt gtttgttgat      900
agtcagcttg atatcctgtg caattggaga acttagtctt ttgtaattga agcagccttc      960
gtccaaacat attctgtaaa gatcacttgg caggtctagt tgttcaccgg tgtgcaattt     1020 ccatttgag tcaaattcta gtgtggccaa gttgaacgag ttctgagcga aatcaatagc     1080
cttcaactga tacgcaaatg tagaccccaa gaaaagaaac aacgtgacga ggctttgtag     1140
ggtagtagcc attgtcgaat agttgaggat aagtagacgg cgagttattc tccttgataa     1200
atgctatcgc gatggatagt gattacagtg cgataatatt atccttttca tccacgtcaa     1260
ccatggttaa caggccattg gacattatga taaaggtcct gctattcctg ctctccctat     1320
caagtcttgt gaaagctttg gatgattcca ttgataagaa ttctgtggta agtcttttaa     1380
tttttgtttt cacaagatca tgccgtgcta actgggtact atagtatacc               1430

<210> SEQ ID NO 20
<211> LENGTH: 1498
<212> TYPE: DNA
<213> ORGANISM: Artificial Sequence
<220> FEATURE:
<223> OTHER INFORMATION: 3' region of Pichia pastoris YOS9

<400> SEQUENCE: 20
ggttcctatt cactgaagac agaataccctc atgacactcc aaactttaga gtgtataacg       60
gagttaatgt gaattaagac aatttatata ctcagtaaaa taaatactag tacttacgtc      120 ttttttagt cagagcacta actctgctgg aagggttctt cgtgtaaatt ggtacagacg      180
ctggtaaagt accactatac gttgtttgac aaataggtag tttgaagctg acatcaagtt      240
tcaagtcctt aggagtcaca ttgcgagttt gaatgaccaa ttgtattaat ctcttaatct      300
tgaagtacaa tctcttctct ttgagactgg gtttcaagac agtgacggga ttagcaggat      360 cgatttggg tgatgcctta tacctttctt gacgtaattg tgacagatct attagcaact      420
tgcttataag ttcttgctct tgttggaac ggatagcctc tatctcatcc tcctcaacga      480
agcttcccgg agtccaggag aggaggttgt ctagcttgat cttatagtct tcggatccat      540
tgacctggac ttccttatct gtgttttcaa gttagttga tgtatctgtc cccgtatggc      600
cattcttagt ctcctggtca acaggtgccg gaagctcttt ttcaattctt tttggttcgt      660
```

```
ccttctgaag ttcattatcc gtctcattt tagatggtct gctcagtttt tctgctatat    720
caccaagctt tctaaaacca gcttgctcca gccacctcag gcccttcaat tcactggaga    780
ttgcagattt ttcttcgtct attgtaggtg caaaactgaa atcgttaccc ttattgtggg    840
tgagccattg acccatcggt aacgcgtacc agttcaaatg aaagaggttt ggcaataaat    900
ccgtaggttt ggtggctggg tgaggttcat tgttgtattg aggagaaatc ttgttaagcg    960
gctgtgaact aatggaaggg catgggggga ttactttcgt cagattaaaa tcgccttcat   1020
tcactacagc ttctctagca tccaagcttg atttattatt cagggacgaa acaatggcg   1080
cattaggtgt gatgaatgta gttaaacatt ctccgttgga tgaaacaaaa atgtggaca   1140
ctttattgaa gtcttttgtc atcgattctt caaactcact ggtgtaatca tctaaaacac   1200
gagagtcaac gctttctctt agttgtctgt agttgaacaa aaatcttcct gcctctctga   1260
tcaataactc aaccatcgac ttgtagaaca aatcaatctt gacgtagtct tccgaatctc   1320
tgttccgttc gtttataagt atcaggcaca ctaaagttag gtcgtgaaat atggaataaa   1380
tagtcttgta gtgaccactc tttattctgt cgctgatggt aaccagctct gtaggtttga   1440
gatccttacc atcaacaagc tgatagtatg atccagctat caaggaagga tcctggac    1498

<210> SEQ ID NO 21
<211> LENGTH: 1699
<212> TYPE: DNA
<213> ORGANISM: Artificial Sequence
<220> FEATURE:
<223> OTHER INFORMATION: 5' region of Pichia pastoris ALG3

<400> SEQUENCE: 21
aaccttcatg gaacgattcg gatacggaaa aacctgagat agttttaact agagtagatg     60
caagatttca cgattctaaa gaccgagaag gagatgtctg atgtcggtaa ctactatccg    120
gtaaatgata ttagcacact atatgctact agcgagtctg gaaccaattc tactatccat    180
tgatgctcta ttagggatgg agaattcaat caaccccctct aattctgatt tcagatgttc    240
caacagcgaa gtagcccttg acaagttctc aacatcactc atcttagcta cattcacgta    300
tgctttgata aaaaactctc tactttttgtc aatgagctct agcctagtct ctggttctat    360
cgtttcctct ttggtctcca gattactctc tggattagaa tctacatcca tcttcatatc    420
tatgtccatg tccagctcaa ttttcatacc gtcagtattc ttagattcga tagcagtatc    480
tgatctggta gatccattag ttgctgcagc ggtatttct ttggaatttg gagcactttc    540
ctgtttctgt ttcataaaga ctcggtagat tgcaatgact atatcgtttc tgtagaactt    600
gtaaccatga gtccaaaatt gggtttcagg catgtatcct agctcatcta aatatccaac    660
cacatcatcc gtgctacata tagtagactc gtagagtgtc tgtgaagaaa cggctctttt    720
tcctgccaaa ggaacgtccg atatttgaag ggtccatata cgattttcct tattaagagc    780
ttcaagatgt ttcttattaa acaattcaaa gtctttaat tcaattgtgt tatcaatagg    840
atcctcaacg tcctgtttcc attcggtgga cattctcatc ttgtattgtt cgatttggtt    900
gacttttcca gtctggaact caggactata aggaaacttt ggagttaaaa taacagtata    960
agttgagagc cttgcgggca ccatacccgt tagagacttc aacgtctcca agatcaactg   1020
cagttgagac tcttggattc tagataccag agacacctgt tgtaccatat aattaagtga   1080
ctgggctggc ttggatacag gatttcgaga agtgcttcga attatcagac cgaaggcagt   1140
tgataatttg tgcctcagcc ttaatgttcc ctataactta aggctataca cagctttatg   1200
attaatgaat ctgggctgct ggtgacgaat ttcgtcaatg accagttgcc tacgggcgat   1260
```

```
aattattttt tcagttggat gaaagaacgg aaaaacccgg tcagattcaa aaagaatatt    1320
gataatcttt gtctagcaca actgaaatgc ttggaaactc tcccaagcat gaatcagacc    1380
tgagattgta ttagacgaaa aaattgtagt atagagttat agacatatag gttgtggcaa    1440
tatcctgtgc aagccaatat ctcacagaaa taaacgtaca caccgataca aactatttcg    1500
aaaagcacac tttgagcgca acagtgattg tcctaacagt ataggtttct aaggccccag    1560
cagaccatga cggcaaatta tttatttccc ctcgtatttg ccttatctcc ttttgttctc    1620
attcttatct tggctactgt aattatctgg ataaccctcg atacttcgct tggtttctac    1680
ctcacaacat atccctacc                                                 1699

<210> SEQ ID NO 22
<211> LENGTH: 1052
<212> TYPE: DNA
<213> ORGANISM: Artificial Sequence
<220> FEATURE:
<223> OTHER INFORMATION: 3' region of Pichia pastoris ALG3

<400> SEQUENCE: 22
atttacaatt agtaatatta aggtggtaaa aacattcgta gaattgaaat gaattaatat      60
agtatgacaa tggttcatgt ctataaatct ccggcttcgg taccttctcc ccaattgaat     120
acattgtcaa aatgaatggt tgaactatta ggttcgccag tttcgttatt aagaaaactg     180
ttaaaatcaa attccatatc atcggttcca gtgggaggac cagttccatc gccaaaatcc     240
tgtaagaatc cattgtcaga acctgtaaag tcagtttgag atgaaatttt tccggtcttt     300
gttgacttgg aagcttcgtt aaggttaggt gaaacagttt gatcaaccag cggctcccgt     360
tttcgtcgct tagtagcagc attattacca ggaatgccgc ctgtagagtt ttgatgtgtc     420
ctagctgcaa ttggagtctg tggagtagtg ggagtcgggg gctcagtagc tttctttgcc     480 ttcttttag ctggctcctt tttctttcgt acaggtgcga cattatttgg tgtagacccc      540
gcagaagtgt taccagtact atgtgcagtg ttttgagttt gtgtaccagg tgaagttccg     600
ggagtattct tcgtgaccac tgcagagttc tggggaggga gcattacatt cacattaaat     660
tttggttcgg gcggtgtgtg ctctggaatt ggatcaaagt tagaaaaatg cccgcttccc     720
ttcttacatg ccatgtcatg acgctgtttg ttctgttttct caagcatcat tagctctttc     780
tgatactcct gtatacctac aattttagaa gcacttgatt gagactgttg cgattgctgg     840
tgttggctct gtgattgtgg ttgtgctatt tgctgatgtt gtgaccctgg agttggaact     900
agctccggct gctgaataga agaaggcgga gaatgttgcg gttgagatgc aggtaaaggc     960
tgctgataaa caggaccagg ttgcgagaat ctaggtgtgg tggacgagtg aggagtaccg    1020
gcggcagaag tagagtgagg cagaggagcc at                                  1052

<210> SEQ ID NO 23
<211> LENGTH: 411
<212> TYPE: DNA
<213> ORGANISM: Artificial Sequence
<220> FEATURE:
<223> OTHER INFORMATION: 5' region of Pichia pastoris BMT1

<400> SEQUENCE: 23
catatggtga gagccgttct gcacaactag atgttttcga gcttcgcatt gtttcctgca      60
gctcgactat tgaattaaga tttccggata tctccaatct cacaaaaact tatgttgacc     120
acgtgctttc ctgaggcgag gtgttttata tgcaagctgc caaaaatgga aaacgaatgg     180
```

```
ccattttttcg cccaggcaaa ttattcgatt actgctgtca taaagacagt gttgcaaggc    240
tcacattttt ttttaggatc cgagataaag tgaatacagg acagcttatc tctatatctt    300
gtaccattcg tgaatcttaa gagttcggtt aggggggactc tagttgaggg ttggcactca    360
cgtatggctg ggcgcagaaa taaaattcag gcgcagcagc acttatcgat g             411
```

<210> SEQ ID NO 24
<211> LENGTH: 692
<212> TYPE: DNA
<213> ORGANISM: Artificial Sequence
<220> FEATURE:
<223> OTHER INFORMATION: 3' region of Pichia pastoris BMT1

<400> SEQUENCE: 24

```
gaattcacag ttataaataa aaacaaaaac tcaaaaagtt tgggctccac aaaataactt     60
aatttaaatt tttgtctaat aaatgaatgt aattccaaga ttatgtgatg caagcacagt    120
atgcttcagc cctatgcagc tactaatgtc aatctcgcct gcgagcgggc ctagattttc    180
actacaaatt tcaaaactac gcggatttat tgtctcagag agcaatttgg catttctgag    240
cgtagcagga ggcttcataa gattgtatag gaccgtacca acaaattgcc gaggcacaac    300
acggtatgct gtgcacttat gtggctactt ccctacaacg gaatgaaacc ttcctctttc    360
cgcttaaacg agaaagtgtg tcgcaattga atgcaggtgc ctgtgcgcct tggtgtattg    420 ttttgaggg cccaatttat caggcgcctt ttttcttggt tgttttccct tagcctcaag    480
caaggttggt ctatttcatc tccgcttcta taccgtgcct gatactgttg gatgagaaca    540
cgactcaact tcctgctgct ctgtattgcc agtgttttgt ctgtgatttg gatcggagtc    600
ctccttactt ggaatgataa taatcttggc ggaatctccc taaacggagg caaggattct    660
gcctatgatg atctgctatc attgggaagc tt                                   692
```

<210> SEQ ID NO 25
<211> LENGTH: 1043
<212> TYPE: DNA
<213> ORGANISM: Artificial Sequence
<220> FEATURE:
<223> OTHER INFORMATION: 5' region of Pichia pastoris BMT4

<400> SEQUENCE: 25

```
aagcttgttc accgttggga cttttccgtg gacaatgttg actactccag gagggattcc     60
agctttctct actagctcag caataatcaa tgcagcccca ggcgcccgtt ctgatggctt    120
gatgaccgtt gtattgcctg tcactatagc caggggtagg gtccataaag gaatcatagc    180
agggaaatta aaagggcata ttgatgcaat cactcccaat ggctctcttg ccattgaagt    240
ctccatatca gcactaactt ccaagaagga ccccttcaag tctgacgtga tagagcacgc    300
ttgctctgcc acctgtagtc ctctcaaaac gtcaccttgt gcatcagcaa agactttacc    360
ttgctccaat actatgacgg aggcaattct gtcaaaattc tctctcagca attcaaccaa    420
cttgaaagca aattgctgtc tcttgatgat ggagactttt ttccaagatt gaaatgcaat    480
gtgggacgac tcaattgctt cttccagctc ctcttcggtt gattgaggaa cttttgaaac    540
cacaaaattg gtcgttgggt catgtacatc aaaccattct gtagatttag attcgacgaa    600
agcgttgttg atgaaggaaa aggttggata cggtttgtcg gtctctttgg tatggccggt    660
ggggtatgca attgcagtag aagataattg acagccatt gttgaaggta gagaaaaggt    720
cagggaactt gggggttatt tataccatt taccccacaa ataacaactg aaaagtaccc    780
attccatagt gagaggtaac cgacggaaaa agacgggccc atgttctggg accaatagaa    840
```

```
ctgtgtaatc cattgggact aatcaacaga cgattggcaa tataatgaaa tagttcgttg      900
aaaagccacg tcagctgtct tttcattaac tttggtcgga cacaacattt tctactgttg      960
tatctgtcct actttgctta tcatctgcca cagggcaagt ggatttcctt ctcgcgcggc     1020
tgggtgaaaa cggttaacgt gaa                                             1043
```

<210> SEQ ID NO 26
<211> LENGTH: 695
<212> TYPE: DNA
<213> ORGANISM: Artificial Sequence
<220> FEATURE:
<223> OTHER INFORMATION: 3' region of Pichia pastoris BMT4

<400> SEQUENCE: 26

```
gccttggggg acttcaagtc tttgctagaa actagatgag gtcaggccct cttatggttg       60
tgtcccaatt gggcaatttc actcacctaa aaagcatgac aattatttag cgaaataggt      120
agtatatttt ccctcatctc ccaagcagtt tcgttttttgc atccatatct ctcaaatgag     180
cagctacgac tcattagaac cagagtcaag taggggtgag ctcagtcatc agccttcgtt     240
tctaaaacga ttgagttctt tgttgctac aggaagcgcc ctagggaact ttcgcacttt      300
ggaaatagat tttgatgacc aagagcggga gttgatatta gagaggctgt ccaaagtaca     360
tgggatcagg ccggccaaat tgattggtgt gactaaacca ttgtgtactt ggacactcta     420
ttacaaaagc gaagatgatt tgaagtatta caagtcccga agtgttagag gattctatcg     480
agcccagaat gaaatcatca accgttatca gcagattgat aaactcttgg aaagcggtat     540
cccattttca ttattgaaga actacgataa tgaagatgtg agagacggcg accctctgaa     600
cgtagacgaa gaaacaaatc tacttttggg gtacaataga gaaagtgaat caagggaggt     660
atttgtggcc ataatactca actctatcat taatg                                695
```

<210> SEQ ID NO 27
<211> LENGTH: 546
<212> TYPE: DNA
<213> ORGANISM: Artificial Sequence
<220> FEATURE:
<223> OTHER INFORMATION: 5' region of Pichia pastoris BMT3

<400> SEQUENCE: 27

```
gatatctccc tggggacaat atgtgttgca actgttcgtt gttggtgccc cagtccccca       60
accggtacta atcggtctat gttcccgtaa ctcatattcg gttagaacta gaacaataag      120
tgcatcattg ttcaacattg tggttcaatt gtcgaacatt gctggtgctt atatctacag     180
ggaagacgat aagcctttgt acaagagagg taacagacag ttaattggta tttctttggg     240
agtcgttgcc ctctacgttg tctccaagac atactacatt ctgagaaaca gatggaagac     300
tcaaaaatgg gagaagctta gtgaagaaga gaaagttgcc tacttggaca gagctgagaa     360
ggagaacctg ggttctaaga ggctggactt tttgttcgag agttaaactg cataattttt     420
tctaagtaaa tttcatagtt atgaaatttc tgcagcttag tgtttactgc atcgtttact     480
gcatcaccct gtaaataatg tgagcttttt tccttccatt gcttggtatc ttccttgctg     540
ctgttt                                                                 546
```

<210> SEQ ID NO 28
<211> LENGTH: 378
<212> TYPE: DNA
<213> ORGANISM: Artificial Sequence
<220> FEATURE:

<223> OTHER INFORMATION: 3' region of Pichia pastoris BMT3

<400> SEQUENCE: 28

| | | |
|---|---|---|
| acaaaacagt catgtacaga actaacgcct ttaagatgca gaccactgaa aagaattggg | 60 | |
| tcccattttt cttgaaagac gaccaggaat ctgtccattt tgtttactcg ttcaatcctc | 120 | |
| tgagagtact caactgcagt cttgataacg gtgcatgtga tgttctattt gagttaccac | 180 | |
| atgattttgg catgtcttcc gagctacgtg gtgccactcc tatgctcaat cttcctcagg | 240 | |
| caatcccgat ggcagacgac aaagaaattt gggtttcatt cccaagaacg agaatatcag | 300 | |
| attgcgggtg ttctgaaaca atgtacaggc caatgttaat gcttttgtt agagaaggaa | 360 | |
| caaacttttt tgctgagc | 378 | |

<210> SEQ ID NO 29
<211> LENGTH: 1494
<212> TYPE: DNA
<213> ORGANISM: Artificial Sequence
<220> FEATURE:
<223> OTHER INFORMATION: Trichoderma reesie mannosidase I catalytic
      domain

<400> SEQUENCE: 29

| | | |
|---|---|---|
| cgcgccggat ctcccaaccc tacgagggcg gcagcagtca aggccgcatt ccagacgtcg | 60 | |
| tggaacgctt accaccattt tgcctttccc catgacgacc tccacccggt cagcaacagc | 120 | |
| tttgatgatg agagaaacgg ctggggctcg tcggcaatcg atggcttgga cacggctatc | 180 | |
| ctcatggggg atgccgacat tgtgaacacg atccttcagt atgtaccgca gatcaacttc | 240 | |
| accacgactg cggttgccaa ccaaggcatc tccgtgttcg agaccaacat tcggtacctc | 300 | |
| ggtggcctgc tttctgccta tgacctgttg cgaggtcctt tcagtccctt ggcgacaaac | 360 | |
| cagacccctgg taaacagcct tctgaggcag gctcaaacac tggccaacgg cctcaaggtt | 420 | |
| gcgttcacca ctcccagcgg tgtcccggac cctaccgtct tcttcaaccc tactgtccgg | 480 | |
| agaagtggtg catctagcaa caacgtcgct gaaattggaa gcctggtgct cgagtggaca | 540 | |
| cggttgagcg acctgacggg aaaccccgcag tatgcccagc ttgcgcagaa gggcgagtcg | 600 | |
| tatctcctga atccaaaggg aagcccggag gcatggcctg gctgattgg aacgtttgtc | 660 | |
| agcacgagca acggtacctt tcaggatagc agcggcagct ggtccggcct catggacagc | 720 | |
| ttctacgagt acctgatcaa gatgtacctg tacgacccgg ttgcgtttgc acactacaag | 780 | |
| gatcgctggg tccttgctgc cgactcgacc attgcgcatc tcgcctctca cccgtcgacg | 840 | |
| cgcaaggact tgacctttt gtcttcgtac aacggacagt ctacgtcgcc aaactcagga | 900 | |
| catttggcca gtttttgccgg tggcaacttc atcttgggag gcattctcct gaacgagcaa | 960 | |
| aagtacattg actttggaat caagcttgcc agctcgtact ttgccacgta caaccagacg | 1020 | |
| gcttctggaa tcggccccga aggcttcgcg tgggtggaca gcgtgacggg cgccggcggc | 1080 | |
| tcgccgccct cgtcccagtc cgggttctac tcgtcggcag gattctgggt gacggcaccg | 1140 | |
| tattacatcc tgcggccgga gacgctggag agcttgtact acgcataccg cgtcacgggc | 1200 | |
| gactccaagt ggcaggacct ggcgtgggaa gcgttcagtg ccattgagga cgcatgccgc | 1260 | |
| gccggcagcg cgtactcgtc catcaacgac gtgacgcagg ccaacggcgg gggtgcctct | 1320 | |
| gacgatatgg agagcttctg gtttgccgag gcgctcaagt atgcgtacct gatctttgcg | 1380 | |
| gaggagtcgg atgtgcaggt gcaggccaac ggcgggaaca aatttgtctt taacacggag | 1440 | |
| gcgcaccccct ttagcatccg ttcatcatca cgacggggcg gccaccttgc ttaa | 1494 | |

<210> SEQ ID NO 30
<211> LENGTH: 1231
<212> TYPE: DNA
<213> ORGANISM: Artificial Sequence
<220> FEATURE:
<223> OTHER INFORMATION: 5' region of Pichia pastoris PRO1

<400> SEQUENCE: 30

```
gaagggccat cgaattgtca tcgtctcctc aggtgccatc gctgtgggca tgaagagagt      60
caacatgaag cggaaaccaa aaaagttaca gcaagtgcag gcattggctg ctataggaca     120
aggccgtttg ataggacttt gggacgacct tttccgtcag ttgaatcagc ctattgcgca     180
gattttactg actagaacgg atttggtcga ttacacccag tttaagaacg ctgaaaatac     240
attggaacag cttattaaaa tgggtattat tcctattgtc aatgagaatg cacccctatc     300
cattcaagaa atcaaatttg gtgacaatga caccttatcc gccataacag ctggtatgtg     360
tcatgcagac tacctgtttt tggtgactga tgtggactgt ctttacacgg ataaccctcg     420
tacgaatccg gacgctgagc caatcgtgtt agttagaaat atgaggaatc taaacgtcaa     480
taccgaaagt ggaggttccg ccgtaggaac aggaggaatg caactaaat tgatcgcagc     540
tgatttgggt gtatctgcag gtgttacaac gattatttgc aaaagtgaac atcccgagca     600
gattttggac attgtagagt acagtatccg tgctgataga gtcgaaaatg aggctaaata     660
tctggtcatc aacgaagagg aaactgtgga acaatttcaa gagatcaatc ggtcagaact     720
gagggagttg aacaagctgg acattccttt gcatacacgt ttcgttggcc acagttttaa     780
tgctgttaat aacaaagagt tttggttact ccatggacta aaggccaacg gagccattat     840
cattgatcca ggttgttata aggctatcac tagaaaaaac aaagctggta ttcttccagc     900
tggaattatt tccgtagagg gtaatttcca tgaatacgag tgtgttgatg ttaaggtagg     960
actaagagat ccagatgacc cacattcact agaccccaat gaagaacttt acgtcgttgg    1020
ccgtgcccgt tgtaattacc ccagcaatca aatcaacaaa attaagggtc tacaaagctc    1080
gcagatcgag caggttctag gttacgctga cggtgagtat gttgttcaca gggacaactt    1140
ggctttccca gtatttgccg atccagaact gttggatgtt gttgagagta ccctgtctga    1200
acaggagaga gaatccaaac caaataaata g                                   1231
```

<210> SEQ ID NO 31
<211> LENGTH: 1425
<212> TYPE: DNA
<213> ORGANISM: Artificial Sequence
<220> FEATURE:
<223> OTHER INFORMATION: 3' region of Pichia pastoris PRO1

<400> SEQUENCE: 31

```
aatttcacat atgctgcttg attatgtaat tataccttgc gttcgatggc atcgatttcc      60
tcttctgtca atcgcgcatc gcattaaaag tatactttt ttttttttcct atagtactat     120
tcgccttatt ataaactttg ctagtatgag ttctaccccc aagaaagagc ctgatttgac     180
tcctaagaag agtcagcctc caaagaatag tctcggtggg ggtaaaggct ttagtgagga     240
gggtttctcc caaggggact tcagcgctaa gcatatacta atcgtcgcc ctaacaccga     300
aggctcttct gtggcttcga acgtcatcag ttcgtcatca ttgcaaaggt taccatcctc     360
tggatctgga agcgttgctg tgggaagtgt gttgggatct tcgccattaa ctctttctgg     420
agggttccac gggcttgatc caaccaagaa taaaatagac gttccaaagt cgaaacagtc     480
aaggagacaa agtgttcttt ctgacatgat ttccacttct catgcagcta gaaatgatca     540
```

```
ctcagagcag cagttacaaa ctggacaaca atcagaacaa aaagaagaag atggtagtcg    600
atcttctttt tctgtttctt cccccgcaag agatatccgg cacccagatg tactgaaaac    660
tgtcgagaaa catcttgcca atgacagcga gatcgactca tctttacaac ttcaaggtgg    720
agatgtcact agaggcattt atcaatgggt aactggagaa agtagtcaaa agataaccc     780 gcctttgaaa cgagcaaata gttttaatga ttttctttct gtgcatggtg acgaggtagg    840
caaggcagat gctgaccacg atcgtgaaag cgtattcgac gaggatgata tctccattga    900
tgatatcaaa gttccgggag ggatgcgtcg aagttttta ttacaaaagc atagagacca     960
acaactttct ggactgaata aaacggctca ccaaccaaaa caacttacta aacctaattt    1020
cttcacgaac aactttatag agttttggc attgtatggg cattttgcag gtgaagattt     1080
ggaggaagac gaagatgaag atttagacag tggttccgaa tcagtcgcag tcagtgatag    1140
tgagggagaa ttcagtgagg ctgacaacaa tttgttgtat gatgaagagt ctctcctatt    1200
agcacctagt acctccaact atgcgagatc aagaatagga agtattcgta ctcctactta    1260
tggatctttc agttcaaatg ttggttcttc gtctattcat cagcagttaa tgaaaagtca    1320
aatcccgaag ctgaagaaac gtggacagca caagcataaa acacaatcaa aaatacgctc    1380
gaagaagcaa actaccaccg taaaagcagt gttgctgcta ttaaa                    1425

<210> SEQ ID NO 32
<211> LENGTH: 1350
<212> TYPE: DNA
<213> ORGANISM: Artificial Sequence
<220> FEATURE:
<223> OTHER INFORMATION: DNA encodes Anti-Her2 Heavy chain (VH + IgG1
      constant region)

<400> SEQUENCE: 32
gaggttcagt tggttgaatc tggaggagga ttggttcaac ctggtggttc tttgagattg     60
tcctgtgctg cttccggttt caacatcaag gacacttaca tccactgggt tagacaagct    120
ccaggaaagg gattggagtg ggttgctaga atctacccaa ctaacggtta cacaagatac    180
gctgactccg ttaagggaag attcactatc tctgctgaca cttccaagaa cactgcttac    240
ttgcagatga actccttgag agctgaggat actgctgttt actactgttc cagatggggt    300
ggtgatggtt tctacgctat ggactactgg ggtcaaggaa ctttggttac tgttcctcc     360 gcttctacta agggaccatc tgttttccca ttggctccat cttctaagtc tacttccggt    420
ggtactgctg ctttgggatg tttggttaaa gactacttcc cagagccagt tactgtttct    480
tggaactccg gtgctttgac ttctggtgtt cacactttcc cagctgtttt gcaatcttcc    540
ggtttgtact ctttgtcctc cgttgttact gttccatcct cttccttggg tactcagact    600
tacatctgta acgttaacca caagccatcc aacactaagg ttgacaagaa ggttgagcca    660
aagtcctgtg acaagacaca tacttgtcca ccatgtccag ctccagaatt gttgggtggt    720
ccatccgttt tcttgttccc accaaagcca aaggacactt tgatgatctc cagaactcca    780
gaggttacat gtgttgttgt tgacgtttct cacgaggacc cagaggttaa gttcaactgg    840
tacgttgacg gtgttgaagt tcacaacgct aagactaagc caagagaaga gcagtacaac    900
tccacttaca gagttgtttc cgttttgact gttttgcacc aggactggtt gaacggtaaa    960
gaatacaagt gtaaggtttc caacaaggct ttgccagctc caatcgaaaa gactatctcc    1020
aaggctaagg gtcaaccaag agagccacag gtttacactt tgccaccatc cagagaagag    1080
atgactaaga accaggtttc cttgacttgt ttggttaaag gattctaccc atccgacatt    1140
```

```
gctgttgagt gggaatctaa cggtcaacca gagaacaact acaagactac tccaccagtt    1200
ttggattctg atggttcctt cttcttgtac tccaagttga ctgttgacaa gtccagatgg    1260
caacagggta acgttttctc ctgttccgtt atgcatgagg ctttgcacaa ccactacact    1320
caaaagtcct tgtctttgtc ccctggttaa                                     1350

<210> SEQ ID NO 33
<211> LENGTH: 57
<212> TYPE: DNA
<213> ORGANISM: Artificial Sequence
<220> FEATURE:
<223> OTHER INFORMATION: DNA encodes Saccharomyces mating factor pre
      signal sequence

<400> SEQUENCE: 33
atgagattcc catccatctt cactgctgtt tgttcgctg cttcttctgc tttggct        57

<210> SEQ ID NO 34
<211> LENGTH: 414
<212> TYPE: DNA
<213> ORGANISM: Artificial Sequence
<220> FEATURE:
<223> OTHER INFORMATION: Pichia pastoris CIT1 transcription termination
      sequence

<400> SEQUENCE: 34
ccggccattt aaatatgtga cgactgggtg atccgggtta gtgagttgtt ctcccatctg    60 tatattttc atttacgatg aatacgaaat gagtattaag aaatcaggcg tagcaatatg    120
ggcagtgttc agtcctgtca tagatggcaa gcactggcac atccttaata ggttagagaa    180
aatcattgaa tcatttgggt ggtgaaaaaa aattgatgta acaagccac ccacgctggg    240 agtcgaaccc agaatctttt gattagaagt caaacgcgtt aaccattacg ctacgcaggc    300
atgtttcacg tccattttg attgctttct atcataatct aaagatgtga actcaattag    360
ttgcaatttg accaattctt ccattacaag tcgtgcttcc tccgttgatg caac          414

<210> SEQ ID NO 35
<211> LENGTH: 645
<212> TYPE: DNA
<213> ORGANISM: Artificial Sequence
<220> FEATURE:
<223> OTHER INFORMATION: DNA encodes Anti-Her2 light chain (VL + Kappa
      constant region)

<400> SEQUENCE: 35
gacatccaaa tgactcaatc cccatcttct ttgtctgctt ccgttggtga cagagttact    60
atcacttgta gcttccca ggacgttaat actgctgttg cttggtatca acagaagcca     120
ggaaaggctc caagttgtt gatctactcc gcttccttct tgtactctgg tgttccatcc    180
agattctctg gttccagatc cggtactgac ttcactttga ctatctcctc cttgcaacca    240
gaagatttcg ctacttacta ctgtcagcag cactacacta ctccaccaac tttcggacag    300
ggtactaagg ttgagatcaa gagaactgtt gctgctccat ccgtttttcat tttcccacca    360 tccgacgaac agttgaagtc tggtacagct tccgttgttt gtttgttgaa caacttctac    420
ccaagagagg ctaaggttca gtggaaggtt gacaacgctt tgcaatccgg taactcccaa    480
gaatccgtta ctgagcaaga ctctaaggac tccacttact ccttgtcctc cactttgact    540
ttgtccaagg ctgattacga aagcacaag gtttacgctt gtgaggttac acatcagggt    600
ttgtcctccc cagttactaa gtccttcaac agaggagagt gttaa                    645
```

<210> SEQ ID NO 36
<211> LENGTH: 427
<212> TYPE: DNA
<213> ORGANISM: Artificial Sequence
<220> FEATURE:
<223> OTHER INFORMATION: Saccharomyces cerevisea TEF1 promoter

<400> SEQUENCE: 36

```
gatcccccac acaccatagc ttcaaaatgt ttctactcct tttttactct tccagatttt      60
ctcggactcc gcgcatcgcc gtaccacttc aaaacaccca agcacagcat actaaatttc     120
ccctcttttct tcctctaggg tgtcgttaat tacccgtact aaaggtttgg aaaagaaaaa    180
agagaccgcc tcgtttctt ttcttcgtcg aaaaaggcaa taaaaatttt tatcacgttt      240
cttttcttg aaaattttt tttttgattt ttttctcttt cgatgacctc ccattgatat       300
ttaagttaat aaacggtctt caatttctca agtttcagtt tcatttttct tgttctatta    360
caacttttttt tacttcttgc tcattagaaa gaaagcatag caatctaatc taagttttaa    420
ttacaaa                                                               427
```

<210> SEQ ID NO 37
<211> LENGTH: 1793
<212> TYPE: DNA
<213> ORGANISM: Pichia pastoris

<400> SEQUENCE: 37

```
ggtttctcaa ttactatata ctactaacca tttacctgta gcgtatttct tttccctctt     60
cgcgaaagct caagggcatc ttcttgactc atgaaaaata tctggatttc ttctgacaga    120
tcatcaccct tgagcccaac tctctagcct atgagtgtaa gtgatagtca tcttgcaaca    180
gattatttg gaacgcaact aacaaagcag atacacccctt cagcagaatc ctttctggat    240
attgtgaaga atgatcgcca aagtcacagt cctgagacag ttcctaatct ttaccccatt   300
tacaagttca tccaatcaga cttcttaacg cctcatctgg cttatatcaa gcttaccaac    360
agttcagaaa ctcccagtcc aagtttcttg cttgaaagtg cgaagaatgg tgacaccgtt    420
gacaggtaca cctttatggg acattcccccc agaaaaataa tcaagactgg gcctttagag   480
ggtgctgaag ttgacccctt ggtgcttctg gaaaaagaac tgaagggcac cagacaagcg    540
caacttcctg gtattcctcg tctaagtggt ggtgccatag gatacatctc gtacgattgt    600
attaagtact ttgaaccaaa aactgaaaga aaactgaaag atgttttgca acttccggaa    660
gcagctttga tgttgttcga cacgatcgtg gcttttgaca atgtttatca aagattccag    720
gtaattggaa acgtttctct atccgttgat gactcggacg aagctattct tgagaaatat    780
tataagacaa gagaagaagt ggaaaagatc agtaaagtgg tatttgacaa taaaactgtt    840
ccctactatg aacagaaaga tattattcaa ggccaaacgt tcacctctaa tattggtcag    900
gaagggtatg aaaaccatgt tcgcaagctg aagaacata ttctgaaagg agacatcttc     960
caagctgttc cctctcaaag ggtagccagg ccgacctcat tgcaccctt caacatctat    1020
cgtcatttga gaactgtcaa tccttctcca tacatgttct atattgacta tctagacttc   1080
caagttgttg gtgcttcacc tgaattacta gttaaatccg acaacaacaa caaaatcatc   1140
acacatccta ttgctggaac tcttcccaga ggtaaaacta tcgaagagga cgacaattat   1200
gctaagcaat tgaagtcgtc tttgaaagac agggccgagc acgtcatgct ggtagatttg    1260
gccagaaatg atattaaccg tgtgtgtgag cccaccagta ccacggttga tcgtttattg   1320
```

```
actgtggaga gattttctca tgtgatgcat cttgtgtcag aagtcagtgg aacattgaga   1380
ccaaacaaga ctcgcttcga tgcttttcaga tccattttcc cagcaggaac cgtctccggt   1440
gctccgaagg taagagcaat gcaactcata ggagaattgg aaggagaaaa gagaggtgtt   1500
tatgcggggg ccgtaggaca ctggtcgtac gatggaaaat cgatggacac atgtattgcc   1560
ttaagaacaa tggtcgtcaa ggacggtgtc gcttaccttc aagccggagg tggaattgtc   1620
tacgattctg accccatga cgagtacatc gaaaccatga acaaaatgag atccaacaat   1680
aacaccatct tggaggctga gaaaatctgg accgataggt tggccagaga cgagaatcaa   1740
agtgaatccg aagaaaacga tcaatgaacg gaggacgtaa gtaggaattt atg          1793
```

<210> SEQ ID NO 38
<211> LENGTH: 2559
<212> TYPE: DNA
<213> ORGANISM: Leishmania major

<400> SEQUENCE: 38

```
atgccagcta agaaccaaca taagggtggt ggtgatggtg atccagaccc aacttctact     60
ccagctgctg agtccactaa ggttacaaac acttccgatg gtgctgctgt tgattctact    120
ttgccaccat ccgacgagac ttacttgttc cactgtagag ctgctccata ctccaagttg    180
tcctacgctt tcaagggtat catgactgtt ttgatcttgt gtgctatcag atccgcttac    240
caagttagat tgatctccgt tcaaatctac ggttacttga tccacgaatt tgacccatgg    300
ttcaactaca gagctgctga gtacatgtct actcacggtt ggtctgcttt tttctcctgg    360
ttcgattaca tgtcctggta tccattgggt agaccagttg gttctactac ttacccagga    420
ttgcagttga ctgctgttgc tatccataga gctttggctg ctgctggaat gccaatgtcc    480
ttgaacaatg tttgtgtttt gatgccagct tggtttggtg ctatcgctac tgctactttg    540
gctttgatcg ctttcgaagt ttccgagtcc atttgtatgg ctgcttgggc tgctttgtcc    600
ttctccatta tccctgctca cttgatgaga tccatggctg tgagttcga caacgagtgt    660 attgctgttg ctgctatgtt gttgactttc tactgttggg ttagatcctt gagaactaga    720
tcctcctggc caatcggtgt tttgactggt gttgcttacg gttacatggc tgctgcttgg    780
ggaggttaca tcttcgtttt gaacatggtt gctatgcacg ctggtatctc ttctatggtt    840
gactgggcta gaaacactta caacccatcc ttgttgagag cttacacttt gttctacgtt    900
gttggtactg ctatcgctgt tgtgttcca ccagttggaa tgtctccatt caagtccttg    960
gagcagttgg gagctttgtt ggttttggtt ttcttgtgtg gattgcaagt ttgtgaggtt   1020
ttgagagcta gagctggtgt tgaagttaga tccagagcta atttcaagat cagagttaga   1080
gttttctccg ttatggctgg tgttgctgct tggctatct ctgttttggc tccaactggt   1140
tactttggtc cattgtctgt tagagttaga gctttgttcg ttgagcacac tagaactggt   1200
aacccattgg ttgactccgt tgctgaacat catccagctg acgctttggc ttacttgaac   1260
tacttgcaca tcgttcactt gatgtggatc tgttccttgc cagttcagtt gatcttgcca   1320
tccagaaacc agtacgctgt tttgttcgtt ttggtctact ccttcatggc ttactacttc   1380
tccactagaa tggttagatt gttgatcttg gctggtccag ttgcttgttt gggagcttct   1440
gaagttggtg gtactttgat ggaatggtgt ttccagcaat tgttctggga caacggaatg   1500
agaactgcta atatggttgc tgctggtgac atgccatacc aaaaggacga tcacacttcc   1560
agaggtgctg gtgctagaca aaagcagcag aagcaaaagc aggtcaagt ttctgctaga    1620 ggatcttcta cttcctccga ggaaagacca tacagaactt tgatcccagt tgacttcaga   1680
```

-continued

```
agagatgctc agatgaacag atggtccgct ggtaaaacta acgctgcttt gatcgttgct    1740
ttgactatcg gagttttgtt gccattggct ttcgttttcc acttgtcctg tatctcttcc    1800
gcttactctt ttgctggtcc aagaatcgtt ttccagactc agttgcacac tggtgaacag    1860
gttatcgtta aggactactt ggaagcttac gagtggttga gagactctac tccagaggac    1920
gctagagttt tggcttggtg ggactacggt taccaaatca ctggtatcgg taacagaact    1980
tccttggctg atggtaacac ttggaaccac gagcacattg ctactatcgg aaagatgttg    2040
acttctccag ttgctgaagc tcactccttg gttagacaca tggctgacta cgttttgatt    2100
tgggctggtc aatctggtga cttgatgaag tctccacaca tggctagaat cggtaactct    2160
gtttaccacg acatttgtcc agatgaccca ttgtgtcagc aattcggttt ccacagaaac    2220
gattactcca gaccaactcc aatgatgaga gcttccttgt tgtacaactt gcacgaggct    2280
ggaaagacta agggtgttaa ggttaaccca tctttgttcc aagaggttta ctcctccaag    2340
tacggtttgg ttagaatctt caaggttatg aacgtttccg ctgagtctaa gaagtgggtt    2400
gcagacccag ctaacagagt tgtcacccca cctggttctt ggatttgtcc tggtcaatac    2460
ccacctgcta aagaaatcca agagatgttg gctcacagag ttccattcga ccaaatggac    2520
aagcacaagc agcacaaaga aactcaccac aaggcataa                           2559
```

<210> SEQ ID NO 39
<211> LENGTH: 2322
<212> TYPE: DNA
<213> ORGANISM: Leishmania major

<400> SEQUENCE: 39

```
atgttgttgt tgttcttctc cttcttgtac tgtttgaaga acgcttacgg attgagaatg      60
atctccgttc aaatctacgg ttacttgatc cacgaatttg acccatggtt caactacaga    120
gctgctgagt acatgtctac tcacggttgg tctgcttttt tctcctggtt cgattacatg    180
tcctggtatc cattgggtag accagttggt tctactactt acccaggatt gcagttgact    240
gctgttgcta tccatagagc tttggctgct gctggaatgc caatgtcctt gaacaatgtt    300
tgtgttttga tgccagcttg gtttggtgct atcgctactg ctactttggc tttgatgact    360
tacgaaatgt ccggttccgg tattgctgct gctattgctg cttttcatct tctccatcatc    420 ccagctcatt tgatgagatc catggctggt gagttcgaca acgagtgtat tgctgttgct    480
gctatgttgt tgactttcta ctgttgggtt agatccttga aactagatc ctcctggcca    540 atcggtgttt tgactggtgt tgcttacggt tacatggcag ctgcttgggg aggttacatc    600
ttcgttttga acatggttgc tatgcacgct ggtatctctt ctatggttga ctgggctaga    660
aacacttaca acccatcctt gttgagagct tacactttgt tctacgttgt tggtactgct    720
atcgctgttt gtgttccacc agttggaatg tctccattca agtccttgga gcagttggga    780
gctttgttgg ttttggtttt cttgtgtgga ttgcaagttt tgtgaggtttt gagagctaga    840 gctggtgttg aagttagatc cagagctaat ttcaagatca gagttagagt tttctccgtt    900
atggctggtg ttgctgcttt ggctatctct gttttggctc caactggtta ctttggtcca    960
ttgtctgtta gagttagagc tttgttcgtt gagcacacta gaactggtaa cccattggtt   1020
gactccgttg ctgaacacag aatgacttcc ccaaaggctt acgctttctt cttggacttc   1080
acttacccag tttggttgtt gggtactgtt ttgcagttgt tggggagcatt catgggttcc   1140 agaaaagagg ctagattgtt catgggattg cattccttgg ctacttacta cttcgctgat   1200
```

```
agaatgtcca gattgatcgt tttggctggt ccagctgctg ctgctatgac tgctggaatc    1260
ttgggattgg tttacgaatg gtgttgggct caattgactg gatgggcttc tcctggtttg    1320
tctgctgctg gttctggtgg aatggatgac ttcgacaaca agagaggaca aactcaaatc    1380
cagtcctcca ctgctaatag aaacagaggg gttagagcac atgctatcgc tgctgttaag    1440
tccattaagg ctggtgttaa cttgttgcca ttggttttga gagttggtgt tgctgttgct    1500
attttggctg ttactgttgg tactccatac gtttcccagt tccaggctag atgtattcaa    1560
tccgcttact cctttgctgg tccaagaatc gttttccagg ctcagttgca cactggtgaa    1620
caggttatcg ttaaggacta cttggaagct tacgagtggt tgagagactc tactccagag    1680
gacgctagag ttttggcttg gtgggactac ggttaccaaa tcactggtat cggtaacaga    1740
acttccttgg ctgatggtaa cacttggaac cacgagcaca ttgctactat cggaaagatg    1800
ttgacttctc cagttgctga agctcactcc ttggttagac acatggctga ctacgttttg    1860
atttgggctg gtcaatctgg tgacttgatg aagtctccac acatggctag aatcggtaac    1920
tctgtttacc acgacatttg tccagatgac ccattgtgtc agcaattcgg tttccacaga    1980
aacgattact ccagaccaac tccaatgatg agagcttcct tgttgtacaa cttgcacgag    2040
gctggtaaaa ctaagggtgt taaggttaac ccatctttgt tccaagaggt ttactcctcc    2100
aagtacggtt tggttagaat cttcaaggtt atgaacgttt ccgctgagtc taagaagtgg    2160
gttgcagacc cagctaacag agtttgtcac ccacctggtt cttggatttg tcctggtcaa    2220
tacccacctg ctaaagaaat ccaagagatg ttggctcaca gagttccatt cgaccaaatg    2280
gacaagcaca agcagcacaa agaaactcac cacaaggcat aa                       2322
```

<210> SEQ ID NO 40
<211> LENGTH: 2502
<212> TYPE: DNA
<213> ORGANISM: Leishmania major

<400> SEQUENCE: 40

```
atggctgccg catcaaacgt taatgctcct gaaagtaacg tcatgactac aagatccgca     60
gttgcaccac cttccaccgc tgcaccaaag gaggcttctt ccgaaacttt gcttattgga    120
ctttacaaaa tgccttcaca gactagaagt ttgatctatt caagttgttt cgctgttgcc    180
atggcaattg ctttgccaat cgcttacgat atgagagtta gatcaattgg tgtctacgga    240
tatttgttcc attcttccga cccttggttt aattacagag cagctgagta tatgtctact    300
cacggttggt ctgctttctt ttcttggttt gattacatga gttggtatcc attgggtaga    360
cctgttggat ctaccactta tccaggactt caattgacag ccgttgcaat tcatagagct    420
ttggccgcag ctggtatgcc aatgagtctt aacaatgttt gtgtcttgat gcctgcttgg    480
ttctcattgg tttcaagtgc aatggccgca ttgcttgctc atgaaatgtc tggaaacatg    540
gctgttgcct ccatttcttc catcttgttt tctgttgtcc ctgctcactt gatgagatcc    600
atggccggag agttcgataa tgaatgtatt gctgttgctg ccatgttgct acatttttac    660
tgctgggtta gatccttgag aaccagatca agttggccaa tcggtgtttt gactggagtc    720
gcttacggtt atatggcagc tgcctggggt ggatacattt tgttttgaa catggtcgct    780 atgcacgccg gtatctcttc catggttgac tgggctagaa acacttataa tccatctttg    840
cttagagctt acaccttgtt ctatgttgtc ggaactgcaa ttgctgtttg tgtcccacct    900 gttgaatgt cacctttaa gagtcttgaa cagttgggag ctttgcttgt tttggtcttt    960
attttcggac agtcagtttg cgaggctcaa agaagaagac ttggaatcgc cagattgtct   1020
```

```
aaggaaggtg ttgcattgct tattagaatc gatgcagctt tctttgtcgg aattgttgcc    1080
gtcgcaacaa tcgctccagc cggtttcttt aaacctcttt ccttgcaagc aaacgctatt    1140
atcaccggag tttcaagaac tggtaataca ttggtcgata ttttgcttgc acaggacgct    1200
tctaacttgc ttatggtttg gcaattgttt ttgttcccat ttttgggttg ggttgcagga    1260
atgtccgctt tcttagaga gttgatcaga aactacactt acgctaagtc attcatcttg    1320
atgtacggtg ttgtcggaat gtattttgct tctcaatccg ttagaatgat ggtcatgatg    1380
gccccagttg catgtatttt caccgccttg ctttttagat gggcacttga ttacttgttg    1440
ggttctttgt tctgggcaga atgccacct tcatttgata ctgacgccca gagaggtaga    1500
caacagcaaa ctgctgaaga gtctgaggcc gaaacaaaga gaaggaaga ggaatacaac    1560 actatgcaag ttaagaaaat gtccgtcaga atgttgcctt tcatgttgct tttgcttttg    1620
ttcagattgt ccggttttat tgaggacgtt gccgcaatct caagaaagat ggaagctcca    1680
ggaattgttt ttcctagtga gcaggttcaa ggtgtctctg aaaagaaagt tgatgactac    1740
tatgctggat acctttattt gagagattcc acacctgaag acgccagagt tttggcatgg    1800
tgggattacg gttatcaaat tacaggtatc ggaaatagaa cctctttggc tgacggaaac    1860
acctggaatc atgagcacat tgctactatc ggtaaaatgt tgacatcccc agtcgccgaa    1920
gcacattcac ttgttagaca catggcagat tacgtcttga tttctgctgg agatacttat    1980
ttctcagact tgaacagaag tccaatgatg gctagaattg gtaattctgt ttaccatgac    2040
atctgtccag atgaccctct tgctcccag tttgttttgc aaaagagacc taaagctgcc    2100
gcagctaaga gatccagaca tgtttccgtc gatgccttgg aggaagatga cactgcagag    2160
cacatggttt acgaaccatc aagtttgatc gctaagagtc ttatctatca tttgcactct    2220
acaggagttg tcaccggtgt tactcttaac gagacattgt tccagcatgt ctttacctct    2280
ccacaaggtt tgatgagaat tttcaaggtt atgaacgtct ctactgaatc caagaaatgg    2340
gttgctgata gtgccaatag agtctgtcac ccacctggat cttggatttg cccaggtcaa    2400
tacccacctg ctaaggagat ccaggaaatg ttggcccatc aacacactaa ttttaaggat    2460
ttgttggacc ctagaacaac ctggtcaggt agtagaagat aa                       2502
```

<210> SEQ ID NO 41
<211> LENGTH: 957
<212> TYPE: DNA
<213> ORGANISM: Artificial Sequence
<220> FEATURE:
<223> OTHER INFORMATION: DNA encodes Pichia pastoris URA5 marker

<400> SEQUENCE: 41

```
tctagaggga cttatctggg tccagacgat gtgtatcaaa agacaaatta gagtatttat     60
aaagttatgt aagcaaatag gggctaatag ggaaagaaaa attttggttc tttatcagag    120
ctggctcgcg cgcagtgttt ttcgtgctcc tttgtaatag tcattttga ctactgttca    180 gattgaaatc acattgaaga tgtcactgga ggggtaccaa aaaaggtttt tggatgctgc    240
agtggcttcg caggccttga gtttggaac tttcaccttg aaaagtggaa gacagtctcc    300
atacttcttt aacatgggtc ttttcaacaa agctccatta gtgagtcagc tggctgaatc    360
ttatgctcag gccatcatta acagcaacct ggagatagac gttgtatttg gaccagctta    420
taaaggtatt cctttggctg ctattaccgt gttgaagttg tacgagctgg gcggcaaaaa    480
atacgaaaat gtcggatatg cgttcaatag aaaagaaaag aaagaccacg gagaaggtgg    540
```

```
aagcatcgtt ggagaaagtc taaagaataa aagagtactg attatcgatg atgtgatgac    600
tgcaggtact gctatcaacg aagcatttgc tataattgga gctgaaggtg ggagagttga    660
aggttgtatt attgccctag atagaatgga gactacagga gatgactcaa ataccagtgc    720
tacccaggct gttagtcaga gatatggtac ccctgtcttg agtatagtga cattggacca    780
tattgtggcc catttgggcg aaactttcac agcagacgag aaatctcaaa tggaaacgta    840
tagaaaaaag tatttgccca ataagtatg aatctgcttc gaatgaatga attaatccaa     900
ttatcttctc accattattt tcttctgttt cggagctttg ggcacggcgg cggatcc       957
```

<210> SEQ ID NO 42
<211> LENGTH: 709
<212> TYPE: DNA
<213> ORGANISM: Artificial Sequence
<220> FEATURE:
<223> OTHER INFORMATION: DNA encodes part of the E. coli lacZ gene that
      was used to construct the PpURA5 blaster

<400> SEQUENCE: 42

```
cctgcactgg atggtggcgc tggatggtaa gccgctggca agcggtgaag tgcctctgga     60
tgtcgctcca caaggtaaac agttgattga actgcctgaa ctaccgcagc ggagagcgc    120 cgggcaactc tggctcacag tacgcgtagt gcaaccgaac gcgaccgcat ggtcagaagc    180
cgggcacatc agcgcctggc agcagtggcg tctggcggaa aacctcagtg tgacgctccc    240
cgccgcgtcc cacgccatcc cgcatctgac caccagcgaa atggattttt gcatcgagct    300
gggtaataag cgttggcaat ttaaccgcca gtcaggcttt cttttcacaga tgtggattgg    360 cgataaaaaa caactgctga cgccgctgcg cgatcagttc acccgtgcac cgctggataa    420
cgacattggc gtaagtgaag cgacccgcat tgaccctaac gcctgggtcg aacgctggaa    480
ggcggcgggc cattaccagg ccgaagcagc gttgttgcag tgcacggcag atacacttgc    540
tgatgcggtg ctgattacga ccgctcacgc gtggcagcat caggggaaaa ccttatttat    600
cagccggaaa acctaccgga ttgatggtag tggtcaaatg gcgattaccg ttgatgttga    660
agtggcgagc gatacaccgc atccggcgcg gattggcctg aactgccag              709
```

<210> SEQ ID NO 43
<211> LENGTH: 542
<212> TYPE: PRT
<213> ORGANISM: Saccharomyces cerevisea

<400> SEQUENCE: 43

```
Met Gln Ala Lys Ile Ile Tyr Ala Leu Ser Ala Ile Ser Ala Leu Ile
1               5                   10                  15

Pro Leu Gly Ser Ser Leu Leu Ala Pro Ile Glu Asp Pro Ile Val Ser
            20                  25                  30

Asn Lys Tyr Leu Ile Ser Tyr Ile Asp Glu Asp Asp Trp Ser Asp Arg
        35                  40                  45

Ile Leu Gln Asn Gln Ser Val Met Asn Ser Gly Tyr Ile Val Asn Met
    50                  55                  60

Gly Asp Asp Leu Glu Cys Phe Ile Gln Asn Ala Ser Thr Gln Leu Asn
65                  70                  75                  80

Asp Val Leu Glu Asp Ser Asn Glu His Ser Asn Ser Glu Lys Thr Ala
                85                  90                  95

Leu Leu Thr Lys Thr Leu Asn Gln Gly Val Lys Thr Ile Phe Asp Lys
            100                 105                 110

Leu Asn Glu Arg Cys Ile Phe Tyr Gln Ala Gly Phe Trp Ile Tyr Glu
```

```
                115                 120                 125
Tyr Cys Pro Gly Ile Glu Phe Val Gln Phe His Gly Arg Val Asn Thr
    130                 135                 140
Lys Thr Gly Glu Ile Val Asn Arg Asp Glu Ser Leu Val Tyr Arg Leu
145                 150                 155                 160
Gly Lys Pro Lys Ala Asn Val Glu Glu Arg Glu Phe Glu Leu Leu Tyr
                165                 170                 175
Asp Asp Val Gly Tyr Tyr Ile Ser Glu Ile Gly Ser Gly Asp Ile
                180                 185                 190
Cys Asp Val Thr Gly Ala Glu Arg Met Val Glu Ile Gln Tyr Val Cys
            195                 200                 205
Gly Gly Ser Asn Ser Gly Pro Ser Thr Ile Gln Trp Val Arg Glu Thr
210                 215                 220
Lys Ile Cys Val Tyr Glu Ala Gln Val Thr Ile Pro Glu Leu Cys Asn
225                 230                 235                 240
Leu Glu Leu Leu Ala Lys Asn Glu Asp Gln Lys Asn Ala Ser Pro Ile
                245                 250                 255
Leu Cys Arg Met Pro Ala Lys Ser Lys Ile Gly Ser Asn Ser Ile Asp
            260                 265                 270
Leu Ile Thr Lys Tyr Glu Pro Ile Phe Leu Gly Ser Gly Ile Tyr Phe
            275                 280                 285
Leu Arg Pro Phe Asn Thr Asp Glu Arg Asp Lys Leu Met Val Thr Asp
            290                 295                 300
Asn Ala Met Ser Asn Trp Asp Glu Ile Thr Glu Thr Tyr Tyr Gln Lys
305                 310                 315                 320
Phe Gly Asn Ala Ile Asn Lys Met Leu Ser Leu Arg Leu Val Ser Leu
                325                 330                 335
Pro Asn Gly His Ile Leu Gln Pro Gly Asp Ser Cys Val Trp Leu Ala
            340                 345                 350
Glu Val Val Asp Met Lys Asp Arg Phe Gln Thr Thr Leu Ser Leu Asn
            355                 360                 365
Ile Leu Asn Ser Gln Arg Ala Glu Ile Phe Phe Asn Lys Thr Phe Thr
    370                 375                 380
Phe Asn Glu Asp Asn Gly Asn Phe Leu Ser Tyr Lys Ile Gly Asp His
385                 390                 395                 400
Gly Glu Ser Thr Glu Leu Gly Gln Ile Thr His Ser Asn Lys Ala Asp
                405                 410                 415
Ile Asn Thr Ala Glu Ile Arg Ser Asp Glu Tyr Leu Ile Asn Thr Asp
            420                 425                 430
Asn Glu Leu Phe Leu Arg Ile Ser Lys Glu Ile Ala Glu Val Lys Glu
            435                 440                 445
Leu Leu Asn Glu Ile Val Ser Pro His Glu Met Glu Val Ile Phe Glu
        450                 455                 460
Asn Met Arg Asn Gln Pro Asn Asn Asp Phe Glu Leu Ala Leu Met Asn
465                 470                 475                 480
Lys Leu Lys Ser Ser Leu Asn Asp Asp Asn Lys Val Glu Gln Ile Asn
                485                 490                 495
Asn Ala Arg Met Asp Asp Asp Glu Ser Thr Ser His Thr Thr Arg Asp
            500                 505                 510
Ile Gly Glu Ala Gly Ser Gln Thr Thr Gly Asn Thr Glu Ser Glu Val
        515                 520                 525
Thr Asn Val Ala Ala Gly Val Phe Ile Glu His Asp Glu Leu
    530                 535                 540
```

<210> SEQ ID NO 44
<211> LENGTH: 1629
<212> TYPE: DNA
<213> ORGANISM: Saccharomyces cerevisea

<400> SEQUENCE: 44

```
atgcaagcta aaattatata tgctctgagc gcaatttctg cgttgattcc gttaggatca      60
tcactattag cacctataga agaccccata gtatcgaata agtacctcat atcttacatc     120
gatgaggacg actggagtga taggatatta caaaatcagt ctgtcatgaa ctcgggatat     180
atagtgaata tgggcgacga ccttgaatgc tttattcaaa atgcaagcac tcaattgaat     240
gatgtattgg aagactcaaa tgagcatagc aatagtgaaa agacagcatt attaactaaa     300
accctgaatc aaggtgttaa gacaattttc gataaattaa atgaacggtg catcttctac     360
caagccggat tttggattta cgagtactgt cctggcatag aatttgttca gttccatggt     420
agagtaaata caaaaactgg tgaaatagta atcgagatg aatctttggt ctaccgcctg     480
ggaaaaccaa agcaaatgt agaagagaga gaatttgaac tactttatga cgatgtagga     540
tattacatca gcgaaattat agggtcaggt gatatttgcg atgtgacggg ggctgaaaga     600
atggttgaaa tacaatatgt ctgtggcggc tcaaactctg gaccatcgac tattcaatgg     660
gtgagagaaa caaaaatttg tgtttatgaa gcccaagtta ccatacctga attgtgcaat     720
ttagaattac tagccaaaaa tgaagaccaa agaacgcct cacctatact ttgcaggatg     780
cccgcaaaat caaaaattgg tagtaactct attgatttaa tcaccaaata tgaaccgatt     840
tttttaggtt ctggaatata ctttctaagg ccctttaaca ccgacgaaag agacaaatta     900
atggttactg acaatgccat gtcaaattgg gatgagatta cggaaacata ttaccagaaa     960
tttggaaatg ccataaacaa aatgcttagt ttgagattag tatcgttacc taatggacat    1020
attctccagc ctggtgactc atgtgtttgg ttggcggaag tggttgatat gaaagatcgg    1080
tttcaaacca ctttatcgtt gaacatactt aattcacaga gagcagagat atttttcaac    1140
aagacgttta catttaatga agataatgga aacttcctat catacaaaat tggggatcat    1200
ggcgagtcaa ctgaacttgg tcaaataacc cactcaaaca aagcagatat aaataccgca    1260
gaaattcggt cagatgaata cttaattaac actgataatg agctattctt gaggatttct    1320
aaggagatag cagaagtgaa agaattatta acgaaatcg taagtccaca tgaaatggaa    1380
gtaatatttg aaaacatgag aaatcaaccg aataatgatt ttgaactggc gttgatgaac    1440
aagttgaaat cctcattaaa tgatgataac aaagttgagc agataaacaa cgcaaggatg    1500
gatgatgatg aaagcactag tcatacaacc agagacatcg gggaagctgg atcacaaacg    1560
acagggaata ctgaatcgga ggtaacaaac gtagcagctg gtgttttcat cgaacatgat    1620
gagctttaa                                                           1629
```

<210> SEQ ID NO 45
<211> LENGTH: 360
<212> TYPE: PRT
<213> ORGANISM: Pichia pastoris

<400> SEQUENCE: 45

```
Met Ile Lys Val Leu Leu Phe Leu Leu Ser Leu Ser Ser Leu Val Lys
  1               5                  10                  15

Ala Leu Asp Asp Ser Ile Asp Lys Asn Ser Val Tyr Thr Ile Asn Tyr
             20                  25                  30
```

```
Leu Asn His Ala Ile Ser Pro Thr Ser Glu Lys Ile Val Thr Leu Arg
             35                  40                  45

Ser Thr Asp Asp Gln Tyr Phe Glu Cys Leu Phe Asn Asp Glu Ile Asp
 50                  55                  60

Thr Asp Gln Lys Leu His Gln Lys Gln Ile Leu Lys Thr Leu Pro Ala
 65                  70                  75                  80

Gln Tyr Asn Leu Ser Glu Ile Pro Glu Leu Gln Thr Glu Ile Asn Ser
                 85                  90                  95

Ala Phe Asn Ile Leu Glu Asn Tyr Asn Leu Asn Asp Ala Gln Pro Thr
                100                 105                 110

Lys Asp Arg Tyr Trp Thr Tyr Gln Ile Ile Asn Gly Lys Leu Tyr Gln
            115                 120                 125

Tyr Asn Gly Asn Leu Arg Ile Val Leu Ala Asn Ile Pro Lys Asn Leu
        130                 135                 140

Thr Arg Glu Asp Ile Val Leu Glu Lys Asn Met His Gln Ser Val Phe
145                 150                 155                 160

Leu Ser Leu Ser Leu Gln Asn Gly Ala Ile Cys Asp Leu Thr Phe Thr
                165                 170                 175

Pro Arg Lys Thr Asn Ile Arg Phe Gln Tyr Val Asn Lys Leu Asn Thr
            180                 185                 190

Leu Gly Ile Val Ser Ala Asp Glu Ile Gln Thr Cys Glu Tyr Glu Ile
        195                 200                 205

Leu Ile Asn Val Pro Lys Phe Lys Asp Thr Ile Phe Gln Tyr Gly Phe
    210                 215                 220

Leu Glu Pro Leu Lys Lys Ile Asp Cys Tyr Ser Ser Asp Ser Ser Met
225                 230                 235                 240

Ile Asn Leu Ala Asp Tyr Gln Ile Ser Val Leu Ser His Lys Trp Phe
                245                 250                 255

Leu Gly Ala Lys Asp Phe Arg Leu Ile Leu Ile Thr Asp Val Ser Asn
            260                 265                 270

Pro Pro Val Ile Ser Ile Glu Glu Leu Asn Leu Ile Phe Gln Thr Phe
        275                 280                 285

Pro Lys Tyr Gly Pro Pro Glu Leu Gly Ile Thr Gly Glu Ile Ser Pro
    290                 295                 300

His Asp Thr Phe Ile Phe Arg Ile Pro Val Tyr Ser Tyr Asn Arg Thr
305                 310                 315                 320

Lys Phe Gly Asp Val Leu Val Glu Gln Asn Ile Arg Gly Glu Lys Arg
                325                 330                 335

Phe Leu Phe Thr Glu Asp Arg Ile Pro His Asp Thr Pro Asn Phe Arg
            340                 345                 350

Val Tyr Asn Gly Val Asn Val Asn
        355                 360

<210> SEQ ID NO 46
<211> LENGTH: 1140
<212> TYPE: DNA
<213> ORGANISM: Pichia pastoris

<400> SEQUENCE: 46
atgataaagg tcctgctatt cctgctctcc ctatcaagtc ttgtgaaagc tttggatgat    60
tccattgata agaattctgt ggtaagtctt ttaattttg ttttcacaag atcatgccgt   120
gctaactggg tactatagta taccataaac tacttaaatc atgccatctc acccacctca   180
gaaaaaatag tgacattaag atcaacggac gatcaatatt ttgagtgttt gtttaatgat   240
```

```
gaaattgata ctgaccagaa actacatcaa aagcagattc tgaaaactct tccagctcaa    300
tacaacttga gtgaaatacc agaacttcaa actgaaataa actctgcatt caatatactt    360
gaaaactata acctcaacga tgctcagcca accaaggaca gatattggac atatcaaata    420
ataaatggaa aattgtacca atataacggg aacttgcgaa ttgtcctggc taatataccc    480
aagaatctga cgagggaaga catagttctg gagaagaata tgcaccaatc ggtgttttta    540
tcactcagct acaaaacgg tgccatttgt gatttgactt tcactcctag aaagacaaat    600
atacggtttc aatacgttaa caagctcaac actctaggaa ttgtctccgc cgatgaaata    660
cagacctgcg aatatgaaat tcttatcaat gttcctaagt tcaaagatac cattttcag    720
tacggatttt tggagccttt gaagaagatt gattgctact cgagtgatag ctcaatgata    780
aatttggcag actaccaaat atctgtcctt tcccataaat ggttcttagg ggccaaagat    840
ttcaggttga ttttgatcac tgatgtgtct aaccctcccg tgatatcaat agaagaactg    900
aatctcatat ttcaaacatt tcctaaatac ggtcccccag agctcgggat cactggtgag    960
atttcacccc atgacacttt tatcttcaga attcctgtgt acagctacaa taggacaaaa   1020
ttcggtgacg tactggttga gcagaatatc aggggagaga aaaggttcct attcactgaa   1080
gacagaatac ctcatgacac tccaaacttt agagtgtata acggagttaa tgtgaattaa   1140
```

<210> SEQ ID NO 47
<211> LENGTH: 520
<212> TYPE: PRT
<213> ORGANISM: Aspergillus fumigates

<400> SEQUENCE: 47

```
Met Ile Arg Arg Ile Arg Thr Leu Thr Pro Leu Leu Val Leu Ala Cys
1               5                   10                  15

Ala Gly Ser Gly Ala Trp Ala Ser Lys Lys Ala Phe Asn Ile Gln Asp
            20                  25                  30

Asp Leu Leu Ala Tyr Pro Gln Phe Gln Val Phe Phe Pro Asp Glu Tyr
        35                  40                  45

Ile Leu Asp Ala Arg Ala Arg Glu Leu Leu Gln Asn Gln Gln Glu Ser
    50                  55                  60

Ser Ser Ala Ser Ala Asp Lys Thr Phe Ser Glu Gly Asn Asp Ala Gln
65                  70                  75                  80

Val Tyr Leu Gly Ser Arg Lys Asp Gln Ser Glu Asp Val Asn Lys Glu
                85                  90                  95

Thr Ile Glu Gly Ser Gly Phe Thr Tyr Glu Glu Met Leu Leu Glu Gly
            100                 105                 110

Gln Arg Tyr Leu Cys Ser Ile Pro Gln Val Asp Asn Gly Asn Arg Asp
        115                 120                 125

Gln Thr Asn Gly Ala Glu Ser Thr Ser Lys Glu Asp Glu Gln Arg Glu
    130                 135                 140

Ile Ala Arg Ala Thr Asp Arg Gly Leu Glu Leu Leu Arg Glu Met Glu
145                 150                 155                 160

Gly Lys Cys Met Tyr Tyr Ile Ser Gly Trp Trp Ser Tyr Ser Phe Cys
                165                 170                 175

Tyr Lys Lys Gln Ile Lys Gln Phe His Ala Leu Pro Ser Gly Pro Gly
            180                 185                 190

Val Pro Asn Tyr Pro Pro Ile Glu Asp Ser Thr Thr His Ser Phe Val
        195                 200                 205

Leu Gly Arg Phe Pro Asn Ser Gly Asp Asp Glu Asp Leu Glu Gly Asp
    210                 215                 220
```

```
Ala Glu His Lys Lys Thr Thr Thr Asp Val Ala Glu Leu Gln Thr Lys
225                 230                 235                 240

Gly Gly Ser Arg Tyr Leu Val Gln Arg Leu Gly Gly Thr Lys Cys
            245                 250                 255

Asp Leu Thr Gly Lys Asp Arg Lys Ile Glu Val Gln Phe His Cys His
            260                 265                 270

Pro Gln Ser Thr Asp Arg Ile Gly Trp Ile Lys Glu Leu Thr Thr Cys
            275                 280                 285

Ser Tyr Leu Met Val Ile Tyr Thr Pro Arg Leu Cys Asn Asp Val Ala
            290                 295                 300

Phe Leu Pro Pro Gln Gln Asp Glu Ala His Ala Ile Glu Cys Arg Glu
305                 310                 315                 320

Ile Leu Ser Glu Glu Glu Val Ser Asp Trp Glu Ala Asn Arg Glu Tyr
                325                 330                 335

His Leu Ala Gln Gln Leu Val Glu Ser Ala Ile Thr Pro Glu Phe Pro
                340                 345                 350

Val Val Gly Asp Ile Glu Val Gly Ala His Lys Trp Val Gly Ser Glu
            355                 360                 365

Gly Lys Gln Ile Glu Lys Gly Arg Val Ala Ser Ile Gly Glu Glu Lys
    370                 375                 380

Ile Glu Val Val Ala Lys Arg Gln Asn Gly Glu Ile Thr Arg Leu Ser
385                 390                 395                 400

Lys Glu Glu Leu Lys Lys Tyr Gly Leu Asp Pro Glu Lys Ile Glu Thr
                405                 410                 415

Leu Lys Ser Arg Leu Glu Glu Leu Ala Lys Gly Lys Asp Trp Thr Leu
            420                 425                 430

Glu Ile Val Glu Ser Asn Gly Glu Arg Gly Leu Val Gly Thr Val Asp
            435                 440                 445

Ser Asn Asp Asp Glu Lys Glu Asp His Ala Ala Gln Gly Ser Ile Ser
    450                 455                 460

Gln Pro Ala Gln Gly Thr Thr Ala Asp Lys Gly Glu Ser Asn Ala Glu
465                 470                 475                 480

Thr Gly Glu Glu Lys Lys Lys Ala Asp Glu Lys Ile Asp His Tyr Glu
                485                 490                 495

Pro Glu Lys Ser Gly Pro Thr Thr Asp Asp Ala Asp Asp Gly Ser Glu
            500                 505                 510

Glu Ile Phe Phe Lys Asp Glu Leu
            515                 520

<210> SEQ ID NO 48
<211> LENGTH: 1563
<212> TYPE: DNA
<213> ORGANISM: Aspergillus fumigates

<400> SEQUENCE: 48
atgattcgac gtatacggac tcttacccca ttgctggtgc tggcttgtgc tggttccggc      60
gcatgggcca gcaagaaggc gttcaacata caagatgatc tacttgcata tcctcaattt     120
caagtcttct ccctgatga atacattctt gatgcgcgag caagggagtt attacagaat      180
caacaagaga gctcttcggc ttccgctgat aagacattct ccgaaggcaa tgatgcgcaa     240
gtatatctgg aagccgaaa agatcaatct gaagacgtca ataaagagac gatagaagga      300
tctgggttca catacgagga gatgctcctt gagggacaga gatatctctg ttccattccg     360
caagtcgaca acggaaacag ggaccagacg aacggagcgg aaagcaccag taaagaggat     420
```

-continued

```
gaacagcgag aaattgcacg cgcgacggac cgtggcctgg aacttctgcg cgagatggaa      480
ggcaaatgca tgtactacat atccggatgg tggtcatact cattctgcta caagaagcaa      540
atcaagcagt ttcatgcact accgtccggt ccaggcgtgc ccaactaccc gccgatagaa      600
gactctacga cccattcttt cgtgctgggc aggtttccca acagcggcga cgacgaggat      660
ttggaggggg atgcggagca caaaaagaca actacagatg tcgccgagct ccagactaaa      720
ggcgggtcgc ggtacttagt gcagcggctg ggggcggaa ccaagtgcga cttgacaggc       780
aaagaccgga agatcgaagt gcagttccac tgccatccgc aatctacaga tcggatcggt      840
tggatcaagg aacttactac ttgctcatat ctcatggtga tctacactcc gcgcttgtgc      900
aatgatgtcg catttctgcc gcctcagcag gacgaggctc acgcgatcga atgccgcgag      960
attctctccg aggaagaggt ttccgactgg gaagcaaacc gggaatatca tttggctcag     1020
cagctcgtcg aatcagcgat tacacccgag tttcctgttg tcggggatat cgaggtcggg     1080
gcgcacaagt gggtgggatc ggaaggcaag cagatcgaga agggtcgagt ggcatccatt     1140
ggagaagaga agatcgaggt agttgccaag cgccaaaatg gagagatcac aaggttgtcc     1200
aaggaggagt tgaagaaata cggtcttgat cctgagaaga ttgagacgct gaaaagccgc     1260
ctcgaggagc ttgccaaggg taaggactgg acactggaga ttgtcgagtc taacggcgag     1320
cgtggcttag tcggaactgt cggactccaa cgacgatgaga aagaggatca cgccgcacag     1380
ggctctatat cgcagccggc acagggaact acagctgaca agggggaatc caatgcagag     1440
acaggagagg aaaagaagaa ggcagacgag aagatagacc attacgagcc agaaaaatca     1500
gggccgacca ctgatgatgc cgacgacggc agcgaggaaa tcttcttcaa ggatgagctc     1560
tag                                                                   1563
```

<210> SEQ ID NO 49
<211> LENGTH: 305
<212> TYPE: PRT
<213> ORGANISM: Schizosaccharomyces pombe

<400> SEQUENCE: 49

```
Met Phe Pro His Leu Ile Leu Pro Ala Ile Gly Ser Ser Lys Val Arg
1               5                   10                  15

Thr Met Val Leu Pro Phe Ala Phe Val Gly Phe Phe Ile Phe Pro Ile
                20                  25                  30

Cys Leu Ala Ser Leu Leu Asp Trp Asn Asp Ala Tyr Glu Tyr Pro Lys
            35                  40                  45

Tyr Ser Phe Glu Trp Ser Asn Val Ser Ile Leu Glu Gly Asp Ile Asp
        50                  55                  60

Ser Ile Lys Glu Lys Thr Glu Lys Thr Lys Leu Ser Ser Leu Phe Tyr
65                  70                  75                  80

Ala Gly Lys His Glu Tyr Phe Cys Val Tyr Pro Asn Ala Ser Leu Ile
                85                  90                  95

Lys Gln Asn Ser Thr Thr Glu Pro Ser Tyr Asp Leu Gln Glu Leu Arg
            100                 105                 110

Ile Gln Gly Thr Glu Lys Ile Asn Glu Leu Ala Asn Val Phe Leu Ile
        115                 120                 125

Glu Asn Arg Gly Tyr Trp Thr Tyr Asp Tyr Val Tyr Gly Gln His Val
    130                 135                 140

Arg Gln Tyr His Leu Glu Pro Gln Gln Gly Ser Asp Lys Val Leu Ala
145                 150                 155                 160
```

```
Asn Pro Met Tyr Ile Leu Gly Thr Ala Pro Asn Thr Gln Thr Lys Lys
                165                 170                 175

Asn Leu Glu Glu Asn Trp Ala Ile Gly Phe Val Glu Gly Lys Ala Tyr
            180                 185                 190

Leu Gln Thr Thr Phe Arg Asn Gly Thr Met Cys Asp Ile Thr Lys Arg
        195                 200                 205

Pro Arg His Val Ile Leu Ser Tyr Glu Cys Ser Thr Asn Ser Asp Thr
    210                 215                 220

Pro Glu Ile Thr Gln Tyr Gln Glu Val Ser Ser Cys Ala Tyr Ser Met
225                 230                 235                 240

Thr Ile His Val Pro Gly Leu Cys Ser Leu Pro Ala Phe Lys Ile Gln
                245                 250                 255

Glu Asp Ile Pro Ser Glu Lys Ile Val Cys Tyr Asn Val Ile Lys Glu
            260                 265                 270

Lys Ser Asn Glu Val Asp His Lys Asp Ser Gln His Val Val Asp Glu
        275                 280                 285

Val Ala Gln Thr Ser Pro Pro Glu Val Lys Glu Val Glu Thr Gln Ser
    290                 295                 300

Ser
305

<210> SEQ ID NO 50
<211> LENGTH: 918
<212> TYPE: DNA
<213> ORGANISM: Schizosaccharomyces pombe

<400> SEQUENCE: 50
atgtttccac atttgattct acctgcaatc ggctcatcta aagttaggac tatggtgcta      60
ccatttgctt ttgtggggtt ttttattttt ccaatatgtt tagcttcttt gttagactgg     120
aatgatgcat atgaatatcc taaatattcg tttgaatgga gtaatgtgtc aatattagag     180
ggcgacattg actcaattaa agaaaaaact gaaaaaacta attatcgtc attattctat      240 gctggaaagc atgaatattt ttgtgtatat cccaatgcgt ctcttataaa acaaaatagc     300
acaaccgaac caagctatga tttacaagaa ttgcggatac aagggactga aaaaatcaat     360
gagcttgcta atgtattttt aatcgagaat cgtggttatt ggacttatga ctatgtctac     420
ggtcaacacg tgcgtcaata tcatttggag ccgcagcaag ttctgacaa agtccttgct      480 aaccctatgt atatacttgg tacggcacct aacactcaaa ctaaaagaa tttggaagaa      540 aattgggcta ttggatttgt tgaaggtaaa gcatatttgc aaacaacttt ccgaaatggg     600
actatgtgcg acattactaa agaccaaga cacgtaattc taagttatga atgcagtaca      660
aattcggata ctcctgaaat tactcaatat caagaagttt caagctgtgc atattcaatg     720
actattcacg ttcccggttt atgctcatta cctgctttca aaattcaaga ggacataccc     780
tctgaaaaaa ttgtgtgcta taatgtaatt aaagaaaaat caaacgaagt cgaccataag     840
gattcccagc acgttgttga tgaagttgct caaacatctc cgcctgaggt gaaggaggta     900
gagacgcaat caagttag                                                   918

<210> SEQ ID NO 51
<211> LENGTH: 2004
<212> TYPE: DNA
<213> ORGANISM: Artificial Sequence
<220> FEATURE:
<223> OTHER INFORMATION: Pichia pastoris ATT1 5' region

<400> SEQUENCE: 51
```

```
ggccgggact acatgaggcc gattcttcaa gccagggaaa ttaattgctt gaaccggaaa      60
atcattaagg caggcaacga aaatccaac tccttggttg aattgactca aaagtttatc     120
ttacggagaa aagctaaaga catcaatacg aatttccttc cgccaaaaac tgaactgata     180
ctgatggttc caatgactga attacaacag gagctataca aggatataat tgaaactaac     240
caagccaagc ttggcttgat caacgacaga aacttttttc ttcaaaaaat tttgattctt     300
cgtaaaatat gcaattcacc ctccctgctg aaagacgaac ctgattttgc cagatacaat     360
ctcggcaata gattcaatag cggtaagatc aagctaacag tactgctttt acgaaagctg     420
tttgaaacca ccaatgagaa gtgtgtgatt gtttcaaact tcactaaaac tttggacgta     480
cttcagctaa tcatagagca caacaattgg aaataccacc gactagatgg ttcgagtaaa     540
ggacgggaca aaatcgtacg agattttaac gagtcgcctc aaaaagatcg attcatcatg     600
ttgctttctt ccaaggcagg gggagtgggg ctcaacttaa ttggagcctc acgcttaatt     660 cttttttgata cgactggaa tcccagtgtt gacattcaag caatggctag agtgcatcga     720
gacgggcaga aaaggcacac ctttatctat cgtttgtata cgaaaggcac aattgacgaa     780
aagatcctac aaaggcaatt gatgaaacaa atctgagcg acaaattcct ggatgataat     840
gatagcagca aggatgatgt gtttaacgac tacgatctca aagatttgtt tactgtagat     900
cttgacacga attgtagtac acacgatttg atggaatgtt tatgtaatgg gcggctgaga     960
gatccgactc ccgtcttgga agcagaagaa tgcaagacaa accgttgga ggccgttgac    1020 gacacggatg atggttggat gtcagctctg gatttcaaac agttatcaca aaaagaggag    1080
acaggtgctg tgtcaacaat gcgtcaatgt ctgctcggat atcaacacat tgatccaaag    1140
attttggaac caacagaacc tgtagggggac gatttggtat tggcaaacat cctcgcggag    1200
tcctcaggct tggctaaatc tgcattgtca tctgaaaaga aacccaagaa accagtggtg    1260
aactttatct ttgtgtcagg ccaagactaa gctggaagaa cggaacttta atcgaaggaa    1320
aaattaaatg tcaaagtggg tcgatcagga gataatccat gcttcacgtg attttttctta    1380 ataaacgccg gaaaaacttt cttttttgtg accaaaatta tccgatctga aaaaaaatta    1440
cgcatgcgtg aagtaggatg agagacttac tgttgaactt tgtgagacga ggggaaaagg    1500
aatatcctga tcgtaaacaa aaaagttttc cagcccaatc gggaacatct gcgaagtgtt    1560
ggaattcaac ccctctttcg aaaatgttcc attttaccca aaattattgt tattaaataa    1620
tacatgtgtt actagcaaag tctgcgcttt ccatgtctca gattcggcag ataacaaagt    1680
tgacacgttc ttgcgagata cgcatgaatc ttttggctgc ttttgtgaa agagaaatgg    1740 tgccatatat tgcagacgcc cctgaaagat tagtgtgcgg ctgagtcttt ttttttctc    1800 aaccagcttt ttctttttat tgggtaccat cgcgcacgca ggactcatgc tccattagac    1860
ttctgaacca cctgacttaa tattcatgga cggacgcttt tatccttaaa ttgttcatcc    1920
attcctcaat ttttccgttt gccctccctg tactattaaa ttacaaaagc tgatcttttt    1980
caagtgtttc tctttgaatc gctc                                           2004
```

<210> SEQ ID NO 52
<211> LENGTH: 1854
<212> TYPE: DNA
<213> ORGANISM: Artificial Sequence
<220> FEATURE:
<223> OTHER INFORMATION: Pichia pastoris ATT1 3' region

<400> SEQUENCE: 52

```
ggaccctgaa gacgaagaca tgtctgcctt agagtttacc gcagttcgat tccccaactt      60
ttcagctacg acaacagccc cgcctcctac tccagtcaat tgcaacagtc ctgaaaacat     120
caagacctcc actgtggacg atttttttgaa agctactcaa gatccaaata caaagagat     180 actcaacgac atttacagtt tgattttttga tgactccatg gatcctatga gcttcggaag    240
tatggaacca agaaacgatt tggaagttcc ggacactata atggattaat ttgcagcggg     300
cctgtttgta tagtctttga ttgtgtataa tagaattact acgcgtatat cccgatctgg     360
aagtaacatg gaagtttccc attttcgcgc agtctcctac tcgtatcctc cccacccctt     420
accgatgacg caaaggtca ctagataagc atagcatagt ttcatccctt gctctttcct      480
tgtaccaaca gatcatggct gggaatctca aggatattct atccttgtcg aggaagacag     540
caaggaatct gaagcaggct ctggatgagc ttgcggagca ggtgatcaac accaacgga     600 gacgaccagc tctggtccga gttcctatca acaacaacct taggcgcaag agccagcagt    660 ccttttttgaa tcgcaggtca ttccatcttt ggaccagcaa gtacaaccca tactttggga   720
ggggaggcag aagcaacgtt ctggaccagc ttaaccgtga agctttaagg tacagatcgt     780
cttttgcgaa acccggattt tatccaagtg ggctgtatca gtcaactttc cctcaaagag    840
gtagtaggat gttttccacc tgcgcctact catgtcagca ggaggcagtc aaaaacttga     900
cttccgctgt tcgtgctttg ttacaaagtg gtgctaattt cggcagtcaa atgaaacaaa    960
tgaaacactg ttcgcaaaag aagaagcact tctctaaatt ttctaagagg cttacttctt   1020
ccactgccgc tgggtctggc aagaatgctg aacaagctcc ttctggtttg gccgaaggat    1080
ccgctgttgt ttttagcctt gaacgtcaaa gtcacaatac tgagttggaa ggaatcttgg    1140
atcaagaaac ttcttccatt ctcgaggaag aaatggttca acatgagcgt cacctggcta    1200
ttattagaga agaaatccag agaattagtg agaatctagg atcattacca ttaatcatgt     1260
ctggtcacaa gattgaggta tttttccca attgtgacac tgttaaatgt gagcaactga    1320
tgagagattt ggctattacg aaaggggttg tgaggcgtca tgattctact gctgagcatt    1380
caagctccag gtcatttgtt ccagaagatt gcttgtattc ctcagggtca agttcaccga   1440
atcctttatc ctcaacttct tcgaaatcat tgatagagt ctcattggac tacatttcct    1500
ctcggtctac atctgatcaa accactggtt ctgagtacac atctctgtct caacaatatc    1560
acctggttag caattacaac cctgtactat cctcagcccc gggttcttcg agggtcttgg     1620
agctgaatac tcccgagtcc actatggaag gcagtacaga tctggagtat taacgcgag     1680 acgatgtgtt gctgttaaat gtctaatcta gacctatcct tcattctata tagcttagtt     1740
gagttttacg taagccctag ttttttgttaa ttcttatcga tttatggtta gtgtaccact    1800
caactcacga tgatatatcc caggagctgt tgtgcatta taactaccaa tcct           1854
```

<210> SEQ ID NO 53
<211> LENGTH: 1389
<212> TYPE: DNA
<213> ORGANISM: Artificial Sequence
<220> FEATURE:
<223> OTHER INFORMATION: Encodes Mus muscula endomannosidase
(codon-optimized for expression in Pichia pastoris)

<400> SEQUENCE: 53

```
atggctaagt ttagaagaag aacctgtatt tgttgtcct tgtttatcct ttttatttc        60 tccttgatga tgggattgaa gatgctttgg cctaacgctg cctctttttgg tccacctttc    120 ggattggatt tgcttccaga acttcatcct ttgaacgcac actcaggtaa taaggctgat    180
```

```
tttcagagaa gtgacagaat aacatggaa actaacacaa aggctttgaa aggtgccgga      240
atgactgttc ttcctgccaa agcatccgag gtcaaccttg aagagttgcc acctcttaac    300 tacttttgc atgctttcta ctactcatgg tacggtaacc acaattcga tggaaagtac      360 atccattgga atcacccagt tttggaacat tgggacccta gaatcgctaa aaattaccca    420
cagggtcaac actctccacc tgatgacatt ggttcttcct tctaccctga attgggatct    480
tattcaagta gagatccatc cgttattgag actcatatga agcaaatgag atccgcctcc    540
atcggtgtct tggcactttc atggtaccca cctgacagta gagatgacaa cggagaagcc    600
acagatcact tggttcctac cattcttgac aaggcacata agtacaactt gaaggtcact    660
ttccacatcg agccatattc taatagagat gaccagaaca tgcaccaaaa catcaagtac    720
atcatcgata gtacggtaa ccatcctgct ttctacagat ataagaccag aactggacac    780
tctttgccaa tgttctacgt ttatgactcc tacattacaa aacctaccat ctgggctaac    840
ttgcttactc catcaggtag tcagtcggtt agatcctccc cttatgatgg attgtttatt    900
gccttgcttg tcgaagagaa gcataagaac gatatcttgc agtctggttt cgacggaatc    960
tacacatatt ttgctaccaa cggtttcact tacggatcaa gtcaccaaaa ttggaacaat   1020
ttgaagtcct tctgtgaaaa gaacaatctt atgttcatcc catcagttgg tcctggatat   1080
attgatacaa gtatcagacc atggaacact caaaacacaa gaaacagagt taacggtaaa   1140
tactacgagg tcggattgtc tgcagctctt cagactcatc cttccttgat tcaatcaca    1200 agttttaacg aatggcacga gggtactcaa attgaaaagg ctgttccaaa agaaccgcc    1260 aatactatct acttggatta tagaccacat aagccttcat tgtaccttga gttgaccaga   1320
aaatggtctg aaaagttctc caaagagaga atgacttatg cattggacca acagcaacca   1380
gcttcctaa                                                           1389
```

<210> SEQ ID NO 54
<211> LENGTH: 260
<212> TYPE: DNA
<213> ORGANISM: Artificial Sequence
<220> FEATURE:
<223> OTHER INFORMATION: Pichia pastoris AOX1 transcription termination
      sequences

<400> SEQUENCE: 54

```
tcaagaggat gtcagaatgc catttgcctg agagatgcag gcttcatttt gatacttttt     60
tatttgtaac ctatatagta taggattttt tttgtcattt tgtttcttct cgtacgagct    120
tgctcctgat cagcctatct cgcagctgat gaatatcttg tggtaggggt ttgggaaaat    180
cattcgagtt tgatgttttt cttggtattt cccactcctc ttcagagtac agaagattaa    240
gtgagacgtt cgtttgtgca                                                260
```

<210> SEQ ID NO 55
<211> LENGTH: 32
<212> TYPE: PRT
<213> ORGANISM: Artificial Sequence
<220> FEATURE:
<223> OTHER INFORMATION: Insulin analogue

<400> SEQUENCE: 55

```
Asn Gly Thr Phe Val Asn Gln His Leu Cys Gly Ser His Leu Val Glu
1               5                   10                  15

Ala Leu Tyr Leu Val Cys Gly Glu Arg Gly Phe Phe Tyr Thr Asn Lys
            20                  25                  30
```

```
<210> SEQ ID NO 56
<211> LENGTH: 32
<212> TYPE: PRT
<213> ORGANISM: Artificial Sequence
<220> FEATURE:
<223> OTHER INFORMATION: N-glycosylated Insulin analogue
<220> FEATURE:
<221> NAME/KEY: MOD_RES
<222> LOCATION: (1)..(1)
<223> OTHER INFORMATION: Asn beta-1 linked to a paucimannose N-glycan
<220> FEATURE:
<221> NAME/KEY: MOD_RES
<222> LOCATION: (31)..(31)
<223> OTHER INFORMATION: Asn beta-1 linked to a paucimannose N-glycan

<400> SEQUENCE: 56

Asn Gly Thr Phe Val Asn Gln His Leu Cys Gly Ser His Leu Val Glu
1               5                   10                  15

Ala Leu Tyr Leu Val Cys Gly Glu Arg Gly Phe Phe Tyr Thr Asn Lys
            20                  25                  30
```

METHODS FOR INCREASING N-GLYCAN OCCUPANCY AND REDUCING PRODUCTION OF HYBRID N-GLYCANS IN PICHIA PASTORIS STRAINS LACKING ALG3 EXPRESSION

CROSS REFERENCE TO RELATED APPLICATIONS

This application is the National Stage of International Application No. PCT/US2012/61428 filed on Oct. 23, 2012, which claims the benefit under 35 U.S.C. 119(e) of U.S. Provisional Application No. 61/679,212, filed Aug. 3, 2012, and 61/552,720, filed Oct. 28, 2011.

REFERENCE TO SEQUENCE LISTING SUBMITTED ELECTRONICALLY

The sequence listing of the present application is submitted electronically via EFS-Web as an ASCII formatted sequence listing with a file name "23162_US_PCT_SEQLIST_25APRIL2014.txt", creation date of 31 Mar. 2014, and a size of 96 KB. This sequence listing submitted via EFS-Web is part of the specification and is herein incorporated by reference in its entirety.

BACKGROUND OF THE INVENTION (1) Field of the Invention

The present invention relates to methods for increasing the yield and N-glycosylation site occupancy of paucimannose or complex N-glycans of recombinant glycoproteins produced in a recombinant host cell lacking dolichyl-P-Man:Man$_5$GlcNAc$_2$-PP-dolichyl alpha-1,3 mannosyltransferase (Alg3p) activity. In particular, the present invention provides recombinant host cells that comprise a disruption of the expression of an OS-9 family gene in the host cell. In further embodiments, the recombinant host cells further overexpress at least one heterologous single-subunit oligosaccharyltransferase, which in particular embodiments is capable of functionally suppressing the lethal phenotype of a mutation of at least one essential protein of the yeast oligosaccharyltransferase (OTase) complex.

(2) Description of Related Art

The ability to produce recombinant human proteins has led to major advances in human health care and remains an active area of drug discovery. Many therapeutic proteins require the posttranslational addition of glycans to specific asparagine residues (N-glycosylation) of the protein to ensure proper structure-function activity and subsequent stability in human serum. For therapeutic use in humans, glycoproteins require human-like N-glycosylation. Mammalian cell lines (e.g., Chinese hamster ovary (CHO) cells, human retinal cells) that can mimic human-like glycoprotein processing have several drawbacks including low protein titers, long fermentation times, heterogeneous products, and continued viral containment. It is therefore desirable to use an expression system that not only produces high protein titers with short fermentation times, but can also produce human-like glycoproteins.

Fungal hosts such as *Saccharomyces cerevisiae* or methylotrophic yeast such as *Pichia pastoris* have distinct advantages for therapeutic protein expression, for example, they do not secrete high amounts of endogenous proteins, strong inducible promoters for producing heterologous proteins are available, they can be grown in defined chemical media and without the use of animal sera, and they can produce high titers of recombinant proteins (Cregg et al., FEMS Microbiol. Rev. 24: 45-66 (2000)). However, glycosylated proteins expressed in yeast generally contain additional mannose sugars resulting in "high mannose" glycans. Because these high mannose N-glycans can result in adverse responses when administered to certain individuals, yeast have not generally been used to produce therapeutic glycoproteins intended for human use. However, methods for genetically engineering yeast to produce human-like N-glycans are described in U.S. Pat. Nos. 7,029,872 and 7,449,308 along with methods described in U.S. Published Application Nos. 20040230042, 20040171826, 20050170452, 20050208617, 20050208617, and 20060286637. These methods have been used to construct recombinant yeast that can produce therapeutic glycoproteins that have predominantly human-like complex or hybrid N-glycans thereon instead of yeast type N-glycans.

It has been found that while the genetically engineered yeast can produce glycoproteins that have mammalian- or human-like N-glycans, the occupancy of N-glycan attachment sites on glycoproteins varies widely and is generally lower than the occupancy of these same sites in glycoproteins produced in mammalian cells. This has been observed for various recombinant antibodies produced in *Pichia pastoris*. However, variability of occupancy of N-glycan attachment sites has also been observed in mammalian cells as well. For example, Gawlitzek et al., Identification of cell culture conditions to control N-glycosylation site-occupancy of recombinant glycoproteins expressed in CHO cells, Biotechnol. Bioengin. 103: 1164-1175 (2009), disclosed that N-glycosylation site occupancy can vary for particular sites for particular glycoproteins produced in CHO cells and that modifications in growth conditions can be made to control occupancy at these sites. International Published Application No. WO 2006107990 discloses a method for improving protein N-glycosylation of eukaryotic cells using the dolichol-linked oligosaccharide synthesis pathway. Control of N-glycosylation site occupancy has been reviewed by Jones et al., Biochim. Biophys. Acta. 1726: 121-137 (2005).

However, there still remains a need for methods for increasing N-glycosylation site occupancy of therapeutic proteins produced in recombinant host cells having particular genetic backgrounds.

BRIEF SUMMARY OF THE INVENTION

The present invention provides methods for increasing the yield and N-glycosylation site occupancy of paucimannose or complex N-glycans of recombinant glycoproteins produced in a recombinant host cell lacking dolichyl-P-Man:Man$_5$GlcNAc$_2$-PP-dolichyl alpha-1,3 mannosyltransferase (Alg3p) activity. In particular, the present invention provides recombinant host cells that comprise a disruption of the expression of an OS-9 family gene in the host cell. These recombinant host cells may then be used for producing the recombinant glycoproteins having predominantly paucimannose or complex N-glycans. In further embodiments, the recombinant host cells further overexpress at least one heterologous single-subunit oligosaccharyltransferase, which in particular embodiments is capable of functionally suppressing the lethal phenotype of a mutation of at least one essential protein of the yeast oligosaccharyltransferase (OTase) complex. For example, the host cell may further express at least one single-subunit oligosaccharyltransferase is the *Leishmania* sp. STT3A protein (LmSTT3A), STT3B protein (LmSTT3B), STT3D protein LmSTT3D), or combinations thereof. Recombinant host cells that express at least one *Leishmania* sp. STT3, for example LmSTT3D produce glycoproteins that have a greater amount of N-glycosylation site occupancy than recombinant host cells that do not express the oligosaccharyltransferase. In recombinant host cells genetically engineered to produce predominantly paucimannose N-glycans or complex N-glycans, the mole percent of hybrid N-glycans in a composition of glycoproteins produced by the recombinant host cells will be reduced compared to the amount that would be present in host cells that express the OS-9 family gene.

Therefore, in one aspect of the above, provided is a method for producing a heterologous glycoprotein in a recombinant host cell, comprising providing a recombinant host cell that includes a disruption in the expression of the endogenous dolichyl-P-Man:Man$_5$GlcNAc$_2$-PP-dolichyl alpha-1,3 mannosyltransferase (ALG3) gene, a disruption in the expression of the endogenous osteosarcoma 9 (OS-9) family gene or homolog thereof, and a nucleic acid molecule encoding the heterologous glycoprotein, and wherein the endogenous host cell genes encoding the proteins comprising the endogenous OTase complex are expressed; and culturing the host cell under conditions for expressing the heterologous glycoprotein to produce the heterologous glycoprotein.

In a further aspect of the above, provided is a method for producing a heterologous glycoprotein with mammalian- or human-like complex or hybrid N-glycans in a host cell, comprising providing a recombinant host cell that includes a disruption in the expression of the endogenous dolichyl-P-Man:Man$_5$GlcNAc$_2$-PP-dolichyl alpha-1,3 mannosyltransferase (ALG3) gene, a disruption in the expression of the endogenous osteosarcoma 9 (OS-9) family gene or homolog thereof, at least one nucleic acid molecule encoding a heterologous single-subunit oligosaccharyltransferase, and a nucleic acid molecule encoding the heterologous glycoprotein; and culturing the host cell under conditions for expressing the heterologous glycoprotein to produce the heterologous glycoprotein.

In further aspects of the above method, the host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia minuta (Ogataea minuta, Pichia lindneri), Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum*, and *Neurospora crassa*. In other aspects, the host cell is an insect, plant or mammalian host cell.

In a further aspect of the above, provided is a method for producing a heterologous glycoprotein in a lower eukaryote host cell, comprising providing a recombinant lower eukaryote host cell that includes a disruption in the expression of the endogenous dolichyl-P-Man:Man$_5$GlcNAc$_2$-PP-dolichyl alpha-1,3 mannosyltransferase (ALG3) gene, a disruption in the expression of the endogenous osteosarcoma 9 (OS-9) family gene or homolog thereof, at least one nucleic acid molecule encoding a heterologous single-subunit oligosaccharyltransferase, and a nucleic acid molecule encoding the heterologous glycoprotein, and wherein the endogenous host cell genes encoding the proteins comprising the endogenous OTase complex are expressed; and culturing the host cell under conditions for expressing the heterologous glycoprotein to produce the heterologous glycoprotein.

In further aspects of the above method, the lower eukaryote host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia minuta (Ogataea minuta, Pichia lindneri), Pichia* sp., *Saccharomyces cerevisiae, Saccharomyces* sp., *Hansenula polymorphs, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum*, and *Neurospora crassa*.

In a further aspect of the above, provided is a method for producing a heterologous glycoprotein in a recombinant yeast host cell, comprising providing a recombinant yeast host cell that includes a disruption in the expression of the endogenous dolichyl-P-Man:Man$_5$GlcNAc$_2$-PP-dolichyl alpha-1,3 mannosyltransferase (ALG3) gene, a disruption in the expression of the endogenous YOS9 gene or homolog thereof, and a nucleic acid molecule encoding the heterologous glycoprotein; and culturing the host cell under conditions for expressing the heterologous glycoprotein to produce the heterologous glycoprotein.

In the above methods, the recombinant yeast host cell either produces the glycoprotein with a yeast N-glycan pattern or the yeast has been genetically engineered to produce glycoproteins with a yeast pattern but which lack hypermannosylation but which produce high mannose N-glycans. For example, the yeast can be genetically engineered to lack α1,6-mannosyltransferase activity, e.g., Och1p activity. In further aspects, the yeast is genetically engineered to produce glycoproteins that have mammalian or human-like N-glycans.

In further embodiments, the host cell further includes at least one nucleic acid molecule encoding a heterologous single-subunit oligosaccharyltransferase, and a nucleic acid molecule encoding the heterologous glycoprotein. In particular aspects, the single-subunit oligosaccharyltransferase is capable of functionally suppressing the lethal phenotype of a mutation of at least one essential protein of an OTase complex, for example, a yeast OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. In particular aspects, the single-subunit oligosaccharyltransferase is the *Leishmania* sp. STT3A protein, STT3B protein, STT3C protein, STT3D protein, or combinations thereof. In particular aspects, the single-subunit oligosaccharyltransferase is the *Leishmania major* STT3A protein, STT3B protein, STT3D protein, or combinations thereof. In particular aspects, the single-subunit oligosaccharyltransferase is the *Leishmania major* STT3D protein. In further aspects, the for example single-subunit oligosaccharyltransferase is the *Leishmania major* STT3D protein, which is capable of functionally suppressing (or rescuing or complementing) the lethal phenotype of at least one essential protein of the *Saccharomyces cerevisae* OTase complex. In further aspects, the endogenous host cell genes encoding the proteins comprising the endogenous oligosaccharyltransferase (OTase) complex are expressed.

In further aspects of the above method, the yeast host cell is selected from the group consisting of *Pichia pastoris,*

*Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia minuta (Ogataea minuta, Pichia lindneri), Pichia* sp., *Saccharomyces cerevisiae, Saccharomyces* sp., *Hansenula polymorphs, Kluyveromyces* sp., *Kluyveromyces lactis*, and *Candida albicans*.

In a further aspect of the above, provided is a method for producing a heterologous glycoprotein in a recombinant yeast host cell, comprising providing a recombinant host cell that includes a disruption in the expression of the endogenous dolichyl-P-Man:Man$_5$GlcNAc$_2$-PP-dolichyl alpha-1,3 mannosyltransferase (ALG3) gene, a disruption in the expression of the endogenous YOS9 gene or homolog thereof, and a nucleic acid molecule encoding the heterologous glycoprotein, and wherein the endogenous host cell genes encoding the proteins comprising the endogenous OTase complex are expressed; and culturing the host cell under conditions for expressing the heterologous glycoprotein to produce the heterologous glycoprotein.

In the above methods, the recombinant yeast host cell either produces the glycoprotein with a yeast N-glycan pattern or the yeast has been genetically engineered to produce glycoproteins with a yeast pattern that includes high mannose N-glycans but which lack hypermannosylation. For example, the yeast can be genetically engineered to lack α1,6-mannosyltransferase activity, e.g., Och1p activity. In further aspects, the yeast is genetically engineered to produce glycoproteins that have mammalian or human-like N-glycans.

In further embodiments, the host cell further includes at least one nucleic acid molecule encoding a heterologous single-subunit oligosaccharyltransferase, and a nucleic acid molecule encoding the heterologous glycoprotein. In particular aspects, the single-subunit oligosaccharyltransferase is capable of functionally suppressing the lethal phenotype of a mutation of at least one essential protein of an OTase complex, for example, a yeast OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. In particular aspects, the single-subunit oligosaccharyltransferase is the *Leishmania* sp. STT3A protein, STT3B protein, STT3C protein, STT3D protein, or combinations thereof. In particular aspects, the single-subunit oligosaccharyltransferase is the *Leishmania major* STT3A protein, STT3B protein, STT3D protein, or combinations thereof. In particular aspects, the single-subunit oligosaccharyltransferase is the *Leishmania major* STT3D protein. In further aspects, the for example single-subunit oligosaccharyltransferase is the *Leishmania major* STT3D protein, which is capable of functionally suppressing (or rescuing or complementing) the lethal phenotype of at least one essential protein of the *Saccharomyces cerevisae* OTase complex. In further aspects, the endogenous host cell genes encoding the proteins comprising the endogenous oligosaccharyltransferase (OTase) complex are expressed.

In further aspect of the above method, the yeast host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia minuta (Ogataea minuta, Pichia lindneri), Pichia* sp., *Saccharomyces cerevisiae, Saccharomyces* sp., *Hansenula polymorphs, Kluyveromyces* sp., *Kluyveromyces lactis*, and *Candida albicans*.

In a further aspect of the above, provided is a method for producing a heterologous glycoprotein in a filamentous fungus host cell, comprising providing a recombinant filamentous host cell that includes a disruption in the expression of the endogenous dolichyl-P-Man:Man$_5$GlcNAc$_2$-PP-dolichyl alpha-1,3 mannosyltransferase (ALG3) gene, a disruption in the expression of the endogenous YOS9 gene or homolog thereof, and a nucleic acid molecule encoding the heterologous glycoprotein, and wherein the endogenous host cell genes encoding the proteins comprising the endogenous OTase complex are expressed; and culturing the host cell under conditions for expressing the heterologous glycoprotein to produce the heterologous glycoprotein. The filamentous fungus host cell produces the glycoprotein in which the N-glycans have a filamentous fungus pattern or it is genetically engineered to produce glycoproteins that have mammalian or human-like N-glycans.

In further embodiments, the host cell further includes at least one nucleic acid molecule encoding a heterologous single-subunit oligosaccharyltransferase, and a nucleic acid molecule encoding the heterologous glycoprotein. In particular aspects, the single-subunit oligosaccharyltransferase is capable of functionally suppressing the lethal phenotype of a mutation of at least one essential protein of an OTase complex, for example, a yeast OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. In particular aspects, the single-subunit oligosaccharyltransferase is the *Leishmania* sp. STT3A protein, STT3B protein, STT3C protein, STT3D protein, or combinations thereof. In particular aspects, the single-subunit oligosaccharyltransferase is the *Leishmania major* STT3A protein, STT3B protein, STT3D protein, or combinations thereof. In particular aspects, the single-subunit oligosaccharyltransferase is the *Leishmania major* STT3D protein. In further aspects, the for example single-subunit oligosaccharyltransferase is the *Leishmania major* STT3D protein, which is capable of functionally suppressing (or rescuing or complementing) the lethal phenotype of at least one essential protein of the *Saccharomyces cerevisae* OTase complex. In further aspects, the endogenous host cell genes encoding the proteins comprising the endogenous oligosaccharyltransferase (OTase) complex are expressed.

In further aspects of the above, the filamentous fungus host cell is selected from the group consisting of *Aspergillus nidulans, Aspergillus niger, Aspergillus oryzae, Trichoderma reesei, Chrysosporium lucknowense, Fusarium* sp., *Fusarium gramineum, Fusarium venenatum*, and *Neurospora crassa*.

In further embodiments of any one of the above methods, the host cell is genetically engineered to produce glycoproteins comprising one or more N-glycans shown in FIG. 17. In further aspects of any one of the above methods, the host cell is genetically engineered to produce glycoproteins comprising one or more mammalian- or human-like complex N-glycans shown selected from G0, G1, G2, A1, or A2. In further embodiments, the host cell is genetically engineered to produce glycoproteins comprising one or more mammalian- or human-like complex N-glycans that have bisected N-glycans or have multiantennary N-glycans. In other embodiments, the host cell is genetically engineered to produce glycoproteins comprising one or more mammalian- or human-like hybrid N-glycans selected from GlcNAcMan$_3$GlcNAc$_2$; GalGlcNAcMan$_3$GlcNAc$_2$; and NANAGalGlcNAcMan$_3$GlcNAc$_2$. In further embodiments, the N-glycan structure consists of the paucimannose (G-2) structure $Man_3GlcNAc_2$ or the $Man_5GlcNAc_2$ (GS 1.3) structure.

In particular embodiments of any one of the above methods, the heterologous glycoprotein can be for example, erythropoietin (EPO); cytokines such as interferon α, interferon β, interferon γ, and interferon w; and granulocyte-colony stimulating factor (GCSF); granulocyte macrophage-colony stimulating factor (GM-CSF); coagulation factors such as factor VIII, factor IX, and human protein C; antithrombin III; thrombin; soluble IgE receptor α-chain; immunoglobulins such as IgG, IgG fragments, IgG fusions, and IgM; immunoadhesions and other Fc fusion proteins such as soluble TNF receptor-Fc fusion proteins; RAGE-Fc fusion proteins; interleukins; urokinase; chymase; urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4-Ig; transmembrane activator and calcium modulator and cyclophilin ligand; glucagon like protein 1; or IL-2 receptor agonist. In further aspects, the heterologous glycoprotein is a protein that is not normally N-glycosylated but which has been modified to comprise one or more N-glycosylation sites. For example, the glycoprotein may be insulin in which an N-glycosylation site has been introduced into the insulin amino acid sequence.

In further embodiments of any one of the above methods, the heterologous protein is an antibody, examples of which, include but are not limited to, an anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD11a antibody, anti-EGF receptor antibody, or anti-CD20 antibody.

In particular aspects of any one of the above methods, the host cell includes one or more nucleic acid molecules encoding one or more catalytic domains of a glycosidase, mannosidase, or glycosyltransferase activity derived from a member of the group consisting of UDP-GlcNAc transferase (GnT) I, GnT II, GnT III, GnT IV, GnT V, GnT VI, UDP-galactosyltransferase (GalT), fucosyltransferase, and sialyltransferase. In particular embodiments, the mannosidase is selected from the group consisting of C. elegans mannosidase IA, C. elegans mannosidase IB, D. melanogaster mannosidase IA, H. sapiens mannosidase IB, P. citrinum mannosidase I, mouse mannosidase IA, mouse mannosidase IB, A. nidulans mannosidase IA, A. nidulans mannosidase IB, A. nidulans mannosidase IC, mouse mannosidase II, C. elegans mannosidase II, H. sapiens mannosidase II, and mannosidase III.

In certain aspects of any one of the above methods, at least one catalytic domain is localized by forming a fusion protein comprising the catalytic domain and a cellular targeting signal peptide. The fusion protein can be encoded by at least one genetic construct formed by the in-frame ligation of a DNA fragment encoding a cellular targeting signal peptide with a DNA fragment encoding a catalytic domain having enzymatic activity. Examples of targeting signal peptides include, but are not limited to, membrane-bound proteins of the ER or Golgi, retrieval signals, Type II membrane proteins, Type I membrane proteins, membrane spanning nucleotide sugar transporters, mannosidases, sialyltransferases, glucosidases, mannosyltransferases, and phosphomannosyltransferases.

In particular aspects of any one of the above methods, the host cell further includes one or more nucleic acid molecules encode one or more enzymes selected from the group consisting of UDP-GlcNAc transporter, UDP-galactose transporter, GDP-fucose transporter, CMP-sialic acid transporter, and nucleotide diphosphatases.

In further aspects of any one of the above methods, the host cell includes one or more nucleic acid molecules encoding an α1,2-mannosidase activity, a UDP-GlcNAc transferase (GnT) I activity, a mannosidase II activity, and a GnT II activity.

In further still aspects of any one of the above methods, the host cell includes one or more nucleic acid molecules encoding an α1,2-mannosidase activity, a UDP-GlcNAc transferase (GnT) I activity, a mannosidase II activity, a GnT II activity, and a UDP-galactosyltransferase (GalT) activity.

In further still aspects of any one of the above methods, the host cell is deficient in the activity of one or more enzymes selected from the group consisting of mannosyltransferases and phosphomannosyltransferases. In further still aspects, the host cell does not express an enzyme selected from the group consisting of 1,6 mannosyltransferase, 1,3 mannosyltransferase, and 1,2 mannosyltransferase.

In a particular aspect of any one of the above methods, the host cell is an och1 mutant of *Pichia pastoris*.

In a particular aspect of the host cells, the host cell includes a one or more nucleic acid molecules encoding an α1,2-mannosidase activity and a heterologous glycoprotein and the host cell lacks or does not display with respect to an N-glycan on a glycoprotein detectable phosphomannosyltransferase activity, initiating α1,6-mannosyltransferase activity, and β1,2-mannosyltransferase activity. In a further aspect, the host cell includes one or more nucleic acid molecules encoding an α1,2-mannosidase activity and an endomannosidase activity.

Further provided is a host cell, comprising (a) a disruption in the expression of the endogenous dolichyl-P-Man:Man₅GlcNAc₂-PP-dolichyl alpha-1,3 mannosyltransferase (ALG3) gene, and (b) a disruption in the expression of the endogenous osteosarcoma 9 (OS-9) family gene or homolog thereof. In further embodiments, the host cell includes a second nucleic acid molecule encoding a heterologous glycoprotein.

Further provided is a lower eukaryotic host cell, comprising (a) a disruption in the expression of the endogenous dolichyl-P-Man:Man₅GlcNAc₂-PP-dolichyl alpha-1,3 mannosyltransferase (ALG3) gene, and (b) a disruption in the expression of the endogenous osteosarcoma 9 (OS-9) family gene or homolog thereof. In further embodiments, the host cell includes a second nucleic acid molecule encoding a heterologous glycoprotein.

Further provided is a yeast host cell, comprising (a) a disruption in the expression of the endogenous dolichyl-P-Man:Man₅GlcNAc₂-PP-dolichyl alpha-1,3 mannosyltransferase (ALG3) gene, and (b) a disruption in the expression of the endogenous osteosarcoma 9 (OS-9) family gene or homolog thereof. In further embodiments, the host cell includes a second nucleic acid molecule encoding a heterologous glycoprotein.

Further provided is a yeast host cell, comprising (a) a disruption in the expression of the endogenous dolichyl-P-Man:Man₅GlcNAc₂-PP-dolichyl alpha-1,3 mannosyltransferase (ALG3) gene, and (b) a disruption in the expression of the endogenous osteosarcoma 9 (OS-9) family gene or homolog thereof. In further embodiments, the host cell includes a second nucleic acid molecule encoding a heterologous glycoprotein.

Further provided is a filamentous fungus host cell comprising (a) a disruption in the expression of the endogenous dolichyl-P-Man:Man$_5$GlcNAc$_2$-PP-dolichyl alpha-1,3 mannosyltransferase (ALG3) gene, and (b) a disruption in the expression of the endogenous osteosarcoma 9 (OS-9) family gene or homolog thereof. In further embodiments, the host cell includes a second nucleic acid molecule encoding a heterologous glycoprotein.

Further provided is a filamentous fungus host cell, comprising (a) a disruption in the expression of the endogenous dolichyl-P-Man:Man$_5$GlcNAc$_2$-PP-dolichyl alpha-1,3 mannosyltransferase (ALG3) gene. In further embodiments, the host cell includes a second nucleic acid molecule encoding a heterologous glycoprotein.

In further embodiments, the host cell further includes at least one nucleic acid molecule encoding a heterologous single-subunit oligosaccharyltransferase, and a nucleic acid molecule encoding the heterologous glycoprotein. In particular aspects, the single-subunit oligosaccharyltransferase is capable of functionally suppressing the lethal phenotype of a mutation of at least one essential protein of an OTase complex, for example, a yeast OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. In particular aspects, the single-subunit oligosaccharyltransferase is the *Leishmania* sp. STT3A protein, STT3B protein, STT3C protein, STT3D protein, or combinations thereof. In particular aspects, the single-subunit oligosaccharyltransferase is the *Leishmania major* STT3A protein, STT3B protein, STT3D protein, or combinations thereof. In particular aspects, the single-subunit oligosaccharyltransferase is the *Leishmania major* STT3D protein. In further aspects, the for example single-subunit oligosaccharyltransferase is the *Leishmania major* STT3D protein, which is capable of functionally suppressing (or rescuing or complementing) the lethal phenotype of at least one essential protein of the *Saccharomyces cerevisae* OTase complex. In further aspects, the endogenous host cell genes encoding the proteins comprising the endogenous oligosaccharyltransferase (OTase) complex are expressed.

Further provided is a host cell, comprising (a) a disruption in the expression of the endogenous dolichyl-P-Man:Man$_5$GlcNAc$_2$-PP-dolichyl alpha-1,3 mannosyltransferase (ALG3) gene, and (b) a disruption in the expression of the endogenous osteosarcoma 9 (OS-9) family gene or homolog thereof; and (c) a first nucleic acid molecule encoding a heterologous single-subunit oligosaccharyltransferase; and the endogenous host cell genes encoding the proteins comprising the endogenous oligosaccharyltransferase (OTase) complex are expressed. In further embodiments, the host cell includes a second nucleic acid molecule encoding a heterologous glycoprotein.

Further provided is a lower eukaryotic host cell, comprising (a) a disruption in the expression of the endogenous dolichyl-P-Man:Man$_5$GlcNAc$_2$-PP-dolichyl alpha-1,3 mannosyltransferase (ALG3) gene, (b) a disruption in the expression of the endogenous osteosarcoma 9 (OS-9) family gene or homolog thereof; and (c) a first nucleic acid molecule encoding a heterologous single-subunit oligosaccharyltransferase; and the endogenous host cell genes encoding the proteins comprising the endogenous oligosaccharyl- transferase (OTase) complex are expressed. In further embodiments, the host cell includes a second nucleic acid molecule encoding a heterologous glycoprotein.

Further provided is a yeast host cell, comprising (a) a disruption in the expression of the endogenous dolichyl-P-Man:Man$_5$GlcNAc$_2$-PP-dolichyl alpha-1,3 mannosyltransferase (ALG3) gene, (b) a disruption in the expression of the endogenous YOS9 gene or homolog thereof; and (c) a first nucleic acid molecule encoding a heterologous single-subunit oligosaccharyltransferase; and the endogenous host cell genes encoding the proteins comprising the endogenous oligosaccharyltransferase (OTase) complex are expressed. In further embodiments, the host cell includes a second nucleic acid molecule encoding a heterologous glycoprotein.

Further provided is a yeast host cell, comprising (a) a disruption in the expression of the endogenous dolichyl-P-Man:Man$_5$GlcNAc$_2$-PP-dolichyl alpha-1,3 mannosyltransferase (ALG3) gene, (b) a disruption in the expression of the endogenous YOS9 gene or homolog thereof; and (c) a first nucleic acid molecule encoding a heterologous single-subunit oligosaccharyltransferase capable of functionally suppressing the lethal phenotype of a mutation of at least one essential protein of a yeast oligosaccharyltransferase (OTase) complex; and the endogenous host cell genes encoding the proteins comprising the endogenous oligosaccharyltransferase (OTase) complex are expressed. In further embodiments, the host cell includes a second nucleic acid molecule encoding a heterologous glycoprotein.

Further provided is a filamentous fungus host cell comprising (a) a disruption in the expression of the endogenous dolichyl-P-Man:Man$_5$GlcNAc$_2$-PP-dolichyl alpha-1,3 mannosyltransferase (ALG3) gene, (b) a disruption in the expression of the endogenous osteosarcoma 9 (OS-9) family gene or homolog thereof; and (c) a first nucleic acid molecule encoding a heterologous single-subunit oligosaccharyltransferase; and the endogenous host cell genes encoding the proteins comprising the endogenous oligosaccharyltransferase (OTase) complex are expressed. In further embodiments, the host cell includes a second nucleic acid molecule encoding a heterologous glycoprotein.

Further provided is a filamentous fungus host cell, comprising (a) a disruption in the expression of the endogenous dolichyl-P-Man:Man$_5$GlcNAc$_2$-PP-dolichyl alpha-1,3 mannosyltransferase (ALG3) gene, (b) a disruption in the expression of the endogenous osteosarcoma 9 (OS-9) family gene or homolog thereof; and (c) a first nucleic acid molecule encoding a heterologous single-subunit oligosaccharyltransferase capable of functionally suppressing the lethal phenotype of a mutation of at least one essential protein of a yeast or filamentous fungus oligosaccharyltransferase (OTase) complex; and the endogenous host cell genes encoding the proteins comprising the endogenous oligosaccharyltransferase (OTase) complex are expressed. In further embodiments, the host cell includes a second nucleic acid molecule encoding a heterologous glycoprotein.

In particular aspects, the single-subunit oligosaccharyltransferase is capable of functionally suppressing the lethal phenotype of a mutation of at least one essential protein of an OTase complex, for example, a yeast OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. In particular aspects, the single-subunit oligosaccharyltransferase is the *Leishmania* sp. STT3A protein, STT3B protein, STT3C protein, STT3D protein, or combinations thereof. In particular aspects, the single-subunit oligosaccharyltransferase is the *Leishmania major* STT3A protein, STT3B protein, STT3D protein, or combinations thereof. In particular aspects, the single-subunit oligosaccharyltransferase is the *Leishmania major* STT3D protein. In further aspects, the for example single-subunit oligosaccharyltransferase is the *Leishmania major* STT3D protein, which is capable of functionally suppressing (or rescuing or complementing) the lethal phenotype of at least one essential protein of the *Saccharomyces cerevisae* OTase complex. In further aspects, the endogenous host cell genes encoding the proteins comprising the endogenous oligosaccharyltransferase (OTase) complex are expressed.

In further embodiments, the host cell further expresses an endomannosidase activity (e.g., a full-length endomannosidase or a chimeric endomannosidase comprising an endomannosidase catalytic domain fused to a cellular targeting signal peptide not normally associated with the catalytic domain and selected to target the endomannosidase activity to the ER or Golgi apparatus of the host cell. See for example, U.S. Pat. No. 7,332,299) and/or glucosidase II activity (a full-length glucosidase II or a chimeric glucosidase II comprising a glucosidase II catalytic domain fused to a cellular targeting signal peptide not normally associated with the catalytic domain and selected to target the glucosidase II activity to the ER or Golgi apparatus of the host cell. See for example, U.S. Pat. No. 6,803,225). In particular aspects, the host cell further includes a deletion or disruption of the ALG6 (α1,3-glucosylatransferase) gene (alg6Δ), which has been shown to increase N-glycan occupancy of glycoproteins in alg3Δ host cells (See for example, De Pourcq et al., PloSOne 2012; 7(6):e39976. Epub 2012 Jun. 29, which discloses genetically engineering *Yarrowia lipolytica* to produce glycoproteins that have $Man_5GlcNAc_2$ (GS 1.3) or paucimannose N-glycan structures). The nucleic acid sequence encoding the *Pichia pastoris* ALG6 is disclosed in EMBL database, accession number CCCA38426. In further aspects, the host cell further includes a deletion or disruption of the OCH1 gene (och1Δ).

In further embodiments of any one of the above methods, the host cell is genetically engineered to produce glycoproteins comprising one or more N-glycans shown in FIG. 17. In further aspects of any one of the above methods, the host cell is genetically engineered to produce glycoproteins comprising one or more mammalian- or human-like complex N-glycans shown selected from G0, G1, G2, A1, or A2. In further embodiments, the host cell is genetically engineered to produce glycoproteins comprising one or more human-like complex N-glycans that bisected N-glycans or have multiantennary N-glycans. In other embodiments, the host cell is genetically engineered to produce glycoproteins comprising one or more mammalian- or human-like hybrid N-glycans selected from $GlcNAcMan_3GlcNAc_2$; $GalGlcNAcMan_3GlcNAc_2$; and $NANAGalGlcNAcMan_3GlcNAc_2$. In further embodiments, the N-glycan structure consists of the paucimannose (G-2) structure $Man_3GlcNAc_2$ or the $Man_5GlcNAc_2$ (GS 1.3) structure.

In particular embodiments of any one of the above host cells, the heterologous glycoprotein can be for example, selected from the group consisting of erythropoietin (EPO); cytokines such as interferon α, interferon β, interferon γ, and interferon ω; and granulocyte-colony stimulating factor (GCSF); granulocyte macrophage-colony stimulating factor (GM-CSF); coagulation factors such as factor VIII, factor IX, and human protein C; antithrombin III; thrombin; soluble IgE receptor α-chain; immunoglobulins such as IgG, IgG fragments, IgG fusions, and IgM; immunoadhesions and other Fc fusion proteins such as soluble TNF receptor-Fc fusion proteins; RAGE-Fc fusion proteins; interleukins; urokinase; chymase; urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4-Ig; transmembrane activator and calcium modulator and cyclophilin ligand; glucagon like protein 1; and IL-2 receptor agonist. In further aspects, the glycoprotein is a normally non-N-glycosylated protein that has been modified to comprise at least one N-linked glycosylation site. For example, insulin modified to comprise at least one N-linked glycosylation site.

In further embodiments of any one of the above host cells, the heterologous protein is an antibody, examples of which, include but are not limited to, an anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD11a antibody, anti-EGF receptor antibody, or anti-CD20 antibody.

In particular aspects of the above host cells, the host cell includes one or more nucleic acid molecules encoding one or more catalytic domains of a glycosidase, mannosidase, or glycosyltransferase activity derived from a member of the group consisting of UDP-GlcNAc transferase (GnT) I, GnT II, GnT III, GnT IV, GnT V, GnT VI, UDP-galactosyltransferase (GalT), fucosyltransferase, and sialyltransferase. In particular embodiments, the mannosidase is selected from the group consisting of *C. elegans* mannosidase IA, *C. elegans* mannosidase IB, *D. melanogaster* mannosidase IA, *H. sapiens* mannosidase IB, *P. citrinum* mannosidase I, mouse mannosidase IA, mouse mannosidase IB, *A. nidulans* mannosidase IA, *A. nidulans* mannosidase IB, *A. nidulans* mannosidase IC, mouse mannosidase II, *C. elegans* mannosidase II, *H. sapiens* mannosidase II, and mannosidase III.

In certain aspects of any one of the above host cells, at least one catalytic domain is localized by forming a fusion protein comprising the catalytic domain and a cellular targeting signal peptide. The fusion protein can be encoded by at least one genetic construct formed by the in-frame ligation of a DNA fragment encoding a cellular targeting signal peptide with a DNA fragment encoding a catalytic domain having enzymatic activity. Examples of targeting signal peptides include, but are not limited to, those to membrane-bound proteins of the ER or Golgi, retrieval signals such as HDEL or KDEL, Type II membrane proteins, Type I membrane proteins, membrane spanning nucleotide sugar transporters, mannosidases, sialyltransferases, glucosidases, mannosyltransferases, and phosphomannosyltransferases.

In particular aspects of any one of the above host cells, the host cell further includes one or more nucleic acid molecules encoding one or more enzymes selected from the group consisting of UDP-GlcNAc transporter, UDP-galactose transporter, GDP-fucose transporter, CMP-sialic acid transporter, and nucleotide diphosphatases.

In further aspects of any one of the above host cells, the host cell includes one or more nucleic acid molecules encoding an α1,2-mannosidase activity, a UDP-GlcNAc transferase (GnT) I activity, a mannosidase II activity, and a GnT II activity.

In further still aspects of any one of the above host cells, the host cell includes one or more nucleic acid molecules encoding an α1,2-mannosidase activity, a UDP-GlcNAc transferase (GnT) I activity, a mannosidase II activity, a GnT II activity, and a UDP-galactosyltransferase (GalT) activity.

In a particular aspect of the host cells, the host cell includes a one or more nucleic acid molecules encoding an α1,2-mannosidase activity and a heterologous glycoprotein and the host cell lacks or does not display with respect to an N-glycan on a glycoprotein detectable phosphomannosyltransferase activity, initiating α1,6-mannosyltransferase activity, and β1,2-mannosyltransferase activity. In a further aspect, the host cell includes one or more nucleic acid molecules encoding an α1,2-mannosidase activity and an endomannosidase activity.

In further aspects of any one of the above host cells, the host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorphs, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa*, plant cells, insect cells, and mammalian cells.

In further still aspects of any one of the above host cells, the host cell is deficient in or does not display detectable activity of one or more enzymes selected from the group consisting of mannosyltransferases and phosphomannosyltransferases. In further still aspects, the host cell does not express an enzyme selected from the group consisting of 1,6 mannosyltransferase, 1,3 mannosyltransferase, and 1,2 mannosyltransferase.

In a particular aspect of any one of the above host cells, the host cell is *Pichia pastoris*. In a further aspect, the host cell is an och1 mutant of *Pichia pastoris*.

The methods and host cells herein can be used to produce glycoprotein compositions in which at least 70%, 75%, 80%, 85%, 90%, 95%, 98%, or 99% of the N-glycosylation sites of the glycoproteins in the composition are occupied.

Further, the methods and host cells herein can be used to produce glycoprotein compositions in which at least 70%, 75%, 80%, 85%, 90%, 95%, 98%, or 99% of the N-glycosylation sites of the glycoproteins in the composition are occupied and which in further aspects have mammalian- or human-like N-glycans that lack fucose.

Further, the methods and yeast or filamentous fungus host cells are genetically engineered to produce mammalian-like or human-like N-glycans can be used to produce glycoprotein compositions in which at least 70%, 75%, 80%, 85%, 90%, 95%, 98%, or 99% of the N-glycosylation sites of the glycoproteins in the composition are occupied and which in further aspects have mammalian- or human-like N-glycans that lack fucose.

In some aspects, the yeast or filamentous host cells genetically engineered to produce fucosylated mammalian- or human-like N-glycans can be used to produce glycoprotein compositions in which at least 70%, 75%, 80%, 85%, 90%, 95%, 98%, or 99% of the N-glycosylation sites of the glycoproteins in the composition are occupied and which in further aspects have mammalian- or human-like N-glycans that have fucose.

The methods and host cells herein can be used to produce antibody compositions in which at least 70%, 75%, 80%, 85%, 90%, 95%, 98%, or 99% antibody molecules in the compositions have both N-glycosylation sites occupied.

Further, the methods and host cells herein can be used to produce antibody compositions in which at least 70%, 75%, 80%, 85%, 90%, 95%, 98%, or 99% antibody molecules in the compositions have both N-glycosylation sites occupied and the N-glycans lack fucose.

Further, the methods and yeast or filamentous fungus host cells herein can be used to produce antibody compositions in which at least 70%, 75%, 80%, 85%, 90%, 95%, 98%, or 99% antibody molecules in the compositions have both N-glycosylation sites occupied and the N-glycans lack fucose.

Further, the methods and yeast or filamentous fungus host cells genetically engineered to produce mammalian-like or human-like N-glycans can be used to produce antibody compositions in which at least 70%, 75%, 80%, 85%, 90%, 95%, 98%, or 99% antibody molecules in the compositions have both N-glycosylation sites occupied and the antibodies have mammalian- or human-like N-glycans that lack fucose. In some aspects, the yeast or filamentous host cells genetically engineered to produce fucosylated mammalian- or human-like N-glycans can be used to produce antibody compositions in which at least 70%, 75%, 80%, 85%, 90%, 95%, 98%, or 99% antibody molecules in the compositions have both N-glycosylation sites occupied and the antibodies have mammalian- or human-like N-glycans with fucose.

In particular embodiments, the antibodies comprise an antibody selected from the group consisting of anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD11a antibody, anti-EGF receptor antibody, and anti-CD20 antibody.

Further provided are compositions comprising one ore more glycoproteins produced by the host cells and methods described herein.

In particular embodiments, the glycoprotein compositions provided herein comprise glycoproteins having fucosylated and non-fucosylated hybrid and complex N-glycans, including bisected and multiantennary species, including but not limited to N-glycans such as $GlcNAc_{(1-4)}Man_3GlcNAc_2$; $Gal_{(1-4)}GlcNAc_{(1-4)}Man_3GlcNAc_2$; $NANA_{(1-4)}Gal_{(1-4)}GlcNAc_{(1-4)}Man_3GlcNAc_2$.

In particular embodiments, the glycoprotein compositions provided herein comprise glycoproteins having at least one hybrid N-glycan selected from the group consisting of $GlcNAcMan_3GlcNAc_2$; $GalGlcNAcMan_3GlcNAc_2$; $NANAGalGlcNAcMan_3GlcNAc_2$; $GlcNAcMan_5GlcNAc_2$; $GalGlcNAcMan_5GlcNAc_2$; and $NANAGalGlcNAcMan_5GlcNAc_2$. In particular aspects, the hybrid N-glycan is the predominant N-glycan species in the composition. In further aspects, the hybrid N-glycan is a particular N-glycan species that comprises about 30%, 40%, 50%, 60%, 70%, 80%, 90%, 95%, 97%, 98%, 99%, or 100% of the hybrid N-glycans in the composition.

In particular embodiments, the glycoprotein compositions provided herein comprise glycoproteins having at least one complex N-glycan selected from the group consisting of $GlcNAc_2Man_3GlcNAc_2$; $GalGlcNAc_2Man_3GlcNAc_2$; $Gal_2GlcNAc_2Man_3GlcNAc_2$; $NANAGal_2GlcNAc_2Man_3GlcNAc_2$; and $NANA_2Gal_2GlcNAc_2Man_3GlcNAc_2$. In particular aspects, the complex N-glycan is the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition.

In particular embodiments, the N-glycan is fusosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of GlcNAcMan$_5$GlcNAc$_2$(Fuc), GlcNAcMan$_3$GlcNAc$_2$(Fuc), GlcNAc$_2$Man$_3$GlcNAc$_2$(Fuc), GalGlcNAc$_2$Man$_3$GlcNAc$_2$(Fuc), Gal$_2$GlcNAc$_2$Man$_3$GlcNAc$_2$(Fuc), NANAGal$_2$GlcNAc$_2$Man$_3$GlcNAc$_2$(Fuc), and NANA$_2$Gal$_2$GlcNAc$_2$Man$_3$GlcNAc$_2$(Fuc); in an α1,3-linkage or α1,4-linkage fucose to produce a glycoform selected from the group consisting of GlcNAc(Fuc)Man$_5$GlcNAc$_2$, GlcNAc(Fuc)Man$_3$GlcNAc$_2$, GlcNAc$_2$(Fuc$_{1-2}$)Man$_3$GlcNAc$_2$, GalGlcNAc$_2$(Fuc$_{1-2}$)Man$_3$GlcNAc$_2$, Gal$_2$GlcNAc$_2$(Fuc1-2)Man3GlcNAc2, NANAGal2GlcNAc2(Fuc$_{1-2}$)Man$_3$GlcNAc$_2$, and NANA$_2$Gal$_2$GlcNAc$_2$(Fuc$_{1-2}$)Man$_3$GlcNAc$_2$; or in an α1,2-linkage fucose to produce a glycoform selected from the group consisting of Gal(Fuc)GlcNAc$_2$Man$_3$GlcNAc$_2$, Gal$_2$(Fuc$_{1-2}$)GlcNAc$_2$Man$_3$GlcNAc$_2$, NANAGal$_2$(Fuc$_{1-2}$)GlcNAc$_2$Man$_3$GlcNAc$_2$, and NANA$_2$Gal$_2$(Fuc$_{1-2}$)GlcNAc$_2$Man$_3$GlcNAc$_2$.

In further aspects of the above, the complex N-glycans further include fucosylated and non-fucosylated bisected and multiantennary species.

In further aspects, the glycoproteins comprise high mannose N-glycans, including but not limited to, Man$_5$GlcNAc$_2$, or N-glycans that consist of the Man$_3$GlcNAc$_2$ N-glycan structure.

The present invention provides for the use of a host cell comprising (a) a disruption in the expression of the endogenous dolichyl-P-Man:Man$_5$GlcNAc$_2$-PP-dolichyl alpha-1,3 mannosyltransferase (ALG3) gene; and (b) a disruption in the expression of the endogenous osteosarcoma 9 (OS-9) family gene or homolog for the manufacture of a medicament for treating a disease.

The present invention provides for the use of any one of the foregoing host cells for the manufacture of a medicament for treating a disease.

DEFINITIONS

As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetylneuraminic acid (NANA)). The processing of the sugar groups occurs co-translationally in the lumen of the ER and continues post-translationally in the Golgi apparatus for N-linked glycoproteins.

N-glycans have a common pentasaccharide core of Man$_3$GlcNAc$_2$ ("Man" refers to mannose; "Glc" refers to glucose; and "NAc" refers to N-acetyl; GlcNAc refers to N-acetylglucosamine). Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the Man$_3$GlcNAc$_2$ ("Man3") core structure which is also referred to as the "triammnose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

With respect to complex N-glycans, the terms "G-2", "G-1", "G0", "G1", "G2", "A1", and "A2" mean the following. "G-2" refers to an N-glycan structure that can be characterized as Man$_3$GlcNAc$_2$ or paucimannose; the term "G-1" refers to an N-glycan structure that can be characterized as GlcNAcMan$_3$GlcNAc$_2$; the term "G0" refers to an N-glycan structure that can be characterized as GlcNAc$_2$Man$_3$GlcNAc$_2$; the term "G1" refers to an N-glycan structure that can be characterized as GalGlcNAc$_2$Man$_3$GlcNAc$_2$; the term "G2" refers to an N-glycan structure that can be characterized as Gal$_2$GlcNAc$_2$Man$_3$GlcNAc$_2$; the term "A1" refers to an N-glycan structure that can be characterized as NANAGal$_2$GlcNAc$_2$Man$_3$GlcNAc$_2$; and, the term "A2" refers to an N-glycan structure that can be characterized as NANA$_2$Gal$_2$GlcNAc$_2$Man$_3$GlcNAc$_2$. Unless otherwise indicated, the terms G-2", "G-1", "G0", "G1", "G2", "A1", and "A2" refer to N-glycan species that lack fucose attached to the GlcNAc residue at the reducing end of the N-glycan. When the term includes an "F", the "F" indicates that the N-glcyan species contains a fucose residue on the GlcNAc residue at the reducing end of the N-glycan. For example, G0F, G1F, G2F, A1F, and A2F all indicate that the N-glycan further includes a fucose residue attached to the GlcNAc residue at the reducing end of the N-glycan. Lower eukaryotes such as yeast and filamentous fungi do not normally produce N-glycans that produce fucose.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas GlcNAc$_{(2-4)}$ Man$_3$GlcNAc$_2$, Gal$_{(1-4)}$GlcNAc$_{(2-4)}$Man$_3$GlcNAc$_2$, or NANA$_{(1-4)}$Gal$_{(1-4)}$GlcNAc$_{(2-4)}$Man$_3$GlcNAc$_2$. The term "1-4" refers to 1, 2, 3, or 4 residues.

With respect to bisected N-glycans, the term "bisected N-glycan" refers to N-glycans in which a GlcNAc residue is linked to the mannose residue at the reducing end of the N-glycan. A bisected N-glycan can be characterized by the formula GlcNAc$_3$Man$_3$GlcNAc$_2$ wherein each mannose residue is linked at its non-reducing end to a GlcNAc residue. In contrast, when a multiantennary N-glycan is characterized as GlcNAc$_3$Man$_3$GlcNAc$_2$, the formula indicates that two GlcNAc residues are linked to the mannose residue at the non-reducing end of one of the two arms of the N-glycans and one GlcNAc residue is linked to the mannose residue at the non-reducing end of the other arm of the N-glycan.

Abbreviations used herein are of common usage in the art, see, e.g., abbreviations of sugars, above. Other common abbreviations include "PNGase", or "glycanase" or "glucosidase" which all refer to peptide N-glycosidase F (EC 3.2.2.18).

As used herein, the term "glycoprotein" refers to any protein having one or more N-glycans attached thereto. Thus, the term refers both to proteins that are generally recognized in the art as a glycoprotein and to proteins which have been genetically engineered to contain one or more N-linked glycosylation sites, for example insulin modified to comprise one or more N-linked glycosylation sites.

As used herein, a "humanized glycoprotein" or a "human-like glycoprotein" refers alternatively to a protein having attached thereto N-glycans having fewer than four mannose residues, and synthetic glycoprotein intermediates (which are also useful and can be manipulated further in vitro or in vivo) having at least five mannose residues. Preferably, glycoproteins produced according to the invention contain at least 30 mole %, preferably at least 40 mole % and more preferably 50, 60, 70, 80, 90, or even 100 mole % of the Man$_5$GlcNAc$_2$ intermediate, at least transiently. This may be achieved, e.g., by engineering a host cell of the invention to express a "better", i.e., a more efficient glycosylation enzyme. For example, a mannosidase is selected such that it will have optimal activity under the conditions present at the site in the host cell where proteins are glycosylated and is introduced into the host cell preferably by targeting the enzyme to a host cell organelle where activity is desired.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism. Preferred host cells are yeasts and fungi.

When referring to "mole percent" of a glycan present in a preparation of a glycoprotein, the term means the molar percent of a particular glycan present in the pool of N-linked oligosaccharides released when the protein preparation is treated with PNGase and then quantified by a method that is not affected by glycoform composition, (for instance, labeling a PNGase released glycan pool with a fluorescent tag such as 2-aminobenzamide and then separating by high performance liquid chromatography or capillary electrophoresis and then quantifying glycans by fluorescence intensity). For example, 50 mole percent GlcNAc$_2$Man$_3$GlcNAc$_2$Gal$_2$NANA$_2$ means that 50 percent of the released glycans are GlcNAc$_2$Man$_3$GlcNAc$_2$Gal$_2$NANA$_2$ and the remaining 50 percent are comprised of other N-linked oligosaccharides. In embodiments, the mole percent of a particular glycan in a preparation of glycoprotein will be between 20% and 100%, preferably above 25%, 30%, 35%, 40% or 45%, more preferably above 50%, 55%, 60%, 65% or 70% and most preferably above 75%, 80% 85%, 90% or 95%.

The term "operably linked" expression control sequences refers to a linkage in which the expression control sequence is contiguous with the gene of interest to control the gene of interest, as well as expression control sequences that act in trans or at a distance to control the gene of interest.

The term "expression control sequence" or "regulatory sequences" are used interchangeably and as used herein refer to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "transfect", transfection", "transfecting" and the like refer to the introduction of a heterologous nucleic acid into eukaryote cells, both higher and lower eukaryote cells. Historically, the term "transformation" has been used to describe the introduction of a nucleic acid into a yeast or fungal cell; however, herein the term "transfection" is used to refer to the introduction of a nucleic acid into any eukaryote cell, including yeast and fungal cells.

The term "eukaryotic" refers to a nucleated cell or organism, and includes insect cells, plant cells, mammalian cells, animal cells and lower eukaryotic cells.

The term "lower eukaryotic cells" includes yeast and filamentous fungi. Yeast and filamentous fungi include, but are not limited to *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorphs, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* p., *Fusarium gramineum, Fusarium venenatum, Physcomitrella patens* and *Neurospora crassa. Pichia* sp., any *Saccharomyces* sp., *Hansenula polymorphs*, any *Kluyveromyces* sp., *Candida albicans*, any

*Aspergillus* sp., *Trichoderma reesei*, *Chrysosporium lucknowense*, any *Fusarium* sp. and *Neurospora crassa*.

As used herein, the terms "antibody," "immunoglobulin," "immunoglobulins" and "immunoglobulin molecule" are used interchangeably. Each immunoglobulin molecule has a unique structure that allows it to bind its specific antigen, but all immunoglobulins have the same overall structure as described herein. The basic immunoglobulin structural unit is known to comprise a tetramer of subunits. Each tetramer has two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Light chains are classified as either kappa or lambda. Heavy chains are classified as gamma, mu, alpha, delta, or epsilon, and define the antibody's isotype as IgG, IgM, IgA, IgD, and IgE, respectively.

The light and heavy chains are subdivided into variable regions and constant regions (See generally, Fundamental Immunology (Paul, W., ed., 2nd ed. Raven Press, N.Y., 1989), Ch. 7. The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. The terms include naturally occurring forms, as well as fragments and derivatives. Included within the scope of the term are classes of immunoglobulins (Igs), namely, IgG, IgA, IgE, IgM, and IgD. Also included within the scope of the terms are the subtypes of IgGs, namely, IgG1, IgG2, IgG3, and IgG4. The term is used in the broadest sense and includes single monoclonal antibodies (including agonist and antagonist antibodies) as well as antibody compositions which will bind to multiple epitopes or antigens. The terms specifically cover monoclonal antibodies (including full length monoclonal antibodies), polyclonal antibodies, multispecific antibodies (for example, bispecific antibodies), and antibody fragments so long as they contain or are modified to contain at least the portion of the CH2 domain of the heavy chain immunoglobulin constant region which comprises an N-linked glycosylation site of the CH2 domain, or a variant thereof. Included within the terms are molecules comprising only the Fc region, such as immunoadhesions (U.S. Published Patent Application No. 2004/0136986; the disclosure of which is incorporated herein by reference), Fc fusions, and antibody-like molecules.

The term "Fc fragment" refers to the 'fragment crystallized' C-terminal region of the antibody containing the CH2 and CH3 domains. The term "Fab fragment" refers to the 'fragment antigen binding' region of the antibody containing the VH, CH1, VL and CL domains.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, monoclonal antibodies are advantageous in that they can be produced, for example, by hybridoma culture, uncontaminated by other immunoglobulins. The term "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975) Nature, 256:495, or may be made by recombinant DNA methods (See, for example, U.S. Pat. No. 4,816,567; the disclosure of which is incorporated herein by reference).

The term "fragments" within the scope of the terms "antibody" or "immunoglobulin" include those produced by digestion with various proteases, those produced by chemical cleavage and/or chemical dissociation and those produced recombinantly, so long as the fragment remains capable of specific binding to a target molecule. Among such fragments are Fc, Fab, Fab', Fv, F(ab')2, and single chain Fv (scFv) fragments. Hereinafter, the term "immunoglobulin" also includes the term "fragments" as well.

Immunoglobulins further include immunoglobulins or fragments that have been modified in sequence but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (See, for example, Intracellular Antibodies: Research and Disease Applications, (Marasco, ed., Springer-Verlag New York, Inc., 1998).

The term "catalytic antibody" refers to immunoglobulin molecules that are capable of catalyzing a biochemical reaction. Catalytic antibodies are well known in the art and have been described in U.S. Pat. Nos. 7,205,136; 4,888,281; 5,037,750 to Schochetman et al., U.S. Pat. Nos. 5,733,757; 5,985,626; and 6,368,839 to Barbas, III et al. (the disclosures of which are all incorporated herein by reference).

The interaction of antibodies and antibody-antigen complexes with cells of the immune system and the variety of responses, including antibody-dependent cell-mediated cytotoxicity (ADCC) and complement-dependent cytotoxicity (CDC), clearance of immunocomplexes (phagocytosis), antibody production by B cells and IgG serum half-life are defined respectively in the following: Daeron et al., Annu Rev. Immunol. 15: 203-234 (1997); Ward and Ghetie, Therapeutic Immunol. 2:77-94 (1995); Cox and Greenberg, Semin. Immunol. 13: 339-345 (2001); Heyman, Immunol. Lett. 88:157-161 (2003); and Ravetch, Curr. Opin. Immunol. 9: 121-125 (1997).

As used herein, the term "consisting essentially of" will be understood to imply the inclusion of a stated integer or group of integers; while excluding modifications or other integers which would materially affect or alter the stated integer. With respect to species of N-glycans, the term "consisting essentially of" a stated N-glycan will be understood to include the N-glycan whether or not that N-glycan is fucosylated at the N-acetylglucosamine (GlcNAc) which is directly linked to the asparagine residue of the glycoprotein.

As used herein, the term "predominantly" or variations such as "the predominant" or "which is predominant" will be understood to mean the glycan species that has the highest mole percent (%) of total neutral N-glycans after the glycoprotein has been treated with PNGase and released glycans analyzed by mass spectroscopy, for example, MALDI-TOF MS or HPLC. In other words, the phrase "predominantly" is defined as an individual entity, such as a specific glycoform, is present in greater mole percent than any other individual entity. For example, if a composition consists of species A at 40 mole percent, species B at 35 mole percent and species C at 25 mole percent, the composition comprises predominantly species A, and species B would be the next most predominant species. Some host cells may produce compositions comprising neutral N-glycans and charged N-glycans such as mannosylphosphate. Therefore, a composition of glycoproteins can include a plurality of charged and uncharged or neutral N-glycans. In the present invention, it is within the context of the total plurality of neutral N-glycans in the composition in which the predominant N-glycan determined. Thus, as used herein, "predominant N-glycan" means that of the total plurality of neutral N-glycans in the composition, the predominant N-glycan is of a particular structure.

As used herein, the term "essentially free of" a particular sugar residue, such as fucose, or galactose and the like, is used to indicate that the glycoprotein composition is substantially devoid of N-glycans which contain such residues. Expressed in terms of purity, essentially free means that the amount of N-glycan structures containing such sugar residues does not exceed 10%, and preferably is below 5%, more preferably below 1%, most preferably below 0.5%, wherein the percentages are by weight or by mole percent. Thus, substantially all of the N-glycan structures in a glycoprotein composition according to the present invention are free of, for example, fucose, or galactose, or both.

As used herein, a glycoprotein composition "lacks" or "is lacking" a particular sugar residue, such as fucose or galactose, when no detectable amount of such sugar residue is present on the N-glycan structures at any time. For example, in preferred embodiments of the present invention, the glycoprotein compositions are produced by lower eukaryotic organisms, as defined above, including yeast (for example, *Pichia* sp.; *Saccharomyces* sp.; *Kluyveromyces* sp.; *Aspergillus* sp.), and will "lack fucose," because the cells of these organisms do not have the enzymes needed to produce fucosylated N-glycan structures. Thus, the term "essentially free of fucose" encompasses the term "lacking fucose." However, a composition may be "essentially free of fucose" even if the composition at one time contained fucosylated N-glycan structures or contains limited, but detectable amounts of fucosylated N-glycan structures as described above.

DETAILED DESCRIPTION OF THE INVENTION

Figure 1C:
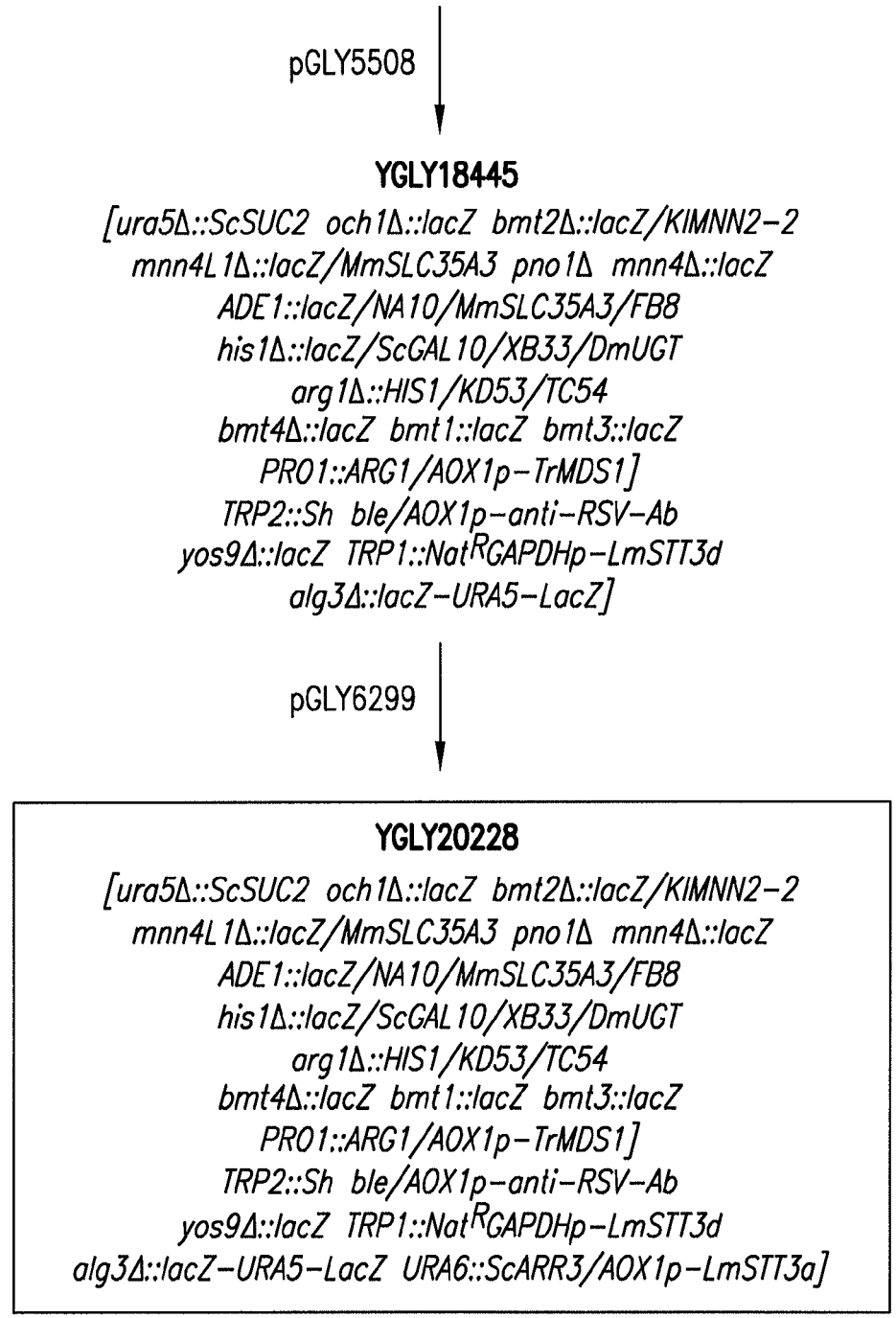
FIGS. 1 A-E shows the genealogy of ALG3-engineered *P. pastoris* strains (GS 5.0) beginning from wild-type strain NRRL-Y11430. These strains are capable of producing glycoproteins having galactose-terminated complex N-glcyans.
Figure 1D:
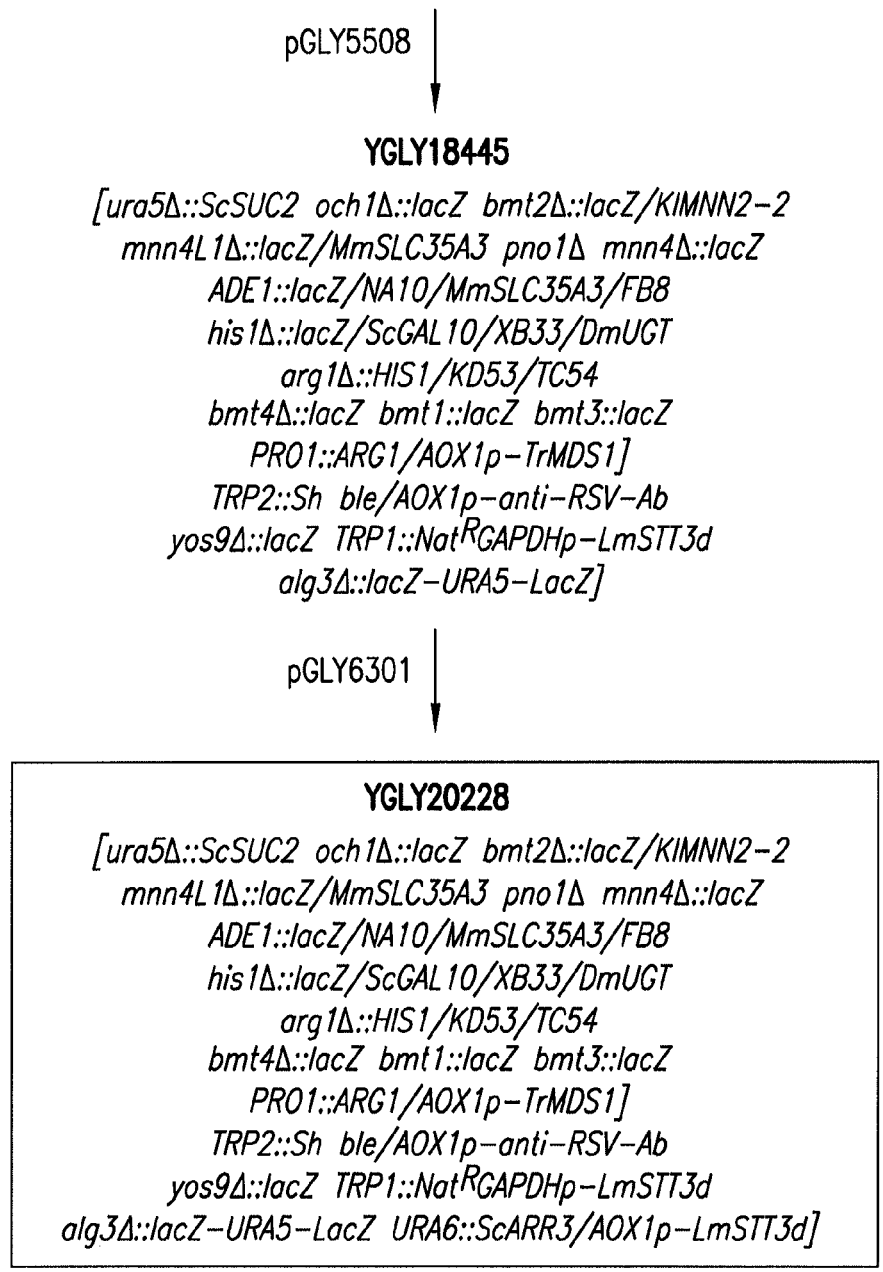

The present invention provides host cells and methods for increasing yield and N-glycosylation site occupancy as well as N-glycan quality, either complex or paucimannose ($Man_3GlcNAc_2$) in recombinant host cells that lack expression of the ALG3 gene encoding dolichyl-P-Man: $Man_5GlcNAc_2$-PP-dolichyl alpha-1,3 mannosyltransferase activity (Alg3p). The increase in N-glycosylation site occupancy and N-glycan quality in recombinant host cells that lack ALG3 expression is achieved by disrupting expression of an osteosarcoma 9 (OS-9) family gene or homolog thereof in the recombinant host cell. Homologs to the OS-9 gene include open reading frames encoding proteins of similar structure found in the genome of organisms including without limitation *Saccharomyces cerevisiae, Pichia pastoris, Schizosaccharomyces pombe, Caenorhabditis elegans*, and *Homo sapiens*.

YOS9 is a yeast homolog of the human gene OS-9, which is overexpressed in osteosarcomas (Friedman et al., J. Biol. Chem. 277: 35274-35281 (2002); GenBank Accession No. CAY70383). The YOS9 gene encodes Yos9p, a lectin protein, which has been shown in *Saccharomyces cerevisiae* to be involved in the ER-associated degradation (ERAD) pathway, a quality control pathway in the ER that detects and targets misfolded glycoproteins for degradation in the cytosol (See Kim et al., Mol. Cell. 16: 741-751 (2005). Quan et al., Mol. Cell. 32: 870-877 (2008) has shown that in the ERAD pathway, misfolded glycoproteins are modified to contain N-glycans that have a terminal α1,6-linked mannose. Yos9p is a sensor protein that recognizes N-glycans containing these terminal α1,6-linked mannose residues and targets glycoproteins that have them for degradation. In alg3Δ strains, the $Man_5GlcNAc_2$ oligosaccharide that is transferred to the N-linked glycosylation site also has a terminal α1,6-linked mannose residues, which may render the glycoprotein a substrate for the ERAD pathway (Clerc et al., J. Cell Biol. 184: 159-172 (2009)). The *Saccharomyces cerevisiae* Yos9p protein has the amino acid sequence shown in SEQ ID NO:43, which is encoded by the YOS9 nucleotide sequence shown in SEQ ID NO:44. The *Pichia pastoris* Yos9p protein has the amino acid sequence shown in SEQ ID NO:45, which is encoded by the YOS9 nucleotide sequence shown in SEQ ID NO:46. The *Aspergillus fumigates* Yos9p protein has the amino acid sequence shown in SEQ ID NO:47, which is encoded by the YOS9 nucleotide sequence shown in SEQ ID NO:48. The *Schizosaccharomyces pombe* Yos9p protein has the amino acid sequence shown in SEQ ID NO:49, which is encoded by the YOS9 nucleotide sequence shown in SEQ ID NO:50.

In the present invention, disruption of YOS9 gene expression in recombinant host cells that lack ALG3 gene expression increases the yield of recombinant glycoproteins and thus improves the yield of paucimannose N-glycans in host cells further modified to include an α1,2-mannosidase activity targeted to the ER or Golgi apparatus or the yield of complex N-glycans when these host cells are further modified to include one more glycosylation enzymes to enable the host cells to produce glycoproteins that have human-like N-glycosylation patterns or that have predominantly particular N-glycan structures.

Figure 17:
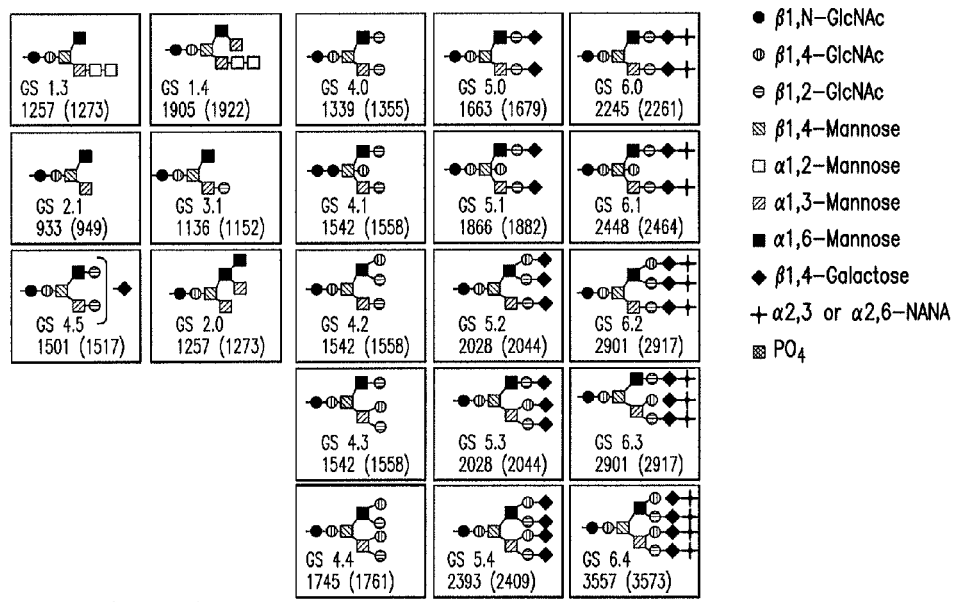
FIG. 17 shows examples of N-glycan structures that can be attached to the asparagine residue in the motif Asn-Xaa-Ser/Thr wherein Xaa is any amino acid other than proline or attached to any amino acid in vitro. Recombinant host cells can be genetically modified to produce glycoproteins that have predominantly particular N-glycan species.

The construction of host cells that do not display Alg3p protein activity or have a disruption of expression from the ALG3 gene has been described in Published U.S. Application No. 20050170452 or US20100227363, which are incorporated herein by reference. Alg3p is $Man_5GlcNAc_2$-PP-dolichyl alpha-1,3 mannosyltransferase that transferase a mannose residue to the mannose residue of the alpha-1,6 arm of lipid-linked $Man_5GlcNAc_2$ (FIG. 17, GS 1.3) in an alpha-1,3 linkage to produce lipid-linked $Man_6GlcNAc_2$ (FIG. 17, GS 1.4), a precursor for the synthesis of lipid-linked $Glc_3Man_9GlcNAc_2$, which is then transferred by an oligosaccharyltransferase to an asparagine residue of a glycoprotein followed by removal of the glucose (Glc) residues. In host cells that lack Alg3p protein activity, the lipid-linked $Man_5GlcNAc_2$ oligosaccharide may be transferred by an oligosaccharyltransferase to an asparagine residue of a glycoprotein. In such host cells that further include an α1,2- mannosidase, the $Man_5GlcNAc_2$ oligosaccharide attached to the glycoprotein is trimmed to a tri-mannose (paucimannose) $Man_3GlcNAc_2$ structure (FIG. 17, GS 2.1). The $Man_5GlcNAc_2$ (GS 1.3) structure is distinguishable from the $Man_5GlcNAc_2$ (GS 2.0) shown in FIG. 17, and which is produced in host cells that express the $Man_5GlcNAc_2$-PP-dolichyl alpha-1,3 mannosyltransferase (Alg3p).

The N-glycosylation site occupancy of glycoproteins comprising paucimannose N-glycans or complex N-glycans produced in the alg3Δ yos9Δ host cells may be substantially increased by expressing in the host cells one or more heterologous single-subunit oligosaccharyltransferases which in particular embodiments, at least one of which is capable of functionally suppressing the lethal phenotype of a mutation of at least one essential protein of the yeast oligosaccharyltransferase (OTase) complex. Published International Application No. WO2011106389, which is incorporated herein by reference, discloses methods for increasing the N-glycosylation site occupancy of a glycoprotein produced in recombinant lower eukaryote host cells genetically engineered to express the glycoprotein. In particular, the method provides recombinant host cells that overexpress a heterologous single-subunit oligosaccharyltransferase, which in particular embodiments is capable of functionally suppressing the lethal phenotype of a mutation of at least one essential protein of the yeast oligosaccharyltransferase (OTase) complex.

Nasab et al., Molecular Biology of the Cell 19: 3758-3768 (2008) expressed each of the four *Leishmania major* STT3 proteins individually in *Saccharomyces cerevisiae* and found that three of them, LmSTT3A protein, LmSTT3B protein, and LmSTT3D protein, were able to complement a deletion of the yeast STT3 locus. In addition, LmSTT3D expression suppressed the lethal phenotype of single and double deletions in genes encoding various essential OTase subunits. The LmSTT3 proteins did not incorporate into the yeast OTase complex but instead formed a homodimeric enzyme, capable of replacing the endogenous, multimeric enzyme of the yeast cell. The results indicate that while these single-subunit oligosaccharyltransferases may resemble the prokaryotic enzymes, they use substrates typical for eukaryote glycosylation: that is, the N-X-S/T N-glycosylation recognition site and dolicholpyrophosphate-linked high mannose oligosaccharides.

Therefore in particular embodiments of the present invention, the open reading frame encoding at least one heterologous single-subunit oligosaccharyltransferase (for example, selected from the group consisting of LmSTT3A protein, LmSTT3B protein, or LmSTT3D) is overexpressed constitutively or inducibly in the recombinant alg3Δ yos9Δ host cell in which the host cell continues to express its endogenous genes encoding the proteins comprising its oligosaccharyltransferase (OTase) complex, which includes expression of the endogenous host cell STT3 gene. Thus, the host cell expresses both the heterologous single-subunit oligosaccharyltransferase and the endogenous host cell OTase complex, including the endogenous host cell SST3 protein. Furthermore, with respect to recombinant yeast, filamentous fungus, algal, or plant host cells, the host cells can further be genetically engineered to produce glycoproteins that comprise a mammalian or human-like glycosylation pattern comprising complex and/or hybrid N-glycans and not glycoproteins that have the host cells' endogenous glycosylation pattern.

The present invention has been exemplified herein using *Pichia pastoris* alg3Δ yos9Δ host cells genetically engineered to produce mammalian- or human-like complex N-glycans; however, the present invention can be applied to other yeast ost cells (including but not limited to *Saccharomyces cerevisiae*, *Schizosaccharomyces pombe*, *Ogataea minuta*, and *Pichia pastoris*) or filamentous fungi (including but not limited to *Tricoderma reesei*) that produce glycoproteins that have yeast or fungal N-glycans (either hypermannosylated N-glycans or high mannose N-glycans) or genetically engineered to produce glycoproteins that have mammalian- or human-like high mannose, complex, or hybrid N-glycans to improve the overall N-glycosylation site occupancy of glycoproteins produced in the host cell. Furthermore, the present invention can also be applied to plant and mammalian expression system to improve the overall N-glycosylation site occupancy of glycoproteins produced in these plant or mammalian expression systems, particularly glycoproteins that have more than two N-linked glycosylation sites.

Expression of the endogenous host cell genes encoding the proteins comprising the oligosaccharyltransferase (OTase) complex includes expression of the endogenous host cell gene encoding the endogenous STT3 protein or homologue. In the case of yeast host cells, the endogenous host cell genes encoding the proteins comprising the OTase complex are expressed, which includes the expression of the endogenous STT3 gene. Currently, the genes encoding proteins comprising the *Saccharomyces cerevisiae* OTase complex are known to include OST1, OST2, OST3, OST4, OST5, OST6, WBP1, SWP1, and STT3 (See for example, Spirig et al., Molec. Gen. Genet. 256: 628-637 (1997) and in *Pichia pastoris*, the OTase complex appears to include at least Ost1p, Ost2p, Ost3p, Ost4p, Ost6p, Wbp1, Swp1p, and Stt3p (See Shutter et al., op. cit.).

In general, the heterologous single-subunit oligosaccharyltransferase is capable of functionally suppressing the lethal phenotype of a mutation of at least one essential protein of an OTase complex, for example, a yeast OTase complex. Thus, the heterologous single-subunit oligosaccharyltransferase is capable of functionally complementing or rescuing a lethal mutation of at least one essential protein of an OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. In general, heterologous single-subunit oligosaccharyltransferases that can be used in the methods herein for increasing N-glycosylation site occupancy is a heterologous single-subunit oligosaccharyltransferase that in particular embodiments is capable of functionally suppressing (or rescuing or complementing) the lethal phenotype of at least one essential protein of the *Saccharomyces cerevisiae* and/or *Pichia pastoris* OTase complex. For example, in further aspects, the heterologous single-subunit oligosaccharyltransferase is the *Leishmania major STT*3D protein, which is capable of functionally suppressing (or rescuing or complementing) the lethal phenotype of at least one essential protein of the *Saccharomyces cerevisiae* or *Pichia pastoris* OTase complex. Therefore, for a particular host cell, a particular heterologous single-subunit oligosaccharyltransferase is suitable for expression in the particular host cell provided the single-subunit heterologous oligosaccharyltransferase is capable of suppressing the lethal phenotype of at least one essential protein of the yeast OTase complex. In further aspect, a heterologous single-subunit heterologous oligosaccharyltransferase is selected for expression in a particular host cell provided the single-subunit heterologous oligosaccharyltransferase is capable of suppressing the lethal phenotype of at least one essential protein of the Saccharomyces cerevisiae and/or Pichia pastoris OTase complex. The essential proteins include OST1, OST2, WBP1, SWP1, and STT3.

As used herein, a lethal mutation includes a deletion or disruption of the gene encoding the essential protein of the OTase complex or a mutation in the coding sequence that renders the essential protein non-functional. The term can further include knock-down mutations wherein production of a functional essential protein is abrogated using shRNA or RNAi.

Therefore, the present invention provides a recombinant host cell that does not display dolichyl-P-Man: Man$_5$GlcNAc$_2$-PP-dolichyl alpha-1,3 mannosyltransferase activity (Alg3p) activity and an osteosarcoma 9 (OS-9) family gene or homolog thereof activity and which further includes a nucleic acid molecule encoding a heterologous recombinant protein. In further embodiments, the host cell further includes a nucleic acid molecule encoding at least one heterologous single-subunit oligosaccharyltransferase (for example, selected from the group consisting of LmSTT3A protein, LmSTT3B protein, and LmSTT3D) operably linked to a constitutively or inducible promoter.

In particular aspects, the recombinant host cell does not express the dolichyl-P-Man:Man$_5$GlcNAc$_2$-PP-dolichyl alpha-1,3 mannosyltransferase activity (ALG3) gene and the osteosarcoma 9 (OS-9) family gene or homolog thereof gene and which further includes a nucleic acid molecule encoding a heterologous recombinant protein. In further embodiments, the host cell further includes a nucleic acid molecule encoding at least one heterologous single-subunit oligosaccharyltransferase (for example, selected from the group consisting of LmSTT3A protein, LmSTT3B protein, and LmSTT3D) operably linked to a constitutively or inducible promoter.

In particular aspects of the above, the host cell is a lower eukaryote. In further aspects, the lower eukaryote is selected from the group consisting of Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Ogataea minuta, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, and Neurospora crassa. Various yeasts, such as Ogataea minuta, Kluyveromyces lactis, Pichia pastoris, Pichia methanolica, and Hansenula polymorpha are particularly suitable for cell culture because they are able to grow to high cell densities and secrete large quantities of recombinant protein. Likewise, filamentous fungi, such as Aspergillus niger, Fusarium sp, Neurospora crassa and others can be used to produce glycoproteins of the invention at an industrial scale.

In further still aspects, the host cell is deficient in the activity of one or more enzymes selected from the group consisting of mannosyltransferases and phosphomannosyltransferases. In further still aspects, the host cell does not express an enzyme selected from the group consisting of 1,6 mannosyltransferase, 1,3 mannosyltransferase, and 1,2 mannosyltransferase.

In a particular aspect of any one of the above host cells, the host cell is a yeast host cell, including but not limited to, Pichia pastoris, Shizosaccharomyces pombe, Ogataea minuta, and Saccharomyces cerevisiae. In particular aspects, the host cell is an och1 mutant of Pichia pastoris, Shizosaccharomyces pombe, Ogataea minuta, or Saccharomyces cerevisiae. In yeast, the osteosarcoma 9 (OS-9) family gene is the YOS9 gene, which encodes Yos9p protein. Thus, the present invention provides recombinant yeast host cells that do not display a Man$_5$GlcNAc$_2$-PP-dolichyl alpha-1,3 mannosyltransferase activity (Alg3p) activity and a Yos9p protein or homolog thereof activity and which further includes a nucleic acid molecule encoding a heterologous recombinant protein. In further embodiments, the host cell further includes a nucleic acid molecule encoding at least one heterologous single-subunit oligosaccharyltransferase (for example, selected from the group consisting of LmSTT3A protein, LmSTT3B protein, or LmSTT3D) operably linked to a constitutively or inducible promoter.

In particular aspects of the recombinant yeast host cell, the expression of the dolichyl-P-Man:Man$_5$GlcNAc$_2$-PP-dolichyl alpha-1,3 mannosyltransferase activity (ALG3) gene and the YOS9 gene or homolog thereof are disrupted and the host cell further includes a nucleic acid molecule encoding a heterologous recombinant protein. In further embodiments, the host cell further includes a nucleic acid molecule encoding at least one heterologous single-subunit oligosaccharyltransferase (for example, selected from the group consisting of LmSTT3A protein, LmSTT3B protein, or LmSTT3D) operably linked to a constitutively or inducible promoter.

Further provided are methods for producing recombinant glycoproteins using the host cells disclosed herein. In general, the method comprises providing a recombinant host cell that does not display Alg3p activity and osteosarcoma 9 (OS-9) family gene or homolog thereof activity and introducing into the host cell a nucleic acid molecule encoding the recombinant glycoprotein. The recombinant host cell is cultivated or fermented in a medium for a time sufficient to express the recombinant glycoprotein. In further embodiments, the recombinant glycoprotein is secreted into to the medium where it can be recovered and purified from other components in the medium. In particular aspects, the host cell further includes a nucleic acid molecule encoding at least one heterologous single-subunit oligosaccharyltransferase (for example, selected from the group consisting of LmSTT3A protein, LmSTT3B protein, or LmSTT3D) operably linked to a constitutively or inducible promoter.

In particular aspects of the method, the host cell is a lower eukaryote. In further aspects, the lower eukaryote is selected from the group consisting of Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Ogataea minuta, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, and Neurospora crassa. Various yeasts, such as Ogataea minuta, Kluyveromyces lactis, Pichia pastoris, Pichia methanolica, and Hansenula polymorpha are particularly suitable for cell culture because they are able to grow to high cell densities and secrete large quantities of recombinant protein. Likewise, filamentous fungi, such as Aspergillus niger, Fusarium sp, Neurospora crassa and others can be used to produce glycoproteins of the invention at an industrial scale.

In further still aspects, the host cell is deficient in the activity of one or more enzymes selected from the group consisting of mannosyltransferases and phosphomannosyltransferases. In further still aspects, the host cell does not express an enzyme selected from the group consisting of 1,6 mannosyltransferase, 1,3 mannosyltransferase, and 1,2 mannosyltransferase.

In a particular aspect of any one of the above method, the host cell is a yeast host cell, including but not limited to, *Pichia pastoris, Shizosaccharomyces pombe, Ogataea minuta*, and *Saccharomyces cerevisiae*. In particular aspects, the host cell is an och1 mutant of *Pichia pastoris, Shizosaccharomyces pombe, Ogataea minuta*, or *Saccharomyces cerevisiae*. In yeast, the osteosarcoma 9 (OS-9) family gene is the YOS9 gene, which encodes Yos9p protein.

Thus, the present invention further provides a method for producing a recombinant glycoprotein comprising providing recombinant yeast host cell that does not display a $Man_5GlcNAc_2$-PP-dolichyl alpha-1,3 mannosyltransferase activity (Alg3p) activity and a Yos9p protein or homolog thereof activity and which further includes a nucleic acid molecule encoding a heterologous recombinant protein. The recombinant host cell is cultivated or fermented in a medium for a time sufficient to express the recombinant glycoprotein. In further embodiments, the recombinant glycoprotein is secreted into to the medium where it can be recovered and purified from other components in the medium. In further embodiments, the host cell further includes a nucleic acid molecule encoding at least one heterologous single-subunit oligosaccharyltransferase (for example, selected from the group consisting of LmSTT3A protein, LmSTT3B protein, or LmSTT3D) operably linked to a constitutively or inducible promoter.

In particular aspects of the method, provides is a recombinant yeast host cell in which expression of the dolichyl-P-Man:$Man_5GlcNAc_2$-PP-dolichyl alpha-1,3 mannosyltransferase activity (ALG3) gene and the YOS9 gene or homolog thereof gene has been disrupted and the host cell further includes a nucleic acid molecule encoding a heterologous recombinant protein. The recombinant host cell is cultivated or fermented in a medium for a time sufficient to express the recombinant glycoprotein. In further embodiments, the recombinant glycoprotein is secreted into to the medium where it can be recovered and purified from other components in the medium. In further embodiments, the host cell further includes a nucleic acid molecule encoding at least one heterologous single-subunit oligosaccharyltransferase (for example, selected from the group consisting of LmSTT3A protein, LmSTT3B protein, or LmSTT3D) operably linked to a constitutively or inducible promoter.

The above recombinant host cells may further include any combination of the following genetic manipulations to provide host cells that are capable of expressing glycoproteins in which the N-glycosylation pattern is mammalian-like or human-like or humanized or where a particular N-glycan species is predominant. This may achieved by eliminating selected endogenous glycosylation enzymes and/or supplying exogenous enzymes as described by Gerngross et al., U.S. Pat. No. 7,449,308, the disclosure of which is incorporated herein by reference, and general methods for reducing O-glycosylation in yeast have been described in International Application No. WO2007061631. In this manner, glycoprotein compositions can be produced in which a specific desired glycoform is predominant in the composition. If desired, additional genetic engineering of the glycosylation can be performed, such that the glycoprotein can be produced with or without core fucosylation. Use of lower eukaryotic host cells such as yeast are further advantageous in that these cells are able to produce relatively homogenous compositions of glycoprotein, such that the predominant glycoform of the glycoprotein may be present as greater than thirty mole percent of the glycoprotein in the composition. In particular aspects, the predominant glycoform may be present in greater than forty mole percent, fifty mole percent, sixty mole percent, seventy mole percent and, most preferably, greater than eighty mole percent of the glycoprotein present in the composition. Such can be achieved by eliminating selected endogenous glycosylation enzymes and/or supplying exogenous enzymes as described by Gerngross et al., U.S. Pat. No. 7,029,872 and U.S. Pat. No. 7,449,308, the disclosures of which are incorporated herein by reference. For example, a host cell can be selected or engineered to be depleted in α1,6-mannosyl transferase activities, which would otherwise add mannose residues onto the N-glycan on a glycoprotein. For example, in yeast such an α1,6-mannosyl transferase activity is encoded by the OCH1 gene and deletion or disruption of the OCH1 inhibits the production of high mannose or hypermannosylated N-glycans in yeast such as *Pichia pastoris* or *Saccharomyces cerevisiae*. (See for example, Gerngross et al. in U.S. Pat. No. 7,029,872; Contreras et al. in U.S. Pat. No. 6,803,225; and Chiba et al. in EP1211310B1 the disclosures of which are incorporated herein by reference).

In one embodiment, the host cell further includes an α1,2-mannosidase catalytic domain fused to a cellular targeting signal peptide not normally associated with the catalytic domain and selected to target the α1,2-mannosidase activity to the ER or Golgi apparatus of the host cell. Passage of a recombinant glycoprotein through the ER or Golgi apparatus of the host cell produces a recombinant glycoprotein comprising a $Man_3GlcNAc_2$ glycoform, for example, a recombinant glycoprotein composition comprising predominantly a $Man_3GlcNAc_2$ glycoform. For example, U.S. Published Patent Application No. 2005/0170452, the disclosures of which is incorporated herein by reference, discloses lower eukaryote host cells capable of producing a glycoprotein comprising a $Man_3GlcNAc_2$ glycoform.

In a further embodiment, the immediately preceding host cell further includes an N-acetylglucosaminyltransferase I (GlcNAc transferase I or GnT I) catalytic domain fused to a cellular targeting signal peptide not normally associated with the catalytic domain and selected to target GlcNAc transferase I activity to the ER or Golgi apparatus of the host cell. Passage of the recombinant glycoprotein through the ER or Golgi apparatus of the host cell produces a recombinant glycoprotein comprising a $GlcNAcMan_3GlcNAc_2$ glycoform, for example a recombinant glycoprotein composition comprising predominantly a $GlcNAcMan_3GlcNAc_2$ glycoform. U.S. Pat. No. 7,029,872, U.S. Pat. No. 7,449,308, and U.S. Published Patent Application No. 2005/0170452, the disclosures of which are all incorporated herein by reference, disclose lower eukaryote host cells capable of producing a glycoprotein comprising a $GlcNAcMan_3GlcNAc_2$ glycoform. The glycoprotein produced in the above cells can be treated in vitro with a hexaminidase to produce a recombinant glycoprotein comprising a $Man_3GlcNAc_2$ glycoform.

In a further embodiment, the immediately preceding host cell further includes N-acetylglucosaminyltransferase II (GlcNAc transferase II or GnT II) catalytic domain fused to a cellular targeting signal peptide not normally associated with the catalytic domain and selected to target GlcNAc transferase II activity to the ER or Golgi apparatus of the host cell. Passage of the recombinant glycoprotein through the ER or Golgi apparatus of the host cell produces a recombinant glycoprotein comprising a GlcNAc$_2$Man$_3$GlcNAc$_2$ glycoform, for example a recombinant glycoprotein composition comprising predominantly a GlcNAc$_2$Man$_3$GlcNAc$_2$ glycoform. U.S. Pat. Nos. 7,029,872 and 7,449,308 and U.S. Published Patent Application No. 2005/0170452, the disclosures of which are all incorporated herein by reference, disclose lower eukaryote host cells capable of producing a glycoprotein comprising a GlcNAc$_2$Man$_3$GlcNAc$_2$ glycoform. The glycoprotein produced in the above cells can be treated in vitro with a hexosaminidase that removes the terminal GlcNAc residues to produce a recombinant glycoprotein comprising a Man$_3$GlcNAc$_2$ glycoform or the hexosaminidase can be co-expressed with the glycoprotein in the host cell to produce a recombinant glycoprotein comprising a Man$_3$GlcNAc$_2$ glycoform.

In a further embodiment, the immediately preceding host cell further includes a galactosyltransferase catalytic domain fused to a cellular targeting signal peptide not normally associated with the catalytic domain and selected to target galactosyltransferase activity to the ER or Golgi apparatus of the host cell. Passage of the recombinant glycoprotein through the ER or Golgi apparatus of the host cell produces a recombinant glycoprotein comprising a GalGlcNAc$_2$Man$_3$GlcNAc$_2$ or Gal$_2$GlcNAc$_2$Man$_3$GlcNAc$_2$ glycoform, or mixture thereof for example a recombinant glycoprotein composition comprising predominantly a GalGlcNAc$_2$Man$_3$GlcNAc$_2$ glycoform or Gal$_2$GlcNAc$_2$Man$_3$GlcNAc$_2$ glycoform or mixture thereof. U.S. Pat. No. 7,029,872 and U.S. Published Patent Application No. 2006/0040353, the disclosures of which are incorporated herein by reference, discloses lower eukaryote host cells capable of producing a glycoprotein comprising a Gal$_2$GlcNAc$_2$Man$_3$GlcNAc$_2$ glycoform. The glycoprotein produced in the above cells can be treated in vitro with a galactosidase to produce a recombinant glycoprotein comprising a GlcNAc$_2$Man$_3$GlcNAc$_2$ glycoform, for example a recombinant glycoprotein composition comprising predominantly a GlcNAc$_2$Man$_3$GlcNAc$_2$ glycoform or the galactosidase can be co-expressed with the glycoprotein in the host cell to produce a recombinant glycoprotein comprising the GlcNAc$_2$Man$_3$GlcNAc$_2$ glycoform, for example a recombinant glycoprotein composition comprising predominantly a GlcNAc$_2$Man$_3$GlcNAc$_2$ glycoform.

In a further embodiment, the immediately preceding host cell further includes a sialyltransferase catalytic domain fused to a cellular targeting signal peptide not normally associated with the catalytic domain and selected to target sialyltransferase activity to the ER or Golgi apparatus of the host cell. Passage of the recombinant glycoprotein through the ER or Golgi apparatus of the host cell produces a recombinant glycoprotein comprising predominantly a Sia$_2$Gal$_2$GlcNAc$_2$Man$_3$GlcNAc$_2$ glycoform or SiaGal$_2$GlcNAc$_2$Man$_3$GlcNAc$_2$ glycoform or mixture thereof. For lower eukaryote host cells such as yeast and filamentous fungi, it is useful that the host cell further include a means for providing CMP-sialic acid for transfer to the N-glycan. U.S. Published Patent Application No. 2005/0260729, the disclosure of which is incorporated herein by reference, discloses a method for genetically engineering lower eukaryotes to have a CMP-sialic acid synthesis pathway and U.S. Published Patent Application No. 2006/0286637, the disclosure of which is incorporated herein by reference, discloses a method for genetically engineering lower eukaryotes to produce sialylated glycoproteins. The glycoprotein produced in the above cells can be treated in vitro with a neuraminidase to produce a recombinant glycoprotein comprising predominantly a Gal$_2$GlcNAc$_2$Man$_3$GlcNAc$_2$ glycoform or GalGlcNAc$_2$Man$_3$GlcNAc$_2$ glycoform or mixture thereof or the neuraminidase can be co-expressed with the glycoprotein in the host cell to produce a recombinant glycoprotein comprising predominantly a Gal$_2$GlcNAc$_2$Man$_3$GlcNAc$_2$ glycoform or GalGlcNAc$_2$Man$_3$GlcNAc$_2$ glycoform or mixture thereof.

In a further aspect, the above host cell capable of making glycoproteins having a Man$_5$GlcNAc$_2$ glycoform can further include a mannosidase III catalytic domain fused to a cellular targeting signal peptide not normally associated with the catalytic domain and selected to target the mannosidase III activity to the ER or Golgi apparatus of the host cell. Passage of the recombinant glycoprotein through the ER or Golgi apparatus of the host cell produces a recombinant glycoprotein comprising a Man$_3$GlcNAc$_2$ glycoform, for example a recombinant glycoprotein composition comprising predominantly a Man$_3$GlcNAc$_2$ glycoform. U.S. Pat. No. 7,625,756, the disclosures of which are all incorporated herein by reference, discloses the use of lower eukaryote host cells that express mannosidase III enzymes and are capable of producing glycoproteins having predominantly a Man$_3$GlcNAc$_2$ glycoform.

Any one of the preceding host cells can further include one or more GlcNAc transferase selected from the group consisting of GnT III, GnT IV, GnT V, GnT VI, and GnT IX to produce glycoproteins having bisected (GnT III) and/or multiantennary (GnT IV, V, VI, and IX) N-glycan structures such as disclosed in U.S. Pat. No. 7,598,055 and U.S. Published Patent Application No. 2007/0037248, the disclosures of which are all incorporated herein by reference.

In general yeast and filamentous fungi are not able to make glycoproteins that have N-glycans that include fucose. Therefore, the N-glycans disclosed herein will lack fucose unless the host cell is specifically modified to include a pathway for synthesizing GDP-fucose and a fucosyltransferase. Therefore, in particular aspects where it is desirable to have glycoproteins in which the N-glycan includes fucose, any one of the aforementioned host cells is further modified to include a fucosyltransferase and a pathway for producing fucose and transporting fucose into the ER or Golgi. Examples of methods for modifying *Pichia pastoris* to render it capable of producing glycoproteins in which one or more of the N-glycans thereon are fucosylated are disclosed in Published International Application No. WO 2008112092, the disclosure of which is incorporated herein by reference. In particular aspects of the invention, the *Pichia pastoris* host cell is further modified to include a fucosylation pathway comprising a GDP-mannose-4,6-dehydratase, GDP-keto-deoxy-mannose-epimerase/GDP-keto-deoxy-galactose-reductase, GDP-fucose transporter, and a fucosyltransferase. In particular aspects, the fucosyltransferase is selected from the group consisting of α1,2-fucosyltransferase, α1,3-fucosyltransferase, α1,4-fucosyltransferase, and α1,6-fucosyltransferase.

Various of the preceding host cells further include one or more sugar transporters such as UDP-GlcNAc transporters (for example, *Kluyveromyces lactis* and *Mus musculus* UDP-GlcNAc transporters), UDP-galactose transporters (for example, *Drosophila melanogaster* UDP-galactose transporter), and CMP-sialic acid transporter (for example, human sialic acid transporter). Because lower eukaryote host cells such as yeast and filamentous fungi lack the above transporters, it is preferable that lower eukaryote host cells such as yeast and filamentous fungi be genetically engineered to include the above transporters.

Host cells further include *Pichia pastoris* that are genetically engineered to eliminate glycoproteins having phosphomannose residues by deleting or disrupting one or both of the phosphomannosyltransferase genes PNO1 and MNN4B (See for example, U.S. Pat. Nos. 7,198,921 and 7,259,007; the disclosures of which are all incorporated herein by reference), which in further aspects can also include deleting or disrupting the MNN4A gene. Disruption includes disrupting the open reading frame encoding the particular enzymes or disrupting expression of the open reading frame or abrogating translation of RNAs encoding one or more of the β-mannosyltransferases and/or phosphomannosyltransferases using interfering RNA, antisense RNA, or the like. The host cells can further include any one of the aforementioned host cells modified to produce particular N-glycan structures.

Host cells further include lower eukaryote cells (e.g., yeast such as *Pichia pastoris*) that are genetically modified to control O-glycosylation of the glycoprotein by deleting or disrupting one or more of the protein O-mannosyltransferase (Dol-P-Man:Protein (Ser/Thr) Mannosyl Transferase genes) (PMTs) (See U.S. Pat. No. 5,714,377; the disclosure of which is incorporated herein by reference) or grown in the presence of Pmtp inhibitors and/or an α1,2 mannosidase as disclosed in Published International Application No. WO 2007061631 the disclosure of which is incorporated herein by reference. Disruption includes disrupting the open reading frame encoding the Pmtp or disrupting expression of the open reading frame or abrogating translation of RNAs encoding one or more of the Pmtps using interfering RNA, antisense RNA, or the like. The host cells can further include any one of the aforementioned host cells modified to produce particular N-glycan structures.

Pmtp inhibitors include but are not limited to a benzylidene thiazolidinediones. Examples of benzylidene thiazolidinediones that can be used are 5-[[3,4-bis(phenylmethoxy) phenyl]methylene]-4-oxo-2-thioxo-3-thiazolidineacetic Acid; 5-[[3-(1-Phenylethoxy)-4-(2-phenylethoxy)]phenyl]methylene]-4-oxo-2-thioxo-3-thiazolidineacetic Acid; and 5-[[3-(1-Phenyl-2-hydroxy) ethoxy)-4-(2-phenylethoxy)]phenyl]methylene]-4-oxo-2-thioxo-3-thiazolidineacetic Acid.

In particular embodiments, the function or expression of at least one endogenous PMT gene is reduced, disrupted, or deleted. For example, in particular embodiments the function or expression of at least one endogenous PMT gene selected from the group consisting of the PMT1, PMT2, PMT3, and PMT4 genes is reduced, disrupted, or deleted; or the host cells are cultivated in the presence of one or more PMT inhibitors. In further embodiments, the host cells include one or more PMT gene deletions or disruptions and the host cells are cultivated in the presence of one or more Pmtp inhibitors. In particular aspects of these embodiments, the host cells also express a secreted α-1,2-mannosidase.

PMT deletions or disruptions and/or Pmtp inhibitors control O-glycosylation by reducing O-glycosylation occupancy; that is by reducing the total number of O-glycosylation sites on the glycoprotein that are glycosylated. The further addition of an α-1,2-mannosidase that is secreted by the cell controls O-glycosylation by reducing the mannose chain length of the O-glycans that are on the glycoprotein. Thus, combining PMT deletions or disruptions and/or Pmtp inhibitors with expression of a secreted α-1,2-mannosidase controls O-glycosylation by reducing occupancy and chain length. In particular circumstances, the particular combination of PMT deletions or disruptions, Pmtp inhibitors, and α-1,2-mannosidase is determined empirically as particular heterologous glycoproteins (antibodies, for example) may be expressed and transported through the Golgi apparatus with different degrees of efficiency and thus may require a particular combination of PMT deletions or disruptions, Pmtp inhibitors, and α-1,2-mannosidase. In another aspect, genes encoding one or more endogenous mannosyltransferase enzymes are deleted. The deletion(s) can be in combination with providing the secreted α-1,2-mannosidase and/or PMT inhibitors or can be in lieu of providing the secreted α-1,2-mannosidase and/or PMT inhibitors.

Thus, the control of O-glycosylation can be useful for producing particular glycoproteins in the host cells disclosed herein in better total yield or in yield of properly assembled glycoprotein. The reduction or elimination of O-glycosylation appears to have a beneficial effect on the assembly and transport of glycoproteins such as whole antibodies as they traverse the secretory pathway and are transported to the cell surface. Thus, in cells in which O-glycosylation is controlled, the yield of properly assembled glycoproteins such as antibody fragments is increased over the yield obtained in host cells in which O-glycosylation is not controlled.

To reduce or eliminate the likelihood of N-glycans and O-glycans with β-linked mannose residues, which are resistant to α-mannosidases, the recombinant glycoengineered *Pichia pastoris* host cells are genetically engineered to eliminate glycoproteins having α-mannosidase-resistant N-glycans by deleting or disrupting one or more of the β-mannosyltransferase genes (e.g., BMT1, BMT2, BMT3, and BMT4) (See, U.S. Pat. No. 7,465,577, U.S. Pat. No. 7,713,719, and Published International Application No. WO2011046855, each of which is incorporated herein by reference). The deletion or disruption of BMT2 and one or more of BMT1, BMT3, and BMT4 also reduces or eliminates detectable cross reactivity to antibodies against host cell protein.

In particular embodiments, the host cells do not display Alg3p protein activity or have a deletion or disruption of expression from the ALG3 gene (e.g., deletion or disruption of the open reading frame encoding the Alg3p to render the host cell alg3Δ) as described in Published U.S. Application No. 20050170452 or US20100227363, which are incorporated herein by reference. Alg3p is Man5GlcNAc2-PP-dolichyl alpha-1,3 mannosyltransferase that transferase a mannose residue to the mannose residue of the alpha-1,6 arm of lipid-linked Man5GlcNAc2 (FIG. 17, GS 1.3) in an alpha-1,3 linkage to produce lipid-linked Man6GlcNAc2 (FIG. 17, GS 1.4), a precursor for the synthesis of lipid-linked Glc3Man9GlcNAc$_2$, which is then transferred by an oligosaccharyltransferase to an asparagine residue of a glycoprotein followed by removal of the glucose (Glc) residues. In host cells that lack Alg3p protein activity, the lipid-linked Man$_5$GlcNAc$_2$ oligosaccharide may be transferred by an oligosaccharyltransferase to an asparigine residue of a glycoprotein. In such host cells that further include an α1,2-mannosidase, the Man$_5$GlcNAc$_2$ oligosaccharide attached to the glycoprotein is trimmed to a tri-mannose (paucimannose) Man3GlcNAc2 structure (FIG. 17, GS 2.1). The Man$_5$GlcNAc$_2$ (GS 1.3) structure is distinguishable from the Man$_5$GlcNAc$_2$ (GS 2.0) shown in FIG. 17, and which is produced in host cells that express the Man$_5$GlcNAc$_2$-PP-dolichyl alpha-1,3 mannosyltransferase (Alg3p).

Therefore, provided is a method for producing an N-glycosylated insulin or insulin analogue and compositions of the same in a lower eukaryote host cell, comprising a deletion or disruption ALG3 gene (alg3Δ) and includes a nucleic acid molecule encoding an insulin or insulin analogue having at least one N-glycosylation site; and culturing the host cell under conditions for expressing the insulin or insulin analogue to produce the N-glycosylated insulin or insulin analogue having predominantly a Man$_5$GlcNAc$_2$ (GS 1.3) structure. In further embodiments, the host cell further expresses an endomannosidase activity (e.g., a full-length endomannosidase or a chimeric endomannosidase comprising an endomannosidase catalytic domain fused to a cellular targeting signal peptide not normally associated with the catalytic domain and selected to target the endomannosidase activity to the ER or Golgi apparatus of the host cell. See for example, U.S. Pat. No. 7,332,299) and/or glucosidase II activity (a full-length glucosidase II or a chimeric glucosidase II comprising a glucosidase II catalytic domain fused to a cellular targeting signal peptide not normally associated with the catalytic domain and selected to target the glucosidase II activity to the ER or Golgi apparatus of the host cell. See for example, U.S. Pat. No. 6,803,225). In particular aspects, the host cell further includes a deletion or disruption of the ALG6 (α1,3-glucosylatransferase) gene (alg6Δ), which has been shown to increase N-glycan occupancy of glycoproteins in alg3Δ host cells (See for example, De Pourcq et al., PloSOne 2012; 7(6):e39976. Epub 2012 Jun. 29, which discloses genetically engineering Yarrowia lipolytica to produce glycoproteins that have Man$_5$GlcNAc$_2$ (GS 1.3) or paucimannose N-glycan structures). The nucleic acid sequence encoding the Pichia pastoris ALG6 is disclosed in EMBL database, accession number CCCA38426. In further aspects, the host cell further includes a deletion or disruption of the OCH1 gene (och1Δ).

Further provided is a method for producing an N-glycosylated insulin or insulin analogue and compositions of the same in a lower eukaryote host cell, comprising a deletion or disruption of the ALG3 gene (alg3Δ) and includes a nucleic acid molecule encoding a chimeric α1,2-mannosidase comprising an α1,2-mannosidase catalytic domain fused to a cellular targeting signal peptide not normally associated with the catalytic domain and selected to target the α1,2-mannosidase activity to the ER or Golgi apparatus of the host cell to overexpress the chimeric α1,2-mannosidase and a nucleic acid molecule encoding the insulin or insulin analogue having at least one N-glycosylation site; and culturing the host cell under conditions for expressing the insulin or insulin analogue to produce the N-glycosylated insulin or insulin analogue having predominantly a Man$_3$GlcNAc$_2$ structure. In further embodiments, the host cell further expresses or overexpresses an endomannosidase activity (e.g., a full-length endomannosidase or a chimeric endomannosidase comprising an endomannosidase catalytic domain fused to a cellular targeting signal peptide not normally associated with the catalytic domain and selected to target the endomannosidase activity to the ER or Golgi apparatus of the host cell) and/or a glucosidase II activity (a full-length glucosidase II or a chimeric glucosidease II comprising a glucosidase II catalytic domain fused to a cellular targeting signal peptide not normally associated with the catalytic domain and selected to target the glucosidase II activity to the ER or Golgi apparatus of the host cell). In particular aspects, the host cell further includes a deletion or disruption of the ALG6 gene (alg6Δ). In further aspects, the host cell further includes a deletion or disruption of the OCH1 gene (och1Δ) Example 6 shows the construction of an alg3Δ Pichia pastoris host cell that overexpresses a full-length endomannosidase, which produced an insulin analogue that has paucimannose N-glycans. Similar host cells may be constructed in other yeast or filamentous fungi.

In further embodiments, the above alg3Δ host cells may further include additional mammalian or human glycosylation enzymes (e.g., GnT I, GnT II, galactosylatransferase, fucosyltransferase, sialyl transferase) as disclosed previously to produce N-glycosylated insulin or insulin analogue having predominantly particular hybrid or complex N-glycans.

Yield of glycoprotein can in some situations be improved by overexpressing nucleic acid molecules encoding mammalian or human chaperone proteins or replacing the genes encoding one or more endogenous chaperone proteins with nucleic acid molecules encoding one or more mammalian or human chaperone proteins. In addition, the expression of mammalian or human chaperone proteins in the host cell also appears to control O-glycosylation in the cell. Thus, further included are the host cells herein wherein the function of at least one endogenous gene encoding a chaperone protein has been reduced or eliminated, and a vector encoding at least one mammalian or human homolog of the chaperone protein is expressed in the host cell. Also included are host cells in which the endogenous host cell chaperones and the mammalian or human chaperone proteins are expressed. In further aspects, the lower eukaryotic host cell is a yeast or filamentous fungi host cell. Examples of the use of chaperones of host cells in which human chaperone proteins are introduced to improve the yield and reduce or control O-glycosylation of recombinant proteins has been disclosed in Published International Application No. WO2009105357 and WO2010019487 (the disclosures of which are incorporated herein by reference).

Therefore, the methods disclose herein can use any host cell that has been genetically modified to produce glycoproteins comprising at least N-glycan shown in FIG. 17. The methods disclose herein can use any host cell that has been genetically modified to produce glycoproteins wherein the predominant N-glycan is selected from the group consisting of complex N-glycans, hybrid N-glycans, and high mannose N-glycans wherein complex N-glycans are selected from the group consisting of Man$_3$GlcNAc$_2$ (paucimannose), GlcNAc$_{(1-4)}$Man$_3$GlcNAc$_2$, Gal$_{(1-4)}$GlcNAc$_{(1-4)}$Man$_3$GlcNAc$_2$, and Sia$_{(1-4)}$Gal$_{(1-4)}$Man$_3$GlcNAc$_2$. In further embodiments, the host cell produces glycoproteins that have predominantly an N-glycan structure consisting of the Man$_5$GlcNAc$_2$ (GS 1.3) structure. In general, the strains here will not be expected to produce the Man$_5$GlcNAc$_2$ (GS 2.0) structure shown in FIG. 17.

For genetically engineering yeast, selectable markers can be used to construct the recombinant host cells include drug resistance markers and genetic functions which allow the yeast host cell to synthesize essential cellular nutrients, e.g. amino acids. Drug resistance markers that are commonly used in yeast include chloramphenicol, kanamycin, methotrexate, G418 (geneticin), Zeocin, and the like. Genetic functions that allow the yeast host cell to synthesize essential cellular nutrients are used with available yeast strains having auxotrophic mutations in the corresponding genomic function. Common yeast selectable markers provide genetic functions for synthesizing leucine (LEU2), tryptophan (TRP1 and TRP2), proline (PRO1), uracil (URA3, URA5, URA6), histidine (HIS3), lysine (LYS2), adenine (ADE1 or ADE2), and the like. Other yeast selectable markers include the ARR3 gene from S. cerevisiae, which confers arsenite resistance to yeast cells that are grown in the presence of arsenite (Bobrowicz et al., Yeast, 13:819-828 (1997); Wysocki et al., J. Biol. Chem. 272:30061-30066 (1997)). A number of suitable integration sites include those enumerated in U.S. Pat. No. 7,479,389 (the disclosure of which is incorporated herein by reference) and include homologs to loci known for *Saccharomyces cerevisiae* and other yeast or fungi. Methods for integrating vectors into yeast are well known (See for example, U.S. Pat. No. 7,479,389, U.S. Pat. No. 7,514,253, U.S. Published Application No. 2009012400, and WO2009/085135; the disclosures of which are all incorporated herein by reference). Examples of insertion sites include, but are not limited to, *Pichia* ADE genes; *Pichia* TRP (including TRP1 through TRP2) genes; *Pichia* MCA genes; *Pichia* CYM genes; *Pichia* PEP genes; *Pichia* PRB genes; and *Pichia* LEU genes. The *Pichia* ADE1 and ARG4 genes have been described in Lin Cereghino et al., Gene 263:159-169 (2001) and U.S. Pat. No. 4,818,700 (the disclosure of which is incorporated herein by reference), the HIS3 and TRP1 genes have been described in Cosano et al., Yeast 14:861-867 (1998), HIS4 has been described in GenBank Accession No. X56180.

The transformation of the yeast cells is well known in the art and may for instance be effected by protoplast formation followed by transformation in a manner known per se. The medium used to cultivate the cells may be any conventional medium suitable for growing yeast organisms.

In particular embodiments of any one of the above host cells and methods using the host cells, the recombinant heterologous protein is therapeutic protein or glycoprotein, which in particular embodiments may be for example, selected from the group consisting of erythropoietin (EPO); cytokines such as interferon α, interferon β, interferon γ, and interferon w; and granulocyte-colony stimulating factor (GCSF); granulocyte macrophage-colony stimulating factor (GM-CSF); coagulation factors such as factor VIII, factor IX, and human protein C; antithrombin III; thrombin; soluble IgE receptor α-chain; immunoglobulins such as IgG, IgG fragments, IgG fusions, and IgM; immunoadhesions and other Fc fusion proteins such as soluble TNF receptor-Fc fusion proteins; RAGE-Fc fusion proteins; interleukins; urokinase; chymase; urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4-Ig; transmembrane activator and calcium modulator and cyclophilin ligand; glucagon-like protein 1; insulin, and IL-2 receptor agonist.

In further embodiments of any one of the above host cells, the therapeutic glycoprotein is an antibody, examples of which, include but are not limited to, an anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD11a antibody, anti-EGF receptor antibody, or anti-CD20 antibody.

The following examples are intended to promote a further understanding of the present invention.

EXAMPLE 1

Plasmids comprising expression cassettes encoding the *Leishmania major* STT3D (LmSTT3D) open reading frame (ORF) operably linked to an inducible or constitutive promoter were constructed as follows.

The open reading frame encoding the LmSTT3D (SEQ ID NO:1) was codon-optimized for optimal expression in *P. pastoris* and synthesized by GeneArt AG, Brandenburg, Germany. The codon-optimized nucleic acid molecule encoding the LmSTT3D was designated pGLY6287 and has the nucleotide sequence shown in SEQ ID NO:2.

Figure 2:
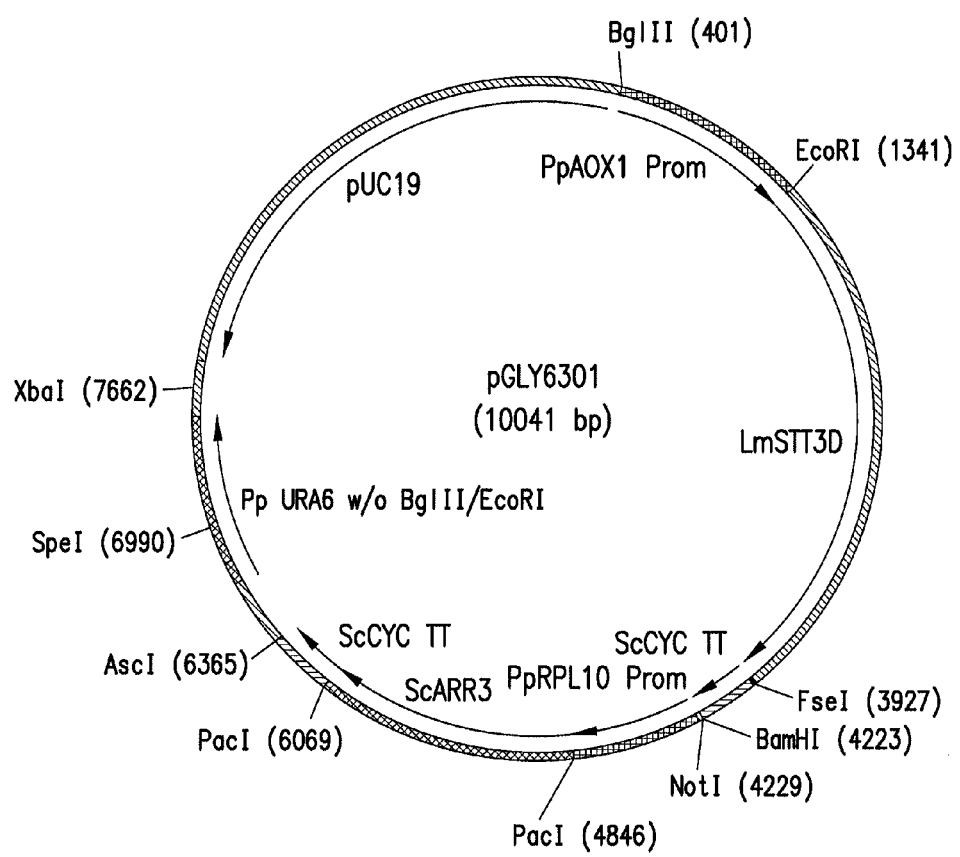
FIG. 2 shows a map of plasmid pGLY6301 encoding the LmSTT3D ORF under the control of the *Pichia pastoris* alcohol oxidase I (AOX1) promoter and *S. cerevisiae* CYC transcription termination sequence. The plasmid is a roll-in vector that targets the URA6 locus. The selection of transformants uses arsenic resistance encoded by the *S. cerevisiae* ARR3 ORF under the control of the *P. pastoris* RPL10 promoter and *S. cerevisiae* CYC transcription termination sequence.

Plasmid pGLY6301 (FIG. 2) is a roll-in integration plasmid that targets the URA6 locus in *P. pastoris*. The expression cassette encoding the LmSTT3D comprises a nucleic acid molecule encoding the LmSTT3D ORF codon-optimized for effective expression in *P. pastoris* operably linked at the 5' end to a nucleic acid molecule that has the inducible *P. pastoris* AOX1 promoter sequence (SEQ ID NO:3) and at the 3' end to a nucleic acid molecule that has the *S. cerevisiae* CYC transcription termination sequence (SEQ ID NO:4). For selecting transformants, the plasmid comprises an expression cassette encoding the *S. cerevisiae* ARR3 ORF in which the nucleic acid molecule encoding the ORF (SEQ ID NO:5) is operably linked at the 5' end to a nucleic acid molecule having the *P. pastoris* RPL10 promoter sequence (SEQ ID NO:6) and at the 3' end to a nucleic acid molecule having the *S. cerevisiae* CYC transcription termination sequence. The plasmid further includes a nucleic acid molecule for targeting the URA6 locus (SEQ ID NO:7). Plasmid pGLY6301 was constructed by cloning the DNA fragment encoding the codon-optimized LmSTT3D ORF (pGLY6287) flanked by an EcoRI site at the 5' end and an FseI site at the 3' end into plasmid pGFI30t, which had been digested with EcoRI and FseI.

Figure 3:
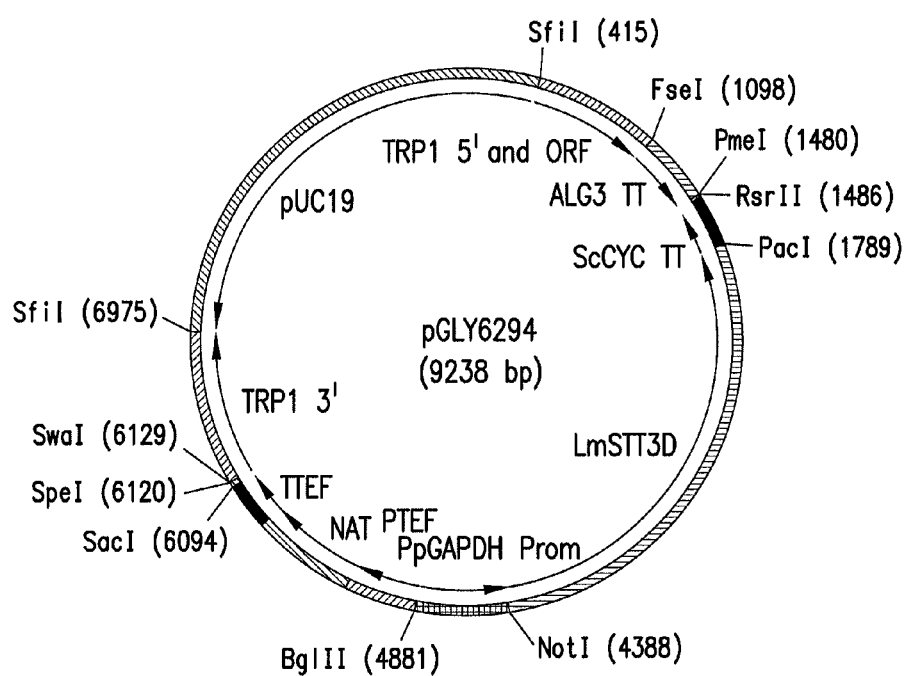
FIG. 3 shows a map of plasmid pGLY6294 encoding the LmSTT3D ORF under the control of the *P. pastoris* GAPDH promoter and *S. cerevisiae* CYC transcription termination sequence. The plasmid is a KINKO vector that targets the TRP1 locus: the 3' end of the TRP1 ORF is adjacent to the *P. pastoris* ALG3 transcription termination sequence. The selection of transformants uses nourseothricin resistance encoded by the *Streptomyces noursei* nourseothricin acetyltransferase (NAT) ORF under the control of the *Ashbya gossypii* TEF1 promoter (PTEF) and *Ashbya gossypii* TEF1 termination sequence (TTEF).

Plasmid pGLY6294 (FIG. 3) is a KINKO integration vector that targets the TRP1 locus in *P. pastoris* without disrupting expression of the locus. KINKO (Knock-In with little or No Knock-Out) integration vectors enable insertion of heterologous DNA into a targeted locus without disrupting expression of the gene at the targeted locus and have been described in U.S. Published Application No. 20090124000. The expression cassette encoding the LmSTT3D comprises a nucleic acid molecule encoding the LmSTT3D ORF operably linked at the 5' end to a nucleic acid molecule that has the constitutive *P. pastoris* GAPDH promoter sequence (SEQ ID NO:8) and at the 3' end to a nucleic acid molecule having the *S. cerevisiae* CYC transcription termination sequence. For selecting transformants, the plasmid comprises an expression cassette encoding the Nourseothricin resistance (NATR) ORF (originally from pAG25 from EROSCARF, Scientific Research and Development GmbH, Daimlerstrasse 13a, D-61352 Bad Homburg, Germany, See Goldstein et al., Yeast 15: 1541 (1999); GenBank Accession Nos. CAR31387.1 and CAR31383.1); wherein the nucleic acid molecule encoding the ORF (SEQ ID NO:9) is operably linked to at the 5' end to a nucleic acid molecule having the *Ashbya gossypii* TEF1 promoter sequence (SEQ ID NO:10) and at the 3' end to a nucleic acid molecule that has the *Ashbya gossypii* TEF1 termination sequence (SEQ ID NO:11). The two expression cassettes are flanked on one side by a nucleic acid molecule comprising a nucleotide sequence from the 5' region of the ORF encoding Trp1p ending at the stop codon (SEQ ID NO:12) linked to a nucleic acid molecule having the *P. pastoris* ALG3 termination sequence (SEQ ID NO:13) and on the other side by a nucleic acid molecule comprising a nucleotide sequence from the 3' region of the TRP1 gene (SEQ ID NO:14). Plasmid pGLY6294 was constructed by cloning the DNA fragment encoding the codon-optimized LmSTT3D ORF (pGLY6287) flanked by a NotI site at the 5' end and a PadI site at the 3' end into plasmid pGLY597, which had been digested with NotI and FseI. An expression cassette comprising a nucleic acid molecule encoding the Nourseothricin resistance ORF (NAT) operably linked to the *Ashbya gos-* sypii TEF1 promoter (PTEF) and *Ashbya gossypii* TEF1 termination sequence (TTEF).

The above plasmids can be used to introduce the LmSTT3D expression cassettes into *P. pastoris* to increase the N-glycosylation site occupancy on glycoproteins produced therein as shown in the following examples.

EXAMPLE 2

Genetically engineered *Pichia pastoris* strains YGLY14401, YGLY18445, YGLY28158, and YGLY20228 are all strains that produce recombinant human anti-RSV antibodies in a host cell genetically engineered to be capable of producing galactose-terminated complex N-glycans. Strain YGLY18445 over expresses LmSTT3D, strain YGLY 28158 overexpressed LmSTT3D from two copies of the gene integrated into the genome, YGLY20228 expresses LmSTT3D and LmSTT3A. Construction of these strains is illustrated schematically in FIG. 1A-1L. Briefly, the strains were constructed as follows.

In general, the strains were constructed from wild-type *Pichia pastoris* strain NRRL-Y 11430 using methods described earlier (See for example, U.S. Pat. No. 7,449,308; U.S. Pat. No. 7,479,389; U.S. Published Application No. 20090124000; Published PCT Application No. WO2009085135; Nett and Gerngross, Yeast 20:1279 (2003); Choi et al., Proc. Natl. Acad. Sci. USA 100:5022 (2003); Hamilton et al., Science 301:1244 (2003)). All plasmids were made in a pUC19 plasmid using standard molecular biology procedures. For nucleotide sequences that were optimized for expression in *P. pastoris*, the native nucleotide sequences were analyzed by the GENEOPTIMIZER software (GeneArt, Regensburg, Germany) and the results used to generate nucleotide sequences in which the codons were optimized for *P. pastoris* expression. Yeast strains were transformed by electroporation (using standard techniques as recommended by the manufacturer of the electroporator BioRad). From a series of transformations beginning with strain NRRL-Y 11430, strain YGLY8323 was produced. Strain YGLY8323 is capable of producing glycoproteins that have predominately galactose-terminated N-glycans. Construction of this strain from the wild-type NRRL-Y 11430 strain is described in detail in Example 2 of Published International Application No. WO2011106389 and which is incorporated herein by reference.

Figure 4:
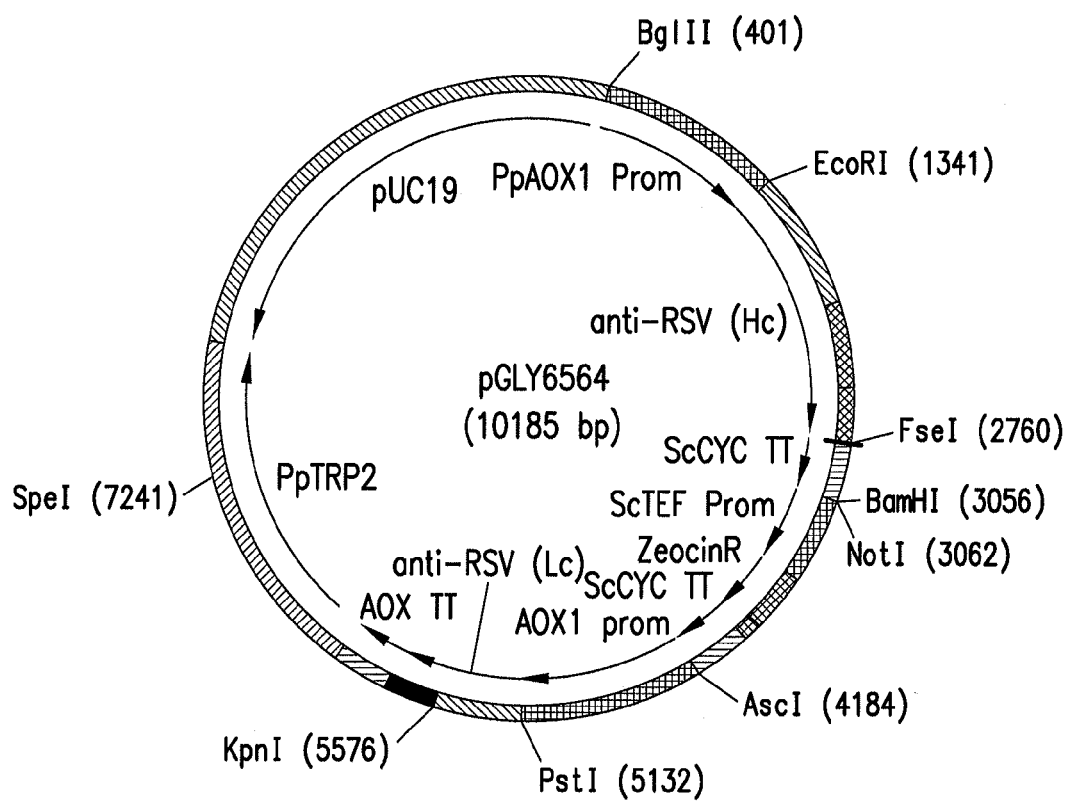
FIG. 4 shows a map of pGLY6564 encoding the light and heavy chains of an anti-RSV antibody. The plasmid is a roll-in vector that targets the TRP2 locus. The ORF encoding the heavy chain is under the control of a *P. pastoris* AOX1 promoter and the *S. cerevisiae* CYC transcription termination sequence. The ORF encoding the light chain is under the control of a *P. pastoris* AOX1 promoter and the *P. pastoris* AOX1 transcription termination sequence. Selection of transformants uses zeocin resistance encoded by the zeocin resistance protein (ZeocinR) ORF under the control of the *P. pastoris* TEE1 promoter and *S. cerevisiae* CYC termination sequence.

Plasmid pGLY6564 (FIG. 4) is a roll-in integration plasmid encoding the light and heavy chains of an anti-RSV antibody that targets the TRP2 locus in *P. pastoris*. The expression cassette encoding the anti-RSV heavy chain comprises a nucleic acid molecule encoding the heavy chain ORF codon-optimized for effective expression in *P. pastoris* (SEQ ID NO:15) operably linked at the 5' end to a nucleic acid molecule (SEQ ID NO:33) encoding the *Saccharomyces cerevisiae* mating factor pre-signal sequence which in turn is fused at its N-terminus to a nucleic acid molecule that has the inducible *P. pastoris* AOX1 promoter sequence and at the 3' end to a nucleic acid molecule that has the *S. cerevisiae* CYC transcription termination. The expression cassette encoding the anti-RSV light chain comprises a nucleic acid molecule encoding the light chain ORF codon-optimized for effective expression in *P. pastoris* (SEQ ID NO:16) operably linked at the 5' end to a nucleic acid molecule encoding the *Saccharomyces cerevisiae* mating factor pre-signal sequence which in turn is fused at its N-terminus to a nucleic acid molecule that has the inducible *P. pastoris* AOX1 promoter sequence and at the 3' end to a nucleic acid molecule that has the *P. pastoris* AOX1 transcription termination sequence (SEQ ID NO:17). For selecting transformants, the plasmid comprises an expression cassette encoding the Zeocin ORF in which the nucleic acid molecule encoding the ORF (SEQ ID NO:18) is operably linked at the 5' end to a nucleic acid molecule having the *S. cerevisiae* TEF promoter sequence (SEQ ID NO:36) and at the 3' end to a nucleic acid molecule having the *S. cerevisiae* CYC transcription termination sequence. The plasmid further includes a nucleic acid molecule for targeting the TRP2 locus.

Strain YGLY14401 was generated by transforming plasmid pGLY6564, which encodes the anti-RSV antibody, into YGLY8323. The strain YGLY14401 was selected from the strains produced. In this strain, the expression cassettes encoding the anti-RSV heavy and light chains are targeted to the *Pichia pastoris* TRP2 locus (PpTRP2). This strain does not include the LmSTT3D expression cassette. The strain YGLY14401 was counterselected in the presence of 5-FOA to produce strain YGLY15820 in which the URA5 gene has been lost and only the lacZ repeats remain.

Figure 5:
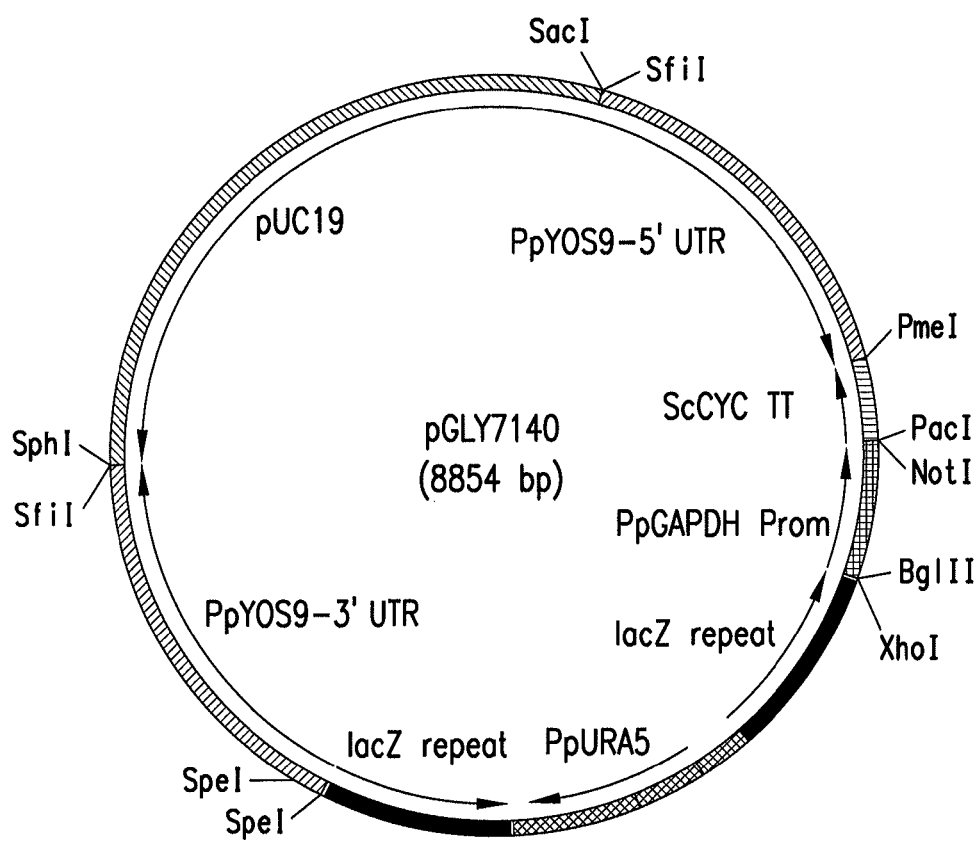
FIG. 5 shows a map of plasmid pGLY7140. The plasmid is a knock-out vector that targets the YOS9 locus comprising the *P. pastoris* URA5 gene or transcription unit (PpURA5) flanked by lacZ repeats (lacZ repeat) flanked on one side with the 5' nucleotide sequence of the *P. pastoris* YOS9 gene (PpYOS9-5') and on the other side with the 3' nucleotide sequence of the *P. pastoris* YOS9 gene (PpYOS9-3').

Strain YGLY15820 was transformed with plasmid pGLY7140 (FIG. 5), a knock-out vector that targets the YOS9 locus and contains a nucleic acid molecule comprising the *P. pastoris* URA5 gene (SEQ ID NO:41) or transcription unit flanked by nucleic acid molecules comprising lacZ repeats (SEQ ID NO:42) which in turn is flanked on one side by a nucleic acid molecule comprising a nucleotide sequence from the 5' region of the YOS9 gene (SEQ ID NO:19) and on the other side by a nucleic acid molecule comprising a nucleotide sequence from the 3' region of the YOS9 gene (SEQ ID NO:20). Plasmid pGLY7140 was linearized with SfiI and the linearized plasmid transformed into strain YGLY15820 to produce a number of strains in which the URA5 gene flanked by the lacZ repeats has been inserted into the YOS9 locus by double-crossover homologous recombination. Strain YGLY15019 was selected from the strains produced.

Strain YGLY17327 was generated by transforming plasmid pGLY6294, a KINKO plasmid encoding the LmSTT3D ORF under the control of the *P. pastoris* GAPDH promoter into strain YGLY15019 in which the LmSTT3D targets the TRP1 locus in *P. pastoris*. The strain YGLY17327 was counterselected in the presence of 5-FOA to produce strain YGLY17331 in which the URA5 gene has been lost and only the lacZ repeats remain.

Figure 6:
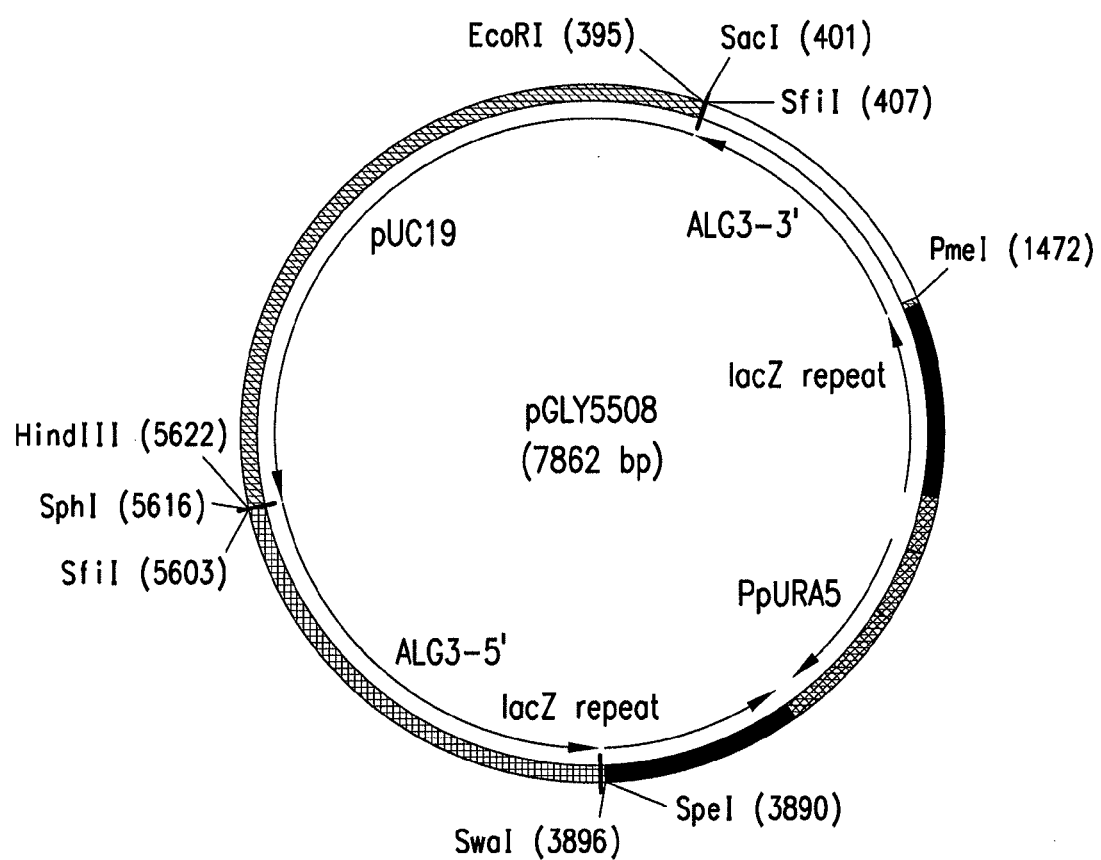
FIG. 6 shows a map of plasmid pGLY5508. The plasmid is a knock-out vector that targets the ALG3 locus comprising the *P. pastoris* URA5 gene or transcription unit (PpURA5) flanked by lacZ repeats (lacZ repeat) flanked on one side with the 5' nucleotide sequence of the *P. pastoris* ALG3 gene (PpALG3-5') and on the other side with the 3' nucleotide sequence of the *P. pastoris* ALG3 gene (PpALG3-3').

Strain YGLY18445 was generated by transforming plasmid pGLY5508 (FIG. 6), a knock-out vector that targets the ALG3 locus and contains a nucleic acid molecule comprising the *P. pastoris* URA5 gene or transcription unit flanked by nucleic acid molecules comprising lacZ repeats which in turn is flanked on one side by a nucleic acid molecule comprising a nucleotide sequence from the 5' region of the ALG3 gene (SEQ ID NO:21) and on the other side by a nucleic acid molecule comprising a nucleotide sequence from the 3' region of the ALG3 gene (SEQ ID NO:22).

Plasmid pGLY5508 was linearized with SfiI and the linearized plasmid transformed into strain YGLY17331 to produce a number of strains in which the URA5 gene flanked by the lacZ repeats has been inserted into the ALG3 locus by double-crossover homologous recombination. Strain YGLY18445 was selected from the strains produced.

Transformation of the appropriate strains disclosed herein with the above LmSTT3D expression/integration plasmid vectors was performed essentially as follows. Appropriate *Pichia pastoris* strains were grown in 50 mL YPD media (yeast extract (1%), peptone (2%), and dextrose (2%)) overnight to an OD of about 0.2 to 6. After incubation on ice for 30 minutes, cells were pelleted by centrifugation at 2500-3000 rpm for five minutes. Media was removed and the cells washed three times with ice cold sterile 1 M sorbitol before resuspension in 0.5 mL ice cold sterile 1 M sorbitol. Ten µL linearized DNA (5-20 µg) and 100 µL cell suspension was combined in an electroporation cuvette and incubated for 5 minutes on ice. Electroporation was in a Bio-Rad GenePulser Xcell following the preset *Pichia pastoris* protocol (2 kV, 25 µF, 200Ω), immediately followed by the addition of 1 mL YPDS recovery media (YPD media plus 1 M sorbitol). The transformed cells were allowed to recover for four hours to overnight at room temperature (24° C.) before plating the cells on selective media.

Strain YGLY18445 was then transformed with pGLY6301, which encodes the LmSTT3D under the control of the inducible AOX1 promoter, or pGLY6299, which encodes the LmSTT3A under the control of the inducible AOX1 promoter as described above to produce strains YGLY28158 and YGLY20228, respectively, as described in Example 3.

EXAMPLE 3

Integration/expression plasmid pGLY6299, which comprises the expression cassette in which the ORF encoding the LmSTT3A is operably-linked to the inducible PpAOX1 promoter, or pGLY6301, which comprises the expression cassette in which the ORF encoding the LmSTT3D is operably-linked to the inducible PpAOX1 promoter, were each linearized with SpeI, and the linearized plasmids transformed into *Pichia pastoris* strain YGLY18445 to produce strains YGLY20228 and YGLY28158, respectively, as shown in Table 1. Transformations were performed essentially as described in Example 2.

TABLE 1

| | | | | |
|---|---|---|---|---|
| | | N-Glycan Occupancy | | |
| Strain | ALG3 | YOS9 | LmSTT3 | N-glycan (mol %) |
| YGLY14401 | WT | WT | None | 79.3 |
| YGLY18445 | Knock-out | Knock-out | GAPDHp-LmSTT3D | 41.8 |
| YGLY20228 | Knock-out | Knock-out | GAPDHp-LmSTT3D AOX1p-LmSTT3A | 81.8 |
| YGLY28158 | Knock-out | Knock-out | GAPDHp-LmSTT3D AOX1p-LmSTT3D | 95.0 |

Table 1 shows the percent N-glycan site occupancy of anti-RSV antibody compositions obtained from strains YGLY18445, YGLY20228, and YGLY28158 in which the ORFs of PpYOS9 and PpALG3 are deleted, and the LmSTT3D is under the control of the constitutive GAPDH promoter. Strain YGLY20228 includes LmSTT3A under the control of the inducible AOX1 promoter and strain YGLY28158 includes an additional copy of LmSTT3D but under the control of the inducible AOX1 promoter.

TABLE 2

| | | | | | | | | | |
|---|---|---|---|---|---|---|---|---|---|
| | | | | Comparison of N-glycans (Complex, Man5, and hybrids) | | | | | |
| Strain | YOS9 | ALG3 | LmSTT3 | % G0 | % G1 | % G2 | % Man5 | % Gal GN M5 | % Gal GN GN M5 |
| YGLY14401 | WT | WT | None | 53.8 | 22.4 | 4.7 | 13.6 | | 5.2 |
| YGLY20228 | Knock-out | Knock-out | GADHp-LmSTT3D AOX1p-LmSTT3A | 57.0 | 24.7 | 1.3 | <1.0 | | <3.4 |

G0—GlcNAc$_2$Man$_3$GlcNAc$_2$
G1—GalGlcNAc$_2$Man$_3$GlcNAc$_2$
G2—Gal2GlcNAc$_2$Man$_3$GlcNAc$_2$
Man5—Man$_5$GlcNAc$_2$ (GS 2.0 produced in YGLY14401)
Hybrid (GNM5 and/or GalGNM5)—GlcNAcMan$_5$GlcNAc$_2$ and/or GalGlcNAcMan$_5$GlcNAc$_2$ in which the Man$_5$GlcNAc$_2$ is GS 2.0.
% is mole %

Table 2 shows a comparison of N-glycans of anti-RSV antibody compositions obtained from the strain YGLY14401 and strain YGLY20228. Strain YGLY14401 does not include an expression cassette encoding the LmSTT3D and LmSTT3A whereas strain YGLY20228 includes the LmSTT3D under the control of the constitutive GAPDH promoter and the LmSTT3A under the control of the inducible AOX1 promoter, and PpYOS9 ORF and PpALG3 ORF are deleted. While strain YGLY20228 is expected to produce Man$_5$GlcNAc$_2$ (GS 1.3) N-glycans, it is expected to produce little if any Man$_5$GlcNAc$_2$ (GS 2.0) N-glycans because the ALG3 disruption prevents the formation of lipid-linked structures that can be transformed by α1,2-mannosidase into Man$_5$GlcNAc$_2$ (GS 2.0) after transferred to an N-linked glycosylation site in a glycoprotein (See FIG. 17 for the structures of GS 2.0 and GS 1.3). The figure shows that YGLY20228 produced little or no detectable Man$_5$GlcNAc$_2$ (GS 2.0) N-glycans. However, the N-glycans in the antibody composition obtained from YGLY20228 included about 4.5 mole % each of M3 (GS 2.1) and M4 N-glycans (GS 1.3 less one alpha1,2-linked mannose), 1.5 mole % GS 3.1 plus 1 glucose linked to the terminus of the 1,3 arm, and 2.9 mole % GS 3.1 plus 2 glucose molecules linked to the terminus of the 1,3 arm.

EXAMPLE 4

Figure 7A:
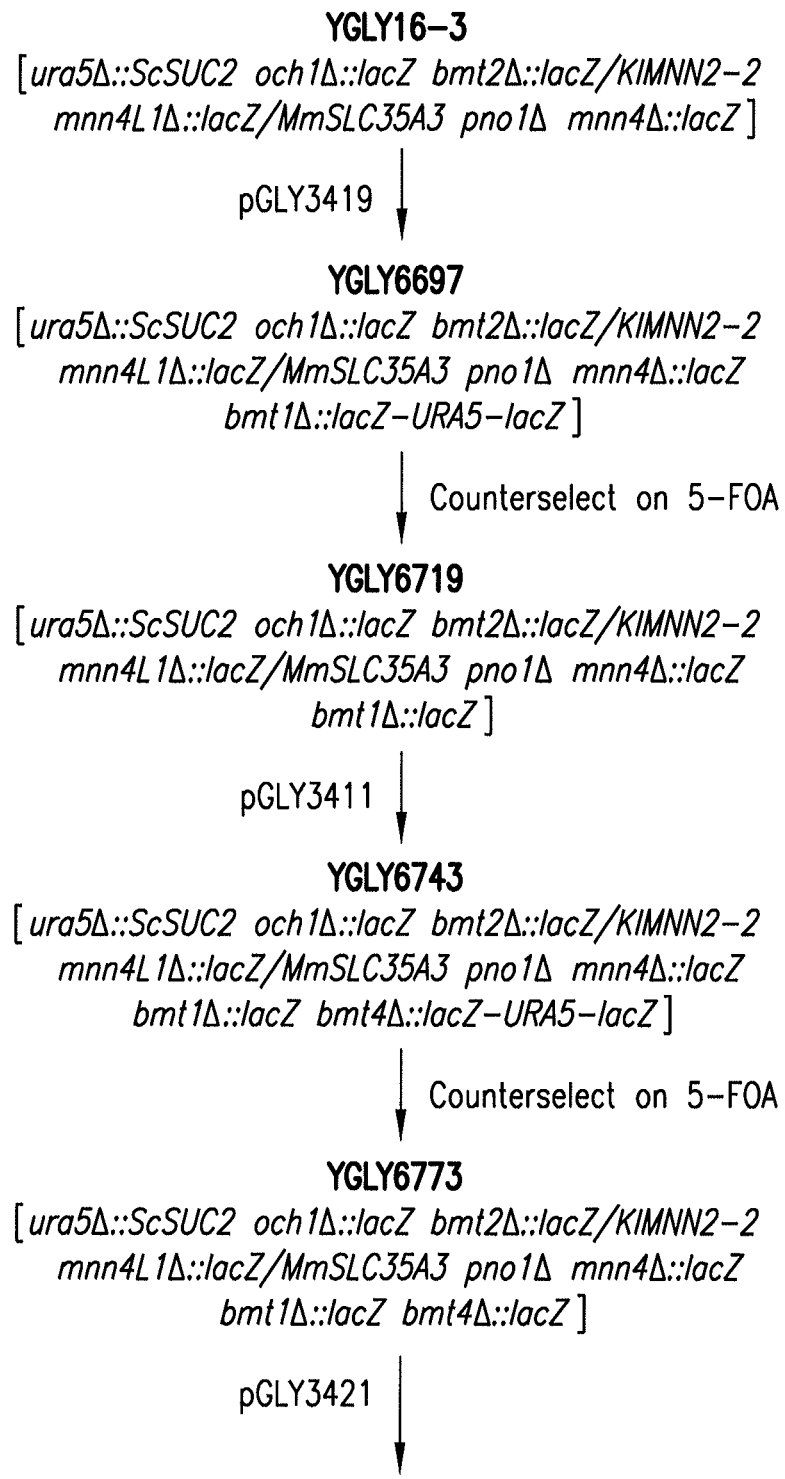
FIG. 7 A-E shows the genealogy of ALG3-engineered *P. pastoris* strains (GS 2.1) beginning from wild-type strain NRRL-Y11430. These strains are capable of producing glycoproteins having paucimannose N-glycans.
Figure 7B:
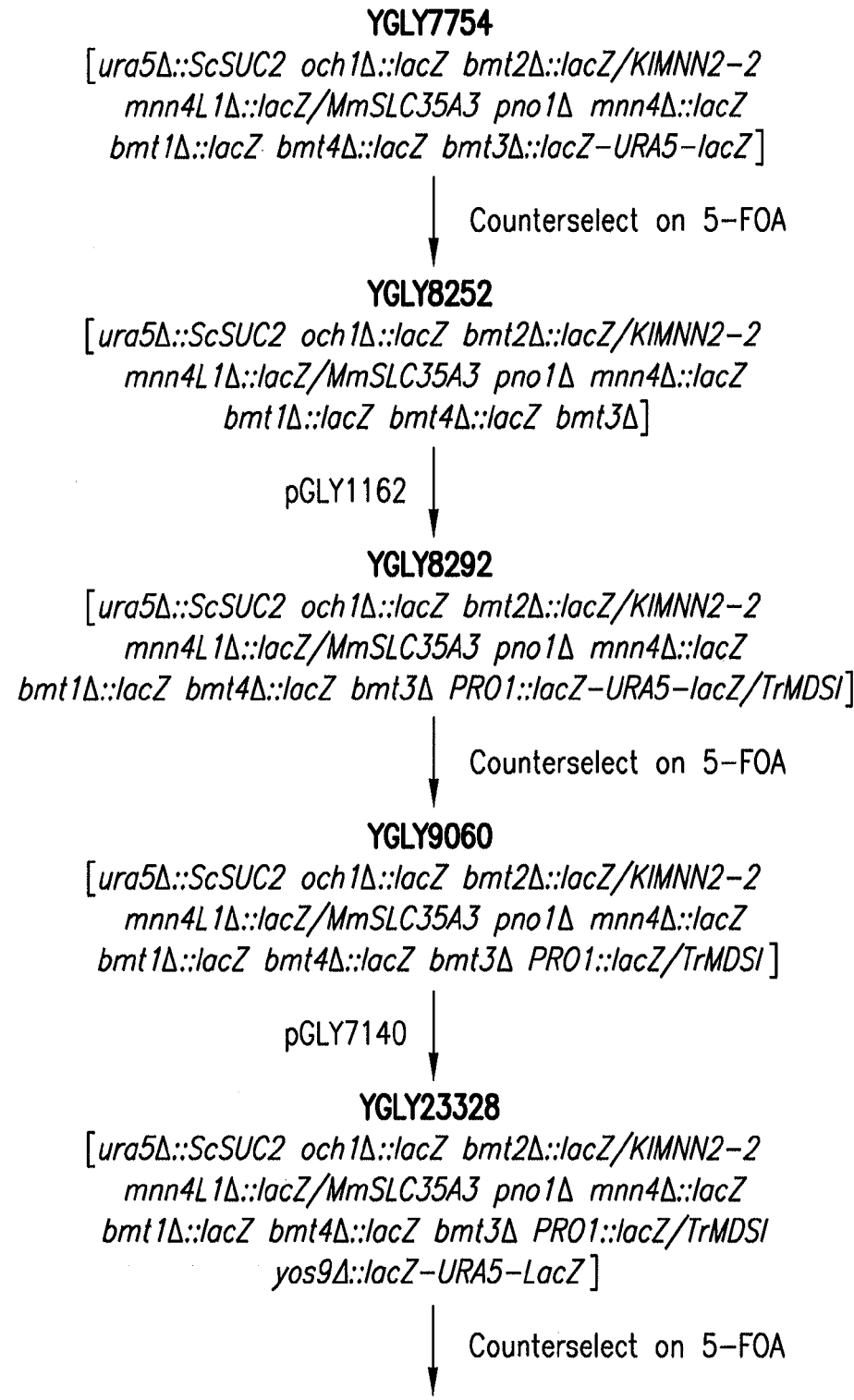
Figure 7C:
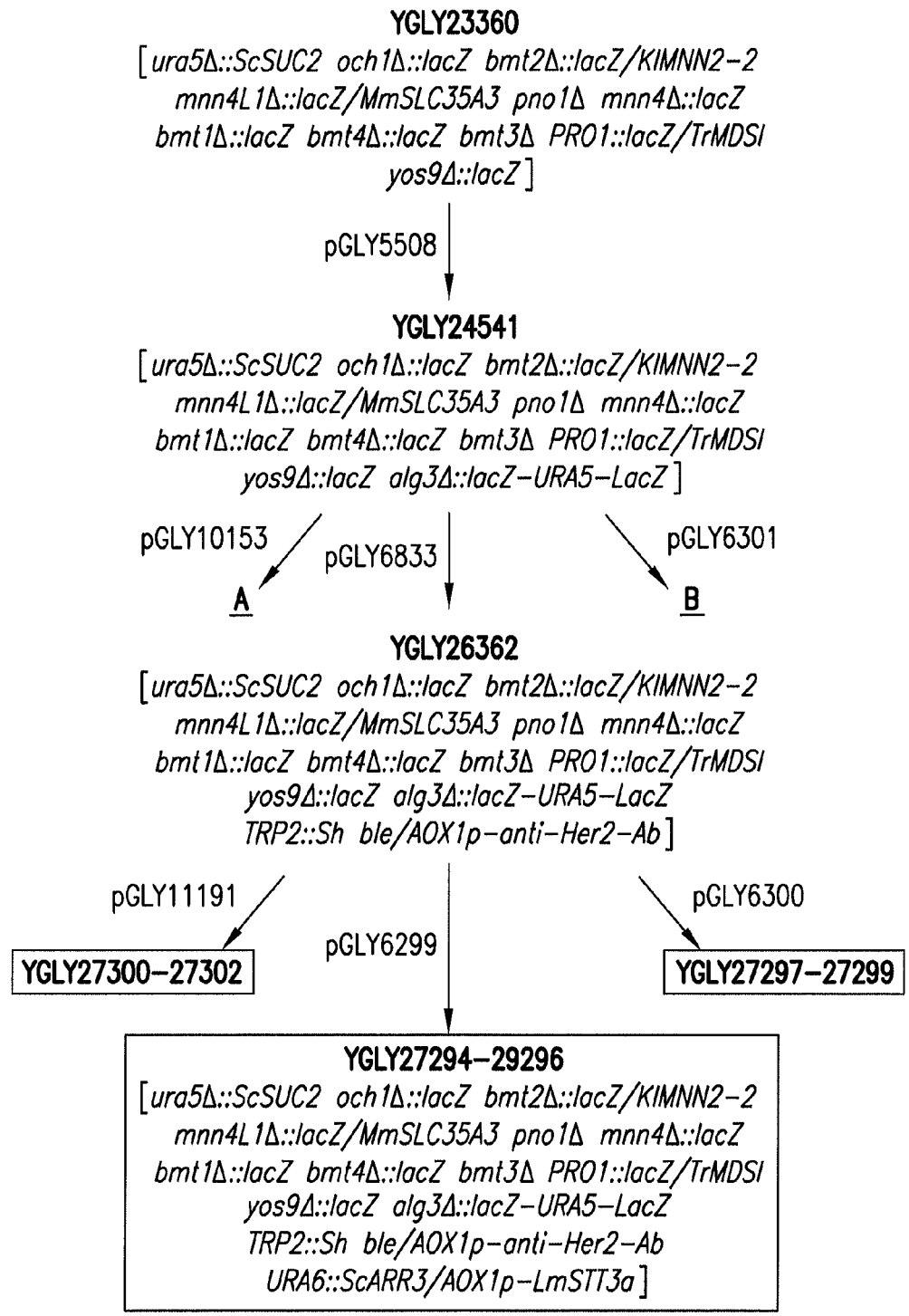

A strain capable of producing the paucimannose Man$_3$GlcNAc$_2$ (GS 2.1) structure was constructed to be used in an evaluation of the yield and quality of the N-glycosylation of an antibody expressed in the strain in the presence of various combinations of LmSTT oligosaccharyltransferases. The strain was designated YGLY24541. Its construction is illustrated schematically in FIG. 7 A-E. Briefly, the strain was constructed as follows.

Figure 8:
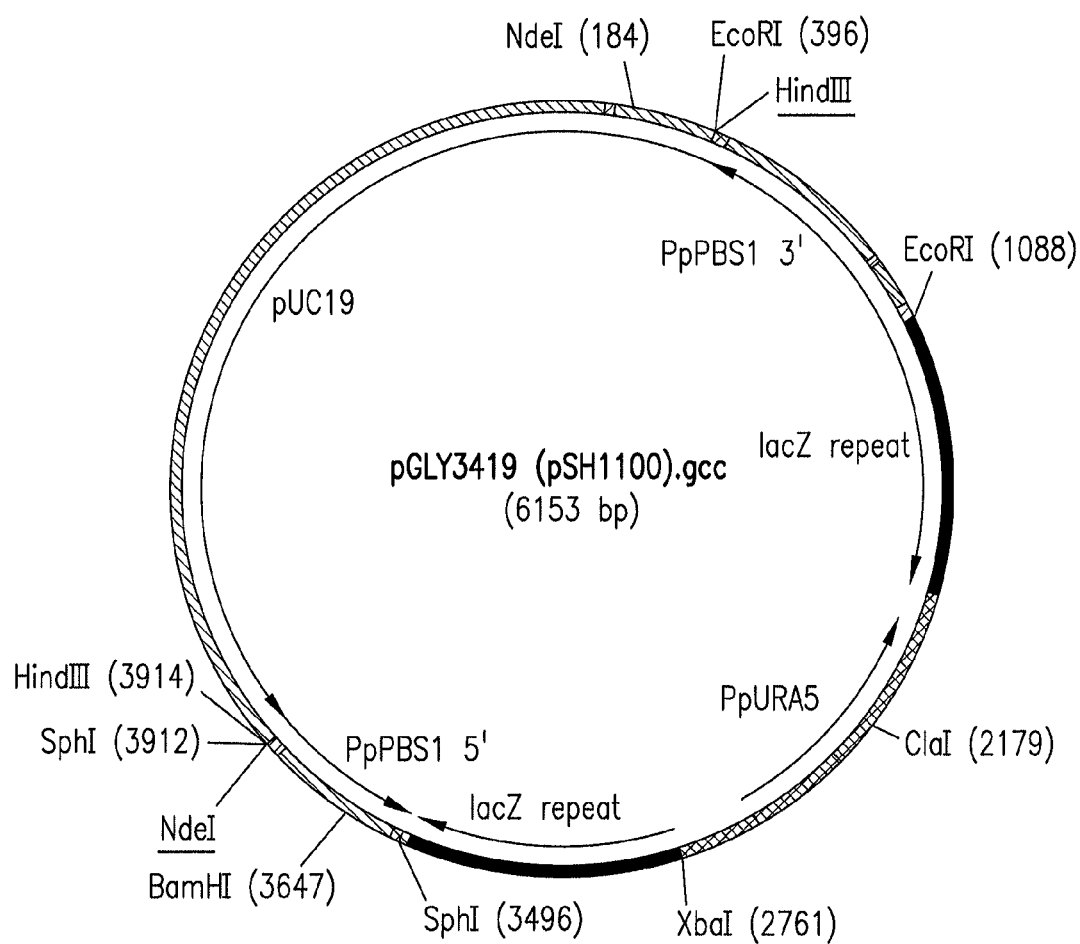
FIG. 8 shows a map of plasmid pGLY3419 (pSH1110). Plasmid pGLY3430 (pSH1115) is an integration vector that contains an expression cassette comprising the *P. pastoris* URA5 gene or transcription unit (PpURA5) flanked by lacZ repeats (lacZ repeat) flanked on one side with the 5' nucleotide sequence of the *P. pastoris* BMT1 gene (PBS 1 5') and on the other side with the 3' nucleotide sequence of the *P. pastoris* BMT1 gene (PBS 1 3').

Construction of beginning strain YGLY16-3 is described in detail in Example 2 of Published International Application No. WO2011106389 and which is incorporated herein by reference. Plasmid pGLY3419 (FIG. 8) is an integration vector that contains the expression cassette comprising the P. pastoris URA5 gene flanked by lacZ repeats flanked on one side with the 5' nucleotide sequence of the P. pastoris BMT1 gene (SEQ ID NO:23) and on the other side with the 3' nucleotide sequence of the P. pastoris BMT1 gene (SEQ ID NO:24). Plasmid pGLY3419 was linearized and the linearized plasmid transformed into strain YGLY16-3 to produce a number of strains in which the URA5 expression cassette has been inserted into the BMT4 locus by double-crossover homologous recombination. The strain YGLY6697 was selected from the strains produced, and counterselected in the presence of 5-FOA to produce strain YGLY6719 in which the URA5 gene has been lost and only the lacZ repeats remain. The strain has disruptions of the BMT2 and BMT1 genes.

Figure 9:
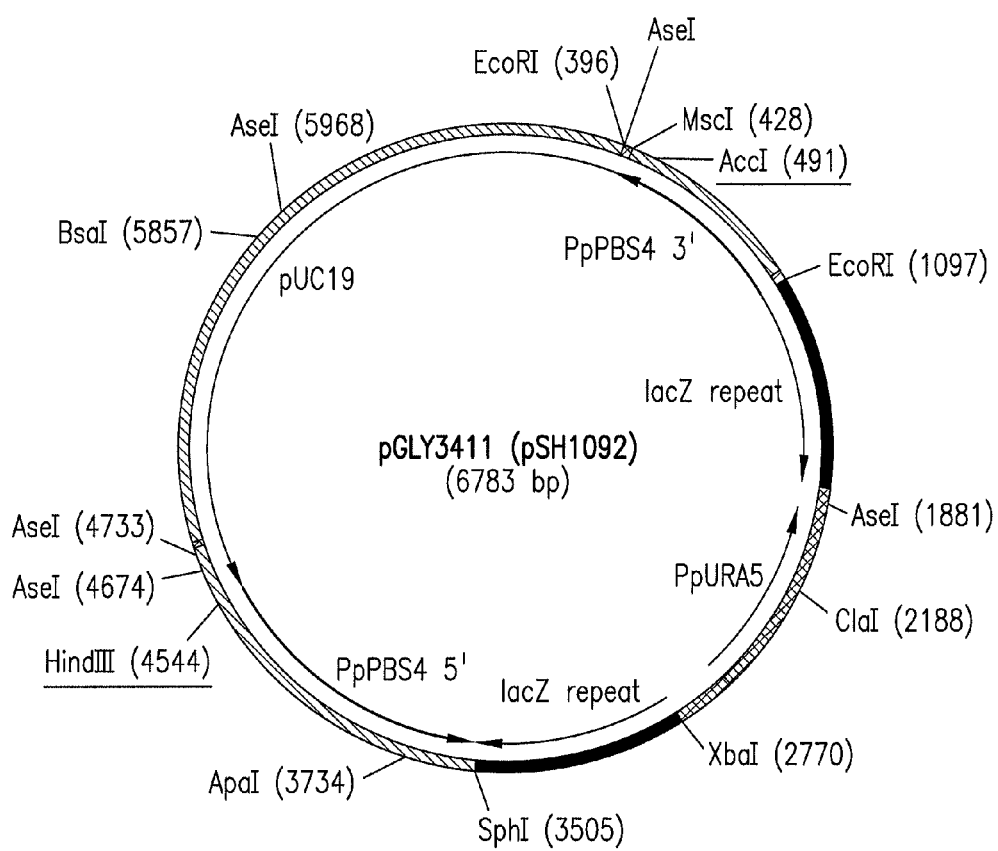
FIG. 9 shows a map of plasmid pGLY3411 (pSH1092). Plasmid pGLY3411 (pSH1092) is an integration vector that contains the expression cassette comprising the *P. pastoris* URA5 gene or transcription unit (PpURA5) flanked by lacZ repeats (lacZ repeat) flanked on one side with the 5' nucleotide sequence of the *P. pastoris* BMT4 gene (PpPBS4 5') and on the other side with the 3' nucleotide sequence of the *P. pastoris* BMT4 gene (PpPBS4 3').

Plasmid pGLY3411 (FIG. 9) is an integration vector that contains the expression cassette comprising the P. pastoris URA5 gene flanked by lacZ repeats flanked on one side with the 5' nucleotide sequence of the P. pastoris BMT4 gene (SEQ ID NO:25) and on the other side with the 3' nucleotide sequence of the P. pastoris BMT4 gene (SEQ ID NO:26). Plasmid pGLY3411 was linearized and the linearized plasmid transformed into strain YGLY6719 to produce a number of strains in which the URA5 expression cassette has been inserted into the BMT4 locus by double-crossover homologous recombination. The strain YGLY6743 was selected from the strains produced, and counterselcted in the presence of 5-FOA to produce strain YGLY6773 in which the URA5 gene has been lost and only the lacZ repeats remain. The strain has disruptions of the BMT2, BMT1, and BMT4 genes.

Figure 10:
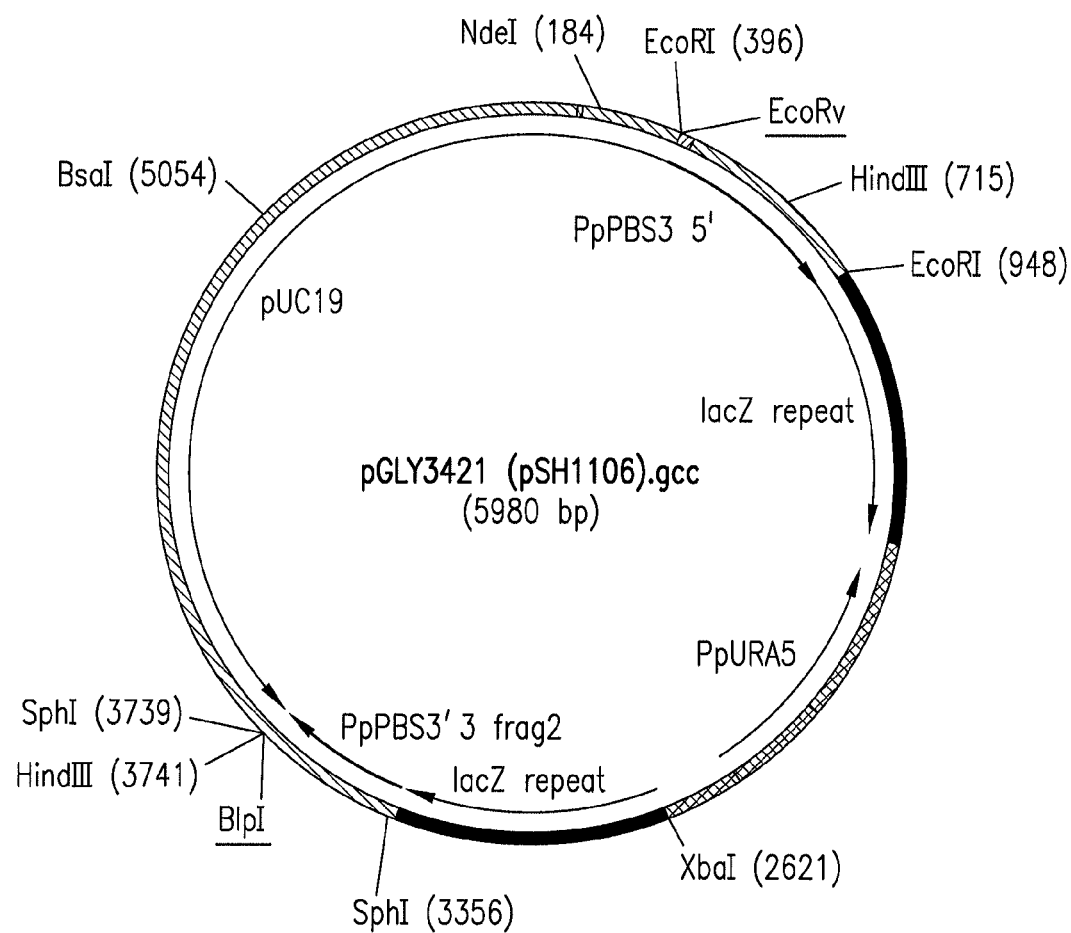
FIG. 10 shows a map of plasmid pGLY3421 (pSH1106). Plasmid pGLY4472 (pSH1186) contains an expression cassette comprising the *P. pastoris* URA5 gene or transcription unit (PpURA5) flanked by lacZ repeats (lacZ repeat) flanked on one side with the 5' nucleotide sequence of the *P. pastoris* BMT3 gene (PpPBS3 5') and on the other side with the 3' nucleotide sequence of the *P. pastoris* BMT3 gene (PpPBS3 3').

Plasmid pGLY3421 (FIG. 10) is an integration vector that contains the expression cassette comprising the P. pastoris URA5 gene flanked by lacZ repeats flanked on one side with the 5' nucleotide sequence of the P. pastoris BMT3 gene (SEQ ID NO:27) and on the other side with the 3' nucleotide sequence of the P. pastoris BMT3 gene (SEQ ID NO:28). Plasmid pGLY3421 was linearized and the linearized plasmid transformed into strain YGLY6733 to produce a number of strains in which the URA5 expression cassette has been inserted into the BMT4 locus by double-crossover homologous recombination. The strain YGLY7754 was selected from the strains produced, and counterselcted in the presence of 5-FOA to produce strain YGLY8252 in which the URA5 gene has been lost and only the lacZ repeats remain. The strain has disruptions of the BMT2, BMT1, BMT4, and BMT3 genes.

Figure 11:
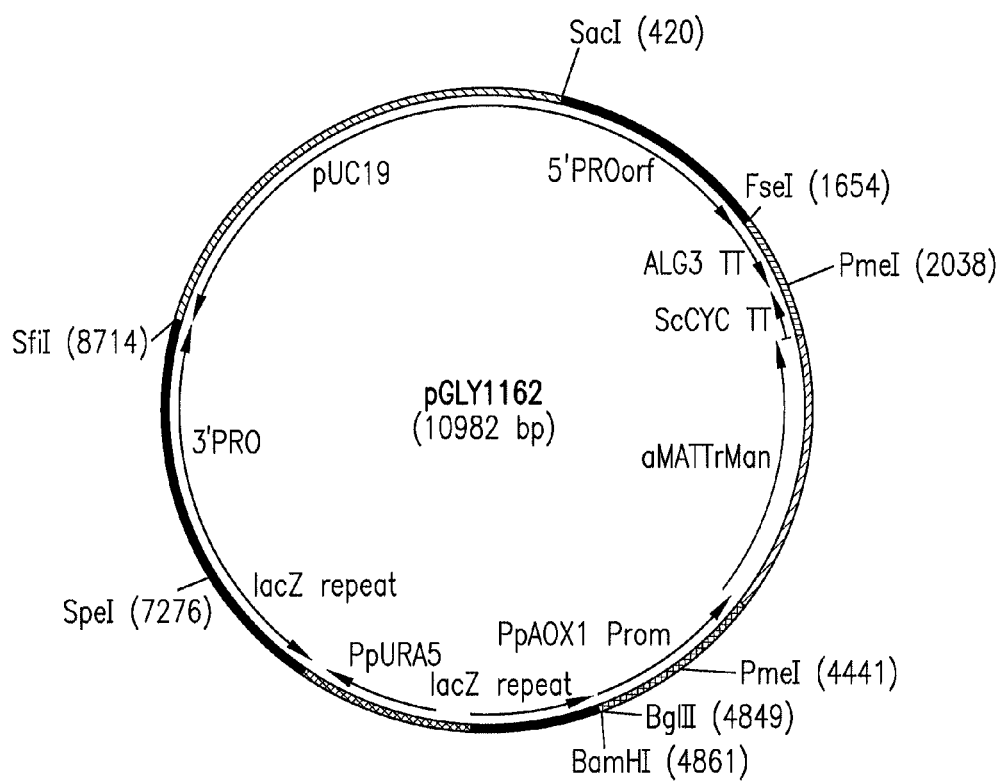
FIG. 11 shows a map of plasmid pGLY1162 cassettes encoding the *T. reesei* α-1,2-mannosidase catalytic domain fused at the N-terminus to *S. cerevisiae* αMATpre signal peptide (aMATTrMan) to target the chimeric protein to the secretory pathway and secretion from the cell.

Plasmid pGLY1162 (FIG. 11) is a KINKO integration vector that targets the PRO1 locus without disrupting expression of the locus and contains expression cassettes encoding the T. reesei α-1,2-mannosidase catalytic domain fused at the N-terminus to S. cerevisiae αMATpre signal peptide (aMATTrMan) to target the chimeric protein to the secretory pathway and secretion from the cell. The expression cassette encoding the aMATTrMan comprises a nucleic acid molecule encoding the T. reesei catalytic domain (SEQ ID NO:29) fused at the 5' end to a nucleic acid molecule (SEQ ID NO:33) encoding the S. cerevisiae αMATpre signal peptide, which is operably linked at the 5' end to a nucleic acid molecule comprising the P. pastoris AOX1 promoter and at the 3' end to a nucleic acid molecule comprising the S. cerevisiae CYC transcription termination sequence. The cassette is flanked on one side by a nucleic acid molecule comprising a nucleotide sequence from the 5' region and complete ORF of the PRO1 gene (SEQ ID NO:30) followed by a P. pastoris ALG3 termination sequence and on the other side by a nucleic acid molecule comprising a nucleotide sequence from the 3' region of the PRO1 gene (SEQ ID NO:31).

Plasmid pGLY1162 was linearized and the linearized plasmid transformed into strain YGLY8252 to produce a number of strains in which the URA5 expression cassette has been inserted into the PRO1 locus by double-crossover homologous recombination. The strain YGLY8292 was selected from the strains produced, and counterselected in the presence of 5-FOA to produce strain YGLY9060 in which the URA5 gene has been lost and only the lacZ repeats remain.

Strain YGLY9060 was transformed with plasmid pGLY7140 to produce a number of strains in which the URA5 gene flanked by the lacZ repeats has been inserted into the YOS9 locus by double-crossover homologous recombination. Strain YGLY23328 was selected from the strains produced. The strain was counterselected in the presence of 5-FOA to produce strain YGLY23360 in which the URA5 gene has been lost and only the lacZ repeats remain.

Strain YGLY24541 was generated by transforming pGLY5508 into strain YGLY23360 to produce a number of strains in which the URA5 gene flanked by the lacZ repeats has been inserted into the ALG3 locus by double-crossover homologous recombination. Strain YGLY24541 was selected from the strains produced.

EXAMPLE 5

Strain YGLY24541 produced in Example 4 was used for the construction of several strains that express an antibody to evaluate the N-glycosylation of antibodies produced in the presence of various LmSTT3 oligosaccharyltransferases. Construction of these strains is as follows.

Figure 12:
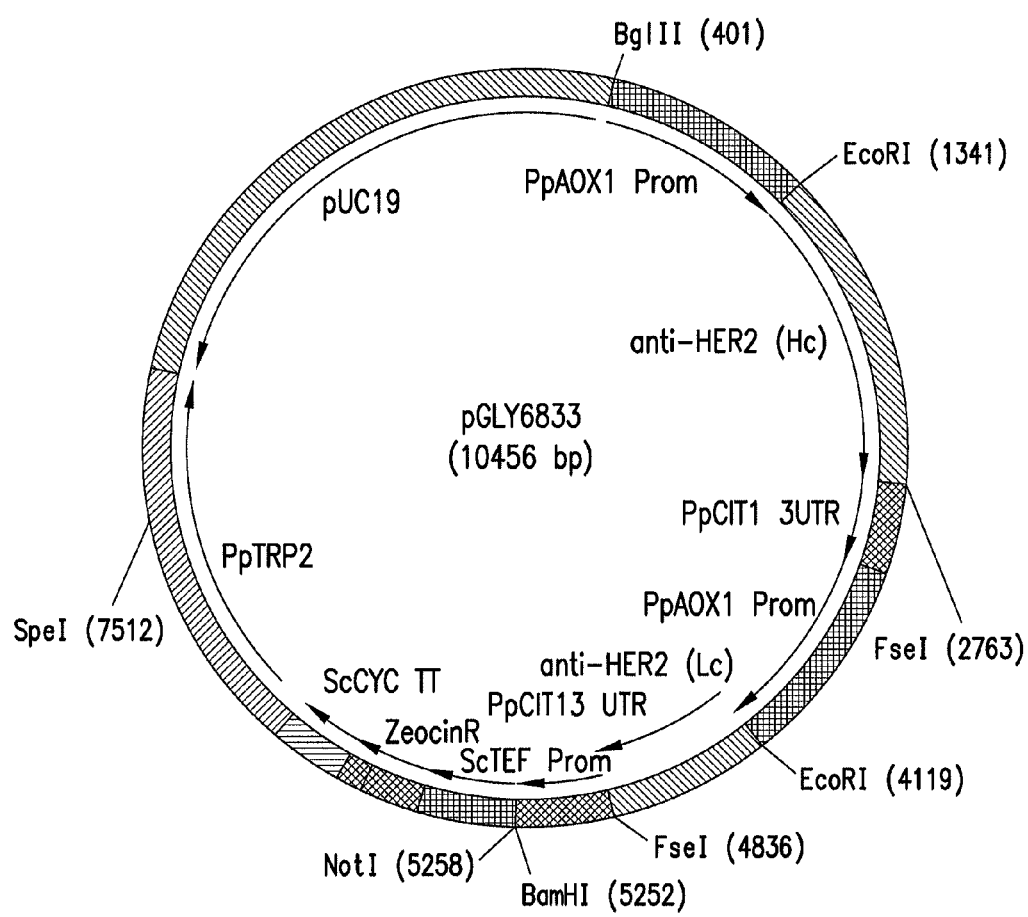
FIG. 12 shows a map of pGLY6833 encoding the light and heavy chains of an anti-Her2 antibody. The plasmid is a roll-in vector that targets the TRP2 locus. The ORFs encoding the light and heavy chains are under the control of a *P. pastoris* AOX1 promoter and the *P. pastoris* CIT1 transcription termination sequence. Selection of transformants uses zeocin resistance encoded by the zeocin resistance protein (ZeocinR) ORF under the control of the *P. pastoris* TEE1 promoter and *S. cerevisiae* CYC termination sequence.

Plasmid pGLY6833 (FIG. 12) is a roll-in integration plasmid encoding the light and heavy chains of an anti-Her2 antibody that targets the TRP2 locus in P. pastoris. The expression cassette encoding the anti-Her2 heavy chain comprises a nucleic acid molecule encoding the heavy chain ORF codon-optimized for effective expression in P. pastoris (SEQ ID NO:32) operably linked at the 5' end to a nucleic acid molecule (SEQ ID NO:33) encoding the Saccharomyces cerevisiae mating factor pre-signal sequence which in turn is fused at its N-terminus to a nucleic acid molecule that has the inducible P. pastoris AOX1 promoter sequence and at the 3' end to a nucleic acid molecule that has the P. pastoris CIT1 transcription termination sequence (SEQ ID NO:34). The expression cassette encoding the anti-Her2 light chain comprises a nucleic acid molecule encoding the light chain ORF codon-optimized for effective expression in *P. pastoris* (SEQ ID NO:35) operably linked at the 5' end to a nucleic acid molecule encoding the *Saccharomyces cerevisiae* mating factor pre-signal sequence which in turn is fused at its N-terminus to a nucleic acid molecule that has the inducible *P. pastoris* AOX1 promoter sequence and at the 3' end to a nucleic acid molecule that has the *P. pastoris* CIT1 transcription termination sequence. For selecting transformants, the plasmid comprises an expression cassette encoding the Zeocin ORF in which the nucleic acid molecule encoding the ORF (SEQ ID NO:18) is operably linked at the 5' end to a nucleic acid molecule having the *S. cerevisiae* TEF promoter sequence (SEQ ID NO:36) and at the 3' end to a nucleic acid molecule having the *S. cerevisiae* CYC transcription termination sequence. The plasmid further includes a nucleic acid molecule for targeting the TRP2 locus (SEQ ID NO:37). Plasmid pGLY6833 was transformed into strain YGLY24541 to produce a number of strains that express the anti-Her2 antibody of which strain YGLY26362 was selected.

Figure 13:
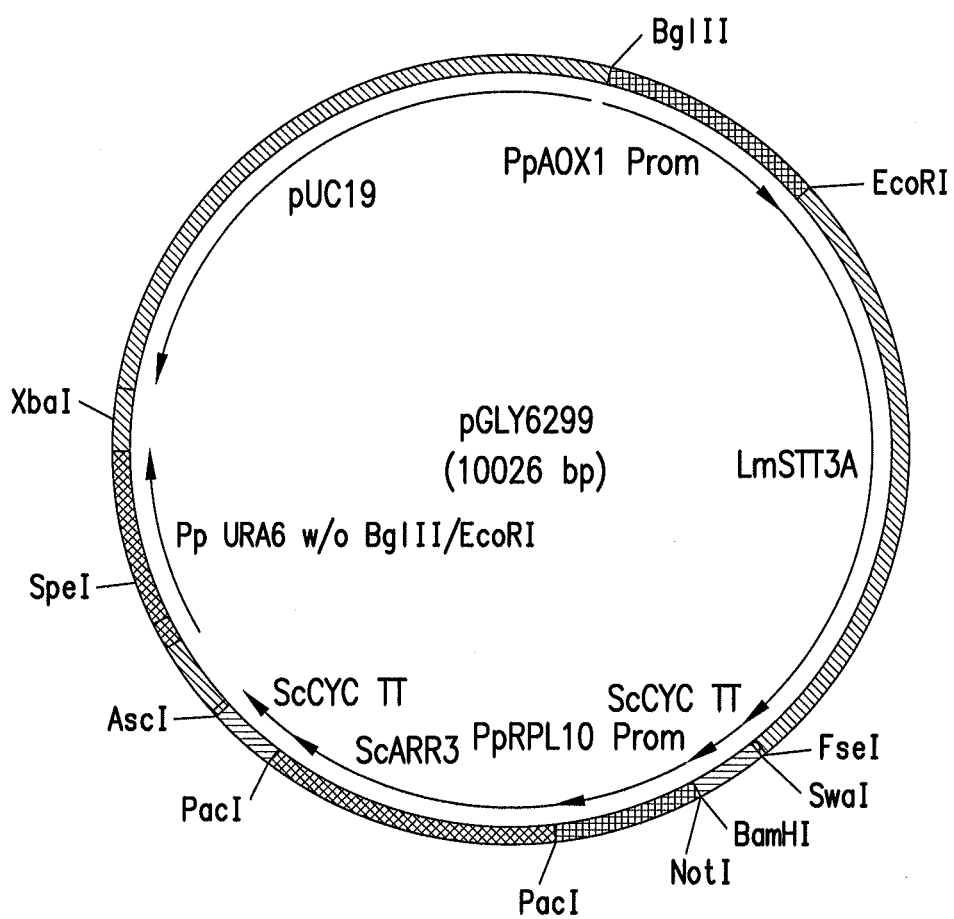
FIG. 13 shows a map of plasmid pGLY6299 encoding the LmSTT3A ORF under the control of the *Pichia pastoris* alcohol oxidase I (AOX1) promoter and *S. cerevisiae* CYC transcription termination sequence. The plasmid is a roll-in vector that targets the URA6 locus. The selection of transformants uses arsenic resistance encoded by the *S. cerevisiae* ARR3 ORF under the control of the *P. pastoris* RPL10 promoter and *S. cerevisiae* CYC transcription termination sequence.

Plasmid pGLY6299 (FIG. 13) is a roll-in integration plasmid that targets the URA6 locus in *P. pastoris*. The expression cassette encoding the LmSTT3A comprises a nucleic acid molecule encoding the LmSTT3D ORF codon-optimized for effective expression in *P. pastoris* (SEQ ID NO:38) operably linked at the 5' end to a nucleic acid molecule that has the inducible *P. pastoris* AOX1 promoter sequence and at the 3' end to a nucleic acid molecule that has the *S. cerevisiae* CYC transcription termination sequence. For selecting transformants, the plasmid comprises an expression cassette encoding the *S. cerevisiae* ARR3 ORF (SEQ ID NO:5) in which the nucleic acid molecule encoding the ORF is operably linked at the 5' end to a nucleic acid molecule having the *P. pastoris* RPL10 promoter sequence (SEQ ID NO:6) and at the 3' end to a nucleic acid molecule having the *S. cerevisiae* CYC transcription termination sequence. Plasmid pGLY6299 was transformed into strain YGLY26362 to produce a number of strains that express the anti-Her2 antibody and LmSTT3A of which strain YGLY27294-27296 was selected.

Figure 14:
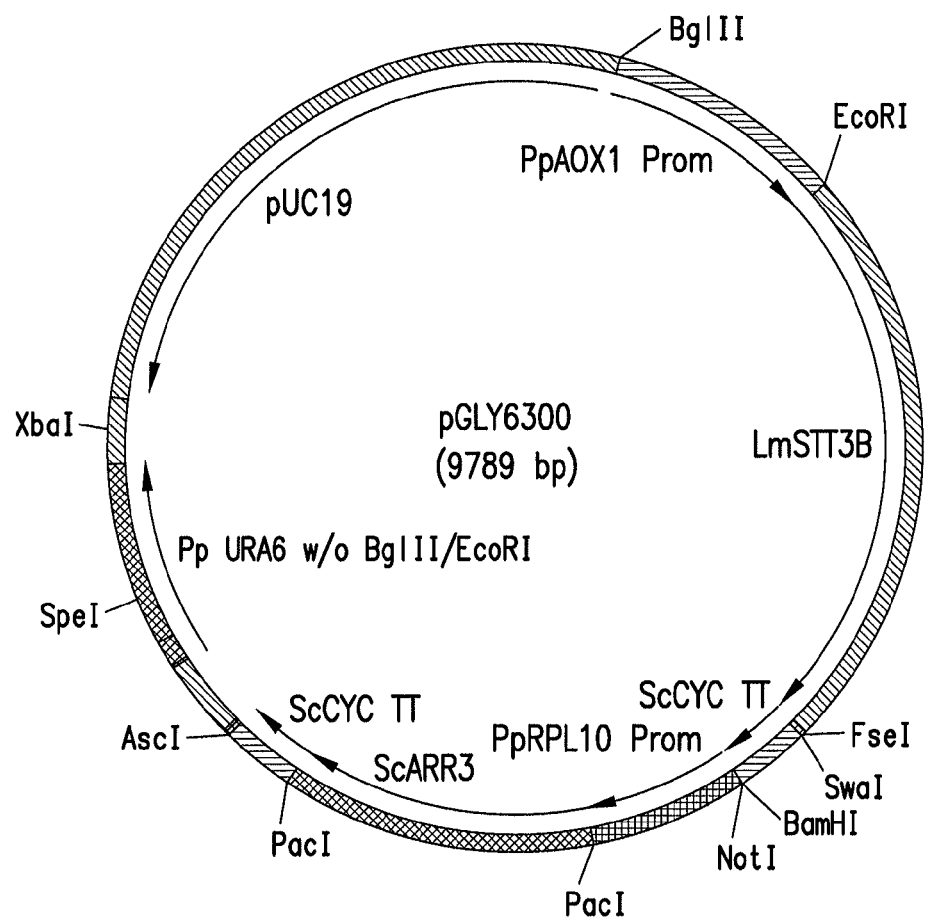
FIG. 14 shows a map of plasmid pGLY6300 encoding the LmSTT3B ORF under the control of the *Pichia pastoris* alcohol oxidase I (AOX1) promoter and *S. cerevisiae* CYC transcription termination sequence. The plasmid is a roll-in vector that targets the URA6 locus. The selection of transformants uses arsenic resistance encoded by the *S. cerevisiae* ARR3 ORF under the control of the *P. pastoris* RPL10 promoter and *S. cerevisiae* CYC transcription termination sequence.

Plasmid pGLY6300 (FIG. 14) is a roll-in integration plasmid that targets the URA6 locus in *P. pastoris*. The expression cassette encoding the LmSTT3B comprises a nucleic acid molecule encoding the LmSTT3B ORF codon-optimized for effective expression in *P. pastoris* (SEQ ID NO:39) operably linked at the 5' end to a nucleic acid molecule that has the inducible *P. pastoris* AOX1 promoter sequence and at the 3' end to a nucleic acid molecule that has the *S. cerevisiae* CYC transcription termination sequence. For selecting transformants, the plasmid comprises an expression cassette encoding the *S. cerevisiae* ARR3 ORF (SEQ ID NO:5) in which the nucleic acid molecule encoding the ORF is operably linked at the 5' end to a nucleic acid molecule having the *P. pastoris* RPL10 promoter sequence (SEQ ID NO:6) and at the 3' end to a nucleic acid molecule having the *S. cerevisiae* CYC transcription termination sequence. Plasmid pGLY6300 was transformed into strain YGLY26362 to produce a number of strains that express the anti-Her2 antibody and LmSTT3B of which strain YGLY27297-27299 was selected.

Figure 15:
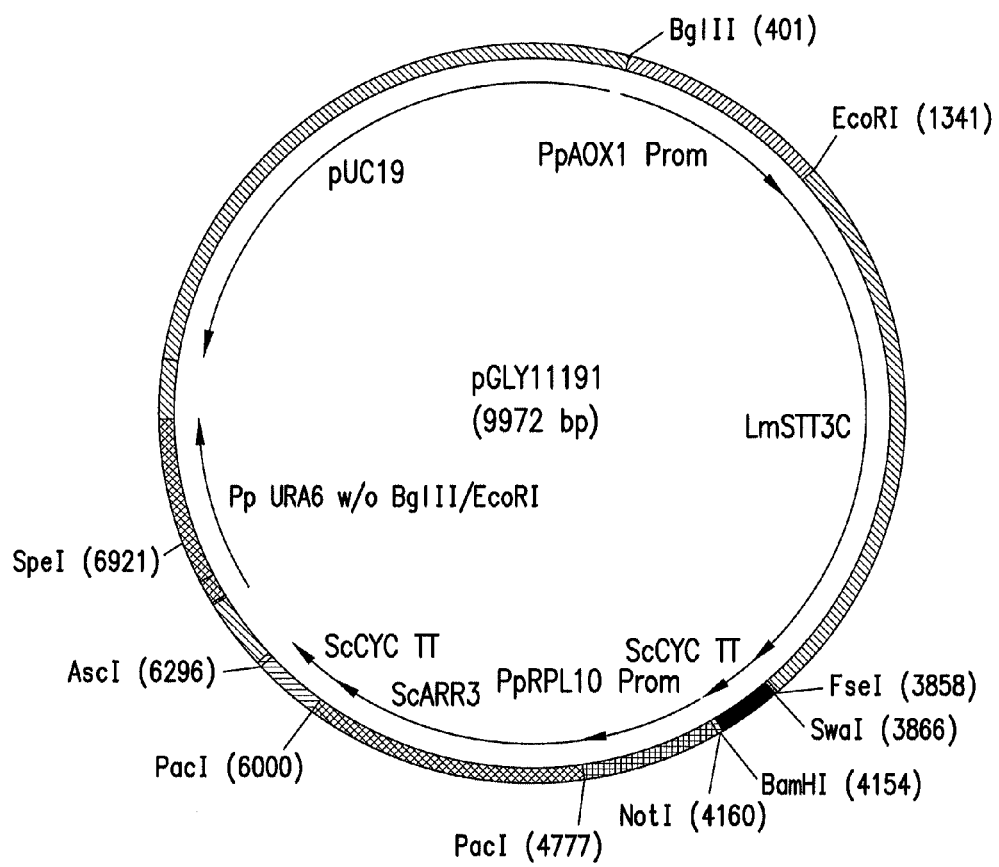
FIG. 15 shows a map of plasmid pGLY11191 encoding the LmSTT3C ORF under the control of the *Pichia pastoris* alcohol oxidase I (AOX1) promoter and *S. cerevisiae* CYC transcription termination sequence. The plasmid is a roll-in vector that targets the URA6 locus. The selection of transformants uses arsenic resistance encoded by the *S. cerevisiae* ARR3 ORF under the control of the *P. pastoris* RPL10 promoter and *S. cerevisiae* CYC transcription termination sequence.

Plasmid pGLY11191 (FIG. 15) is a roll-in integration plasmid that targets the URA6 locus in *P. pastoris*. The expression cassette encoding the LmSTT3C comprises a nucleic acid molecule encoding the LmSTT3C ORF codon-optimized for effective expression in *P. pastoris* (SEQ ID NO:40) operably linked at the 5' end to a nucleic acid molecule that has the inducible *P. pastoris* AOX1 promoter sequence and at the 3' end to a nucleic acid molecule that has the *S. cerevisiae* CYC transcription termination sequence. For selecting transformants, the plasmid comprises an expression cassette encoding the *S. cerevisiae* ARR3 ORF (SEQ ID NO:5) in which the nucleic acid molecule encoding the ORF is operably linked at the 5' end to a nucleic acid molecule having the *P. pastoris* RPL10 promoter sequence (SEQ ID NO:6) and at the 3' end to a nucleic acid molecule having the *S. cerevisiae* CYC transcription termination sequence. Plasmid pGLY11191 was transformed into strain YGLY26362 to produce a number of strains that express the anti-Her2 antibody and LmSTT3C of which strain YGLY27300-27302 was selected.

Figure 16:
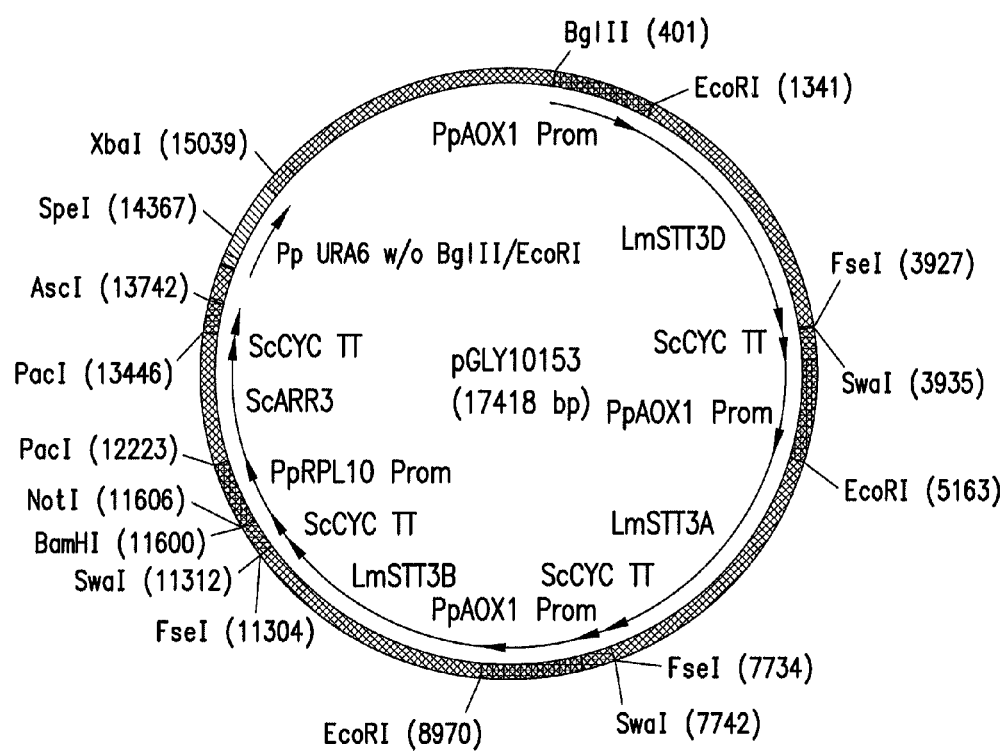
FIG. 16 shows a map of plasmid pGLY10153 encoding the LmSTT3A, LmSTT3B, and LmSTT3D ORFs under the control of the *Pichia pastoris* alcohol oxidase I (AOX1) promoter and *S. cerevisiae* CYC transcription termination sequence. The plasmid is a roll-in vector that targets the URA6 locus. The selection of transformants uses arsenic resistance encoded by the *S. cerevisiae* ARR3 ORF under the control of the *P. pastoris* RPL10 promoter and *S. cerevisiae* CYC transcription termination sequence.

Plasmid pGLY10153 (FIG. 16) is a roll-in integration plasmid that targets the URA6 locus in *P. pastoris* and encodes the LmSTT3A, LmSTT3B, and LmSTT3D ORFs, each under the control of the *Pichia pastoris* AOX1 promoter and *S. cerevisiae* CYC transcription termination sequence. For selecting transformants, the plasmid comprises an expression cassette encoding the *S. cerevisiae* ARR3 ORF in which the nucleic acid molecule encoding the ORF is operably linked at the 5' end to a nucleic acid molecule having the *P. pastoris* RPL10 promoter sequence and at the 3' end to a nucleic acid molecule having the *S. cerevisiae* CYC transcription termination sequence. Plasmid pGLY10153 was transformed into strain YGLY24541 to produce a number of strains of which strain YGLY24558 was selected. Strain YGLY24558 was transformed with plasmid pGLY6833 to produce a number of strains that express the anti-Her2 antibody and LmSTT3A, LmSTT3B, LmSTT3D of which strain YGLY26363-26364 was selected.

Strain YGLY24541 was transformed with plasmid pGLY6301 to produce a number of strains of which strain YGLY25636 was selected. This strain was transformed with plasmid pGLY6833 to produce a number of strains that express the anti-Her2 antibody and LmSTT3D of which strain YGLY26365 was selected.

Table 3 shows a comparison of N-glycan site occupancy of the anti-HER2 antibody compositions obtained from the alg strains carrying individual LmSTT3s under the control of the AOX1 promoter. LmSTT3D demonstrates that N-glycan site occupancy is improved up to 100% in the alg strain background, and LmSTT3A also improves N-glycan site occupancy significantly.

TABLE 3

N-Glycan Occupancy

| Strain | ALG3 | YOS9 | LmSTT3 | N-glycan (mol %) |
|---|---|---|---|---|
| YGLY 26362 | knock-out | knock-out | none | 16.7-22.8 |
| YGLY 27294-27296 | knock-out | knock-out | AOX1p-LmSTT3A | 70.8-74.1 |
| YGLY 27297-27299 | knock-out | knock-out | AOX1p-LmSTT3B | 25.0-28.2 |
| YGLY 27300-27302 | knock-out | knock-out | AOX1p-LmSTT3C | 13.8-14.9 |
| YGLY 26365 | knock-out | knock-out | AOX1p-LmSTT3D | 99.2-100 |
| YGLY 26363-26364 | knock-out | knock-out | AOX1p-LmSTT3 A + B + D | 99.4-100 |

Table 4 shows N-glycan analysis of anti-HER2 antibody compositions produced in the alg strains carrying individual LmSTT3s under the control of the AOX1 promoter. Predominant N-glycan structure is $Man_3GlcNAc_2$ in which Man$_5$GlcNAc$_2$ (alg3 knock-out) is converted into Man$_3$GlcNAc$_2$ by the *T. reesei* α-1,2-mannosidase chimeric enzyme comprising its catalytic domain fused at the N-terminus to *S. cerevisiae* αMATpre signal peptide (aMAT-TrMan) to target the chimeric protein to the secretory pathway and secretion from the cell.

TABLE 4

N-Glycan Occupancy

| Strain | LmSTT3 | M3 | M4 | M5 | M5 + Glc(n) |
|---|---|---|---|---|---|
| YGLY 26362 | none | 87% | 1% | 4% | 8% |
| YGLY 27294-27296 | AOX1p-LmSTT3A | 83~86% | 1-3% | 5-6% | 7-9% |
| YGLY 27297-27299 | AOX1p-LmSTT3B | 84~88% | 1% | 3-4% | 7-10% |
| YGLY 27300-27302 | AOX1p-LmSTT3C | 83~89% | 1-2% | 4-5% | 5-11% |
| YGLY 26365 | AOX1p-LmSTT3D | 90% | 3% | 2% | 5% |

M3—Man$_3$GlcNAc$_2$ (GS 2.1)
M4—Man$_4$GlcNAc$_2$
M5—Man$_5$GlcNAc$_2$ (GS 1.3)
M5 + Glc(n)—Glc$_n$Man$_5$GlcNAc$_2$

Microchip CE-SDS sample preparation was as follows. IgG sample (100-200 μg) was concentrated to about 100 μL and buffer exchanged with 100 mM Tris-HCl pH 9.0 with 1% SDS. Then the sample along with 2 μL of 10 kDa internal standard provided by Beckman was reduced by addition of 5 μL beta mercaptoethanol and boiled for 3 minutes.

Separation Methods by Labchip GXII (Caliper Life Science, CA) was as follows.

The reduced sample was resolved over a bare-fused silica capillary (30.2 cm, 50 μm I.D.) according to the method recommended by manufacturer for reduced IgG in the reverse polarity orientation with a detection window of 20.2 cm from the inlet. For each cycle, the capillary is first preconditioned with 0.1 N NaOH, 0.1 N HCl, HPLC graded water and SDSMW Gel Buffer, provided by manufacturer. Samples are electrokinetically introduced by applying voltage at 5 kV for 20 seconds. Electrophoresis is performed at constant voltage, with an applied field strength of 497 volts/cm with capillary temperature maintained at 25° C. using recirculating liquid coolant. The current generated is approximately 27 μAmps. The peak detection was recorded at 2 Hz at 220 nm of 10 nm bandwidth. The occupancy was determined by percentage of the corrected peak areas corresponding to the glycosylated heavy chain.

N-glycosylation Occupancy analysis was as follows.

Antibody sample (5 μL) at approximately 1-2 mg/mL was added to 7 μL of sample buffer provided with HT Protein Express Labchip® Kit supplemented with 50 mM 2-mercaptoethanol (Sigma-Aldrich; St. Louis, Mo., USA). The sample mixture was then incubated at 75 C for 15 minutes. Prior to microchip analysis, deionized HPLC grade water (35 μL) was added to the sample mixture and added onto the instrument for size separation. The N-glycosylation occupancy was determined by percentage of the corrected peak areas corresponding to the glycosylated heavy chain (GHC). The ratio of heavy and light chains (H:L) was calculated from total corrected peak area of GHC and nonglycosylated heavy (NGHC) against that of light chain. The impurity was reported as the total corrected peak area of protein bands that do not belong to GHC, NGHC or light chain.

The DasGip Protocol for growing the recombinant host cells is substantially as follows.

The inoculum seed flasks were inoculated from yeast patches (isolated from a single colony) on agar plates into 0.1 L of 4% BSGY in a 0.5-L baffled flask. Seed flasks were grown at 180 rpm and 24° C. (Innova 44, New Brunswick Scientific) for 48 hours. Cultivations were done in 1 L (fedbatch-pro, DASGIP BioTools) bioreactors. Vessels were charged with 0.54 L of 0.22 μm filtered 4% BSGY media and autoclaved at 121° C. for 45 minutes. After sterilization and cooling; the aeration, agitation and temperatures were set to 0.7 vvm, 400 rpm and 24° C. respectively. The pH was adjusted to and controlled at 6.5 using 30% ammonium hydroxide. Inoculation of a prepared bioreactor occurred aseptically with 60 mL from a seed flask. Agitation was ramped to maintain 20% dissolved oxygen (DO) saturation. After the initial glycerol charge was consumed, denoted by a sharp increase in the dissolved oxygen, a 50% w/w glycerol solution containing 5 mg/L biotin and 32.3 mg/L PMTi-4 was triggered to feed at 3.68 mL/hr for eight hours. During the glycerol fed-batch phase 0.375 mL of PTM2 salts were injected manually. Completion of the glycerol fed-batch was followed by a 0.5 hour starvation period and initiation of the induction phase. A continuous feed of a 50% v/v methanol solution containing 2.5 mg/L biotin and 6.25 mL/L PTM2 salts was started at a flat rate of 2.16 mL/hour. Injections of 0.25 mL of 1.9 mg/mL PMTi-4 (in methanol) were added after each 24 hours of induction. In general, individual fermentations were harvested within 36-110 hours of induction. The culture broth was clarified by centrifugation (Sorvall Evolution RC, Thermo Scientific) at 8500 rpm for 40 min and the resulting supernatant was submitted for purification.

| Component | Concentration (g/L) |
|---|---|
| 4% BSGY with 100 mM Sorbitol | |
| KH$_2$PO$_4$ (monobasic) | 11.9 |
| K$_2$HPO$_4$ (dibasic) | 2.5 |
| Sorbitol | 18.2 |
| Yeast Extract | 10 |
| Soytone | 20 |
| Glycerol | 40 |
| YNB | 13.4 |
| Biotin | 20 (ml/L) |
| Anti-foam | 8 drops/L* |
| Solution to be autoclaved once made | |
| PTM2 Salts | |
| CuSO$_4$—5H$_2$O | 1.50 |
| NaI | 0.08 |
| MnSO$_4$—H$_2$O | 1.81 |
| H$_3$BO$_4$ | 0.02 |
| FeSO$_4$—7H$_2$O | 6.50 |
| ZnCl$_2$ | 2.00 |
| CoCl$_2$—6H$_2$O | 0.50 |
| Na$_2$MoO$_4$—2H$_2$O | 0.20 |
| Biotin (dry stock) | 0.20 |
| 98% H$_2$SO$_4$ | 5 mL/L |

Dissolve in 80% of the desired total volume of DI water.
Once dissolved make up to final total volume with DI water
Filter under vacuum through 0.22 micron filter into sterile bottle.
Label with Solution Name, Batch Number, and Date. Store at 4° C.

PMTi-4 is a PMT inhibitor disclosed in U.S. Published Application No. 20110076721 as Example 4 compound. PMTi-4 has the structure

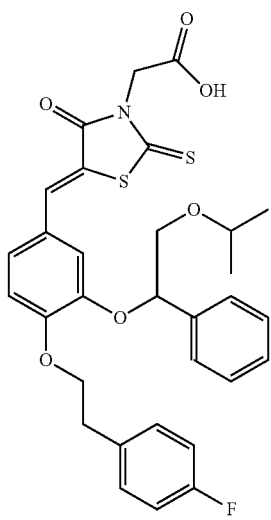

EXAMPLE 6

This example describes construction of strain YGLY29365. Strain YGLY29365 is capable of producing a glycosylated insulin analogue precursor with GS2.1 (Man$_3$GlcNAc$_2$) N-glycans at position B(−2) and position B28. The glycosylated insulin precursor can be processed in vitro to glycosylated insulin analog 210-2-B. 210-B-2 is a heterodimer comprising a native insulin A-chain and a B-chain (des(B30)) having the amino acid sequence N*GTFVNQHLCGSHLVEALYLVCGERGFFYTN*K (SEQ ID NO:56) wherein the Asn residues N* at positions 1 and 31 (B-2 & B28) are each covalently linked in a 131 linkage to a Man$_3$GlcNAc$_2$ (paucimannose) N-glycan.

The construction of strain YGLY29365 is the product of numerous genetic modifications beginning with the strain YGLY9060.

Strain YGLY24542 was generated by transforming plasmid pGLY5508, a knock-out vector that targets the ALG3 locus and contains a nucleic acid molecule comprising the P. pastoris URA5 gene or transcription unit flanked by nucleic acid molecules comprising lacZ repeats which in turn is flanked on one side by a nucleic acid molecule comprising a nucleotide sequence from the 5' region of the ALG3 gene and on the other side by a nucleic acid molecule comprising a nucleotide sequence from the 3' region of the ALG3 gene. Plasmid pGLY5508 was linearized with SfiI and the linearized plasmid transformed into strain YGLY23360 to produce a number of strains in which the URA5 gene flanked by the lacZ repeats has been inserted into the ALG3 locus by double-crossover homologous recombination. Strain YGLY24542 was selected from the strains produced.

Plasmid pGLY10153 is a roll-in integration plasmid that targets the URA6 locus in P. pastoris and encodes the LmSTT3A, LmSTT3B, and LmSTT3D ORFs. Overexpressing the LmSTT3 proteins may enhance N-glycosylation site occupancy of the insulin analogues. The expression cassette encoding the LmSTT3A comprises a nucleic acid molecule encoding the LmSTT3D ORF codon-optimized for effective expression in P. pastoris operably linked at the 5' end to a nucleic acid molecule that has the inducible P. pastoris AOX1 promoter sequence and at the 3' end to a nucleic acid molecule that has the S. cerevisiae CYC transcription termination sequence. The expression cassette encoding the LmSTT3B comprises a nucleic acid molecule encoding the LmSTT3B ORF codon-optimized for effective expression in P. pastoris operably linked at the 5' end to a nucleic acid molecule that has the inducible P. pastoris AOX1 promoter sequence and at the 3' end to a nucleic acid molecule that has the S. cerevisiae CYC transcription termination sequence. The expression cassette encoding the LmSTT3D comprises a nucleic acid molecule encoding the LmSTT3D ORF codon-optimized for effective expression in P. pastoris operably linked at the 5' end to a nucleic acid molecule that has the inducible P. pastoris AOX1 promoter sequence and at the 3' end to a nucleic acid molecule that has the S. cerevisiae CYC transcription termination sequence. For selecting transformants, the plasmid comprises an expression cassette encoding the S. cerevisiae ARR3 ORF in which the nucleic acid molecule encoding the ORF is operably linked at the 5' end to a nucleic acid molecule having the P. pastoris RPL10 promoter sequence and at the 3' end to a nucleic acid molecule having the S. cerevisiae CYC transcription termination sequence. Plasmid pGLY10153 was transformed into strain YGLY24542 to produce a number of strains of which strain YGLY24561 was selected. Strain YGLY24561 was counterselected in the presence of 5-FOA to produce strain YGLY24586 in which the URA5 gene has been lost and only the lacZ repeats remain.

Strain YGLY24586 was transformed with plasmid pGLY5933, which disrupts the ATT1 gene. Disruption of the ATT1 gene may provide improve cell fitness during fermentation. The salient features of the plasmid is that it comprises the URA5 expression cassette described above flanked on one end with a nucleic acid molecule comprising the 5' or upstream region of the ATT1 gene (SEQ ID NO:51) and the other end with a nucleic acid molecule encoding the 3' or downstream region of the ATT1 gene (SEQ ID NO:52). YGLY24586 was transformed with plasmid pGLY5933 resulted in a number of strains of which strain YGLY27303 was selected.

Plasmid pGLY11099, which is a roll-in integration plasmid that targets the TRP2 or AOX1p loci, includes an expression cassette encoding an insulin precursor fusion protein comprising a S. cerevisiae alpha mating factor signal sequence and propeptide fused to an N-terminal spacer peptide fused to the human insulin B-chain with NGT(−2) tripeptide addition and a P28N substitution fused to a C-peptide consisting of the amino acid sequence AAK fused to the human insulin A-chain (SEQ ID NO:55). Strain YGLY27303 was transformed with plasmid pGLY11099 to produce a number strains of which strain YGLY28137 was selected.

Plasmid pGLY12027 is a roll-in integration plasmid that targets the URA6 locus in P. pastoris and encodes the murine endomannosidase ORF. The expression cassette encoding the full-length murine endomannosidase comprises a nucleic acid molecule encoding full-length murine endomannosidase ORF codon-optimized for effective expression in P. pastoris (SEQ ID NO:53) operably linked at the 5' end to a nucleic acid molecule that has the inducible P. pastoris AOX1 promoter sequence and at the 3' end to a transcription termination sequence, for example the Pichia pastoris AOX1 transcription termination sequence (SEQ ID NO:54). For selecting transformants, the plasmid includes the NAT$^R$ expression cassette (SEQ ID NO:9) operably regulated to the Ashbya gossypii TEE1 promoter (SEQ ID NO:10) and A. gossypii TEF1 termination sequence (SEQ ID NO:11). The plasmid further includes a nucleic acid molecule as described previously for targeting the URA6 locus. Strain YGLY28137 was transformed with plasmid pGLY12027 to generate a number of strains of which strain YGLY29365 was selected.

Following the fermentation of strain YGLY29365, the insulin analogue precursor was purified from cell-free fermentation supernatant and processed with the LysC endoproteinase to produce the des(B30) heterodimer 210-2-B for in vitro and in vivo testing.

The 210-B-2 heterodimer was obtained from the culture medium and the N-glycan composition determined. Compositions comprising the 210-B-2 analog contained about 93-100% $Man_3GlcNAc_2$ and about 0 to 7% $Man_4GlcNAc_2$.

Sequences

Sequences that were used to produce some of the strains disclosed in the Examples are provided in the following table.

BRIEF DESCRIPTION OF THE SEQUENCES

| SEQ ID NO: | Description | Sequence |
|---|---|---|
| 1 | Leishmania major STT3D (protein) | MGKRKGNSLGDSGSAATASREASAQAEDAA SQTKTASPPAKVILLPKTLTDEKDFIGIFP FPFWPVHFVLTVVALFVLAASCFQAFTVRM ISVQIYGYLIHEFDPWFNYRAAEYMSTHGW SAFFSWFDYMSWYPLGRPVGSTTYPGLQLT AVAIHRALAAAGMPMSLNNVCVLMPAWFGA IATATLAFCTYEASGSTVAAAAAALSFSII PAHLMRSMAGEFDNECIAVAAMLLTFYCWV RSLRTRSSWPIGVLTGVAYGYMAAAWGGYI FVLNMVAMHAGISSMVDWARNTYNPSLLRA YTLFYVVGTAIAVCVPPVGMSPFKSLEQLG ALLVLVFLCGLQVCEVLRARAGVEVRSRAN FKIRVRVFSVMAGVAALAISVLAPTGYFGP LSVRVRALFVEHTRTGNPLVDSVAEHQPAS PEAMWAFLHVCGVTWGLGSIVLAVSTFVHY SPSKVFWLLNSGAVYYFSTRMARLLLLSGP AACLSTGIFVGTILEAAVQLSFWDSDATKA KKQQKQAQRHQRGAGKGSGRDDAKNATTAR AFCDVFAGSSLAWGHRMVLSIAMWALVTTT AVSFFSSEFASHSTKFAEQSSNPMIVFAAV VQNRATGKPMNLLVDDYLKAYEWLRDSTPE DARVLAWWDYGYQITGIGNRTSLADGNTWN HEHIATIGKMLTSPVVEAHSLVRHMADYVL IWAGQSGDLMKSPHMARIGNSVYHDICPDD PLCQQFGFHRNDYSRPTPMMRASLLYNLHE AGKRKGVKVNPSLFQEVYSSKYGLVRIFKV MNVSAESKKWVADPANRVCHPPGSWICPGQ YPPAKEIQEMLAHRVPFDQVTNADRKNNVG SYQEEYMRRMRESENRR |
| 2 | Leishmania major STT3D (DNA) | ATGGGTAAAAGAAAGGGAAACTCCTTGGGAG ATTCTGGTTCTGCTGCTACTGCTTCCAGAGA GGCTTCTGCTCAAGCTGAAGATGCTGCTTCC CAGACTAAGACTGCTTCTCCACCTGCTAAGG TTATCTTGTTGCCAAAGACTTTGACTGACGA GAAGGACTTCATCGGTATCTTCCCATTTCCA TTCTGGCCAGTTCACTTCGTTTTGACTGTTG TTGCTTTGTTCGTTTTGGCTGCTTCCTGTTT CCAGGCTTTCACTGTTAGAATGATCTCCGTT CAAATCTACGGTTACTTGATCCACGAATTTG ACCCATGGTTCAACTACAGAGCTGCTGAGTA CATGTCTACTCACGGATGGAGTGCTTTTTTC TCCTGGTTCGATTACATGTCCTGGTATCCAT TGGGTAGACCAGTTGGTTCTACTACTTACCC AGGATTGCAGTTGACTGCTGTTGCTATCCAT AGAGCTTTGGCTGCTGCTGGAATGCCAATGT CCTTGAACAATGTTTGTGTTTTGATGCCAGC TTGGTTTGGTGCTATCGCTACTGCTACTTTG GCTTTCTGTACTTACGAGGCTTCTGGTTCTA CTGTTGCTGCTGCTGCAGCTGCTTTGTCCTT CTCCATTATCCCTGCTCACTTGATGAGATCC ATGGCTGGTGAGTTCGACAACGAGTGTATTG CTGTTGCTGCTATGTTGTTGACTTTCTACTG TTGGGTTCGTTCCTTGAGAACTAGATCCTCC TGGCCAATCGGTGTTTTGACAGGTGTTGCTT ACGGTTACATGGCTGCTGCTTGGGGAGGTTA CATCTTCGTTTTGAACATGGTTGCTATGCAC GCTGGTATCTCTTCTATGGTTGACTGGGCTA GAAACACTTACAACCCATCCTTGTTGAGAGC TTACACTTTGTTCTACGTTGTTGGTACTGCT ATCGCTGTTTGTGTTCCACCAGTTGGAATGT CTCCATTCAAGTCCTTGGAGCAGTTGGGAGC TTTGTTGGTTTTGGTTTTCTTGTGTGGATTG CAAGTTTGTGAGGTTTTGAGAGCTAGAGCTG GTGTTGAAGTTAGATCCAGAGCTAATTTCAA GATCAGAGTTAGAGTTTTCTCCGTTATGGCT GGTGTTGCTGCTTTGGCTATCTCTGTTTTGG CTCCAACTGGTTACTTTGGTCCATTGTCTGT TAGAGTTAGAGCTTTGTTTGTTGAGCACACT AGAACTGGTAACCCATTGGTTGACTCCGTTG CTGAACATCAACCAGCTTCTCCAGAGGCTAT GTGGGCTTTCTTGCATGTTTGTGGTGTTACT TGGGGATTGGGTTCCATTGTTTTGGCTGTTT CCACTTTCGTTCACTACTCCCCATCTAAGGT TTTCTGGTTGTTGAACTCCGGTGCTGTTTAC TACTTCTCCACTAGAATGGCTAGATTGTTGT TGTTGTCCGGTCCAGCTGCTTGTTTGTCCAC TGGTATCTTCGTTGGTACTATCTTGGAGGCT GCTGTTCAATTGTCTTTCTGGGACTCCGATG CTACTAAGGCTAAGAAGCAGCAAAAGCAGGC TCAAAGACACCAAAGAGGTGCTGGTAAAGGT TCTGGTAGAGATGACGCTAAGAACGCTACTA CTGCTAGAGCTTTCTGTGACGTTTTCGCTGG TTCTTCTTTGGCTTGGGGTCACAGAATGGTT TTGTCCATTGCTATGTGGGCTTTGGTTACTA CTACTGCTGTTTCCTTCTTCTCCTCCGAATT TGCTTCTCACTCCACTAAGTTCGCTGAACAA TCCTCCAACCCAATGATCGTTTTCGCTGCTG TTGTTCAGAACAGAGCTACTGGAAAGCCAAT GAACTTGTTGGTTGACGACTACTTGAAGGCT TACGAGTGGTTGAGAGACTCTACTCCAGAGG ACGCTAGAGTTTTGGCTTGGTGGGACTACGG TTACCAAATCACTGGTATCGGTAACAGAACT TCCTTGGCTGATGGTAACACTTGGAACCACG AGCACATTGCTACTATCGGAAAGATGTTGAC TTCCCCAGTTGTTGAAGCTCACTCCCTTGTT AGACACATGGCTGACTACGTTTTGATTTGGG CTGGTCAATCTGGTGACTTGATGAAGTCTCC ACACATGGCTAGAATCGGTAACTCTGTTTAC CACGACATTTGTCCAGATGACCCATTGTGTC AGCAATTCGGTTTCCACAGAAACGATTACTC CAGACCAACTCCAATGATGAGAGCTTCCTTG TTGTACAACTTGCACGAGGCTGGAAAAAGAA AGGGTGTTAAGGTTAACCCATCTTTGTTCCA AGAGGTTTACTCCTCCAAGTACGGACTTGTT AGAATCTTCAAGGTTATGAACGTTTCCGCTG AGTCTAAGAAGTGGGTTGCAGACCCAGCTAA CAGAGTTTGTCACCCACCTGGTTCTTGGATT TGTCCTGGTCAATACCCACCTGCTAAAGAAA TCCAAGAGATGTTGGCTCACAGAGTTCCATT CGACCAGGTTACAAACGCTGACAGAAAGAAC AATGTTGGTTCCTACCAAGAGGAATACATGA GAAGAATGAGAGAGTCCGAGAACAGAAGATA ATAG |
| 3 | Pp AOX1 promoter | AACATCCAAAGACGAAAGGTTGAATGAAACC TTTTTGCCATCCGACATCCACAGGTCCATTC TCACACATAAGTGCCAAACGCAACAGGAGGG GATACACTAGCAGCAGACCGTTGCAAACGCA GGACCTCCACTCCTCTTCCTCAACACCCA CTTTTGCCATCGAAAACCAGCCCAGTTATT GGGCTTGATTGGAGCTCGCTCATTCCAATTC CTTCTATTAGGCTACTAACACCATGACTTTA TTAGCCTGTCTATCCTGGCCCCCCTGGCGAG |

BRIEF DESCRIPTION OF THE SEQUENCES

| SEQ ID NO: Description | Sequence |
|---|---|
| | GTTCATGTTTGTTTATTTCCGAATGCAACAA GCTCCGCATTACACCCGAACATCACTCCAGA TGAGGGCTTTCTGAGTGTGGGGTCAAATAGT TTCATGTTCCCCAAATGGCCCAAAACTGACA GTTTAAACGCTGTCTTGGAACCTAATATGAC AAAAGCGTGATCTCATCCAAGATGAACTAAG TTTGGTTCGTTGAAATGCTAACGGCCAGTTG GTCAAAAAGAAACTTCCAAAAGTCGGCATAC CGTTTGTCTTGTTTGGTATTGATTGACGAAT GCTCAAAAATAATCTCATTAATGCTTAGCGC AGTCTCTCTATCGCTTCTGAACCCCGGTGCA CCTGTGCCGAAACGCAAATGGGGAAACACCC GCTTTTTGGATGATTATGCATTGTCTCCACA TTGTATGCTTCCAAGATTCTGGTGGGAATAC TGCTGATAGCCTAACGTTCATGATCAAATT TAACTGTTCTAACCCCTACTTGACAGCAATA TATAAACAGAAGGAAGCTGCCCTGTCTTAAA CCTTTTTTTTTATCATCATTATTAGCTTACT TTCATAATTGCGACTGGTTCCAATTGACAAG CTTTTGATTTTAACGACTTTTAACGACAACT TGAGAAGATCAAAAAACAACTAATTATTCGA AACG |
| 4 ScCYC TT | ACAGGCCCCTTTTCCTTTGTCGATATCATGT AATTAGTTTATGTCACGCTTACATTCACGCCC TCCTCCCACATCCGCTCTAACCGAAAAGGAA GGAGTTAGACAACCTGAAGTCTAGGTCCCTA TTTATTTTTTTAATAGTTATGTTAGTATTA AGAACGTTATTTATATTTCAAATTTTTCTTT TTTTTCTGTACAAACGCGTGTACGCATGTAA CATTATACTGAAAACCTTGCTTGAGAAGGTT TTGGGACGCTCGAAGGCTTTAATTTGCAAGC TGCCGGCTCTTAAG |
| 5 ScARR3 ORF | ATGTCAGAAGATCAAAAAAGTGAAAATTCCG TACCTTCTAAGGTTAATATGGTGAATCGCAC CGATATACTGACTACGATCAAGTCATTGTCA TGGCTTGACTTGATGTTGCCATTTACTATAA TTCTCTCCATAATCATTGCAGTAATAATTTC TGTCTATGTGCCTTCTTCCCGTCACACTTTT GACGCTGAAGGTCATCCCAATCTAATGGGAG TGTCCATTCCTTTGACTGTTGGTATGATTGT AATGATGATTCCCCCGATCTGCAAAGTTTCC TGGGAGTCTATTCACAAGTACTTCTACAGGA GCTATATAAGGAAGCAACTAGCCCTCTCGTT ATTTTTTGAATTGGGTCATCGGTCCTTTGTTG ATGACAGCATTGGCGTGGATGGCGCTATTCG ATTATAAGGAATACCGTCAAGGCATTATTAT GATCGGAGTAGCTAGATGCATTGCCATGGTG CTAATTTGGAATCAGATTGCTGGAGGAGACA ATGATCTCTGCGTCGTGCTTGTTATTACAAA CTCGCTTTTACAGATGGTATTATATGCACCA TTGCAGATATTTTACTGTTATGTTATTTCTC ATGACCACCTGAATACTTCAAATAGGGTATT ATTCGAAGAGGTTGCAAAGTCTGTCGGAGTT TTTCTCGGCATACCACTGGGAATTGGCATTA TCATACGTTGGGAAGTCTTACCATAGCTGG TAAAAGTAATTATGAAAATACATTTTGAGA TTTATTTCTCCATGGGCAATGATCGGATTTC ATTACACTTTATTTGTTATTTTTATTAGTAG AGGTTATCAATTTATCCACGAAATTGGTCT GCAATATTGTGCTTTGTCCCATTGGTGCTTT ACTTCTTTATTGCATGGTTTTTGACCTTCGC ATTAATGAGGTACTTATCAATATCTAGGAGT GATACACAAAGAGAATGTAGCTGTGACCAAG AACTACTTTTAAAGAGGGTCTGGGGAAGAAA GTCTTGTGAAGCTAGCTTTTCTATTACGATG ACGCAATGTTTCACTATGGCTTCAAATAATT TTGAACTATCCCTGGCAATTGCTATTTCCTT ATATGGTAACAATAGCAAGCAAGCAATAGCT GCAACATTTGGGCCGTTGCTAGAAGTTCCAA |

| SEQ ID NO: Description | Sequence |
|---|---|
| | TTTTATTGATTTTGGCAATAGTCGCGAGAAT CCTTAAACCATATTATATATGGAACAATAGA AATTAA |
| 6 PpRPL10 promoter | GTTCTTCGCTTGGTCTTGTATCTCCTTACAC TGTATCTTCCCATTTGCGTTTAGGTGGTTAT CAAAAACTAAAAGGAAAAATTTCAGATGTTT ATCTCTAAGGTTTTTTCTTTTTACAGTATAA CACGTGATGCGTCACGTGGTACTAGATTACG TAAGTTATTTTGGTCCGGTGGGTAAGTGGGT AAGAATAGAAAGCATGAAGGTTTACAAAAAC GCAGTCACGAATTATTGCTACTTCGAGCTTG GAACCACCCCAAAGATTATATTGTACTGATG CACTACCTTCTCGATTTTGCTCCTCCAAGAA CCTACGAAAAACATTTCTTGAGCCTTTTCAA CCTAGACTACACATCAAGTTATTTAAGGTAT GTTCCGTTAACATGTAAGAAAAGGAGAGGAT AGATCGTTTATGGGGTACGTCGCCTGATTCA AGCGTGACCATTCGAAGAATAGGCCTTCGAA AGCTGAATAAAGCAAATGTCAGTTGCGATTG GTATGCTGACAAATTAGCATAAAAAGCAATA GACTTTCTAACCACCTGTTTTTTTCCTTTTA CTTTATTTATATTTTGCCACCGTACTAACAA GTTCAGACAAA |
| 7 URA6 region | CAAATGCAAGAGGACATTAGAAATGTGTTTG GTAAGAACATGAAGCCGGAGGCATACAAACG ATTCACAGATTTGAAGGAGGAAAACAAACTG CATCCACCGGAAGTGCCAGCAGCCGTGTATG CCAACCTTGCTCTCAAAGGCATTCCTACGGA TCTGAGTGGGAAATATCTGAGATTCACAGAC CCACTATTGGAACAGTACCAAACCTAGTTTG GCCGATCCATGATTATGTAATGCATATAGTT TTTGTCGATGCTCACCCGTTTCGAGTCTGTC TCGTATCGTCTTACGTATAAGTTCAAGCATG TTTACCAGGTCTGTTAGAAACTCCTTTGTGA GGGCAGGACCTATTCGTCTCGGTCCCGTTGT TTCTAAGAGACTGTACAGCCAAGCGCAGAAT GGTGGCATTAACCATAAGAGGATTCTGATCG GACTTGGTCTATTGGCTATTGGAACCACCCT TTACGGGACAACCAACCCTACCAAGACTCCT ATTGCATTTGTGGAACAGCCACGGAAAGAG CGTTTAAGGACGGAGACGTCTCTGTGATTTT TGTTCTCGGAGGTCCAGGAGCTGGAAAAGGT ACCCAATGTGCCAAACTAGTGAGTAATTACG GATTTGTTCACCTGTCAGCTGGAGACTTGTT ACGTGCAGAACAGAAGAGGGAGGGTCTAAG TATGGAGAGATGATTTCCCAGTATATCAGAG ATGGACTGATAGTACCTCAAGAGGTCACCAT TGCGCTCTTGGAGCAGGCCATGAAGGAAAAC TTCGAGAAAGGGAAGACACGGTTCTTGATTG ATGGATTCCCTCGTAAGATGGACCAGGCCAA AACTTTTGAGGAAAAAGTCGCAAAGTCCAAG GTGACACTTTTCTTTGATTGTCCCGAATCAG TGCTCCTTGAGAGATTACTTAAAAGAGGACA GACAAGCGGAAGAGAGGATGATAATGCGGAG AGTATCAAAAAAAGATTCAAAACATTCGTG AACTTCGATGCCTGTGGTGGACTATTTCGG GAAGCAAGGACGCGTTTTGAAGGTATCTTGT GACCACCCTGTGGATCAAGTGTATTCACAGG TTGTGTCGGTGCTAAAAGAGAAGGGGATCTT TGCCGATAACGAGACGGAGAATAAATAA |
| 8 PpGAPDH promoter | TTTTTGTAGAAATGTCTTGGTGTCCTCGTCC AATCAGGTAGCCATCTCTGAAATATCTGGCT CCGTTGCAACTCCGAACGACCTGCTGGCAAC GTAAAATTCTCCGGGGTAAAACTTAAATGTG GAGTAATGGAACCAGAAACGTCTCTTCCCTT CTCTCTCCTTCCACCGCCCGTTACCGTCCCT AGGAAATTTTACTCTGCTGGAGAGCTTCTTC TACGGCCCCCTTGCAGCAATGCTCTTCCCAG CATTACGTTGCGGGTAAACGGAGGTCGTGT ACCCGACCTAGCAGCCCAGGGATGGAAAAGT |

BRIEF DESCRIPTION OF THE SEQUENCES

| SEQ ID NO: | Description | Sequence |
|---|---|---|
| | | CCCGGCCGTCGCTGGCAATAATAGCGGGCGG ACGCATGTCATGAGATTATTGGAAACCACCA GAATCGAATATAAAAGGCGAACACCTTTCCC AATTTTGGTTTCTCCTGACCCAAAGACTTTA AATTTAATTTATTTGTCCCTATTTCAATCAA TTGAACAACTATCAAAACACA |
| 9 | NatR ORF | ATGGGTACCACTCTTGACGACACGGCTTACC GGTACCGCACCAGTGTCCCGGGGGACGCCGA GGCCATCGAGGCACTGGATGGGTCCTTCACC ACCGACACCGTCTTCCGCGTCACCGCCACCG GGGACGGCTTCACCCTGCGGGAGGTGCCGGT GGACCCGCCCCTGACCAAGGTGTTCCCCGAC GACGAATCGGACGACGAATCGGACGACGGGG AGGACGGCGACCCGGACTCCCGGACGTTCGT CGCGTACGGGGACGACGGCGACCTGGCGGGC TTCGTGGTCATCTCGTACTCGGCGTGAACC GCCGGCTGACCGTCGAGGACATCGAGGTCGC CCCCGGAGCACCGGGGGCACGGGGTCGGGCGC GCGTTGATGGGGCTCGCGACGGAGTTCGCCG GCGAGCGGGGCGCCGGGCACCTCTGGCTGGA GGTCACCAACGTCAACGCACCGGCGATCCAC GCGTACCGGCGGATGGGGGTTCACCCTCTGCG GCCTGGACACCGCCCTGTACGACGGCACCGC CTCGGACGGCGAGCGGCAGGCGCTCTACATG AGCATGCCCTGCCCC |
| 10 | Ashbya gossypii TEF1 promoter | GATCTGTTTAGCTTGCCTCGTCCCCGCCGGG TCACCCGGCCAGCGACATGGAGGCCCAGAAT ACCCTCCTTGACAGTCTTGACGTGCGCAGCT CAGGGGCATGATGTGACTGTCGCCCGTACAT TTAGCCCATACATCCCATGTATAATCATTT GCATCCATACATTTTGATGGCCGCACGGCGC GAAGCAAAAATTACGGCTCCTCGCTGCAGAC CTGCGAGCAGGGAAACGCTCCCCTCACAGAC GGCGTTGAATTGTCCCCACGCCGCGCCCTG TAGAGAAATATAAAAGGTTAGATTTGCCACT GAGGTTCTTCTTTCATATACTTCCTTTTAAA ATCTTGCTAGGATACAGTTCTCACATCACAT CCGAACATAAACAACC |
| 11 | Ashbya gossypii TEF1 termination sequence | TAATCAGTACTGACAATAAAAAGATTCTTGT TTTCAAGAACTTGTCATTTGTATAGTTTTTT TATATTGTAGTTGTTCTATTTTAATCAAATG TTAGCGTGATTTATATTTTTTTCGCCTCGA CATCATCTGCCCAGATGCGAAGTTAAGTGCG CAGAAAGTAATATCATGCGTCAATCGTATGT GAATGCTGGTCGCTATACTGCTGTCGATTCG ATACTAACGCCGCCATCCAGTGTCGAAAAC |
| 12 | PpTRP1 5' region and ORF | GCGGAAACGGCAGTAAACAATGGAGCTTCAT TAGTGGGTGTTATTATGGTCCCTGGCCGGGA ACGAACGGTGAAACAAGAGGTTGCGAGGGAA ATTTCGCAGATGGTGCGGGAAAAGAGAATTT CAAAGGGCTCAAAATACTTGGATTCCAGACA ACTGAGGAAAGAGTGGGACGACTGTCCTCTG GAAGACTGGTTTGAGTACAACGTGAAAGAAA TAAACAGCAGTGGTCCATTTTTAGTTGGAGT TTTTCGTAATCAAAGTATAGATGAAATCCAG CAAGCTATCCACACTCATGGTTTGGATTTCG TCCAACTACATGGGTCTGAGGATTTTGATTC GTATATACGCAATATCCCAGTTCCTGTGATT ACCAGATACACAGATAATGCCGTCGATGGTC TTACCGGAGAAGACCTCGCTATAAATAGGGC CCTGGTGCTACTGGACAGCGAGCAAGGAGGT GAAGGAAAAACCATCGATTGGGCTCGTGCAC AAAATTTGGAGAACGTAGAGGAAAAATATT ACTAGCCGGAGGTTTGACACCTGATAATGTT GCTCATGCTCGATCTCATACTGGCTGTATTG GTGTTGACGTCTCTGGTGGGGTAGAAACAAA TGCCTCAAAAGATATGGACAAGATCACACAA TTTATCAGAAACGCTACATAA |
| 13 | PpALG3 TT | ATTTACAATTAGTAATATTAAGGTGGTAAAA ACATTCGTAGAATTGAAATGAATTAATATAG TATGACAATGGTTCATGTCTATAAATCTCCG GCTTCGGTACCTTCTCCCCAATTGAATACAT TGTCAAAATGAATGGTTGAACTATTAGGTTC GCCAGTTTCGTTATTAAGAAAACTGTTAAAA TCAAATTCCATATCATCGGTTCCAGTGGGAG GACCAGTTCCATCGCCAAAATCCTGTAAGAA TCCATTGTCAGAACCTGTAAAGTCAGTTTGA GATGAAATTTTTCCGGTCTTTGTTGACTTGG AAGCTTCGTTAAGGTTAGGTGAAACAGTTTG ATCAACCAGCGGCTCCCGTTTTCGTCGCTTA GTAG |
| 14 | PpTRP1 3' region | AAGTCAATTAAATACACGCTTGAAAGGACAT TACATAGCTTTCGATTTAAGCAGAACCAGAA ATGTAGAACCACTTGTCAATAGATTGGTCAA TCTTAGCAGGAGCGGCTGGGCTAGCAGTTGG AACAGCAGAGGTTGCTGAAGGTGAGAAGGAT GGAGTGGATTGCAAAGTGGTGTTGGTTAAGT CAATCTCACCAGGGCTGGTTTTGCCAAAAAT CAACTTCTCCCAGGCTTCACGGCATTCTTGA ATGACCTCTTCTGCATACTTCTTGTTCTTGC ATTCACCAGAGAAAGCAAACTGGTTCTCAGG TTTTCCATCAGGGATCTTGTAAATTCTGAAC CATTCGTTGGTAGCTCTCAACAAGCCCGGCA TGTGCTTTTCAACATCCTCGATGTCATTGAG CTTAGGAGCCAATGGGTCGTTGATGTCGATG ACGATGACCTTCCAGTCAGTCTCTCCCTCAT CCAACAAAGCCATAACACCGAGGACCTTGAC TTGCTTGACCTGTCCAGTGTAACCTACGGCT TCACCAATTTCGCAAACGTCCAATGGATCAT TGTCACCCTTGGCCTTGGTCTCTGGATGAGT GACGTTAGGGTCTTCCCATGTCTGAGGGAAG GCACCGTAGTTGTGAATGTATCCGTGGTGAG GGAAACAGTTACGAACGAAACGAAGTTTTCC CTTCTTTGTGTCCTGAAGAATTGGGTTCAGT TTCTCCTCCTTGGAAATCTCCAACTTGGCGT TGGTCCAACGGGGGACTTCAACAACCATGTT GAGAACCTTCTTGGATTCGTCAGCATAAAGT GGGATGTCGTGAAAGGAGATACGACTT |
| 15 | Anti-RSV Heavy chain (VH + IgG1 constant region) (DNA) | CAGGTTACATTGAGAGAATCCGGTCCAGCTT TGGTTAAGCCAACTCAGACTTTGACTTTGAC TTGTACTTTCTCCGGTTTCTCCTTGTCTACT TCCGGAATGTCTGTTGGATGGATCAGACAAC CACCTGGAAAGGCTTTGGAATGGCTTGCTGA CATTTGGTGGGATGACAAGAAGGACTACAAC CCATCCTTGAAGTCCAGATTGACTATCTCCA AGGACACTTCCAAGAATCAAGTTGTTTTGAA GGTTACAAACATGGACCCAGCTGACACTGCT ACTTACTACTGTGCTAGATCCATGATCACTA ACTGGTACTTCGATGTTTGGGGTGCTGGTAC TACTGTTACTGTCTCGAGTGCTTCTACTAAG GGACCATCCGTTTTTCCATTGGCTCCATCCT CTAAGTCTACTTCCGGTGGAACCGCTGCTTT GGGATGTTTGGTTAAAGACTACTTCCCAGAG CCAGTTACTGTTTCTTGGAACTCCGGTGCTT TGACTTCTGGTGTTCACACTTTCCCAGCTGT TTTGCAATCTTCCGGTTTGTACTCTTTGTCC TCCGTTGTTACTGTTCCATCCTCTTCCTTGG GTACTCAGACTTACATCTGTAACGTTAACCA CAAGCCATCCAACACTAAGGTTGACAAGAGA GTTGAGCCAAAGTCCTGTGACAAGACACATA CTTGTCCACCATGTCCAGCTCCAGAATTGTT GGGTGGTCCATCCGTTTTCTTGTTCCCACCA AAGCCAAAGGACACTTTGATGATCTCCAGAA CTCCAGAGGTTACATGTGTTGTTGTTGACGT TTCACGAGGACCCAGAGGTTAAGTTCAAC TGGTACGTTGACGGTGTTGAAGTTCACAACG CTAAGACTAAGCCAAGAGAAGAGCAGTACAA CTCCACTTACAGAGTTGTTTCCGTTTTGACT GTTTTGCACCAGGACTGGTTGAACGGTAAAG |

| SEQ ID NO: | Description | Sequence |
|---|---|---|
| | | AATACAAGTGTAAGGTTTCCAACAAGGCTTT GCCAGCTCCAATCGAAAAGACTATCTCCAAG GCTAAGGGTCAACCAAGAGAGCCACAGGTTT ACACTTTGCCACCATCCAGAGAAGAGATGAC TAAGAACCAGGTTTCCTTGACTTGTTTGGTT AAAGGATTCTACCCATCCGACATTGCTGTTG AGTGGGAATCTAACGGTCAACCAGAGAACAA CTACAAGACTACTCCACCAGTTTTGGATTCT GATGGTTCCTTCTTCTTGTACTCCAAGTTGA CTGTTGACAAGTCCAGATGGCAACAGGGTAA CGTTTTCTCCTGTTCCGTTATGCATGAGGCT TTGCACAACCACTACACTCAAAAGTCCTTGT CTTTGTCCCCTGGTTAA |
| 16 | Anti-RSV light chain (VL + Kappa constant region (DNA) | ATGAGAATTCCCATCCATCTTCACTGCTGTTT TGTTCGCTGCTTCTTCTGCTTTGGCTGACAT TCAGATGACACAGTCCCCATCTACTTTGTCT GCTTCCGTTGGTGACAGAGTTACTATCACTT GTAAGTGTCAGTTGTCCGTTGGTTACATGCA CTGGTATCAGCAAAAGCCAGGAAAGGCTCCA AAGTTGTTGATCTACGACACTTCCAAGTTGG CTTCCGGTGTTCCATCTAGATTCTCTGGTTC CGGTTCTGGTACTGAGTTCACTTTGACTATC TCTTCCTTGCAACCAGACGACTTCGCTACTT ACTACTGTTTCCAGGGTTCTGGTTACCCATT CACTTTCGGTGGTGGTACTAAGTTGGAGATC AAGAGAACTGTTGCTGCTCCATCCGTTTTCA TTTTCCCACCATCCGACGAACAATTGAAGTC CGGTACCGCTTCCGTTGTTTGTTTGTTGAAC AACTTCTACCCACGTGAGGCTAAGGTTCAGT GGAAGGTTGACAACGCTTTGCAATCCGGTAA CTCCCAAGAATCCGTTACTGAGCAGGATTCT AAGGATTCCACTTACTCATTGTCCTCCACTT TGACTTTGTCCAAGGCTGATTACGAGAAGCA CAAGGTTTACGCTTGCGAGGTTACACATCAG GGTTTGTCCTCCCCAGTTACTAAGTCCTTCA ACAGAGGAGAGTGTTAA |
| 17 | PpAOX1 TT | TCAAGAGGATGTCAGAATGCCATTTGCCTGA GAGATGCAGGCTTCATTTTGATACTTTTTTA TTTGTAACCTATATAGTATAGGAAGTTTTTT GTCATTTTGTTTCTTCTCGTACGAGCTTGCT CCTGATCAGCCTATCTCGCAGCTGATGAATA TCTTGTGGTAGGGGTTTGGGAAAATCATTCG AGTTTGATGTTTTTTCTTGGTATTTCCCACTC CTCTTCAGAGTACAGAAGATTAAGTGAGACG TTCGTTTGTGCA |
| 18 | Sequence of the Sh ble ORF (Zeocin resistance marker): | ATGGCCAAGTTGACCAGTGCCGTTCCGGTGC TCACCGCGCGCGACGTCGCCGGAGCGGTCGA GTTCTGGACCGACCGGCTCGGGTTCTCCCGG GACTTCGTGGAGGACGACTTCGCCGGTGTGG TCCGGGAGCGCGTGACCCGTTCATCAGCGC GGTCCAGGACCAGGTGGTGCCGGACAACACC CTGGCCTGGGTGTGGGTGCGCGGCCTGGACG AGCTGTACGCCGAGTGGTCGGAGGTCGTGTC CACGAACTTCCGGGACGCCTCCGGGCCGGCC ATGACCGAGATCGCGAGCAGCCGTGGGGGC GGGAGTTCGCCCTGCGCGACCCGGCCGGCAA CTGCGTGCACTTCGTGGCCGAGGAGCAGGAC TGA |
| 19 | Sequence of the 5'-Region used for knock out of YOS9 | CCATAGCCTCTGATTGATGTAAGCACCGACA GTACCTGGCTCTAACTTGTTAGAGGTTTTGG TGGTCAAGACATATCTGTTATCACAAATAAC ATAATGGTTATCGGGAAAGTCATTGGGATGA ACAGCAAGTGTTTCATGATGGCAAATTCAT TACCCGGAGAGTTGACTATCTTCAATACATG CACCTTTGGAGCATTTCTCTTTGTGAATCCC AGTTTTTCCATGGTTGTGGCAAAGTGTAGAG ATGTTAAGTGCAGCGAGCAAAGACAAGTAGA TAGACTGTATGGTGTTCTGATGTTATAGTTG TAGTGAATAATCTATAAATGCCTTATTTGAA GGTTTATGTAATAGATTTACCCGTGTGTAGC AAGTGTACTGCTAAGAGGTACTATAAAGTTA TTCATGTGGATATATTCAGTAGATAATAACA AAGCTACAAGGAGATCAAGAAACCATATGAG TTGTTCGTCACATAAGAGATTACGTAATGAC AAATCGGGGAACTAGTACCAATTCTGTCTTA AGTAGTGTCTCTCTAAGCATAACGACCTAT TTGATAACTGGGCTGAACTCCAAGCAGCCTG ATGATGTTGACCTGACTTATTCAGAAGGGCT ATTGGTTTTGATTTCCAGATATTAGCATAAT TAGCAATGCCGGAACAATATACATCCAATAT TTTTGAATGAATGAACGGTTATCAACATTTA CTTCTGCCTCCTCGTCTATGACTTCCTTGAG TTCCAGCTTGTTATCGGATCTGATTTTTTTG ATTTTCTTTTCTTTTCTTGGTAGTTTGGGAA TTGGTGCCTGTCGAATTTGTTCAACTATTAG GTTAAGACCTTTCTGACTAGCATCGAAGAAG GCTACATTTTCGATGTCGTTGTGTTTGTTGA TAGTCAGCTTGATATCCTGTGCAATTGGAGA ACTTAGTCTTTTGTAATTGAAGCAGCCTTCG TCCAAACATATTCTGTAAAGATCACTTGGCA GGTCTAGTTGTTCACCGGTGTGCAATTTCCA TTTTGAGTCAAATTCTAGTGTGGCCAAGTTG AACGAGTTCTGAGCGAAATCAATAGCCTTCA ACTGATACGCAAATGTAGACCCCAAGAAAAG AAACAACGTGACGAGGCTTTGTAGGGTAGTA GCCATTGTCGAATAGTTGAGGATAAGTAGAC GGCGAGTTATTCTCCTTGATAAATGCTATTG CGATGGATAGTGATTACAGTGCGATAATATT ATCCTTTTCATCCACGTCAACCATGGTTAAC AGGCCATTGGACATTATGATAAAGGTCCTGC TATTCCTGCTCTCCCTATCAAGTCTTGTGAA AGCTTTGGATGATTCCATTGATAAGAATTCT GTGGTAAGTCTTTTAATTTTTGTTTTCACAA GATCATGCCGTGCTAACTGGGTACTATAGTA TACC |
| 20 | Sequence of the 3'-Region used for knock out of YOS9 | GGTTCCTATTCACTGAAGACAGAATACCTCA TGACACTCCAAACTTTAGAGTGTATAACGGA GTTAATGTGAATTAAGACAATTTATATACTC AGTAAAATAAATACTAGTACTTACGTCTTTT TTTAGTCAGAGCACTAACTCTGCTGGAAGGG TTCTTCGTGTAAATTGGTACAGACGCTGGTA AAGTACCACTATACGTTGTTTGACAAATAGG TAGTTTGAAGCTGACATCAAGTTTCAAGTCC TTAGGAGTCACATTGCGAGTTTGAATGACCA ATTGTATTAATCTCTTAATCTTGAAGTACAA TCTCTTCTCTTTGAGACTGGGTTTCAAGACA GTGACGGATTAGCAGGATCGATTTTGGGTG ATGCCTTATACCTTTCTTGACGTAATTGTGA CAGATCTATTAGCAACTTGCTTATAAGTTCC TGCTCTTTGTTGGAACGGATAGCCTCTATCT CATCCTCCTCAACGAAGCTTCCCGGAGTCCA GGAGAGGAGGTTGTCTAGCTTGATCTTATAG TCTTCGGATCCATTGACCTGGACTTCCTTAT CTGTGTTTTCAAGTTTAGTTGATGTATCTGT CCCCGTATGCCATTCTTAGTCTCCTGGTCA ACAGGTGCCGGAAGCTCTTTTTTCAATTCTTT TTGGTTCGTCCTTCTGAAGTTCATTATCCGT CTCATTTTTAGATGGTCTGCTCAGTTTTTCT GCTATATCACCAAGCTTTCTAAAACCAGCTT GCTCCAGCCACCTCAGGCCCTTCAATTCACT GGAGATTCAGATTTTTCTTCGTCTATTGTA GGTGCAAAACTGAAATCGTTACCCTTATTGT GGGTGAGCCATTGACCCATCGGTAACGCGTA CCAGTTCAAATGAAAGAGGTTTGGCAATAAA TCCGTAGGTTTGGTGGCTGGGTGAGGTTCAT TGTTGTATTGAGGAGAAATCTTGTTAAGCAG CTGTGAACTAATGGAAGGGACATGGGGGATT ACTTTCGTCAGATTAAAATCGCCTTCATTCA CTACAGCTTCTCTAGCATCCAAGCTTGATTT ATTATTCAGGGACGAAAACAATGCGCATTA GGTGTGATGAATGTAGTTAAACATTCTCCGT |

BRIEF DESCRIPTION OF THE SEQUENCES

| SEQ ID NO: | Description | Sequence |
|---|---|---|
| | | TGGATGAAACAAAAAATGTGGACACTTTATT GAAGTCTTTTGTCATCGATTCTTCAAACTCA CTGGTGTAATCATCTAAAACACGAGAGTCAA CGCTTTCTCTTAGTTGTCTGTAGTTGAACAA AAATCTTCCTGCCTCTCTGATCAATAACTCA ACCATCGACTTGTAGAACAAATCAATCTTGA CGTAGTCTTCCGAATCTCTGTTCCGTTCGTT TATAAGTATCAGGCACACTAAAGTTAGGTCG TGAAATATGGAATAAATAGTCTTGTAGTGAC CACTCTTTATTCTGTCGCTGATGGTAACCAG CTCTGTAGGTTTGAGATCCTTACCATCAACA AGCTGATAGTATGATCCAGCTATCAAGGAAG GATCCTGGAC |
| 21 | Sequence of the 5'-Region used for knock out of ALG3 | AACCTTCATGGAACGATTCGGATACGGAAAA ACCTGAGATAGTTTTAACTAGAGTAGATGCA AGATTTCACGATTCTAAAGACCGAGAAGGAG ATGTCTGATGTCGGTAACTACTATCCGGTAA ATGATATTAGCACACTATATGCTACTAGCGA GTCTGGAACCAATTCTACTATCCATTGATGC TCTATTAGGGATGGAGAATTCAATCAACCCC TCTAATTCTGATTTCAGATGTTCCAACAGCG AAGTAGCCCTTGACAAGTTCTCAACATCACT CATCTTAGCTACATTCACGTATGCTTTGATA AAAAACTCTCTACTTTTGTCAATGAGCTCTA GCCTAGTCTCTGGTTCTATCGTTTCCTCTTT GGTCTCCAGATTACTCTCTGGATTAGAATCT ACATCCATCTTCATATCTATGTCCATGTCCA GCTCAATTTTCATACCGTCAGTATTCTTAGA TTCGATAGCAGTATCTGATCTGGTAGATCCA TTAGTTGCTGCAGCGGTATTTTCTTTGGAAT TTGGAGCACTTTCCTGTTTCTGTTTCATAAA GACTCGGTAGATTGCAATGACTATATCGTTT CTGTAGAACTTGTAACCATGAGTCCAAAATT GGGTTTCAGGCATGTATCCTAGCTCATCTAA ATATCCAACCACATCATCCGTGCTACATATA GTAGACTCGTAGAGTGTCTGTGAAGAAACGG CTCTTTTTCCTGCCAAAGGAACGTCCGATAT TTGAAGGGTCCATATACGATTTTCCTTATTA AGAGCTTCAAGATGTTTCTTATTAAACAATT CAAAGTCTTTTAATTCAATTGTGTTATCAAT AGGATCCTCAACGTCCTGTTTCCATTCGGTG GACATTCTCATCTTGTATTGTTCGATTTGGT TGACTTTTCCAGTCTGGAACTCAGGACTATA AGGAAACTTTGGAGTTAAAATAACAGTATAA GTTGAGAGCCTTGCGGGCACCCATACCCGTTA GAGACTTCAACGTCTCCAAGATCAACTGCAG TTGAGACTCTTGGATTCTAGATACCAGAGAC ACCTGTTGTACCATATAATTAAGTGACTGGG CTGGCTTGGATACAGGATTTCGAGAAGTGCT TCGAATTATCAGACCGAAGGCAGTTGATATT TTGTGCCTCAGCCTTAATGTTCCCTATAACT TAAGGCTATACACAGCTTTATGATTAATGAA TCTGGGCTGCTGGTGACGAATTTCGTCAATG ACCAGTTGCCTACGGGCGATAATTATTTTTT CAGTTGGATGAAAGAACGGAAAAACCCGGTC AGATTCAAAAAGAATATTGAATAATCTTTGTC TAGCACAACTGAAATGCTTGGAAACTCTCCC AAGCATGAATCAGACCTGAGATTGTATTAGA CGAAAAAATTGTAGTATAGAGTTATAGACAT ATAGGTTGTGGCAATATCCTGTGCAAGCCAA TATCTCACAGAAATAAACGTACACACCAGAT ACAACTATTTCGAAAAGCACACTTTGAGCGC AACAGTGATTGTCCTAACAGTATAGGTTTCT AAGGCCCCAGCAGACCATGACGGCAAATTAT TTATTTCCCCTCGTATTTGCCTTATCTCCTT TTGTTCTCATTCTTATCTTGGCTACTGTAAT TATCTGGATAACCCTCGATACTTCGCTTGGT TTCTACCTCACAACATATCCCTACC |
| 22 | Sequence of the 3'-Region used for knock out of | ATTTACAATTAGTAATATTAAGGTGGTAAAA ACATTCGTAGAATTGAAATGAATTAATATAG TATGACAATGGTTCATGTCTATAAATCTCCG |
| | ALG3 | GCTTCGGTACCTTCTCCCCAATTGAATACAT TGTCAAAATGAATGGTTGAACTATTAGGTTC GCCAGTTTCGTTATTAAGAAAACTGTTAAAA TCAAATTCCATATCATCGGTTCCAGTGGGAG GACCAGTTCCATCGCCAAAATCCTGTAAGAA TCCATTGTCAGAACCTGTAAAGTCAGTTTGA GATGAAATTTTTCCGGTCTTTGTTGACTTGG AAGCTTCGTTAAGGTTAGGTGAAACAGTTTG ATCAACCAGCGGCTCCCGTTTTCGTCGCTTA GTAGCAGCATTATTACCAGGAATGCCGCCTG TAGAGTTTTGATGTGTCCTAGCTGCAATTGG AGTCTGTGGAGTAGTGGGAGTCGGGGGCTCA GTAGCTTTCTTTGCCTTCTTTTTAGCTGGCT CCTTTTTCTTTCGTACAGGTGCGACATTATT TGGTGTAGACCCCGCAGAAGTGTTACCAGTA CTATGTGCAGTGTTTTGAGTTTGTGTACCAG GTGAAGTTCCGGGAGTATTCTTCGTGACCAC TGCAGAGTTCTGGGGAGGGAGCATTACATTC ACATTAAATTTTGGTTCGGGCGGTGTGTGCT CTGGAATTGGATCAAAGTTAGAAAAATGCCC GCTTCCCTTCTTACATGCCATGTCATGACGC TGTTTGTTCTGTTTCTCAAGCATCATTAGCT CTTTCTGATACTCCTGTATACCTACAATTTT AGAAGCACTTGATTGAGACTGTTGCGATTGC TGGTGTTGGCTCTGTGATTGTGGTTGTGCTA TTTGCTGATGTTGTGACCCTGGAGTTGGAAC TAGCTCCGGCTGCTGAATAGAAGAAGGCGGA GAATGTTGCGGTTGAGATGCAGGTAAAGGCT GCTGATAAACAGGACCAGGTTGCGAGAATCT AGGTGTGGTGGACGAGTGAGGAGTACCGGCG GCAGAAGTAGAGTGAGGCAGAGGAGCCAT |
| 23 | Sequence of the 5'-Region used for knock out of BMT1 | CATATGGTGAGAGCCGTTCTGCACAACTAGA TGTTTTCGAGCTTCGCATTGTTTCCTGCAGC TCGACTATTGAATTAAGATTTCCGGATATCT CCAATCTCACAAAAACTTATGTTGACCACGT GCTTTCCTGAGGCGAGGTGTTTTATATGCAA GCTGCCAAAAATGGAAAACGAATGGCCATTT TTCGCCCAGGCAAATTATTCGATTACTGCTG TCATAAAGACAGTGTTGCAAGGCTCACATTT TTTTTTAGGATCCGAGATAAAGTGAATACAG GACAGCTTATCTCTATATCTTGTACCATTCG TGAATCTTAAGAGTTCGGTTAGGGGGACTCT AGTTGAGGGTTGGCACTCACGTATGGCTGGG CGCAGAAATAAAATTCAGGCGCAGCAGCACT TATCGATG |
| 24 | Sequence of the 3'-Region used for knock out of BMT1 | GAATTCACAGTTATAAATAAAAACAAAAACT CAAAAAGTTTGGGCTCCACAAAATAACTTAA TTTAAATTTTTTGTCTAATAAATGAATGTAAT TCCAAGATTATGTGATGCAAGCACAGTATGC TTCAGCCCTATGCAGCTACTAATGTCAATCT CGCCTGCGAGCGGGCCTAGATTTTCACTACA AATTTCAAAACTACGCGGATTATTGTCTCA GAGAGCAATTTGGCATTTCTGAGCGTAGCAG GAGGCTTCATAAGATTGTATAGGACCGTACC AACAAATTGCCGAGGCACAACACGGTATGCT GTGCACTTATGTGGCTACTTCCCTACAACGG AATGAAACCTTCCTCTTTCCGCTTAAACGAG AAAGTGTGTCGCAATTGAATGCAGGTGCCTG TGCGCCTTGGTGTATTGTTTTGAGGGCCCA ATTTATCAGGCGCCTTTTTTCTTGGTTGTTT TCCCTTAGCCTCAAGCAAGGTTGGTCTATTT CATCTCCGCTTCTATACCGTGCCTGATACTG TTGGATGAGAACACGACTCAACTTCCTGCTG CTCTGTATTGCCAGTGTTTTGTCTGTGATTT GGATCGGAGTCCTTCCTTACTTGGAATGATAA TAATTGGCGGAATCTCCCTAAACGGAGGC AAGGATTCTGCCTATGATGATCTGCTATCAT TGGGAAGCTT |
| 25 | Sequence of the 5'-Region used | AAGCTTGTTCACCGTTGGGACTTTTCCGTGG ACAATGTTGACTACTCCAGGAGGGATTCCAG |

BRIEF DESCRIPTION OF THE SEQUENCES

| SEQ ID NO: | Description | Sequence |
|---|---|---|
| | for knock out of BMT4 | CTTTCTCTACTAGCTCAGCAATAATCAATGC AGCCCCAGGCGCCCGTTCTGATGGCTTGATG ACCGTTGTATTGCCTGTCACTATAGCCAGGG GTAGGGTCCATAAAGGAATCATAGCAGGGAA ATTAAAAGGGCATATTGATGCAATCACTCCC AATGGCTCTCTTGCCATTGAAGTCTCCATAT CAGCACTAACTTCCAAGAAGGACCCCTTCAA GTCTGACGTGATAGAGCACGCTTGCTCTGCC ACCTGTAGTCCTCTCAAAACGTCACCTTGTG CATCAGCAAAGACTTTACCTTGCTCCAATAC TATGACGGAGGCAATTCTGTCAAAATTCTCT CTCAGCAATTCAACCAACTTGAAAGCAAATT GCTGTCTCTTGATGATGGAGACTTTTTTCCA AGATTGAAATGCAATGTGGGACGACTCAATT GCTTCTTCCAGCTCCTCTTCGGTTGATTGAG GAACTTTTGAAACCACAAAATTGGTCGTTGG GTCATGTACATCAAACCATTCTGTAGATTTA GATTCGACGAAAGCGTTGTTGATGAAGGAAA AGGTTGGATACGGTTTGTCGGTCTCTTTGGT ATGGCCGGTGGGGTATGCATGGGATAACCGACGG AAAAAGACGGGCCCATGTTCTGGGACCAATA GAACTGTGTAATCCATTGGGACTAATCAACA GACGATTGGCAATATAATGAAATAGTTCGTT GAAAAGCCACGTCAGCTGCTTTTCATTAAC TTTGGTCGGACACAACATTTTCTACTGTTGT ATCTGTCCTACTTTGCTTATCATCTGCCACA GGGCAAGTGGATTTCCTTCTCGCGCGGCTGG GTGAAAACGGTTAACGTGAA |
| 26 | Sequence of the 3'-Region used for knock out of BMT4 | GCCTTGGGGGACTTCAAGTCTTTGCTAGAAA CTAGATGAGGTCAGGCCCTCTTATGGTTGTG TCCCAATTGGGCAATTTCACTCACCTAAAAA GCATACAATTATTTAGCGAAATAGGTAGTA TATTTTCCCTCATCTCCCAAGCAGTTTCGTT TTTGCATCCATATCTCTCAAATGAGCAGCTA CGACTCATTAGAACCAGAGTCAAGTAGGGGT GAGCTCAGTCATCAGCCTTCGTTTCTAAAAC GATTGAGTTCTTTTGTTGCTACAGGAAGCGC CCTAGGGAACTTTCGCACTTTGGAAATAGAT TTTGATGACCAAGAGCGGGAGTTGATATTAG AGAGGCTGTCCAAAGTACATGGGATCAGGCC GGCCAAATTGATTGGTGTGACTAAACCATTG TGTACTTGGACACTCTATTACAAAAGCGAAG ATGATTTGAAGTATTACAAGTCCCGAAGTGT TAGAGGATTCTATCGAGCCCAGAATGAAATC ATCAACCGTTATCAGCAGATTGATAAACTCT TGGAAAGCGGTATCCCATTTTCATTATTGAA GAACTACGATAATGAAGATGTGAGAGACGGC GACCCTCTGAACGTAGACGAAGAAACAAATC TACTTTTGGGGTACAATAGAGAAAGTGAATC AAGGGAGGTATTGTGGCCATAATACTCAAC TCTATCATTAATG |
| 27 | Sequence of the 5'-Region used for knock out of BMT3 | GATATCTCCCTGGGGACAATATGTGTTG- CAACTGTTCG TTGTTGGTGCCCCAGTCCCCCAACCGGTACT AATCGGTCTATGTTCCCGTAACTCATATTCG GTTAGAACTAGAACAATAAGTGCATCATTGT TCAACATTGTGGTTCAATTGTCGAACATTGC TGGTGCTTATATCTACAGGGAAGACGATAAG CCTTTGTACAAGAGAGGTAACAGACAGTTAA TTGGTATTTCTTTGGGAGTCGTTGCCCTCTA CGTTGTCTCCAAGACATACTACATTCTGAGA AACAGATGGAAGACTCAAAAATGGGAGAAGC TTAGTGAAGAAGAGAAAGTTGCCTACTTGGA CAGAGCTGAGAAGGAGAACCTGGGTTCTAAG AGGCTGGACTTTTTGTTCGAGAGTTAAACTG CATAATTTTTTCTAAGTAAATTTCATAGTTA TGAAATTTCTGCAGCTTAGTGTTTACTGCAT CGTTTACTGCATCACCCTGTAAATAATGTGA |
| | | GCTTTTTTCCTTCCATTGCTTGGTATCTTCC TTGCTGCTGTTT |
| 28 | Sequence of the 3'-Region used for knock out of BMT3 | ACAAAACAGTCATGTACAGAACTAACGCCTT TAAGATGCAGACCACTGAAAAGAATTGGGTC CCATTTTTCTTGAAAGACGACCAGGAATCTG TCCATTTTGTTTACTCGTTCAATCCTCTGAG AGTACTCAACTGCAGTCTTGATAACGGTGCA TGTGATGTTCTATTTGAGTTACCACATGATT TTGGCATGTCTTCCGAGCTACGTGGTGCCAC TCCTATGCTCAATCTTCCTCAGGCAATCCCG ATGGCAGACGACAAAGAAATTTGGGTTTCAT TCCCAAGAACGAGAATATCAGATTGCGGGTG TTCTGAAACAATGTACAGGCCAATGTTAATG CTTTTTGTTAGAGAAGGAACAAACTTTTTTG CTGAGC |
| 29 | DNA encodes Tr ManI catalytic domain | CGCGCCGGATCTCCCAACCCTACGAGGGCGG CAGCAGTCAAGGCCGCATTCCAGACGTCGTG GAACGCTTACCACCATTTTGCCTTTCCCCAT GACGACCTCCACCCGGTCAGCAACAGCCTTTG ATGATGAGAGAAACGGCTGGGGCTCGTCGGC AATCGATGGCTTGGACACGGCTATCCTCATG GGGGATGCCGACATTGTGAACACGATCCTTC AGTATGTACCGCAGATCAACTTCACCACGAC TGCGGTTGCCAACCAAGGCATCTCCGTGTTC GAGACCAACATTCGGTACCTCGGTGGCCTGC TTTCTGCCTATGACCTGTTGCGAGGTCCTTT CAGCTCCTTGGCGACAAACCAGACCCTGGTA AACAGCCTTCTGAGGCAGGCTCAAACACTGG CCAACGGCCTCAAGGTTGCGTTCACCACTCC CAGCGGTGTCCCGGACCCTACCGTCTTCTTC AACCCTACTGTCCGGAGAAGTGGTGCATCTA GCAACAACGTCGCTGAAATTGGAAGCCTGGT GCTCGAGTGGACACGGTTGAGCGACCTGACG GGAAACCCGCAGTATGCCCAGCTTGCGCAGA AGGGCGAGTCGTATCTCCTGAATCCAAAGGG AAGCCCGGAGGCATGGCCTGGCCTGATTGGA ACGTTTGTCAGCACGAGCAACGGTACCTTTC AGGATAGCAGCGGCAGCTGGTCCGGCCTCAT GGACAGCTTCTACAGTACCTGATCAAGATG TACCTGTACGACCCGGTTGCGTTTGCACACT ACAAGGATCGCTGGGTCCTTGCTGCCGACTC GACCATTGCGCATCTCGCCTCTCACCCGTCG ACGCGCAAGACTTGACCTTTTTTGTCTTCGT ACAACGGACAGTCTACGTCGCCAAACTCAGG ACATTTGGCCAGTTTTGCCGGTGCAACTTC ATCTTGGGAGGCATTCTCCTGAACGAGCAAA AGTACATTGACTTTGGAATCAAGCTTGCCAG CTCGTACTTTGCCACGTACAACCAGACGGCT TCTGGAATCGGCCCCGAAGGCTTCGCGTGGG TGGACAGCGTGACGGGCGCCGGCGGCTCGCC GCCCTCGTCCCAGTCCGGGTTCTACTCGTCG GCAGGATTCTGGGTGACGGCACCGTATTACA TCCTGCGGCCGGAGACGCTGGAGAGCTTGTA CTACGCATACCGCGTCACGGGCGACTCCAAG TGGCAGGACCTGGCGTGGGAAGCGTTCAGTG CCATTGAGGACGCATGCCGCGCCGGCAGCGC GTACTCGTCCATCAACGACGTGACGCAGGCC AACGGCGGGGTGCCTCTGACGATATGGAGA GCTTCTGGTTTGCCGAGGCGCTCAAGTATGC GTACCTGATCTTTGCGGAGGAGTCGGATGTG CAGGTGCAGGCCAACGGCGGGAACAAATTTG TCTTTAACACGGAGGCGCACCCCTTTAGCAT CCGTTCATCATCACGACGGGGCGGCCACCTT GCTTAA |
| 30 | Sequence of the 5'-region that was used to knock into the PpPRO1 locus: | GAAGGGCCATCGAATTGTCATCGTCTCCTCA GGTGCCATCGCTGTGGGCATGAAGAGAGTCA ACATGAAGCGGAAACCAAAAAGTTACAGCA AGTGCAGGCATTGGCTGCTATAGGACAAGGC CGTTTGATAGGACTTTGGGACGACCTTTTCC GTCAGTTGAATCAGCCTATTGCGCAGATTTT |

BRIEF DESCRIPTION OF THE SEQUENCES

| SEQ ID NO: | Description | Sequence |
|---|---|---|
| | | ACTGACTAGAACGGATTTGGTCGATTACACC CAGTTTAAGAACGCTGAAAATACATTGGAAC AGCTTATTAAAATGGGTATTATTCCTATTGT CAATGAGAATGACACCCTATCCATTCAAGAA ATCAAATTTGGTGACAATGACACCTTATCCG CCATAACAGCTGGTATGTGTCATGCAGACTA CCTGTTTTTGGTGACTGATGTGGACTGTCTT TACACGGATAACCCTCGTACGAATCCGGACG CTGAGCCAATCGTGTTAGTTAGAAATATGAG GAATCTAAACGTCAATACCGAAAGTGGAGGT TCCGCCGTAGGAACAGGAGGAATGACAACTA AATTGATCGCAGCTGATTTGGGTGTATCTGC AGGTGTTACAACGATTATTTGCAAAAGTGAA CATCCCGAGCAGATTTTGGACATTGTAGAGT ACAGTATCCGTGCTGATAGAGTCGAAAATGA GGCTAAATATCTGGTCATCAACGAAGAGGAA ACTGTGGAACAATTTCAAGAGATCAATCGGT CAGAACTGAGGGAGTTGAACAAGCTGGACAT TCCTTTGCATACACGTTTCGTTGGCCACAGT TTTAATGCTGTTAATAACAAGAAGAGTTTTGGT TACTCCATGGACTAAAGGCCAACGGAGCCAT TATCATTGATCCAGGTTGTTATAAGGCTATC ACTAGAAAAACAAAGCTGGTATTCTTCCAG CTGGAATTATTTCCGTAGAGGGTAATTTCCA TGAATACGAGTGTGTTGATGTTAAGGTAGGA CTAAGAGATCCAGATGACCCACATTCACTAG ACCCCAATGAAGAACTTTACGTCGTTGGCCG TGCCCGTTGTAATTACCCCAGCAATCAAATC AACAAAATTAAGGGTCTACAAAGCTCGCAGA TCGAGCAGGTTCTAGGTTACGCTGACGGTGA GTATGTTGTTCACAGGGACAACTTGGCTTTC CCAGTATTTGCCGATCCAGAACTGTTGGATG TTGTTGAGAGTACCCTGTCTGAACAGGAGAG AGAATCCAAACCAAATAAATAG |
| 31 | Sequence of the 3'-region that was used to knock into the PpPRO1 locus: | AATTTCACATATGCTGCTTGATTATGTAATT ATACCTTGCGTTCGATGGCATCGATTTCCTC TTCTGTCAATCGCGCATCGCATTAAAAGTAT ACTTTTTTTTTTTTCCTATAGTACTATTCGC CTTATTATAAACTTTGCTAGTATGAGTTCTA CCCCCAAGAAAGAGCCTGATTTGACTCCTAA GAAGAGTCAGCCTCCAAAGAATAGTCTCGGT GGGGGTAAAGGCTTTAGTGAGGAGGGTTTCT CCCAAGGGGACTTCAGCGCTAAGCATATACT AAATCGTCGCCCTAACACCGAAGGCTCTTCT GTGGCTTCGAACGTCATCAGTTCGTCATCAT TGCAAAGGTTACCATCCTCTGGATCTGGAAG CGTTGCTGTGGGAAGTGTGTTGGGATCTTCG CCATTAACTCTTTCTGGAGGGTTCCACGGGC TTGATCCAACCAAGAATAAAATAGACGTTCC AAAGTGAAACAGTCAAGGAGACAAAGTGTT CTTTCTGACATGATTTCCACTTCTCATGCAG CTAGAAATGATCACTCAGAGCAGCAGTTACA AACTGGACAACAATCAGAACAAAAAGAAGAA GATGGTAGTCGATCTTCTTTTTCTGTTTCTT CCCCCGCAAGAGATATCCGGCACCCAGATGT ACTGAAAACTGTCGAGAAACATCTTGCCAAT GACAGCGAGATCGACTCATCTTTACAACTTC AAGGTGGAGATGTCACTAGAGGCATTTATCA ATGGGTAACTGGAGAAAGTAGTCAAAAAGAT AACCCGCCTTTGAAACGAGCAAATAGTTTTA ATGATTTTTCTTCTGTGCATGGTGACGAGGT AGGCAAGGCAGATGCTGACCACGATCGTGAA AGCGTATTCGACGAGGATGATATCTCCATTG ATGATATCAAAGTTCCGGGAGGGATGCGTCG AAGTTTTTTATTACAAAAGCATAGAGACCAA CAACTTTCTGGACTGAATAAAACGGCTCACT AACCAAAACAACTTACTAAACCTAATTTCTT CACGAACAACTTTATAGAGTTTTTGGCATTG TATGGGCATTTTGCAGGTGAAGATTTGGAGG AAGACGAAGATGAAGATTTAGACAGTGGTTC CGAATCAGTCGCAGTCAGTGATAGTGAGGGA GAATTCAGTGAGGCTGACAACAATTTGTTGT ATGATGAAGAGTCTCTCCTATTAGCACCTAG TACCTCCAACTATGCGAGATCAAGAATAGGA AGTATTCGTACTCCTACTTATGGATCTTTCA GTTCAAATGTTGGTTCTTCGTCTATTCATCA GCAGTTAATGAAAAGTCAAATCCCGAAGCTG AAGAAACGTGGACAGCACAAGCATAAAACAC AATCAAAAATACGCTCGAAGAAGCAAACTAC CACCGTAAAAGCAGTGTTGCTGCTATTAAA |
| 32 | Anti-Her2 Heavy chain (VH + IgG1 constant region) (DNA) | GAGGTTCAGTTGGTTGAATCTGGAGGAGGAT TGGTTCAACCTGGTGGTTCTTTGAGATTGTC CTGTGCTGCTTCCGGTTTCAACATCAAGGAC ACTTACATCCACTGGGTTAGACAAGCTCCAG GAAAGGGATTGGAGTGGGTTGCTAGAATCTA CCCAACTAACGGTTACACAAGATACGCTGAC TCCGTTAAGGGAAGATTCACTATCTCTGCTG ACACTTCCAAGAACACTGCTTACTTGCAGAT GAACTCCTTGAGAGCTGAGGATACTGCTGTT TACTACTGTTCCAGATGGGGTGGTGATGGTT TCTACGCTATGGACTACTGGGGTCAAGGAAC TTTGGTTACTGTTTCCTCCGCTTCTACTAAG GGACCATCTGTTTTCCCATTGGCTCCATCTT CTAAGTCTACTTCCGGTGGTACTGCTGCTTT GGGATGTTTGGTTAAAGACTACTTCCCAGAG CCAGTTACTGTTTCTTGGAACTCCGGTGCTT TGACTTCTGGTGTTCACACTTTCCCAGCTGT TTTGCAATCTTCCGGTTTGTACTCTTTGTCC TCCGTTGTTACTGTTCCATCCTCTTCCTTGG GTACTCAGACTTACATCTGTAACGTTAACCA CAAGCCATCCAACACTAAGGTTGACAAGAAG GTTGAGCCAAAGTCCTGTGACAAGACACATA CTTGTCCACCATGTCCAGCTCCAGAATTGTT GGGTGGTCCATCCGTTTTCTTGTTCCCACCA AAGCCAAAGGACACTTTGATGATCTCCAGAA CTCCAGAGGTTACATGTGTTGTTGTTGACGT TTCTCACGAGGACCCAGAGGTTAAGTTCAAC TGGTACGTTGACGGTGTTGAAGTTCACAACG CTAAGACTAAGCCAAGAGAAGAGCAGTACAA CTCCACTTACAGAGTTGTTTCCGTTTTGACT GTTTTGCACCAGGACTGGTTGAACGGTAAAG AATACAAGTGTAAGGTTTCCAACAAGGCTTT GCCAGCTCCAATCGAAAAGACTATCTCCAAG GCTAAGGGTCAACCAAGAGAGCCACAGGTTT ACACTTTGCCACCATCCAGAGAAGAGATGAC TAAGAACCAGGTTTCCTTGACTTGTTTGGTT AAAGGATTCTACCCATCCGACATTGCTGTTG AGTGGGAATCTAACGGTCAACCAGAGAACAA CTACAAGACTACTCCACCAGTTTTGGATTCT GATGGTTCCTTCTTCTTGTACTCCAAGTTGA CTGTTGACAAGTCCAGATGGCAACAGGGTAA CGTTTTCTCCTGTTCCGTTATGCATGAGGCT TTGCACAACCACTACACTCAAAAGTCCTTGT CTTTGTCCCCTGGTTAA |
| 33 | Saccharomyces cerevisiae mating factor pre-signal peptide (DNA) | ATGAGATTCCCATCCATCTTCACTGCTGTTT TGTTCGCTGCTTCTTCTGCTTTGGCT |
| 34 | PpCITI TT | CCGGCCATTTAAATATGTGACGACTGGGTGA TCCGGGTTAGTGAGTTGTTCTCCCATCTGTA TATTTTTCATTTACGATGAATACGAAATGAG TATTAAGAAATCAGGCGTAGCAATATGGGCA GTGTTCAGTCCTGTCATAGATGGCAAGCACT GGCACATCCTTAATAGGTTAGAGAAAATCAT TGAATCATTTTGGGTGGTGAAAAAAAATTGAT GTAAACAAGCCACCCACGCTGGGAGTCGAAC CCAGAATCTTTTGATTAGAAGTCAAACGCGT TAACCATTACGCTACGCAGGCATGTTTCACG TCCATTTTTGATTGCTTTCTATCATAATCTA AAGATGTGAACTCAATTAGTTGCAATTTGAC |

| SEQ ID NO: | Description | Sequence |
|---|---|---|
| | | CAATTCTTCCATTACAAGTCGTGCTTCCTCC<br>GTTGATGCAAC |
| 35 | Anti-Her2 light chain (VL + Kappa constant region) (DNA) | GACATCCAAATGACTCAATCCCCATCTTCTT<br>TGTCTGCTTCCGTTGGTGACAGAGTTACTAT<br>CACTTGTAGAGCTTCCCAGGACGTTAATACT<br>GCTGTTGCTTGGTATCAACAGAAGCCAGGAA<br>AGGCTCCAAAGTTGTTGATCTACTCCGCTTC<br>CTTCTTGTACTCTGGTGTTCCATCCAGATTC<br>TCTGGTTCCAGATCCGGTACTGACTTCACTT<br>TGACTATCTCCTCCTTGCAACCAGAAGATTT<br>CGCTACTTACTACTGTCAGCAGCACTACACT<br>ACTCCACCAACTTTCGGACAGGGTACTAAGG<br>TTGAGATCAAGAGAACTGTTGCTGCTCCATC<br>CGTTTTCATTTTCCCACCATCCGACGAACAG<br>TTGAAGTCTGGTACAGCTTCCGTTGTTTGTT<br>TGTTGAACAACTTCTACCCAAGAGAGGCTAA<br>GGTTCAGTGGAAGGTTGACAACGCTTTGCAA<br>TCCGGTAACTCCCAAGAATCCGTTACTGAGC<br>AAGACTCTAAGGACTCCACTTACTCCTTGTC<br>CTCCACTTTGACTTTGTCCAAGGCTGATTAC<br>GAGAAGCACAAGGTTTACGCTTGTGAGGTTA<br>CACATCAGGGTTTGTCCTCCCCAGTTACTAA<br>GTCCTTCAACAGAGGAGAGTGTTAA |
| 36 | ScTEF1 promoter | GATCCCCCACACACCATAGCTTCAAAATGTT<br>TCTACTCCTTTTTTACTCTTCCAGATTTTCT<br>CGGACTCCGCGCATCGCCGTACCACTTCAAA<br>ACACCCAAGCACAGCATACTAAATTTCCCCT<br>CTTTCTTCCTCTAGGGTGTCGTTAATTACCC<br>GTACTAAAGGTTTGGAAAGAAAAAAGAGAC<br>CGCCTCGTTTCTTTTTCTTCGTCGAAAAAGG<br>CAATAAAAATTTTTATCACGTTTCTTTTTCT<br>TGAAAATTTTTTTTTTGATTTTTTTCTCTT<br>TCGATGACCTCCCATTGATATTTAAGTTAAT<br>AAACGGTCTTCAATTTCTCAAGTTTCAGTTT<br>CATTTTTCTTGTTCTATTACAACTTTTTTTA<br>CTTCTTGCTCATTAGAAAGAAAGCATAGCAA<br>TCTAATCTAAGTTTTAATTACAAA |
| 37 | Sequence of the PpTRP2 gene integration locus: | GGTTTCTCAATTACTATATACTACTAACCAT<br>TTACCTGTAGCGTATTTCTTTTCCCTCTTCG<br>CGAAAGCTCAAGGGCATCTTCTTGACTCATG<br>AAAAATATCTGGATTTCTTCTGACAGATCAT<br>CACCCTTGAGCCCAACTCTCTAGCCTATGAG<br>TGTAAGTGATAGTCATCTTGCAACAGATTAT<br>TTTGAACGCAACTAACAAAGCAGATACACC<br>CTTCAGCAGAATCCTTTCTGGATATTGTGAA<br>GAATGATCGCCAAAGTCAAGTCCTGAGACA<br>GTTCCTAATCTTTACCCCATTTACAAGTTCA<br>TCCAATCAGACTTCTTAACGCCTCATCTGGC<br>TTATATCAAGCTTACCAACAGTTCAGAAACT<br>CCCAGTCCAAGTTCTCATTTGTTGAAAGTGCGA<br>AGAATGGTGACACCGTTGACAGGTACACCTT<br>TATGGGACATTCCCCAGAAAAATAATCAAG<br>ACTGGGCCTTTAGAGGGTGCTGAAGTTGACC<br>CCTTGGTGCTTCTGGAAAAAGAACTGAAGGG<br>CACCAGACAAGCGCAACTTCCTGGTATTCCT<br>CGTCTAAGTGGTGGTGCCATAGGATACATCT<br>CGTACGATTGTATTAAGTACTTTGAACCAAA<br>AACTGAAAGAAAACTGAAAGATGTTTTGCAA<br>CTTCCGGAAGCAGCTTTGTTGTTGACA<br>CGATCGTGGCTTTTGACAATGTTTATCAAAG<br>ATTCCAGGTAATTGGAAACGTTTCTCTATCC<br>GTTGATGACTCGGACGAAGCTATTCTTGAGA<br>AATATTATAAGACAAGAGAAGAAGTGGAAAA<br>GATCAGTAAAGTGGTATTTGACAATAAAACT<br>GTTCCCTACTATGAACAGAAAGATATTATTC<br>AAGGCCAAACGTTCACCTCTAATATTGGTCA<br>GGAAGGGTATGAAAACCATGTTCGCAAGCTG<br>AAAGAACATATTCTGAAAGGAGACATCTTCC<br>AAGCTGTTCCCTCTCAAAGGGTAGCCAGGCC<br>GACCTCATTGCACCCTTTCAACATCTATCGT |
| | | CATTTGAGAACTGTCAATCCTTCTCCATACA<br>TGTTCTATATTGACTATCTAGACTTCCAAGT<br>TGTTGGTGCTTCACCTGAATTACTAGTTAAA<br>TCCGACAACAACAACAAAATCATCACACATC<br>CTATTGCTGGAACTCTTCCCAGAGGTAAAAC<br>TATCGAAGAGGACGACAATTATGCTAAGCAA<br>TTGAAGTCGTCTTTGAAAGACAGGGCCGAGC<br>ACGTCATGCTGGTAGATTTGGCCAGAAATGA<br>TATTAACCGTGTGTGTGAGCCCACCAGTACC<br>ACGGTTGATCGTTTATTGACTGTGGAGAGAT<br>TTTCTCATGTGATGCATCTTGTGTCAGAAGT<br>CAGTGGAACATTGAGACCAAACAAGACTCGC<br>TTCGATGCTTTCAGATCCATTTTCCCAGCAG<br>GAACCGTCTCCGGTGCTCCGAAGGTAAGAGC<br>AATGCAACTCATAGGAGAATTGGAAGGAGAA<br>AAGAGAGGTGTTTATGCGGGAGCCGTAGGAC<br>ACTGGTCGTACGATGGAAAATCGATGGACAC<br>ATGTATTGCCTTAAGAACAATGGTCGTCAAG<br>GACGGTGTCGCTTACCTTCAAGCCGGAGGTG<br>GAATTGTCTACGATTCTGACCCCTATGACGA<br>GTACATCGAAACCATGAACAAAATGAGATCC<br>AACAATAACACCATCTTGGAGGCTGAGAAAA<br>TCTGGACCGATAGGTTGGCCAGAGACGAGAA<br>TCAAAGTGAATCCGAAGAAAACGATCAATGA<br>ACGGAGGACGTAAGTAGGAATTTATG |
| 38 | LmSTT3A (DNA) | ATGCCAGCTAAGAACCAACATAAGGGTGGTG<br>GTGATGGTGATCCAGACCCAACTTCTACTCC<br>AGCTGCTGAGTCCACTAAGGTTACAAACACT<br>TCCGATGGTGCTGCTGTTGATTCTACTTTGC<br>CACCATCCGACGAGACTTACTTGTTCCACTG<br>TAGAGCTGCTCCATATCCCAAGTTGTCCTAC<br>GCTTTCAAGGGTATCATGACTGTTTTGATCT<br>TGTGTGCTATCAGATCCGCTTACCAAGTTAG<br>ATTGATCTCCGTTCAAATCTACGGTTACTTG<br>ATCCACGAATTTGACCCATGGTTCAACTACA<br>GAGCTGCTGAGTACATGTCTACTCACGGTTG<br>GTCTGCTTTTTCTCCTGGTTCGATTACATG<br>TCCTGGTATCCATTGGGTAGACCAGTTGGTT<br>CTACTACTTACCCAGGATTGCAGTTGACTGC<br>TGTTGCTATCCATAGAGCTTTGGCTGCTGCT<br>GGAATGCCAATGTCCTTGAACAATGTTTGTG<br>TTTTGATGCCAGCTTGGTTGGTGCTATCGC<br>TACTGCTACTTTGGCTTTGATCGCTTTCGAA<br>GTTTCCGAGTCCATTTGTATGGCTGCTTGGG<br>CTGCTTTGTCCTTCTCCATTATCCCTGCTCA<br>CTTGATGAGATCCATGGCTGGTGAGTTCGAC<br>AACGAGTGTATTGCTGTTGCTGCTATGTTGT<br>TGACTTTCTACTGTTGGGTTAGATCCTTGAG<br>AACTAGATCCTCCTGGCCAATCGGTGTTTTG<br>ACTGGTGTTGCTTACGGTTACATGGCTGCTG<br>CTTGGGGAGGTTACATCTTCGTTTTGAACAT<br>GGTTGCTATGCACGCTGGTATCTCTTCTATG<br>GTTGACTGGGCTAGAAACACTTACAACCCAT<br>CCTTGTTGAGAGCTTACACTTTGTTCTACGT<br>TGTTGGTACTGCTATCGCTGTTTGTGTTCCA<br>CCAGTTGGAATGTCTCCATTCAAGTCCTTGG<br>AGCAGTTGGGAGCTTTGTTGGTTTTGGTTTT<br>CTTGTGTGGATTGCAAGTTTGTGAGGTTTTG<br>AGAGCTAGAGCTGGTGTTGAAGTTAGATCCA<br>GAGCTAATTTCAAGATCAGAGTTAGAGTTTT<br>CTCCGTTATGGCTGGTGTTGCTGCTTTGGCT<br>ATCTCTGTTTTGGCTCCAACTGGTTACTTTG<br>GTCCATTGTCTGTTAGAGTTAGAGCTTTGTT<br>CGTTGAGCACACTAGAACTGGTAACCCATTG<br>GTTGACTCCGTTGCTGAACATCATCCAGCTG<br>ACGCTTTGGCTTACTTGAACTACTTGCACAT<br>CGTTCACTTGATGTGGATCGTGTTCCTTGCCA<br>GTTCAGTTGATCTTGCCATCCAGAAACCAGT<br>ACGCTGTTTTGTTCGTTTTGGTCTACTCCTT<br>CATGGCTTACTACTTCTCCACTAGAATGGTT<br>AGATTGTTGATCTTGGCTGGTCCAGTTGCTT<br>GTTTGGGAGCTTCTGAAGTTGGTGGTACTTT |

BRIEF DESCRIPTION OF THE SEQUENCES

| SEQ ID NO: | Description | Sequence |
|---|---|---|
| | | GATGGAATGGTGTTTCCAGCAATTGTTCTGG GACAACGGAATGAGAACTGCTGATATGGTTG CTGCTGGTGACATGCCATACCAAAAGGACGA TCACACTTCCAGAGGTGCTGGTGCTAGACAA AAGCAGCAGAAGCAAAAGCCAGGTCAAGTTT CTGCTAGAGGATCTTCTACTTCCTCCGAGGA AAGACCATACAGAACTTTGATCCCAGTTGAC TTCAGAAGAGATGCTCAGATGAACAGATGGT CCGCTGGTAAAACTAACGCTGCTTTGATCGT TGCTTTGACTATCGGAGTTTTGTTGCCATTG GCTTTCGTTTTCCACTTGTCCTGTATCTCTT CCGCTTACTCTTTTGCTGGTCCAAGAATCGT TTTCCAGACTCAGTTGCACACTGGTGAACAG GTTATCGTTAAGGACTACTTGGAAGCTTACG AGTGGTTGAGAGACTCTACTCCAGAGGACGC TAGAGTTTTGGCTTGGTGGGACTACGGTTAC CAAATCACTGGTATCGGTAACAGAACTTCCT TGGCTGATGGTAACACTTGGAACCACGAGCA CATTGCTACTATCGGAAAGATGTTGACTTCT CCAGTTGCTGAAGCTCACTCCTTGGTTAGAC ACATGGCTGACTACGTTTTGATTTGGGCTGG TCAATCTGGTGACTTGATGAAGTCTCCACAC ATGGCTAGAATCGGTAACTCTGTTTACCACG ACATTTGTCCAGATGACCCATTGTTGTCAGCA ATTCGGTTTCCACAGAAACGATTACTCCAGA CCAACTCCAATGATGAGAGCTTCCTTGTTGT ACAACTTGCACGAGGCTGGAAAGACTAAGGG TGTTAAGGTTAACCCATCTTGTTCTTGAAGAG GTTTACTCCTCCAAGTACGGTTTGGTTAGAA TCTTCAAGGTTATGAACGTTTCCGCTGAGTC TAAGAAGTGGGTTGCAGACCCAGCTAACAGA GTTTGTCACCCACCTGGTTCTTGGATTTGTC CTGGTCAATACCCACCTGCTAAAGAAATCCA AGAGATGTTGGCTCACAGAGTTCCATTCGAC CAAATGGACAAGCACAAGCAGCACAAAGAAA CTCACCACAAGGCATAA |
| 39 | LmSTT3B (DNA) | ATGTTGTTGTTGTTCTTCTCCTTCTTGTACT GTTTGAAGAACGCTTACGGATTGAGAATGAT CTCCGTTCAAATCTACGGTTACTTGATCCAC GAATTTGACCCATGGTTCAACTACAGAGCTG CTGAGTACATGTCTACTCACGGTTGGTCTGC TTTTTTCTCCTGGTTCGATTACATGTCCTGG TATCCATTGGGTAGACCAGTTGGTTCTACTA CTTACCCAGGATTGCAGTTGACTGCTGTTGC TATCCATAGAGCTTTGGCTGCTGCTGGAATG CCAATGTCCTTGAACATGTTTGTGTTTTGA TGCCAGCTTGGTTTGGTGCTATCGCTACTGC TACTTTGGCTTTTGATGACTTACGAAATGTCC GGTTCCGGTATTGCTGCTGCTATTGCTGCTT TCATCTTCTCCATCATCCCAGCTCATTTGAT GAGATCCATGGCTGGTGAGTTCGACAACGAG TGTATTGCTGTTGCTGTATGTTGTTGACTT TCTACTGTTGGGTTAGATCCTTGAGAACTAG ATCCTCCTGGCCAATCGGTGTTTTGACTGGT GTTGCTTACGGTTACATGGCAGCTGCTTGGG GAGGTTACATCTTCGTTTTGAACATGGTTGC TATGCACGCTGGTATCTCTTCTATGGTTGAC TGGGCTAGAAACACTTACAACCCATCCTTGT TGAGAGCTTACACTTTGTTCTACGTTGTTGG TACTGCTATCGCTGTTTGTGTTCCACCAGTT GGAATGTCTCCATTCAAGTCCTTGGAGCAGT TGGGAGCTTTGTTGGTTTTGGTTTTCTTGTG TGGATTGCAAGTTTGTGAGGTTTTGAGAGCT AGAGCTGGTGTTGAAGTTAGATCCAGAGCTA ATTTCAAGATCAGAGTTAGAGTTTCTCCGT TATGGCTGGTGTTGCTGTTGGCTATCTCT GTTTTGGCTCCAACTGGTTACTTTGGTCCAT TGTCTGTTAGAGTTAGAGCTTTGTTCGTTGA GCACACTAGAACTGGTAACCCATTGGTTGAC TCCGTTGCTGAACACAGAATGACTTCCCCAA AGGCTTACGCTTTCTTCTTGGACTTCACTTA CCCAGTTTGGTTGTTGGGTACTGTTTTGCAG |
| | | TTGTTGGGAGCATTCATGGGTTCCAGAAAAG AGGCTAGATTGTTCATGGGATTGCATTCCTT GGCTACTTACTACTTCGCTGATAGAATGTCC AGATTGATCGTTTTGGCTGGTCCAGCTGCTG CTGCTATGACTGCTGGAATCTTGGGATTGGT TTACGAATGGTGTTGGGCTCAATTGACTGGA TGGGCTTCTCCTGGTTTGTCTGCTGCTGGTT CTGGTGGAATGGATGACTTCGACAACAAGAG AGGACAAACTCAAATCCAGTCCTCCACTGCT AATAGAAACAGAGGTGTTAGAGCACATGCTA TCGCTGCTGTTAAGTCCATTAAGGCTGGTGT TAACTTGTTGCCATTGGTTTTGAGAGTTGGT GTTGCTGTTGCTATTTTGGCTGTTACTGTTG GTACTCCATACGTTTCCCAGTTCCAGGCTAG ATGTATTCAATCCGCTTACTCCTTTGCTGGT CCAAGAATCGTTTTCCAGGCTCAGTTGCACA CTGGTGAACAGGTTATCGTTAAGGACTACTT GGAAGCTTACGAGTGGTTGAGAGACTCTACT CCAGAGGACGCTAGAGTTTTGGCTTGGTGGG ACTACGGTTACCAAATCACTGGTATCGGTAA CAGAACTTCCTTGGCTGATGGTAACACTTGG AACCACGAGCACATTGCTACTATCGGAAAGA TGTTGACTTCTCCAGTTGCTGAAGCTCACTC CTTGGTTAGACACATGGCTGACTACGTTTTG ATTTGGGCTGGTCAATCTGGTGACTTGATGA AGTCTCCACACATGGCTAGAATCGGTAACTC TGTTTACCACGACATTTGTCCAGATGACCCA TTGTGTCAGCAATTCGGTTTCCACAGAAACG ATTACTCCAGACCAACTCCAATGATGAGAGC TTCCTTGTTGTACAACTTGCACGAGGCTGGT AAAACTAAGGGTGTTAAGGTTAACCCATCTT GTTCTTGAAGAGGTTTACTCCTCCAAGTACGG TTTGGTTAGAATCTTCAAGGTTATGAACGTT TCCGCTGAGTCTAAGAAGTGGGTTGCAGACC CAGCTAACAGAGTTTGTCACCCACCTGGTTC TTGGATTTGTCCTGGTCAATACCCACCTGCT AAAGAAATCCAAGAGATGTTGGCTCACAGAG TTCCATTCGACCAAATGGACAAGCACAAGCA GCACAAAGAAACTCACCACAAGGCATAA |
| 40 | LmSTT3C (DNA) | ATGGCTGCCGCATCAAACGTTAATGCTCCTG AAAGTAACGTCATGACTACAAGATCCGCAGT TGCACCACCTTCCACCGCTGCACCAAAGGAG GCTTCTTCCGAAACTTTGCTTATTGGACTTT ACAAAATGCCTTCACAGACTAGAAGTTTGAT CTATTCAAGTTGTTTCGCTGTTGCCATGGCA ATTGCTTTGCCAATCGCTTACGATATGAGAG TTAGATCAATTGGTGTCTACGGATATTTGTT CCATTCTTCCGACCCTTGTTTAATTACAGA GCAGCTGAGTATATGTCTACTCACGGTTGGT CTGCTTTCTTTTCTTGGTTTGATTACATGAG TTGGTATCCATTGGGTAGACCTGTTGGATCT ACCACTTACTCCAGGACTTCAATTGACAGCCG TTGCAATTCATAGAGCTTTGGCCGCAGCTGG TATGCCAATGAGTCTTAACATGTTTGTGTC TTGATGCCTGCTTGGTTCTCATTGGTTTCAA GTGCAATGGCCGCATTGCTTTGCTCATGAAAT GTCTGGAAACATGGCTGTTGCCTCCATTTCT TCCATCTTGTTTCTGTTGTCCCTGCTCACT TGATGAGATCCATGGCGGAGAGTTCGATAA TGAATGTATTGCTGTTGCTGCCATGTTGCTT ACATTTTTACTGCTGGGTTAGATCCTTGAGAA CCAGATCAAGTTGGCCAATCGGTGTTTTGAC TGGAGTCGCTTACGGTTATATGGCAGCTGCC TGGGGTGGATACATTTTTGTTTTGAACATGG TCGCTATGCACGCCGGTATCTCTTCCATGGT TGACTGGGCTAGAAACACTTATAATCCATCT TTGCTTAGAGCTTACACCTTGTTCTATGTTG TCGGAACTGCAATTGCTGTTTGTGTCCCACC TGTTGGAATGTCACCTTTTAAGAGTCTTGAA CAGTTGGGAGCTTTGCTTGTTTTGGTCTTTA TTTTCGGACAGTCAGTTTGCGAGGCTCAAAG AAGAAGACTTGGAATCGCCAGATTGTCTAAG |

BRIEF DESCRIPTION OF THE SEQUENCES

| SEQ ID NO: | Description | Sequence |
|---|---|---|
| | | GAAGGTGTTGCATTGCTTATTAGAATCGATG CAGCTTTCTTTGTCGGAATTGTTGCCGTCGC AACAATCGCTCCAGCCGGTTTCTTTAAACCT CTTTCCTTGCAAGCAAACGCTATTATCACCG GAGTTTCAAGAACTGGTAATACATTGGTCGA TATTTTGCTTGCACAGGACGCTTCTAACTTG CTTATGGTTTGGCAATTGTTTTTGTTCCCAT TTTTGGGTTGGGTTGCAGGAATGTCCGCTTT TCTTAGAGAGTTGATCAGAAACTACACTTAC GCTAAGTCATTCATCTTGATGTACGGTGTTG TCGGAATGTATTTTGCTTCTCAATCCGTTAG AATGATGGTCATGATGGCCCCAGTTGCATGT ATTTTCACCGCCTTGCTTTTAGATGGGCAC TTGATTACTTGTTGGGTCTTTGTTCGGGC AGAAATGCCACCTTCATTTGATACTGACGCC CAGAGAGGTAGACAACAGCAACTGCTGAAG AGTCTGAGGCCGAAACAAAGAGAAAGGAAGA GGAATACAACACTATGCAAGTTAAGAAAATG TCCGTCAGAATGTTGCCTTTCATGTTGCTTT TGCTTTTGTTCAGATTGTTCCGGTTTATTGA GGACGTTGCCGCAATCTCAAGAAAGATGAA GCTCCAGGAATTGTTTTCCTAGTGAGCAGG TTCAAGGTGTCTCTGAAAAGAAAGTTGATGA CTACTATGCTGACATTGTCCGGTTTATTGAGAGAT TCCACACCTGAAGACGCCAGAGTTTTGGCAT GGTGGGATTACGGTTATCAAATTACAGGTAT CGGAAATAGAACCTCTTTGGCTGACGAAAC ACCTGGAATCATGAGCACATTGCTACTATCG GTAAAATGTTGACATCCCCAGTCGCCGAAGC ACATTCACTTGTTAGACACATGGCAGATTAC GTCTTGATTTCTGCTGGAGATACTTATTTCT CAGACTTGAACAGAAGTCCAATGATGGCTAA AATTGGTAATTCTGTTTACCATGACATCTGT CCAGATGACCCTCTTTGCTCCCAGTTTGTTT TGCAAAAGAGACCTAAAGCTGCCGCAGCTAA GAGATCCAGACATGTTTCCGTCGATGCCTTG GAGGAAGATGACATGTCCAGAGCACATGGTTT ACGAACCATCAAGTTTGATCGCTAAGAGTCT TATCTATCATTTGCACTCTACAGGAGTTGTC ACCGGTGTTACTCTTAACGAGACATTGTTCC AGCATGTCTTTACCTCTCCAAGGTTTGAT GAGAATTTTCAAGGTTATGAACGTCTCTACT GAATCCAAGAAATGGGTTGCTGATAGTGCCA ATAGAGTCTGTCACCCACCTGGATCTTGGAT TTGCCCAGGTCAATACCCACCCAGTTGCATGT ATCCAGGAAATGTTGGCCCATCAACACACTA ATTTTAAGGATTTGTTGGACCCTAGAACAAC CTGGTCAGGTAGTAGAAGATAA |
| 41 | Sequence of the PpURA5 auxotrophic marker: | TCTAGAGGGACTTATCTGGGTCCAGACGATG TGTATCAAAAGACAAATTAGAGTATTTATAA AGTTATGTAAGCAAATAGGGGCTAATAGGGA AAGAAAAATTTTGGTTCTTTATCAGACGTGG CTCGCGCGCAGTGTTTTTCGTGCTCCTTTGT AATAGTCATTTTTGACTACTGTTCAGATTGA AATCACATTGAAGATGTCACTGGAGGGGTAC CAAAAAAGGTTTTTGGATGCTGCAGTGGCTT CGCAGGCCTTGAAGTTTGGAACTTTCACCTT GAAAAGTGGAAGACAGTCTCCATACTTCTTT AACATGGGTCTTTTCAACAAAGCTCCATTAG TGAGTCAGCTGGCTGAATCTTATGCTCAGGC CATCATTAACAGCAACCTGGAGATAGACGTT GTATTTGGACCAGCTTATAAAGGTATTCCTT TGGCTGCTATTACCGTGTTGAAGTTGTACGA GCTGGGCGGCAAAAAATACGAAATGTCGGA TATGCGTTCAATAGAAAAGAAAAGAAAGACC ACGGAGAAGGTGGAAGCATCGTTGGAGAAAG TCTAAAGAATAAAAGATACTGATTATCGAT GATGTGATGACTGCAGGTACTGCTATCAACG AAGCATTTGCTATAATTGGAGCTGAAGGTGG GAGAGTTGAAGGTTGTATTATTGCCCTAGAT AGAATGGAGACTACAGGAGATGACTCAAATA CCAGTGCTACCCAGGCTGTTAGTCAGAGATA TGGTACCCCTGTCTTGAGTATAGTGACATTG GACCATATTGTGGCCCATTTGGGCGAAACTT TCACAGCAGACAGACGAGAAATCTCAAATGGAAAC GTATAGAAAAAAGTATTTGCCCAAATAAGTA TGAATCTGCTTCGAATGAATGAATTAATCCA ATTATCTTCTCACCATTATTTTCTTCTGTTT CGGAGCTTTGGGCACGGCGGCGGATCC |
| 42 | Sequence of the part of the Ec lacZ gene that was used to construct the PpURA5 blaster (recyclable auxotrophic marker) | CCTGCACTGGATGGTGGCGCTGGATGGTAAG CCGCTGGCAAGCGGTGAAGTGCCTCTGGATG TCGCTTCCACAAGGTAAACAGTTGATTGAACT GCCTGAACTACCGCAGCCGGAGAGCGCCGGG CAACTCTGGCTCACAGTACGCGTAGTGCAAC CGAACGCGACCGCATGGTCAGAAGCCGGGCA CATCAGCGCCTGGCAGCAGTGGCGTCTGGCG GAAAACCTCAGTGTGACGCTCCCCGCCGCGT CCCACGCCATCCCGCATCTGACCACCAGCGA AATGGATTTTGCATCGAGCTGGGTAATAAG CGTTGGCAATTTAACCGCCAGTCAGGCTTTC TTTCACAGATGTGGATTGGCGATAAAAAACA ACTGCTGACGCCGCTGCGCGATCAGTTCACC CGTGCACCGCTGGATAACGACATTGGCGTAA GTGAAGCGACCCGCATTGACCCTAACGCCTG GGTCGAACGCTGGAAGGCGGCGGGCCATTAC CAGGCCGAAGCAGCGTTGTTGCAGTGCACGG CAGATACACTTGCTGATGCGGTGCTGATTAC GACCGCTCACGCGTGGCAGCATCAGGGGAAA ACCTTATTTATCAGCCGGAAAACCTACCGGA TTGATGGTAGTGGTCAAATGGCGATTACCGT TGATGTTGAAGTGGCGAGCGATACACCGCAT CCGGCGCGGATTGGCCTGAACTGCCAG |
| 43 | ScYos9p (protein) | MQAKIIYALSAISALIPLGSSLLAPIEDPIV SNKYLISYIDEDDWSDRILQNQSVMNSGYIV NMGDDLECFIQNASTQLNDVLEDSNEHSNSE KTALLTKTLNQGVKTIFDKLNERCIFYQAGF WIYEYCPGIEFVQFHGRVNTKTGEIVNRDES LVYRLGKPKANVEEREFELLYDDVGYYISEI IGSGDICDVTGAERMVEIQYVCGGSNSGPST IQWVRETKICVYEAQVTIPELCNLELLAKNE DQKNASPILCRMPAKSKIGSNSIDLITKYEP IFLGSGIYFLRPFNTDERDKLMVTDNAMSNW DEITETYYQKFGNAINKMLSLRLVSLPNGHI LQPGDSCVWLAEVVDMKDRFQTTLSLNILNS QRAEIFFNKTFTFNEDNGNFLSYKIGDHGES TELGQITHSNKADINTAEIRSDEYLINTDNE LFLRISKEIAEVKELLNEIVSPHEMEVIFEN MRNQPNNDFELALMNKLKSSLNDDNKVEQIN NARMDDDESTSHTTRDIGEAGSQTTGNTESE VTNVAAGVFIEHDEL |
| 44 | ScYOS9 DNA | ATGCAAGCTAAAATTATATATGCTCTGAGCG CAATTTCTGCGTTGATTCCGTTAGGATCATC ACTATTAGCACCTATAGAAGACCCCATAGTA TCGAATAAGTACCTCATATCTTACATCGATG AGGACGACTGGAGTGATAGGATATTACAAA TCAGTCTGTCATGAACTCGGGATATAGTG AATATGGGCGACGACCTTGAATGCTTTATTC AAAATGCAAGCACTCAATTGAATGATGTATT GGAAGACTCAAATGAGCATAGCAATAGTGAA AAGACAGCATTATTAACTAAAACCCTGAATC AAGGTGTTAAGACAATTTTCGATAAATTAAA TGAACGGTGCATCTTCTACCAAGCCGGATTT TGGATTTACGAGTACTGTCCTGGCATAGAAT TTGTTCAGTTCCATGGTAGAGTAAATACAAA AACTGGTGAAATAGTAAATCGAGATGAATCT TTGGTCTACCGCCTGGGAAAACCAAAAGCAA ATGTAGAAGAGAGAATTTGAACTACTTTA TGACGATGTAGGATATTACATCAGCGAAATT ATAGGGTCAGGTGATATTTGCGATGTGACGG GGGCTGAAAGAATGGTTGAAATACAATATGT CTGTGGCGGCTCAAACTCTGGACCATCGACT ATTCAATGGGTGAGAGAAACAAAAATTTGTG |

BRIEF DESCRIPTION OF THE SEQUENCES

| SEQ ID NO: Description | Sequence |
|---|---|
| | TTTATGAAGCCCAAGTTACCATACCTGAATT GTGCAATTTAGAATTACTAGCCAAAAATGAA GACCAAAAGAACGCCTCACCTATACTTTGCA GGATGCCCGCAAAATCAAAAATTGGTAGTAA CTCTATTGATTTAATCACCAAATATGAACCG ATTTTTTAGGTTCTGGAATATACTTTCTAA GGCCCTTTAACACCGACGAAAGAGACAAATT AATGGTTACTGACAATGCCATGTCAAATTGG GATGAGATTACGGAAACATATTACCAGAAAT TTGGAAATGCCATAAACAAAATGCTTAGTTT GAGATTAGTATCGTTACCTAATGGACATATT CTCCAGCCTGGTGACTCATGTGTTTGGTTGG CGGAAGTGGTTGATATGAAAGATCGGTTTCA AACCACTTTATCGTTAACATACTTAATTCA CAGAGAGCAGAGATATTTTCAACAAGACGT TTACATTTAATGAAGATAATGAAACTTCCT ATCATACAAAATTGGGGATCATGGCGAGTCA ACTGAACTTGGTCAAATAACCCACTCAAACA AAGCAGATATAAATACCGCAGAAATTCGGTC AGATGAATACTTAATTAACACTGATAATGAG CTATTCTTGAGGATTTCTAAGGAGATAGCAG AAGTGAAAGAATTATTAAACGAAATCGTAAG TCCACATGAAATGGAAGTAATATTTGAAAAC ATGAGAAATCAACCGAATAATGATTTTGAAC TGGCGTTGATGAACAAGTTGAAATCCTCATT AAATGATGATAACAAAGTTGAGCAGATAAAC AACGCAAGGATGGATGATGATGAAAGCACTA GTCATACAACCAGAGACATCGGGGAAGCTGG ATCACAAACGACAGGGAATACTGAATCGGAG GTAACAAACGTAGCAGCTGGTGTTTTCATCG AACATGATGAGCTTTAA |
| 45 PpYos9p (protein) | MIKVLLFLLSLSSLVKALDDSIDKNSVYTIN YLNHAISPTSEKIVTLRSTDDQYFECLFNDE IDTDQKLHQKQILKTLPAQYNLSEIPELQTE INSAFNILENYNLNDAQPTKDRYWTYQIING KLYQYNGNLRIVLANIPKNLTREDIVLEKNM HQSVFLSLSLQNGAICDLTFTPRKTNIRFQY VNKLNTLGIVSADEIQTCEYEILINVPKFKD TIFQYGFLEPLKKIDCYSSDSSMINLADYQI SVLSHKWFLGAKDFRLILITDVSNPPVISIE ELNLIFQTFPKYGPPELGITGEISPHDTFIF RIPVYSYNRTKFGDVLVEQNIRGEKRFLFTE DRIPHDTPNFRVYNGVNVN |
| 46 PpYOS9 (DNA) | ATGATAAAGGTCCTGCTATTCCTGCTCTCCC TATCAAGTCTTGTGAAAGCTTTGGATGATTC CATTGATAAGAATTCTGTGGTAAGTCTTTTA ATTTTTGTTTTCACAAGATCATGCCGTGCTA ACTGGGTACTATAGTATACCATAAACTACTT AAATCATGCCATCTCACCCACCTCAGAAAAA ATAGTGACATTAAGATCAACGGACGATCAAT ATTTTGAGTGTTTGTTTAATGATGAAATTGA TACTGACCAGAAACTACATCAAAAGCAGATT CTGAAAACTCTTCCAGCTCAATACAACTTGA GTGAAATACCAGAACTTCAAACTGAAATAAA CTCTGCATTCAATATACTTGAAAACTATAAC CTCAACGATGCTCAGCCAACCAAGGACAGAT ATTGGACATATCAAATAATAAATGGAAAATT GTACCAATATAACGGGAACTTGCGAATTGTC CTGGCTAATATACCCAAGAATCTGACGAGGG AAGACATAGTTCTGGAGAAGAATATGCACCA ATCGGTGTTTTATCACTCAGCTTACAAAAC GGTGCCATTTGTGATTTGACTTTCACTCCTA GAAAGACAAATATACGTTTCAATACGTTAA CAAGCTCAACACTCTAGGAATTGTCTCCGCC GATGAAATACAGACCTGTGAATATGAAATTC TTATCAATGTTCCTAAGTTCAAAGATACCAT TTTTCAGTACGGATTTTTGGAGCCTTTGAAG AAGATTGATTGCTACTCGAGTGATAGCTCAA TGATAAATTTGGCAGACTACCAAATATCTGT CCTTTCCCATAAATGGTTCTTAGGGGCCAAA GATTTCAGGTTGATTTTGATCACTGATGTGT |
| 47 AfYos9p (protein) | MIRRIRTLTPLLVLACAGSGAWASKKAFNIQ DDLLAYPQFQVFFPDEYILDARARELLQNQQ ESSSASADKTFSEGNDAQVYLGSRKDQSEDV NKETIEGSGFTYEEMLLEGQRYLCSIPQVDN GNRDQTNGAESTSKEDEQREIARATDRGLEL LREMEGKCMYYISGWWSYSFCYKKQIKQFHA LPSGPGVPNYPPIEDSTTHSFVLGRFPNSGD DEDLEGDAEHKKTTTDVAELQTKGGSRYLVQ RLGGGTKCDLTGKDRKIEVQFHCHPQSTDRI GWIKELTTCSYLMVIYTPRLCNDVAFLPPQQ DEAHAIECREILSEEEVSDWEANREYHLAQQ LVESAITPEFPVVGDIEVGAHKWVGSEGKQI EKGRVASIGEEKIEVVAKRQNGEITRLSKEE LKKYGLDPEKIETLKSRLEELAKGKDWTLEI VESNGERGLVGTVDSNDDEKEDHAAQGSISQ PAQGTTADKGESNAETGEEKKKADEKIDHYE PEKSGPTTDDADDGSEEIFFKDEL |
| 48 AfYOS9 (DNA) | ATGATTCGACGTATACGGACTCTTACCCCAT TGCTGGTGCTGGCTTGTGCTGGTTCCGGCGC ATGGGCCAGCAAGAAGGCGTTCAACATACAA GATGATCTACTTGCATATCCTCAATTTCAAG TCTTCTTCCCTGATGAATACATTCTTGATGC GCGAGCAAGGGAGTTATTACAGAATCAACAA GAGAGCTCTTCGGCTTCCGCTGATAAGCAT TCTCCGAAGGCAATGATGCGCAAGTATATCT GGGAAGCCGAAAAGATCAATCTGAAGACGTC AATAAAGACGATAGAAGGATCTGGGTTCA CATACGAGGAGATGCTCCTTGAGGGACAGAG ATATCTCTGTTCCATTCCGCAAGTCGACAAC GGAAACAGGGACCAGACGAACGGAGCGGAAA GCACCAGTAAAGAGGATGAACAGCGAGAAAT TGCACGCGCGACGACCGTGGCCTGGAACTT CTGCGCGAGATGGAAGGCAAATGCATGTACT ACATATCCGGATGGTGGTCATACTCATTCTG CTACAAGAAGCAAATCAAGCAGTTTCATGCA CTACCGTCCGGTCCAGGCGTGCCCAACTACC CGCCGATAGAAGACTCTACGACCCATTCTTT CGTGCTGGGCAGGTTTCCCAACAGCGGCGAC GACGAGGATTTGGAGGGGGATGCGGAGCACA AAAAGACAACTACAGATGTCGCCGAGCTCCA GACTAAAGGCGGGTCGCGGTACTTAGTGCAG CGGCTGGGGGGCGGAACCAAGTGCGACTTGA CAGGCAAAGACCGGAAGATCGAAGTGCAGTT CCACTGCCATCCGCAATCTACAGATCGGATC GGTTGGATCAAGGAACTTACTACTTGCTCAT ATCTCATGGTGATCTACACTCCGCGCTTGTG CAATGATGTCGCATTTCTGCCGCCTCAGCAG GACGAGGCTCACGCGATCGAATGCCGCGAGA TTCTCTCCGAGGAAGAGGTTTCCGACTGGGA AGCAAACCGGGAATATCATTTGGCTCAGCAG CTCGTCGAATCAGCGATTACACCCGAGTTTC CTGTTGTCGGGGATATCGAGGTCGGGGCGCA CAAGTGGGTGGGATCGGAAGGCAAGCAGATC GAGAAGGGTCGAGTGGCATCCATTGGAGAAG AGAAGATCGAGGTAGTTGCCAAGCGCCAAAA TGGAGAGATCACAAGGTTGTCCAAGGAGGAG TTGAAGAAATACGGTCTTGATCCTGAGAAGA TTGAGACGCTGAAAAGCCGCCTCGAGGAGCT TGCCAAGGGTAAGGACTGGACACTGGAGATT GTCGAGTCTAACGGCGAGCGTGGCTTAGTCG GAACTGTCGACTCCAACGACGATGAGAAAGA GGATCACGCCGCACAGGGCTCTATATCGCAG |

| SEQ ID NO: | Description | Sequence |
|---|---|---|
| | | CCGGCACAGGGAACTACAGCTGACAAGGGGG AATCCAATGCAGAGACAGGAGAGGAAAAGAA GAAGGCAGACGAGAAGATAGACCATTACGAG CCAGAAAAATCAGGGCCGACCACTGATGATG CCGACGACGGCAGCGAGGAAATCTTCTTCAA GGATGAGCTCTAG |
| 49 | SpYos9p (protein) | MFPHLILPAIGSSKVRTMVLPFAFVGFFIFP ICLASLLDWNDAYEYPKYSFEWSNVSILEGD IDSIKEKTEKTKLSSLFYAGKHEYFCVYPNA SLIKQNSTTEPSYDLQELRIQGTEKINELAN VFLIENRGYWTYDYVYGQHVRQYHLEPQQGS DKVLANPMYILGTAPNTQTKKNLEENWAIGF VEGKAYLQTTFRNGTMCDITKRPRHVILSYE CSTNSDTPEITQYQEVSSCAYSMTIHVPGLC SLPAFKIQEDIPSEKIVCYNVIKEKSNEVDH KDSQHVVDEVAQTSPPEVKEVETQSS |
| 50 | SpYOS9 (DNA) | ATGTTTCCACATTTGATTCTACCTGCAATCG GCTCATCTAAAGTTAGGACTATGGTGCTACC ATTTGCTTTTGTGGGGTTTTTTATTTTTCCA ATATGTTTAGCTTCTTTGTTAGACTGGAATG ATGCATATGAATATCCTAAATATTCGTTTGA ATGGAGTAATGTGTCAATATTAGAGGGCGAC ATTGACTCAATTAAAGAAAAAACTGAAAAAA CTAAATTATCGTCATTATTCTATGCTGGAAA GCATGAATATTTTTGTGTATATCCCAATGCG TCTCTTATAAAACAAAATAGCACAACCGAAC CAAGCTATGATTTACAAGAATTGCGGATACA AGGGACTGAAAAATCAATGAGCTTGCTAAT GTATTTTTAATCGAGAATCGTGGTTATTGGA CTTATGACTATGTCTACGGTCAACACGTGCG TCAATATCATTTGGAGCCGCAGCAAGGTTCT GACAAAGTCCTTGCTAACCCTATGTATATAC TTGGTACGGCACCTAACACTCAAACTAAAAA GAATTTGGAAGAAAATTGGGCTATTGGATTT GTTGAAGGTAAAGCATATTTGCAAACAACTT TCCGAAATGGGACTATGTGCGACATTACTAA GAGACCAAGACACGTAATTCTAAGTTATGAA TGCAGTACAAATTCGGATACTCCTGAAATTA CTCAATATCAAGAAGTTTCAAGCTGTGCATA TTCAATGACTATTCACGTTCCCGGTTTATGC TCATTACCTGCTTTCAAAATTCAAGAGGACA TACCCTCTGAAAAAATTGTGTGCTATAATGT AATTAAAGAAAAATCAAACGAAGTCGACCAT AAGGATTCCCAGCACGTTGTTGATGAAGTTG CTCAAACATCTCCGCCTGAGGTGAAGGAGGT AGAGACGCAATCAAGTTAG |
| 51 | Pichia pastoris ATT1 5' region in pGLY5933 | GGCCGGGACTACATGAGGCCGATTCTTCAAG CCAGGGAAATTAATTGCTTGAACCGGAAAAT CATTAAGGCAGGCAACGAAAAATCCAACTCC TTGGTTGAATTGACTCAAAAGTTTATCTTAC GGAGAAAAGCTAAAGACATTCAATACGAATTT CCTTCCGCCAAAAACTGAACTGATACTGATG GTTCCAATGACTGAATTACAACAGGAGCTAT ACAAGGATATAATTGAAACTAACCAAGCCAA GCTTGGCTTGATCAACGACAGAAACTTTTTT CTTCAAAAAATTTTGATTCTTCGTAAAATAT GCAATTCACCCTCCCTGCTGAAAGACGAACC TGATTTTGCCAGATACAATCTCGGCAATAGA TTCAATAGCGGTAAGATCAAGCTAACAGTAC TGCTTTTACAAAGCTGTTTGAAACCACCAA TGAGAAGTGTGTGATTGTTTCAAACTTCACT AAAACTTTGGACGTACTTCAGCTAATCATAG AGCACAACAATTGGAAATACCACCGACTAGA TGGTTCGAGTAAAGGACGGGACAAAATCGTA CGAGATTTTAACGAGTCGCCTCAAAAAGATC GATTCATCATGTTGCTTTCTTCCAAGGCAGG GGGAGTGGGGCTCAACTTAATTGGAGCCTCA CGCTTAATTCTTTTTGATAACGACTGGAATC CCAGTGTTGACATTCAAGCAATGGCTAGAGT GCATCGAGACGGGCAGAAAAGGCACACCTTT ATCTATCGTTTGTATACGAAAGGCACAATTG ACGAAAAGATCCTACAAAGGCAATTGATGAA ACAAAATCTGAGCGACAAATTCCTGGATGAT AATGATAGCAGCAAGGATGATGTGTTTAACG ACTACGATCTCAAAGATTTGTTTACTGTAGA TCTTGACACGAATTGTAGTACACACGATTTG ATGGAATGTTTATGTAATGGGCGGCTGAGAG ATCCGACTCCCGTCTTGGAAGCAGAAGAATG CAAGACAAAACCGTTGGAGGCCGTTGACGAC ACGGATGATGGTTGGATGTCAGCTCTGGATT TCAAACAGTTATCACAAAAAGAGGAGACAGG TGCTGTGTCAACAATGCGTCAATGTCTGCTC GGATATATCAACACATTGATCCAAAGATTTTGG AACCAACAGAACCTGTAGGGGACGATTTGGT ATTGGCAAACATCCTCGCGGAGTCCTCAGGC TTGGCTAAATCTGCATTGTCATCTGAAAAGA AACCCAAGAAACCAGTGGTGAACTTTATCTT TGTGTCAGGCCAAGACTAAGCTGGAAGAACG GAACTTTAATCGAAGGAAAAATTAAATGTCA AAGTGGGTCGATCAGGAGATAATCCATGCTT CACGTGATTTTCTTAATAAACGCCGGAAAA ACTTTCTTTTTTGTGACCAAAATTATCCGAT CTGAAAAAAATTACGCATGCGTGAAGTAGG ATGAGAGACTTACTGTTGAACTTTGTGATGAC GAGGGGAAAAGGAATATCCTGATCGTAAACA AAAAAGTTTTCCAGCCCAATCGGGAACATCT GCGAAGTGTTGGAATTCAACCCCTCTTTCGA AAATGTTCCATTTTACCCAAAATTATTGTTA TTAAATAATACATGTGTTACTAGCAAAGTCT GCGCTTTCCATGTCTCAGATTCGGCAGATAA CAAAGTTGACACGTTCTTGCGAGATACGCAT GAATCTTTTGGCTGCTTTTTGTGAAAGAGAA ATGGTGCCATATATTGCAGACGCCCCTGAAA GATTAGTGTGCGGCTGAGTCTTTTTTTTTTC TCAACCAGCTTTTTCTTTTTATTGGGTACCA TCGCGCACGCAGGACTCATGCTCCATTAGAC TTCTGAACCACCTGACTTAATATTCATGGAC GGACGCTTTTATCCTTAAATTGTTCATCCAT TCCTCAATTTTTCCGTTTGCCCTCCCTGTAC TATTAAATTACAAAAGCTGATCTTTTTCAAG TGTTTCTCTTTGAATCGCTC |
| 52 | Pichia pastoris ATT1 3' region in pGLY5933: | GGACCCTGAAGACGAAGACATGTCTGCCTTA GAGTTTACCGCAGTTCGATTCCCCAACTTTT CAGCTACGACAACAGCCCCGCCTCCTACTCC AGTCAATTGCAACAGTCCTGAAAACATCAAG ACCTCCACTGTGGACGATTTTTTGAAAGCTA CTCAAGATCCAAATAACAAAGAGATACTCAA CGACATTTACAGTTTGATTTTTGATGACTCC ATGGATCCTATGAGCTTCGGAAGTATGGAAC CAAGAAACGATTTGGAAGTTCCGGACACTAT AATGGATTAATTTGCAGCGGGCCTGTTTGTA TAGTCTTTGATTGTGTATAATAGAATTACTA CGCGTATATCCCGATCTGGAAGTAACATGGA AGTTTCCCATTTTCGCGCAGTCTCCTACTCG TATCCTCCCCACCCCTTACCGATGACGCAAA AGGTCACTAGATAAGCATAGCATAGTTTCAT CCCTTGCTCTTTCCTTGTACCAACAGATCAT GGCTGGGAATCTCAAGGATATTCTATCCTTG TCGAGGAAGACAGCAAGGAATCTGAAGCAGG CTCTGGATGAGCTTGCGGAGCAGGTGATCAA CCACCAACGGAGACGACCAGCTCTGGTCCGA GTTCCTATCAACAACAACCTTAGGCGCAAGA GCCAGCAGTCCTTTTTGAATCGCAGGTCATT CCATCTTTGGACCAGCAAGTACAACCCATAC TTTTGGAGGGGAGGCAGAAGCAACGTTCTGG ACCAGCTTAACCGTGAAGCTTTAAGGTACAG ATCGTCTTTTGCGAAACCCGGATTTTATCCA AGTGGGCTGTATCAGTCAACTTTCCCTCAAA GAGGGTAGTAGGATGTTTTCCACCTGCGCCTA CTCATGTCAGCAGGAGGCAGTCAAAAACTTG ACTTCCGCTGTTCGTGCTTTGTTACAAAGTG GTGCTAAATTTCGGCAGTCAAATGAACAAAT |

BRIEF DESCRIPTION OF THE SEQUENCES

| SEQ ID NO: | Description | Sequence |
|---|---|---|
| | | GAAACACTGTTCGCAAAAGAAGAAGCACTTC TCTAAATTTTCTAAGAGGCTTACTTCTTCCA CTGCCGCTGGGTCTGGCAAGAATGCTGAACA AGCTCCTTCTGGTTTGGCCGAAGGATCCGCT GTTGTTTTAGCCTTGAACGTCAAAGTCACA ATACTGAGTTGGAAGGAATCTTGGATCAAGA AACTTCTTCCATTCTCGAGGAAGAAATGGTT CAACATGAGCGTCACCTGGCTATTATTAGAG AAGAAATCCAGAGAATTAGTGAGAATCTAGG ATCATTACCATTAATCATGTCTGGTCACAAG ATTGAGGTATTTTTCCCCAATTGTGACACTG TTAAATGTGAGCAACTGATGAGAGATTTGGC TATTACGAAAGGGGTTGTGAGGCGTCATGAT TCTACTGCTGAGCATTCAAGCTCCAGGTCAT TTGTTCCAGAAGATTGCTTGTATTCCTCAGG GTCAAGTTCACCGAATCCTTTATCCTCAACT TCTTCGAAATCATTTGATAGAGTCTCATTGG ACTACATTTCCTCTCGGTCTACATCTGATCA AACCACTGGTTCTGAGTACACATCTCTGTCT CAACATATCACCTGGTTAGCAATTACAACC CTGTACTATCCTCAGCCCCGGGTTCTTCGAG GGTCTTGGAGCTGAATACTCCCGAGTCCACT ATGGAAGGCAGTACAGATCTGGAGTATTTAA CGCGAGACGATGTGTTGCTGTTAAATGTCTA ATCTAGACCTATCCTTCATTCTATATAGCTT AGTTGAGTTTTACGTAAGCCCTAGTTTTTGT TAATTCTTATCGATTTATGGTTAGTGTACCA CTCAACTCACGATGATATATCCCAGGAGCTG TTTGTGCATTATAACTACCAATCCT |
| 53 | DNA encodes *Mus muscula* endomannosidase (codon-optimized for expression in *Pichia pastoris*) | ATGGCTAAGTTTAGAAGAAGAACCTGTATTT TGTTGTCTTGTTTATCCTTTTTATTTTCTC CTTGATGATGGGATTGAAGATGCTTTGGCCT AACGCTGCCTCTTTTGGTCCACCTTTCGGAT TGGATTTGCTTCCAGAACTTCATCCTTTGAA CGCACACTCAGGTAATAAGGCTGATTTTCAG AGAAGTGACAGAATTAACATGGAAACTAACA CAAAGGCTTTGAAAGGTGCCGGAATGACTGT TCTTCCTGCCAAAGCATCCGAGGTCAACCTT GAAGAGTTGCCACCTCTTAACTACTTTTTGC ATGCTTTCTACTACTCATGGTACGGTAACCC ACAATTCGATGGAAAGTACATCCATTGGAAT CACCCAGTTTTGGAACATTGGGACCCTAGAA TCGCTAAAAATTACCCACAGGGTCAACACTC TCCACCTGATGACATTGGTTCTTCCTTCTAC CCTGAATTGGGATCTTATTCAAGTAGAGATC CATCCGTTATTGAGACTCATATGAAGCAAAT GAGATCCGCCTCCATCGGTGTCTTGGCACTTT TCATGGTACCCACCTGACAGTAGAGATGACA ACGGAGAAGCCACAGATCACTTGGTTCCTAC CATTCTTGACAAGGCACATAAGTACAACTTG AAGGTCACTTTCCACATCGAGCCATATTCTA |

| SEQ ID NO: | Description | Sequence |
|---|---|---|
| | | ATAGAGATGACCAGAACATGCACCAAAACAT CAAGTACATCATCGATAAGTACGGTAACCAT CCTGCTTTCTACAGATATAAGACCAGAACTG GACACTCTTTGCCAATGTTCTACGTTTATGA CTCCTACATTACAAAACCTACCATCTGGGCT AACTTGCTTACTCCATCAGGTAGTCAGTCGG TTAGATCCTCCCCTTATGATGGATTGTTTAT TGCCTTGCTTGTCGAAGAGAAGCATAAGAAC GATATCTTGCAGTCTGGTTTCGACGGAATCT ACACATATTTTGCTACCAACGGTTTCACTTA CGGATCAAGTCACCCAAAATTGGAACAATTTG AAGTCCTTCTGTGAAAAGAACAATCTTATGT TCATCCCATCAGTTGGTCCTGGATATATTGA TACAAGTATCAGACCATGGAACACTCAAAAC ACAAGAAACAGAGTTAACGGTAAATACTACG AGGTCGGATTGTCTGCAGCTCTTCAGACTCA TCCTTCCTTGATTTCAATCACAAGTTTTAAC GAATGGCACGAGGGTACTCAAATTGAAAAGG CTGTTCCAAAAAGAACCGCCAATACTATCTA CTTGGATTATAGACCACATAAGCCTTCATTG TACCTTGAGTTGACCAGAAAATGGTCTGAAA AGTTCTCCAAAGAGAGAATGACTTATGCATT GGACCAACAGCAACCAGCTTCCTAA |
| 54 | *Pichia pastoris* AOX1 transcription termination sequences | TCAAGAGGATGTCAGAATGCCATTTGCCTGA GAGATGCAGGCTTCATTTTGATACTTTTTTTA TTTGTAACCTATATAGTATAGGATTTTTTTT GTCATTTTGTTTCTTCTCGTACGAGCTTGCT CCTGATCAGCCTATCTCGCAGCTGATGAATA TCTTGTGGTAGGGGTTTGGGAAAATCATTCG AGTTTGATGTTTTTCTTGGTATTTCCCACTC CTCTTCAGAGTACAGAAGATTAAGTGAGACG TTCGTTTGTGCA |
| 55 | Insulin analogue | <u>N</u>GTFVNQHLCGSHLVEALYLVCGERGFFYT NK |
| 56 | Insulin analogue: Asn at 1 and 31 beta-1 linked to a paucimannose N-glycan | <u>N</u>*GTFVNQHLCGSHLVEALYLVCGERGFFYT <u>N</u>*K |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A host cell comprising:
   (a) a disruption in the expression of the endogenous dolichyl-P-Man:Man5GlcNAc2-PP-dolichyl alpha-1,3 mannosyltransferase (ALG3) gene; and
   (b) a disruption in the expression of the endogenous YOS9 gene; and
   (c) a nucleic acid molecule encoding a heterologous protein having one or more N-linked glycosylation sites,
   wherein the host cell is a mutant of *P. pastoris* having a deletion or disruption of the OCH1 gene.

2. The host cell of claim 1, wherein the disruption in the expression of the endogenous dolichyl-P-Man:Man5GlcNAc2-PP-dolichyl alpha-1,3 mannosyltransferase (ALG3) and endogenous YOS9 gene is achieved by deleting or disrupting the gene.

3. The host cell of claim 1, wherein the host cell further includes at least one nucleic acid molecule encoding a heterologous single-subunit oligosaccharyltransferase.

4. The host cell of claim 3, wherein the single-subunit oligosaccharyltransferase is the *Leishmania* sp. STT3A protein, STT3B protein, STT3C protein, STT3D protein or combinations thereof.

5. The host cell of claim 3, wherein the single-subunit oligosaccharyltransferase is the *Leishmania major* STT3D protein.

6. The host cell of claim 1, wherein the host cell is genetically engineered to produce glycoproteins comprising one or more mammalian- or human-like N-glycans.

7. The host cell of claim 1, wherein the host cell further expresses a protein that has endomannosidase activity.

8. A method for producing a heterologous glycoprotein, comprising providing a host cell comprising:
   (a) a disruption in the expression of the endogenous dolichyl-P-Man:Man5GlcNAc2-PP-dolichyl alpha-1,3 mannosyltransferase (ALG3) gene,
   (b) a disruption in the expression of the endogenous YOS9 gene, and
   (c) a nucleic acid molecule encoding the heterologous protein having one or more N-linked glycosylation sites, and
   culturing the host cell under conditions for expressing the heterologous protein to produce the heterologous glycoprotein,
   wherein the host cell is a mutant of *P. pastoris* having a deletion or disruption of the OCH1 gene.

9. The host cell of claim 8, wherein the disruption in the expression of the endogenous dolichyl-P-Man:Man5GlcNAc2-PP-dolichyl alpha-1,3 mannosyltransferase (ALG3) and endogenous YOS9 gene is achieved by deleting or disrupting the gene.

10. The method of claims 8, wherein the host cell further includes at least one nucleic acid molecule encoding a heterologous single-subunit oligosaccharyltransferase.

11. The method of claim 10, wherein the single-subunit oligosaccharyltransferase is the *Leishmania* sp. STT3A protein, STT3B protein, STT3C protein, STT3D protein or combinations thereof.

12. The method of claim 10, wherein the single-subunit oligosaccharyltransferase is the *Leishmania major* STT3D protein.

13. The method of claim 8, wherein the host cell is genetically engineered to produce glycoproteins comprising one or more mammalian- or human-like N-glycans.

14. The method of claim 8, wherein the host cell further expresses a protein that has endomannosidase activity.

* * * * *